United States Patent [19]

Sasaki et al.

[11] Patent Number: 5,218,092

[45] Date of Patent: Jun. 8, 1993

[54] MODIFIED GRANULOCYTE-COLONY STIMULATING FACTOR POLYPEPTIDE WITH ADDED CARBOHYDRATE CHAINS

[75] Inventors: Katsutoshi Sasaki; Tatsunari Nishi; Shigeyoshi Yasumura; Moriyuki Sato, all of Tokyo; Seiga Itoh, Kanagawa, all of Japan

[73] Assignee: Kyowa Hakko Kogyo Co., Ltd., Tokyo, Japan

[21] Appl. No.: 413,482

[22] Filed: Sep. 27, 1989

[30] Foreign Application Priority Data

Sep. 29, 1988 [JP] Japan .................. 63-245705

[51] Int. Cl.[5] .......................... C07K 13/00
[52] U.S. Cl. .................. 530/351; 530/300; 530/350; 530/395; 930/145; 435/69.1; 435/69.2; 435/69.5; 435/69.51; 435/69.52; 435/69.6; 435/183
[58] Field of Search ........... 530/350, 351, 395, 300; 435/69.1-69.7; 930/145

[56] References Cited

U.S. PATENT DOCUMENTS

| | | | |
|---|---|---|---|
| 4,280,953 | 7/1981 | Guillemin et al. | 260/112.5 |
| 4,478,746 | 10/1984 | Kim et al. | 260/112.7 |
| 4,478,830 | 10/1984 | Kim et al. | 424/178 |
| 4,483,792 | 11/1984 | Kim et al. | 260/112.7 |
| 4,489,064 | 12/1984 | Kim et al. | 424/178 |
| 4,751,084 | 6/1968 | Feder | 435/94.64 |
| 4,810,643 | 3/1989 | Souza | 435/172.3 |
| 4,904,584 | 2/1990 | Shaw | 435/69.4 |

FOREIGN PATENT DOCUMENTS 0276846 4/1988 European Pat. Off. .
63-230083 9/1988 Japan .
WO88/01647 3/1988 PCT Int'l Appl. .
WO89/11531 6/1989 World Int. Prop. O. .

OTHER PUBLICATIONS

*Archives of Biochem*, LaBranche et al, 276, 1990, pp. 153-159.
Stanley, *TIG* 3(3) 1987, pp. 77-81.
Kavshansky, *Biochem* 26, 1987, pp. 4861-4867.
*The Journal of Biological Chemistry*, vol. 263, No. 12, Apr. 1988, pp. 5948-5954 "Influence of New Glycosylation Sites on Expression ...".
*The Journal of Biological Chemistry*, vol. 263, No. 12, Apr. 1988, pp. 5955-5960, "Vesicular Stomatitis Virus G Proteins with Altered ...".
*Methods of Enzymology*, vol. 138, pp. 409-413 (1987).
*Methods of Enzymology*, vol. 138, pp. 413-418, (1987).
*Methods of Enxymology*, vol. 138, pp. 418-424 (1987).
*Biochemical and Biophysical Research Communications*, vol. 159, No. 1 1989, Feb. 28, 1989, pp. 103-111, Kuga et al "Mutagenesis of Human ...".

*Primary Examiner*—Garnette D. Draper
*Attorney, Agent, or Firm*—Nixon & Vanderhye

[57] ABSTRACT

A polypeptide or glycosylated polypeptide with at least one new carbohydrate chain produced by means of recombinant DNA technique, which has protease resistance and thermal stability and is expected to have longer lifetime in blood than those of a naturally-occurring form.

1 Claim, 58 Drawing Sheets

FIG. 1
HIGH MANNOSE TYPE (REPRESENTATIVE)
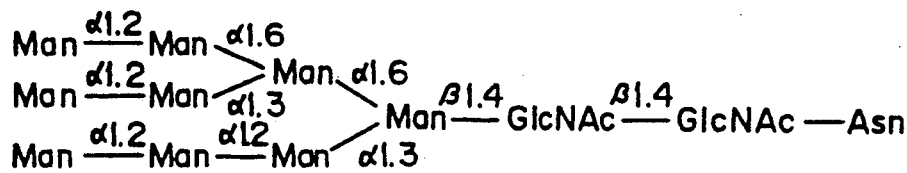
COMPLEX TYPE (REPRESENTATIVE)
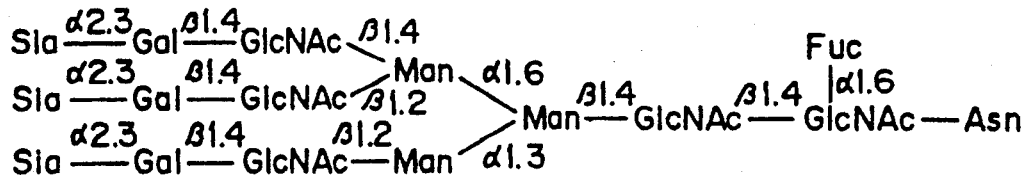
HYBRID TYPE (REPRESENTATIVE)
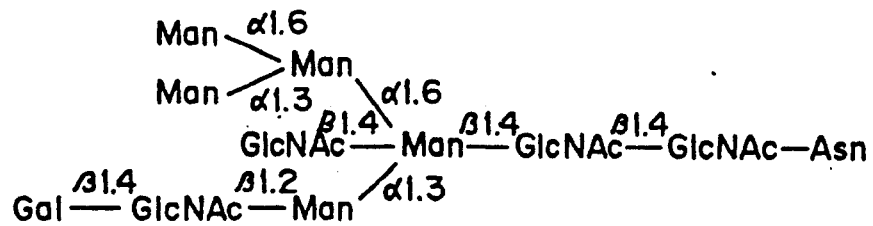

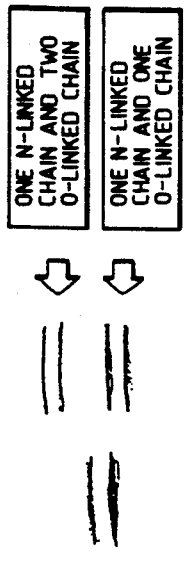
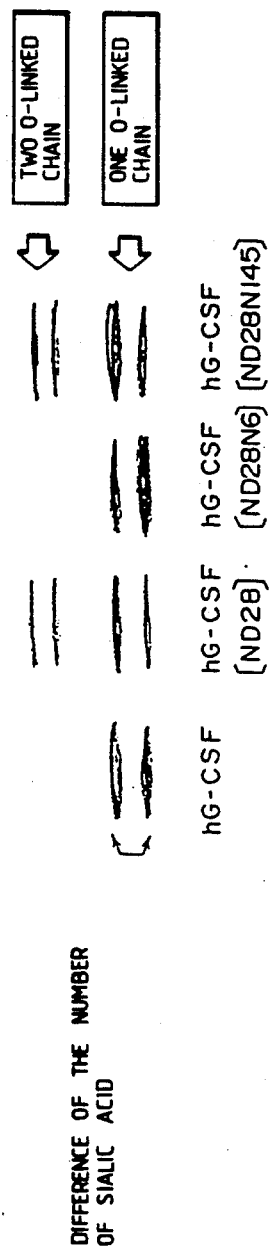
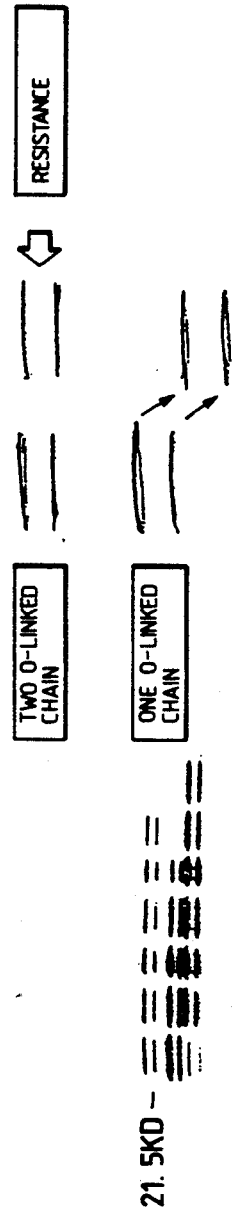
FIG. 8(3)
FIG. 8(4)

FIG. 12

NATURL pro-UK

PROTEIN MOLECULAR WEIGHT MARKER | ⊖ THROMBIN | ⊕ THROMBIN
| 0' 15' 30' 60' 120' | 0' 15' 30' 60' 120'

- 92.5K
- 66.2K
- 45K ← SINGLE-STRANDED pro-UK
- 31K ← DOUBLE-STRANDED B CHAIN
- 21.5K ← DOUBLE-STRANDED A CHAIN

UK-S1

PROTEIN MOLECULAR WEIGHT MARKER | ⊖ THROMBIN | ⊕ THROMBIN

- 92.5K
- 66.2K
- 45K ← SINGLE-STRANDED UK-S1 WITH CARBOHYDRATE CHAIN NEWLY ADDED THERETO
- 31K
- 21.5K

FIG. 26
```
p AGCTTGAGATCCTACAGGAGTCCAGGGCTGGAGAGAAAACCTCTGCG
    ACTCTAGGATGTCCTCAGGTCCCGACCTCTCTTTTGGAGACGC       p
p AGGAAAGGGAAGGAGCAAGCCGTGAATTTAAGGGACGCTGTGAAGCAAT
     CCCTTCCTCGTTCGGCACTTAAATTCCCTGCGACACTTCGTTAGTAC  p
```
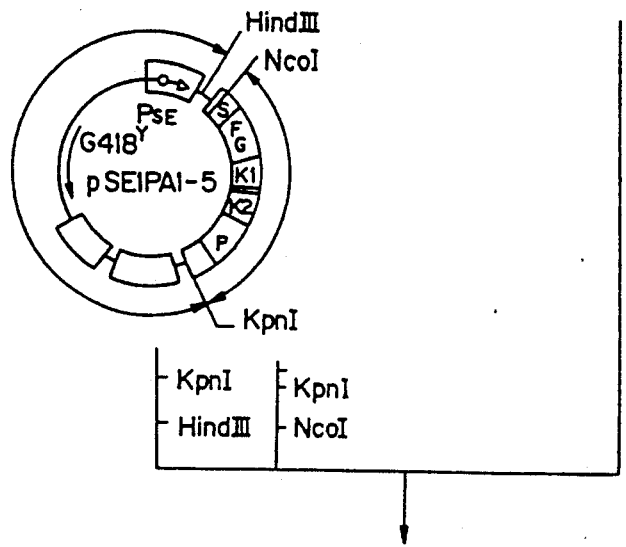
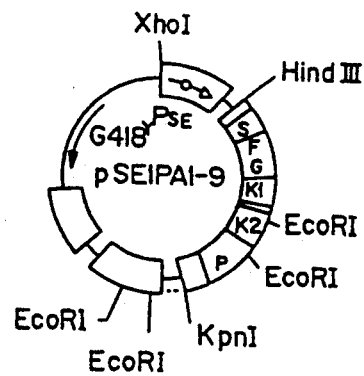

FIG. 32
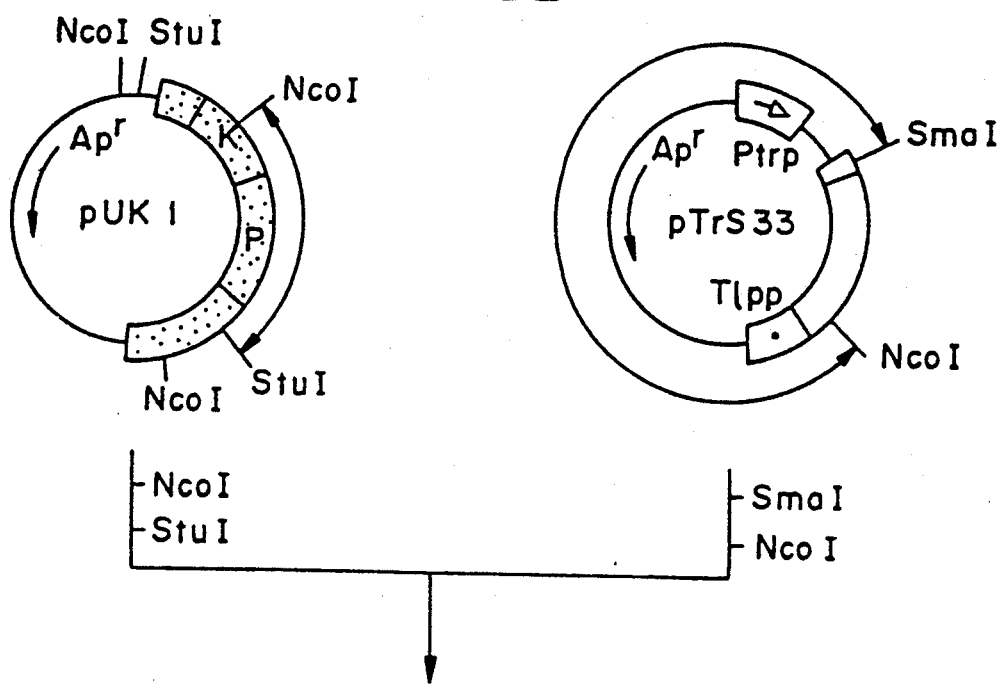
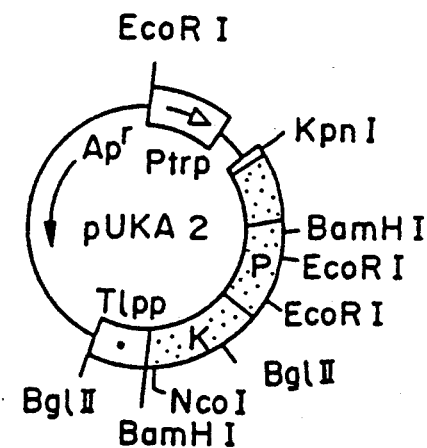

pAGCTTGTCCCCGCAGCGCCGTCGCGCCCTCCTGCCGCAG
ACAGGGGCGTCGCGGCAGCGCGGGAGGACGGCGTCCGGTGGp pGCCACCGAGGCCGCCGCCGTCTAGCGCCCCGACCTCGCCAC
CTCCGGCGGCGGCAGATCGCGGGGCTGGAGCGGTGGTACp pCATG AGA GCC CTG CTG G
TCT CGG GAC GAC C GCGCp

FIG. 36
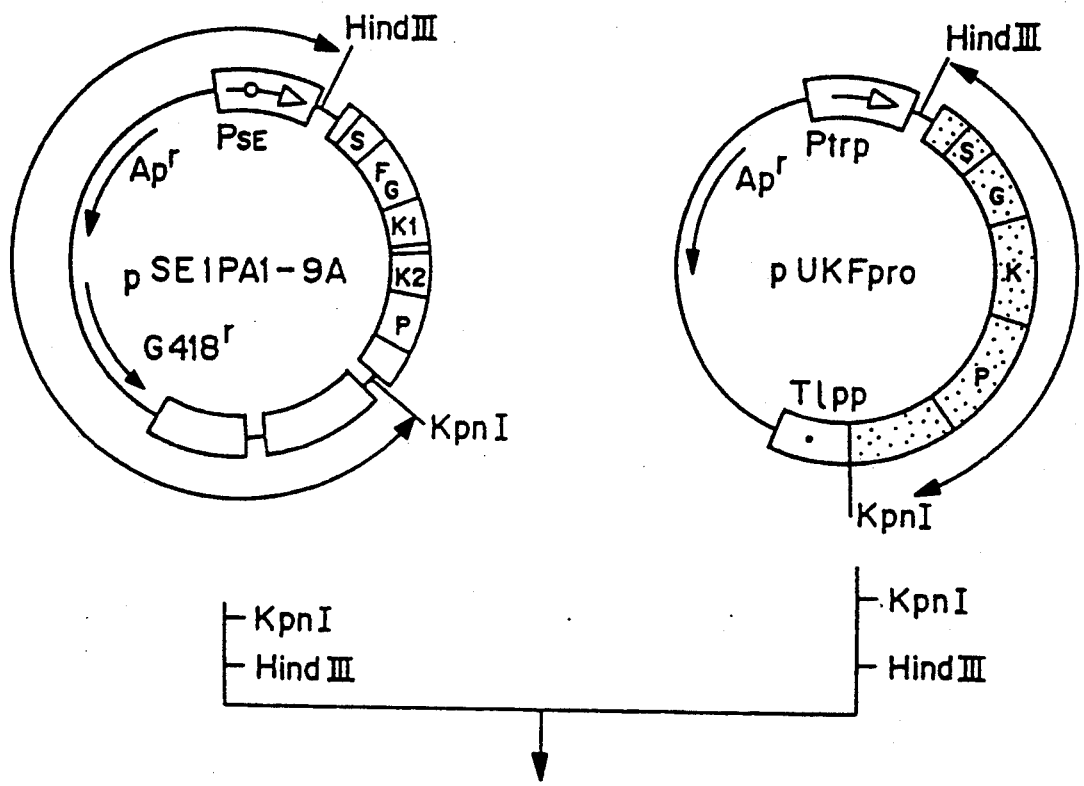
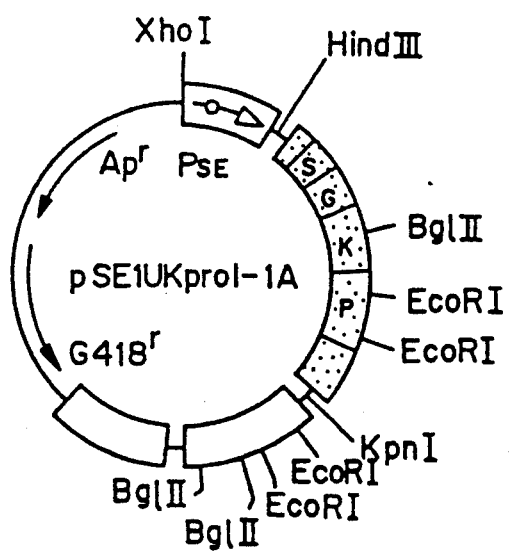

FIG. 39
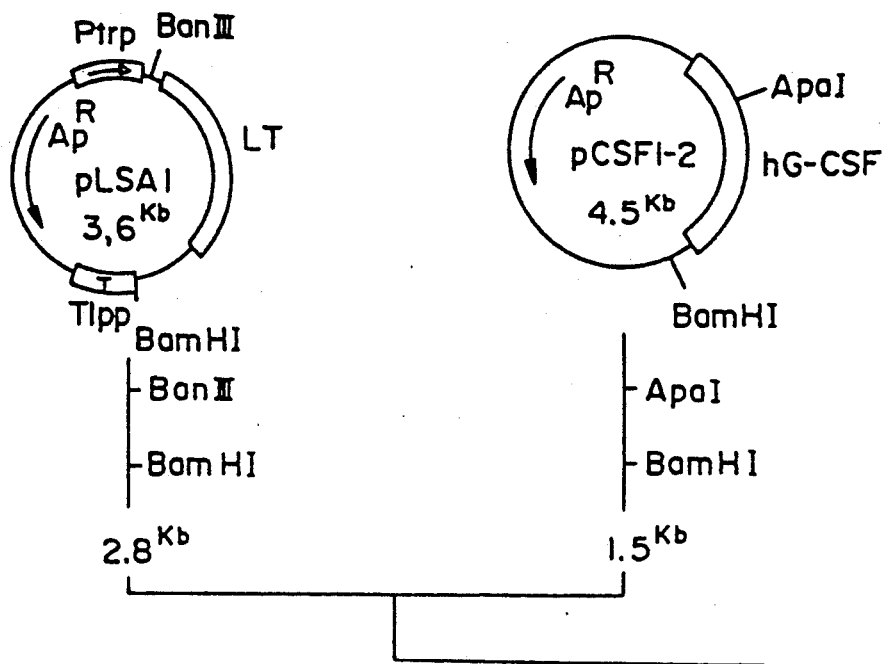
26mer 4mix    Met Thr Pro Leu Gly
5'—CGATAAGCTT ATG ACT CCT CTAGGCC—3'
3'— TATTCGAA TAC TGT GGT GAT ————5'
20mer 4mix
- PHOSPHORYLATION
- T4 LIGASE
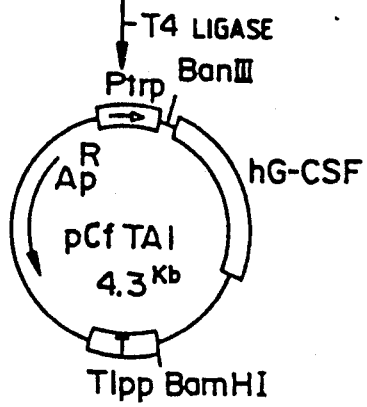

GGCCAAAAGACTATTCGAACGCGTTTTAAGATTATTGGGGGAG
TTTTCTGATAAGCTTGCGCAAAATTCTAATAACCCCCTCTTAA

FIG. 51
p ACTGTGACGTCCCCAGCTGTTCTGAAGGAAATGCA
TGACACTGCAGGGGTCGACAAGACTTCCTTT p
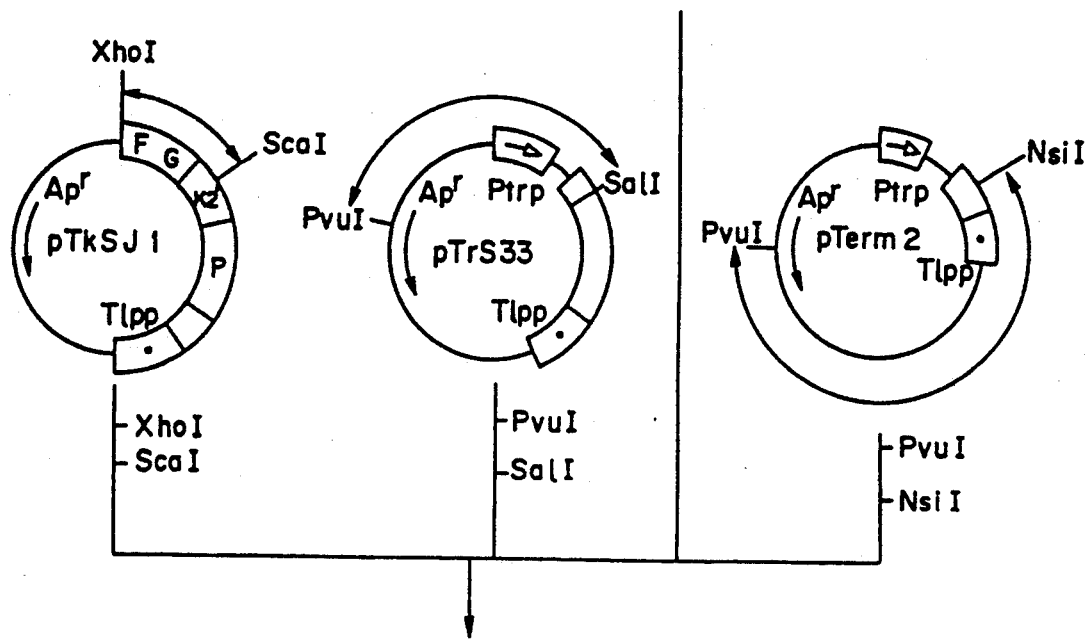
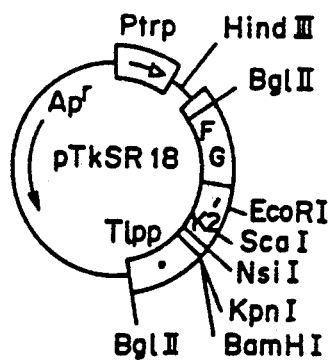

pACTGTGACGTCCCCAGCTGTTCTGAAGGAAATGCA
TGACACTGCAGGGGTCGACAAGACTTCCTTTp

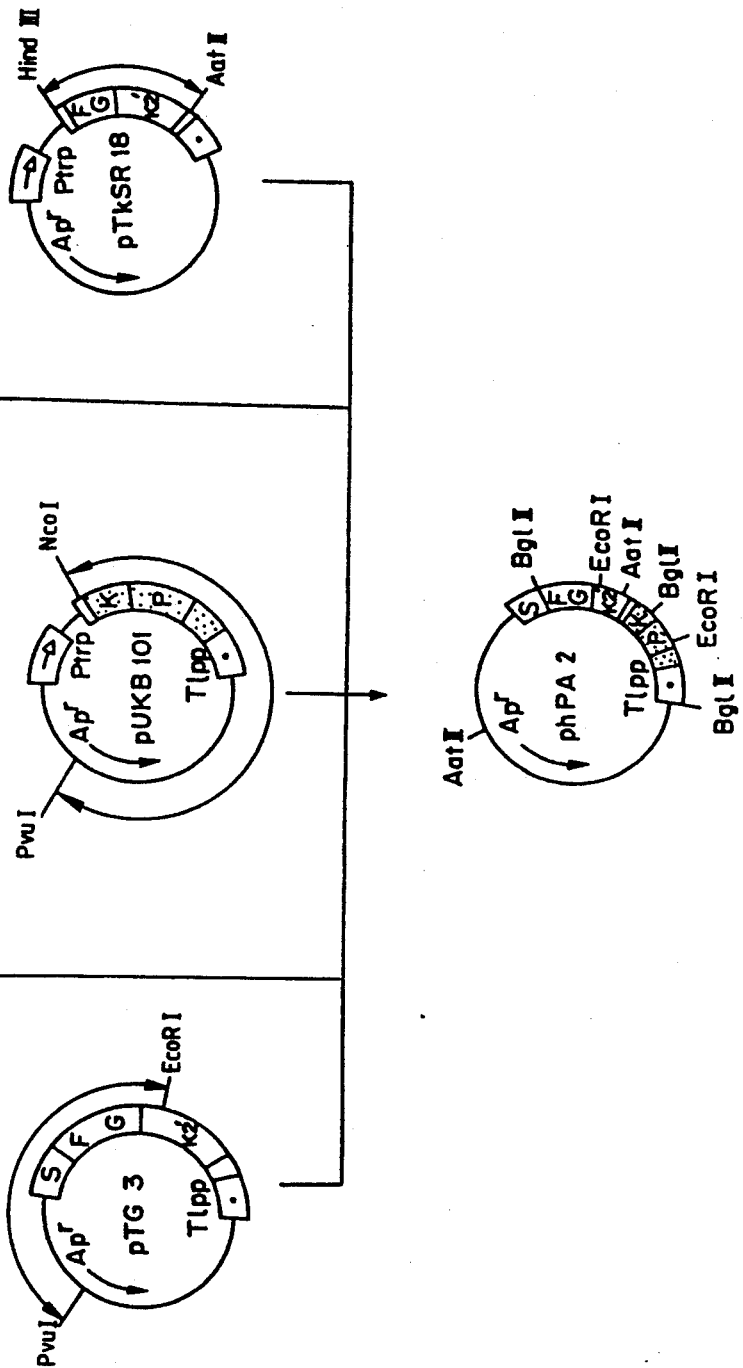

MODIFIED GRANULOCYTE-COLONY STIMULATING FACTOR POLYPEPTIDE WITH ADDED CARBOHYDRATE CHAINS

FIELD OF THE INVENTION

The invention relates to novel polypeptides having an amino acid sequence which allows addition of at least one carbohydrate chain thereto, glycosylated polypeptides derived from said polypeptides, deoxyribonucleic acids (DNA) coding for said polypeptides or glycosylated polypeptides, recombinant plasmids containing said DNA, host cells transformed with said recombinant plasmids, and a method of producing said polypeptides or glycosylated polypeptides which uses the transformant cells.

This invention is applicable to each and every polypeptide. The polypeptides having a newly added carbohydrate (or oligosaccharide) chain as provided by this invention have diverse carbohydrate chain functions added and are superior in physicochemical properties and/or activities to the corresponding naturally occurring proteins. Therefore, the carbohydrate chain-added polypeptides according to the invention are expected to be useful in a wide range of fields.

When the polypeptide or glycosylated polypeptide according to the invention is human granulocyte colony stimulating factor (hG-CSF), for instance, the hG-CSF with an additional carbohydrate chain added at an appropriate site has increased resistance to protease. This novel hG-CSF is fully expected to show slower blood clearance and is expected to be useful as a drug.

When the polypeptide or glycosylated polypeptide according to the invention is urokinase (UK), the UK with an additional carbohydrate chain added at an appropriate site is superior in thrombolytic activity to the corresponding UK having no such chain and is expected to be useful as a therapeutic agent for cerebral thrombosis, myocardial infarction and so forth.

BACKGROUND OF THE INVENTION

While proteins produced in prokaryotes, such as *Escherichia coli*, have no carbohydrate chain, proteins produced in eukaryotes, such as yeasts, fungi, plant cells or animal cells, have a carbohydrate chain or chains in many instances.

Carbohydrate chains involved in glycosylation are roughly classifiable into two main groups. One group includes N-linked or N-glycosylated carbohydrate chains bound to the asparagine (Asn) residue in proteins and the other includes O-linked or O-glycosylated chains bound to the serine (Ser) or threonine (Thr) residue in proteins.

N-glycosylated carbohydrate chains have a common basic core structure composed of five monosaccharide residues, namely two N-acetylglucosamine residues and three mannose residues, and are classified into three types: high mannose type, complex type and hybrid type (FIG. 1). A precursor to these asparagine-linked carbohydrate chains is the lipid intermediate (Glc$_3$Man$_9$GlcNAc$_2$-PP-Dol) (FIG. 2) composed of dolichol, which is polyisoprenoid alcohol comprising 18 to 20 isoprene units, and a carbohydrate chain composed of two N-acetylglucosamine residues, nine mannose residues and three glucose residues and bound to said dolichol via pyrophosphoric acid.

The reaction route leading to the formation of the lipid intermediate is well known as the "dolichol phosphate cycle" (FIG. 3).

The carbohydrate chain portion of the lipid intermediate is transferred as a whole to the Asn residue in an amino acid sequence (N-glycosylation site), such as Asn-X-Ser/Thr, in a polypeptide chain under formation within the cisterna of the rough-surfaced endoplasmic reticulum (rER), whereby an N-glycoside linkage is formed. In the above sequence, X may be any amino acid other than proline (Pro). This reaction is known to be catalyzed by "oligosaccharyl transferase", a kind of membrane enzyme. Thereafter, the carbohydrate chain undergoes trimming and processing in the process of passing through the rER and Golgi body, whereby a carbohydrate chain of the high mannose, hybrid or complex type is worked up (FIG. 4). It is known that a number of glycosidases and glycosyl transferases are involved in the process of trimming and processing.

While high mannose type carbohydrate chains are often encountered in glycoproteins of animal or plant origin as well as in yeast and fungal glycoproteins, it is presumed that carbohydrate chains of the complex type are limited to glycoproteins of the animal origin.

N-Glycosylated carbohydrate chains are bound to the Asn residue in Asn-X-Ser/Thr (X being any amino acid other than Pro) in polypeptides, as mentioned above. However, many proteins contain an unglycosylated Asn-X-Ser/Thr sequence or sequences and the presence of this sequence does not always result in addition of a carbohydrate chain thereto. In fact, William J. Lennarz et al. suggest that the three-dimensional structure of a protein is important in inducing binding of a carbohydrate chain. Their suggestion is based on the finding that simple tripeptides having the sequence Asn-X-Ser/Thr and denatured proteins free of a complicatedly folded spatial structure such as natural proteins have are comparatively readily glycosylated enzymatically in vitro.

On the other hand, O-glycosylated carbohydrate chains are bound to the Ser or Thr residue in polypeptides via N-acetylgalactosamine, which is generally followed by galactose, sialic acid, fucose and N-terminal acetylgalactosamine [Suzuki et al.: Tanpakushitsu, Kakusan, Koso, 30, 513 (1985)]. Unlike the case of the above-mentioned N-glycosylated carbohydrate chains, it is believed that their synthesis does not involve the rER but is always conducted in the Golgi body [Johnson et al.: Cell, 32, 987 (1983)]. Also, unlike the case of the N-glycosylated there is no rule on the amino acid sequence required for glycosylation. It is known, however, that the tendency toward glycosylation increases when Pro occurs in the vicinity, for example in the sequences Pro-Thr/Ser, Thr/Ser-Pro and Thr/Ser-X$_{1-3}$-Pro (X being any amino acid) [Takahashi et al.: Proc. Natl. Acad. Sci. USA, 81, 2021 (1984)].

Many of the substantial biologic functions of carbohydrate chains in glycoproteins remain unknown. However, a number of investigations on glycoproteins have already revealed diverse functions of carbohydrate chains.

Firstly, it is known that carbohydrate chains stabilize proteins. Retardation in blood clearance is an example. It is known that human erythropoietin (having no asparagine-linked carbohydrate chain) produced by means of gene introduction into *Escherichia coli* or human erythropoietin enzymatically treated for carbohydrate chain elimination shows activity in vitro but undergoes rapid clearance and shows decreased activity in vivo [Dordal et al.: Endocrinology, 116, 2293 (1985) and Browne et al.: Cold Spr. Harb. Symp. Quant. Biol., 51, 693 (1986)]. In the case of human granulocyte macrophage colony stimulating factor (hGM-CSF), the natural form of which has two N-glycosylated carbohydrate chains, it is known that the rate of clearance from the rat plasma increases in proportion to the reduction in the number of carbohydrate chains [Donahue et al.: Cold Spr. Harb. Symp. Quant. Biol., 51, 685 (1986)]. The rate of clearance and the site of clearance vary depending on the carbohydrate chain structure as well. Thus, it is known that sialic acid-containing hGM-CSF undergoes clearance in the kidney while hGM-CSF after sialic acid elimination shows an increased rate of clearance and undergoes clearance in the liver. Furthermore, $\alpha_1$-acid glycoproteins differing in carbohydrate structure as biosynthesized in a rat liver primary culture system in the presence of different asparagine-linked carbohydrate chain biosynthesis inhibitors were examined for the rate of clearance from the rat plasma and for the rate of clearance from the rat perfusate. It was found that in both fluids the clearance rates were in the following order: high mannose type > carbohydrate chain-deficient type > hybrid type > complex type (natural form) [Gross et al.: Eur. J. Biochem., 162, 83 (1987)]. As another example of stabilization, it is known that carbohydrate chains provide proteins with protease resistance. In the case of fibronectin, for instance, inhibition of carbohydrate chain formation by means of tunicamycin results in an increased rate of decomposition of the intracellular product protein, i.e. carbohydrate chain-deficient fibronectin [Olden et al.: Cell, 13, 461 (1987)]. It is also known that carbohydrate chain addition increases thermal stability and/or freezing resistance. Furthermore, it is known that carbohydrate chains contribute to increased solubility of proteins, for example in the case of erythropoietin or $\beta$-interferon.

Carbohydrate chains are helpful for proteins to maintain their proper three-dimentional structure. In the case of the vesicular stomatitis virus membrane-bound glycoprotein, it is known that removal of the two naturally occurring N-glycosylated carbohydrate chains results in inhibition of the transport of the protein to the cell surface and that addition of new carbohydrate chains to the protein results in recovery of this transport. In this case, it has been revealed that carbohydrate chain elimination leads to induction of the aggregation of one protein molecule with another via disulfide bond and, as a result, protein transport is inhibited. It is considered that the newly added carbohydrate chains can inhibit this aggregation and maintain the proper three-dimentional structure of the protein, thus making the protein transport again possible. In the case mentioned above, it has been shown that the sites for new carbohydrate chain addition are considerably flexible. To the contrary, it has been found that carbohydrate chain introduction at some sites results in complete inhibition of the transport of the protein having natural carbohydrate chains [Rose et al.: J. Biol. Chem., 263, 5948 and 5955 (1988)].

Instances are also known where antigenic sites on polypeptides are masked by carbohydrate chains. For hGM-CSF, prolactin, interferon-$\gamma$, Rauschcer leukemia virus gp70 and influenza hemagglutinin, experiments using polyclonal antibodies or monoclonal antibodies to specific regions on peptides have led to the conclusion that the carbohydrate chains on these proteins inhibit the reaction with the antibodies. On the other hand, it is also known that carbohydrate chains in some proteins induce immune reactions. It is thus suggested that carbohydrate chains might play a dual role.

It is further known that carbohydrate chains themselves are directly involved in the expression of activity of glycoproteins in some instances. Examples are glycoprotein hormones, such as luteinizing hormone, follicle-stimulating hormone and chorionic gonadotropin.

Finally, involvement in recognition phenomena may be mentioned as an important function of carbohydrate chains. Many instances are known where carbohydrate chains are considered to be involved in cell-cell, protein-protein or cell-protein recognition phenomena. That different carbohydrate chain structures may be indicative of different sites of in vivo clearance is an example.

In the foregoing, mention has been made of the structures and functions of carbohydrate chains in glycoproteins. The means of analyzing the structures and functions of carbohydrates have advanced remarkably, making it possible to analyze physicochemical properties of carbohydrate chains bound to peptide skeletons from various viewpoints.

In particular, it deserves special mentioned that highly specific enzymes (exoglycosidases) eliminating monosaccharides one by one and glycopeptidases or endoglycosidases cleaving the site of binding to a peptide chain without damaging either the peptide chain or the carbohydrate chain are now available for use in detailed investigations as to the biological roles of carbohydrate chains. It is also possible to add one or more additional carbohydrate chains to proteins by using glycosyltransferase. It is further possible to add sialic acid to the end of a carbohydrate chain by using sialyltransferase. Techniques are well known for modifying the carbohydrate chain to be added by using various glycosyltransferase inhibitors or glycosidase inhibitors.

Although there are some cases where the techniques of carbohydrate chain addition were applied for the purpose of investigating the functions of carbohydrate chains, as in the case of the above-mentioned vesicular stomatitis virus membrane glycoprotein, such techniques have never been used for the production of improved polypeptides of high commercial value. Generally, many (physiologically active) polypeptides have undesirable properties; for example, they are readily cleaved with protease and their activity is reduced, heat treatment reduce their activity, they readily undergo clearance when administered to living bodies, and so forth. There have been no cases known as yet in which attempts have been made to increase protease resistance, thermal stability or stability in blood by modifying the amino acid sequences of such polypeptides and intentionally adding one or more new carbohydrate chains to the polypeptide of interest. The present inventors have developed a means of improving various properties of such polypeptides, as mentioned above, through the intentional addition of one or more new carbohydrate chains to such peptides.

Generally, many physiologically active polypeptides are disadvantageous in that their activity is readily reduced by cleavage with protease or upon heat treatment or that they readily undergo clearance when administered to living animals including humans. For instance, urokinase (hereinafter referred to as "UK") is converted to an inactive form upon exposure to a protease called thrombin. It is an important task to improve physiologically active polypeptides with respect to such properties.

SUMMARY OF THE INVENTION

A method has now been developed of providing physiologically active polypeptides with at least one new or additional carbohydrate chain to thereby accomplish the objects described above. The method of modifying the amino acid sequence of a polypeptide is to add at least one new carbohydrate chain to the modified polypeptide at a desired site, for example in the vicinity of a protease cleavage site. This method includes constructing a DNA coding for the modified polypeptide using recombinant DNA technology, constructing a recombinant expression vector with this DNA inserted in it, introducing the vector into a microorganism or animal cells and causing the microorganism or cells to express the thus modified polypeptide. Upon investigating the properties of several glycosylated polypeptides obtained by this method, it was found that these polypeptides had been provided with the properties desired, such as protease resistance. The present invention has been completed based on such findings.

Thus, the invention provides novel polypeptides having an amino acid sequence allowing addition of at least one carbohydrate chain, the resultant glycosylated polypeptides, DNAs coding for these polypeptides or glycosylated polypeptides, recombinant plasmids containing these DNAs, microorganism or animal cells harboring these recombinant plasmids, and a method of producing these polypeptides or glycosylated polypeptides which use the microorganism or animal cells are all within this invention.

BRIEF DESCRIPTION OF THE DRAWINGS

The invention is further illustrated with reference to the following drawings:

FIG. 1 illustrates the classification of N-glycosylated carbohydrate chains. The symbols used in the figure respectively have the following meanings and these definitions shall apply throughout the specification and appended claims: Glc: glucose; Man: mannose; GlcNAc: N-acetylglucosamine; Gal: galactose; Sia: sialic acid; Fuc: fucose.

FIG. 7(2) shows the construction scheme for the plasmid pASN145.

FIG. 8(2) shows the result of enzyme-labeled antibody staining of proteins on the gel shown in FIG. 8(1) after transfer onto a nitrocellulose membrane. An anti-hG-CSF monoclonal antibody was used as the antibody.

FIG. 8(3) is a schematic representation of FIG. 8(2).

FIG. 8(4) shows the result of SDS-polyacrylamide gel electrophoresis of hG-CSF[ND28] with an O-glycosylated carbohydrate chain newly added thereto and hG-CSF[ND28] without the carbohydrate chain such as carried out with respect to chymotrypsin resistance, together with a schematic representation of said result.

FIG. 8(5) shows the result of SDS-polyacrylamide gel electrophoresis of hG-CSF[ND28N6] with an N-glycosylated carbohydrate chain newly added thereto and hG-CSF[ND28N6] without such chain as carried out with respect to chymotrypsin resistance, together with a schematic representation of the same.

FIG. 8(6) shows the result of SDS-polyacrylamide gel electrophoresis of hG-CSF[ND28N145] with an O-glycosylated carbohydrate chain or N-glycosylated carbohydrate chain newly added thereto and hG-CSF[ND28N145] without such chain as carried out with respect to chymotrypsin resistance, together with a schematic representation of the same.

FIG. 8(7) shows the result of a comparative test of hG-CSF[ND28N6] with an N-glycosylated carbohydrate chain newly added thereto and hG-CSF[ND28N6] having no such chain (as a result of elimination of such chain) as carried out with respect to thermal stability. The symbol o indicates N-glycanase treatment (hG-CSF[ND28N6] after N-glycosylated carbohydrate chain elimination) and the symbol [● indicates the control (N-glycosylated carbohydrate chain-added hG-CSF[ND28N6]).

FIG. 12 shows the result of SDS-polyacrylamide gel electrophoresis of naturally occurring pro-UK and the UK derivative UK-S1 as carried out for comparing them with respect to thrombin sensitivity.

FIG. 26 shows the construction scheme for the plasmid pSE1PA1-9.

FIG. 32 shows the construction scheme for the plasmid pUKA2.

FIG. 36 shows the construction scheme for the plasmid pSE1UKpro1-1A.

FIG. 39 shows the construction scheme for the plasmid pCfTA1.

FIG. 51 shows the construction scheme for the plasmid pTkSR18.

FIG. 56 shows the construction scheme for the plasmid phPA2.

DETAILED DESCRIPTION OF THE INVENTION

Figure 2:
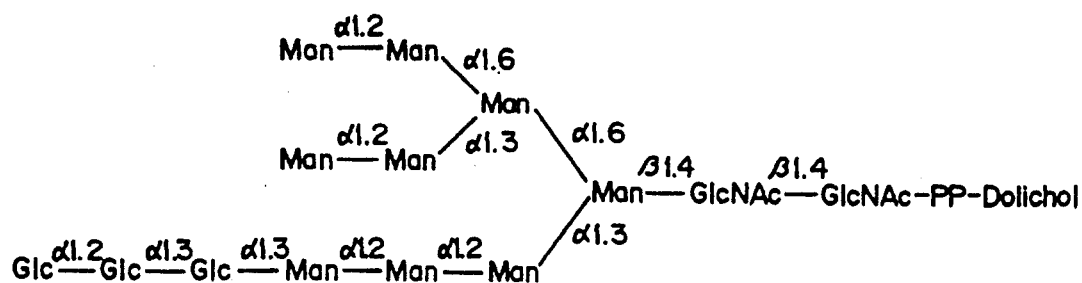
FIG. 2 illustrates the structures of lipid intermediates. In this figure, "PP" stands for pyrophosphoric acid.
Figure 3:
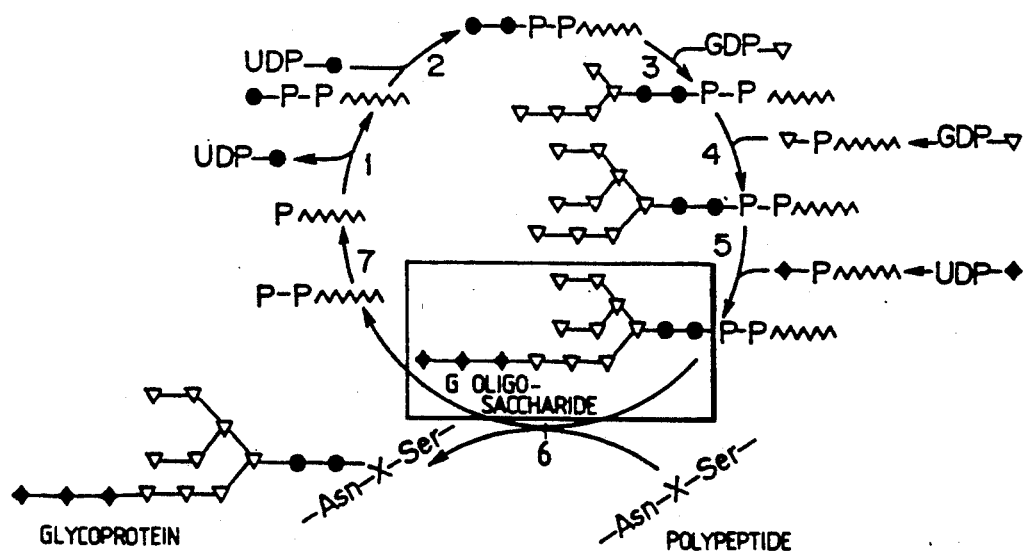
FIG. 3 illustrates the dolichol phosphate cycle. The symbols used in the figure respectively have the following meanings: P∿: dolichol phosphate; P—P∿: dolichol pyrophosphate; GDP: guanidine diphosphate; UDP: uridine diphosphate; ◆: glucose; ∇: mannose; ● : N-acetylglucosamine.
Figure 4:
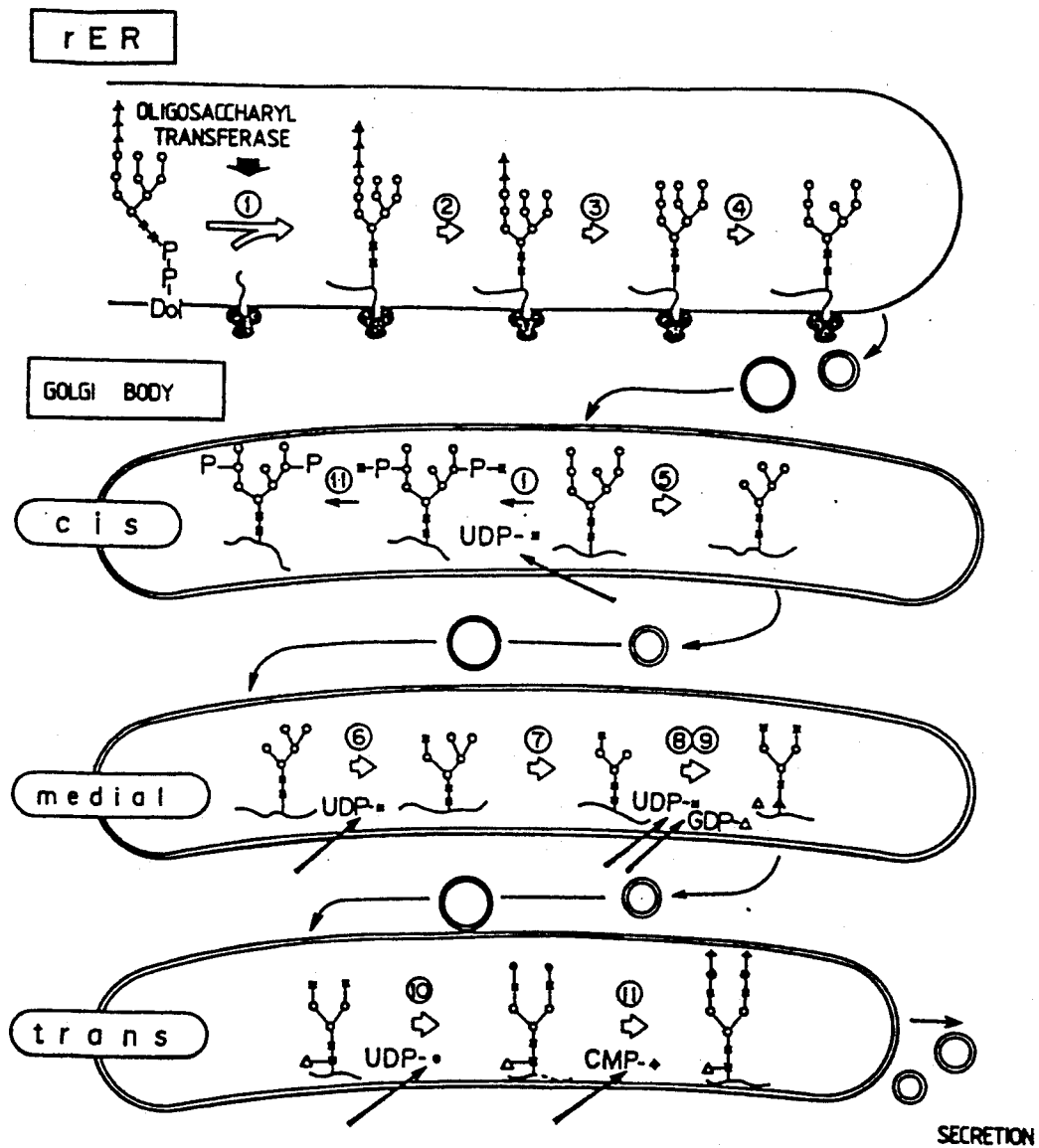
FIG. 4 illustrates the system of biosynthesis of N-glycosylated carbohydrate chains. The symbols used in the figure respectively have the following meanings: ■: N-acetylglucosamine; o: mannose; ● : galactose; ◆: sialic acid; ▲ : glucose; △: fucose.

It is an object of the invention to provide a polypeptide or glycosylated polypeptide with at least one new carbohydrate chain and thereby additionally endow the polypeptide or glycosylated polypeptide with at least one of the above-mentioned functions of carbohydrate chains. Thus, for instance, it is an object of the invention to stabilize polypeptides or glycosylated polypeptides by adding one or more new carbohydrate chains thereto and thereby retard blood clearance and/or direct said polypeptides or glycosylated polypeptides to specific sites in vivo. In cases where protease cleavage of polypeptides exerts a great influence on their physiological activity, the invention makes it possible to increase their protease resistance through carbohydrate chain addition and thus control their physiological activity.

The formation of an amino acid sequence allowing the addition of a new carbohydrate chain in polypeptides can be realized by means such as amino acid substitution in, amino acid deletion from, or amino acid insertion into the polypeptides.

Since asparagine (Asn) is known to be an amino acid for linking an N-glycosylated carbohydrate chain and serine (Ser) and threonine (Thr) are each known to be amino acids suited for linking of an O-glycosylated carbohydrate chain, it is suitable for the intended purpose to locate one of these "linking" amino acids at an appropriate position in the polypeptide to be modified.

Polypeptides modified so that they contain an amino acid to which a carbohydrate chain can be added can be obtained preferably by introducing a tripeptide of the formula Asn-X-Thr/Ser (X being any amino acid other than proline) into the polypeptides to be modified at an appropriate site. This tripeptide introduction can be carried out by the site-directed gene mutation technique.

In adding a new carbohydrate chain, the site of carbohydrate chain addition is important. As mentioned above, carbohydrate chain addition will not occur at certain sites on polypeptides or, in some instances, addition of a new carbohydrate chain, even if it has occurred, may result in destruction of the appropriate three-dimensional structure of the polypeptide, which may lead to inhibition of membrane transport or loss of activity. Therefore, it is necessary that the site of addition of a new carbohydrate chain should be located at least at a surface site region of the polypeptide. When the three-dimensional structure of a polypeptide is already known, the surface sites of this polypeptide are apparent, so that the site or sites of addition can be readily determined. To minimize activity loss due to the addition of one or more carbohydrate chains, it is desirable that the site or sites of addition should be as remote from the active site as possible. In the case of polypeptides the three-dimensional structure and active site of which are known, the addition site or sites can be selected with due consideration for the above. On the other hand, when the three-dimensional structure of a polypeptide is unknown, the surface sites can be estimated by calculating the hydrophilicity of the polypeptide on the basis of its primary structure. It is also possible to estimate the locus or loci where a turn structure is likely formed by anticipating the secondary structure based on the primary structure by the method of Chou and Fasman [Biochemistry, 13, 211 (1974); Biochemistry, 13, 222 (1974); Adv. Enzymol., 47, 45 (1978)] or by the method of Robson [J. Mol. Biol., 107, 327 (1976); ibid., 120, 97 (1978)]. Furthermore, more detailed information may be obtained about the surface sites by treating with various kinds of proteases and identifying readily cleavable sites. Since it is thought highly probable that the vicinity of a protease cleavage site occurs on the surface of the polypeptide in question, such vicinity would become the best target site for carbohydrate chain addition when one attempts to add one or more carbohydrate chains to the polypeptide efficiently or to produce a carbohydrate chain-added (i.e. glycosylated) polypeptide comparable in activity to the corresponding naturally occurring protein. Furthermore, it can be expected that a polypeptide glycosylated in the vicinity of a protease cleavage site would be resistant to the relevant protease. The vicinity of a protease cleavage site thus may be said to be a very suitable carbohydrate chain addition site for stabilizing the polypeptide. It is desirable and preferable that a carbohydrate chain addition site should be introduced into a polypeptide within the range of 8 amino acid residues from a protease cleavage site.

Irrespective of whether the three-dimensional structure is known or unknown, it is necessary to actually introduce carbohydrate addition sites into some of the sites selected in the above manner so that whether glycosylation can actually take place there can be confirmed. It is also necessary to evaluate the glycosylated polypeptides obtained as to whether they retain biologically activity, whether there is a loss in activity or whether they have some or other additional desirable function, and from other viewpoints.

The polypeptide, which is the subject of the present invention, may be any physiologically active polypeptide. As preferred examples, however, there may be mentioned colony stimulating factors (granulocyte-macrophage colony stimulating factor, granulocyte colony stimulating factor, macrophage colony stimulating factor), tissue plasminogen activator (t-PA), urokinase (UK), interferon-α, interferon-β, interferon-γ, lymphotoxln, lipocortin, superoxide dismutase, erythropoietin, interleukin-1, -2, -3, -4, -5, -6 and -7, and the like. Other physiologically active peptides amenable to this invention will suggest themselves.

Polypeptides are glycosylated as follows. First, a DNA coding for a mutant polypeptide so modified that it has, at a desired site, for example in the vicinity of a protease cleavage site, an amino acid sequence which allows new carbohydrate chain addition is constructed by using recombinant DNA techniques. Then, the DNA is inserted into an expression vector and the resulting recombinant is introduced into microbial cells (yeast cells, fungal cells, etc.) or animal cells (CHO cells, Namalwa cells, etc.) and expression is caused, and a newly glycosylated polypeptide can be obtained. For causing addition of an N-glycosylated carbohydrate chain, the DNA should be such that it contains an N-glycosylation site (Asn-X-Ser/Thr; X being any amino acid other than Pro). Such DNA coding for a mutant polypeptide can be constructed in the manner of site-directed mutagenesis or by using a synthetic DNA linker.

The function or functions of a carbohydrate chain greatly depend on the structure thereof. Therefore, it is also important that the structure of the carbohydrate chain to be added should be modified so that the carbohydrate chain selected can add a better property to the glycosylation product. The present invention includes the process for such optimization as well. As the methods for modifying the carbohydrate chain structure, there may be mentioned the following, among others: 1) Change of the protein-producing host; 2) Cultivation of microorganism or animal cells harboring the above-mentioned recombinant plasmid in a medium containing an agent (inhibitor) that inhibits an enzyme involved in biosynthesis or processing of carbohydrate chains, such as 1-deoxynojirimycin, 1-deoxymannonojirimycin or swainsonine; and 3) Treatment of glycosylated proteins with various glycosidases, such as sialidase, β-galactosidase, β-N-acetylglucosaminidase, β-mannosidase and endoglycosidase, or glycosyltransferases, such as sialyltransferase.

A more detailed description will be given below in those cases where the polypeptide or glycosylated polypeptide according to the invention is hG-CSF, UK or t-PA.

(1) The case where the polypeptide or glycosylated polypeptide according to the invention is hG-CSF:

Analysis of hG-CSF and the hG-CSF derivative hG-CSF[ND 28] (cf. Reference Example 16) each produced in and purified from *Escherichia coli* using recombinant DNA techniques has revealed that a site behind the 144th (from the N terminus) amino acid phenylalanine (Phe) residue of the mature hG-CSF polypeptide is susceptible to proteolysis by chymotrypsin. As for hG-CSF[ND28], it has also been revealed that four to seven N-terminal amino acid residues are susceptible to cleavage with various protease species (subtilisin, chymotrypsin, trypsin, etc.). It is known that hG-CSF[ND28] is more active than mature hG-CSF produced in and purified from *Escherichia coli*. On the basis of the above findings, it is estimated that, in hG-CSF[ND28], a portion close to the N terminus and a portion in the vicinity of the 144th (from the N terminus) amino acid are found on the polypeptide surface. Therefore, an attempt was made to add a carbohydrate chain to hG-CSF[ND28] on the 6th or 145th (from the N terminus) amino acid residue thereof. An hG-CSF[ND28] derivative which has a carbohydrate chain addition site on the 6th (from the N terminus) amino acid residue is hG-CSF[ND28N6] and a derivative which has a carbohydrate chain addition site on the 145th (from the N terminus) amino acid residue is hG-CSF[ND28N145]. In these cases, it is expected that the carbohydrate chain addition can result in development of protease resistance. Retardation of blood clearance can also be expected as a result of stabilization of the polypeptide.

The amino acid sequences of hG-CSF, hG-CSF[ND28], hG-CSF[ND28N6] and hG-CSF[ND28N145] used in illustrating the present invention are shown in Table 1, Table 2, Table 3 and Table 4, respectively.

TABLE 1

```
          10         20         30         40         50         60
ACCCCCCTGGGCCCTGCCAGCTCCCTGCCCCAGAGCTTCCTGCTCAAGTGCTTAGAGCAA
Thr Pro Leu Gly Pro Ala Ser Ser Leu Pro Gln Ser Phe Leu Leu Lys Cys Leu Glu Gln 70         80         90        100        110        120
GTGAGGAAGATCCAGGGCGATGGCGCAGCGCTCCAGGAGAAGCTGTGTGCCACCTACAAG
Val Arg Lys Ile Gln Gly Asp Gly Ala Ala Leu Gln Glu Lys Leu Cys Ala Thr Tyr Lys 130        140        150        160        170        180
CTGTGCCACCCCGAGGAGCTGGTGCTGCTCGGACACTCTCTGGGCATCCCCTGGGCTCCC
Leu Cys His Pro Glu Glu Leu Val Leu Leu Gly His Ser Leu Gly Ile Pro Trp Ala Pro 190        200        210        220        230        240
CTGAGCAGCTGCCCCAGCCAGGCCCTGCAGCTGGCAGGCTGCTTGAGCCAACTCCATAGC
Leu Ser Ser Cys Pro Ser Gln Ala Leu Gln Leu Ala Gly Cys Leu Ser Gln Leu His Ser 250        260        270        280        290        300
GGCCTTTTCCTCTACCAGGGGCTCCTGCAGGCCCTGGAAGGGATCTCCCCCGAGTTGGGT
Gly Leu Phe Leu Tyr Gln Gly Leu Leu Gln Ala Leu Glu Gly Ile Ser Pro Glu Leu Gly 310        320        330        340        350        360
CCCACCTTGGACACACTGCAGCTGGACGTCGCCGACTTTGCCACCACCATCTGGCAGCAG
Pro Thr Leu Asp Thr Leu Gln Leu Asp Val Ala Asp Phe Ala Thr Thr Ile Trp Gln Gln 370        380        390        400        410        420
ATGGAAGAACTGGGAATGGCCCCTGCCCTGCAGCCCACCCAGGGTGCCATGCCGGCCTTC
Met Glu Glu Leu Gly Met Ala Pro Ala Leu Gln Pro Thr Gln Gly Ala Met Pro Ala Phe 430        440        450        460        470        480
GCCTCTGCTTTCCAGCGCCGGGCAGGAGGGGTCCTAGTTGCCTCCCATCTGCAGAGCTTC
Ala Ser Ala Phe Gln Arg Arg Ala Gly Gly Val Leu Val Ala Ser His Leu Gln Ser Phe 490        500        510        520
CTGGAGGTGTCGTACCGCGTTCTACGCCACCTTGCCCAGCCCTGA
Leu Glu Val Ser Tyr Arg Val Leu Arg His Leu Ala Gln Pro ***
```

TABLE 2

```
          10         20         30         40         50         60
GCACCAACATATCGCGCCTCGAGTCTACCACAGAGCTTCCTTTTAAAAAGCTTAGAGCAA
Ala Pro Thr Tyr Arg Ala Ser Ser Leu Pro Gln Ser Phe Leu Leu Lys Ser Leu Glu Gln 70         80         90        100        110        120
GTGAGGAAGATCCAGGGCGATGGCGCAGCGCTCCAGGAGAAGCTGTGTGCCACCTACAAG
Val Arg Lys Ile Gln Gly Asp Gly Ala Ala Leu Gln Glu Lys Leu Cys Ala Thr Tyr Lys 130        140        150        160        170        180
CTGTGCCACCCCGAGGAGCTGGTGCTGCTCGGACACTCTCTGGGCATCCCCTGGGCTCCC
Leu Cys His Pro Glu Glu Leu Val Leu Leu Gly His Ser Leu Gly Ile Pro Trp Ala Pro 190        200        210        220        230        240
CTGAGCAGCTGCCCCAGCCAGGCCCTGCAGCTGGCAGGCTGCTTGAGCCAACTCCATAGC
Leu Ser Ser Cys Pro Ser Gln Ala Leu Gln Leu Ala Gly Cys Leu Ser Gln Leu His Ser 250        260        270        280        290        300
GGCCTTTTCCTCTACCAGGGGCTCCTGCAGGCCCTGGAAGGGATCTCCCCCGAGTTGGGT
Gly Leu Phe Leu Tyr Gln Gly Leu Leu Gln Ala Leu Glu Gly Ile Ser Pro Glu Leu Gly 310        320        330        340        350        360
CCCACCTTGGACACACTGCAGCTGGACGTCGCCGACTTTGCCACCACCATCTGGCAGCAG
Pro Thr Leu Asp Thr Leu Gln Leu Asp Val Ala Asp Phe Ala Thr Thr Ile Trp Gln Gln 370        380        390        400        410        420
ATGGAAGAACTGGGAATGGCCCCTGCCCTGCAGCCCACCCAGGGTGCCATGCCGGCCTTC
Met Glu Glu Leu Gly Met Ala Pro Ala Leu Gln Pro Thr Gln Gly Ala Met Pro Ala Phe 430        440        450        460        470        480
GCCTCTGCTTTCCAGCGCCGGGCAGGAGGGGTCCTAGTTGCCTCCCATCTGCAGAGCTTC
Ala Ser Ala Phe Gln Arg Arg Ala Gly Gly Val Leu Val Ala Ser His Leu Gln Ser Phe 490        500        510        520
CTGGAGGTGTCGTACCGCGTTCTACGCCACCTTGCCCAGCCCTGA
Leu Glu Val Ser Tyr Arg Val Leu Arg His Leu Ala Gln Pro ***
```

TABLE 3

```
          10         20         30         40         50         60
GCACCTACATATCGCAACTCGAGTCTACCACAGAGCTTCCTTTTAAAAAGCTTAGAGCAA
Ala Pro Thr Tyr Arg Asn Ser Ser Leu Pro Gln Ser Phe Leu Leu Lys Ser Leu Glu Gln
```

TABLE 3-continued

```
       70        80        90        100       110       120
GTGAGGAAGATCCAGGGCGATGGCGCAGCGCTCCAGGAGAAGCTGTGTGCCACCTACAAG
Val Arg Lys Ile Gln Gly Asp Gly Ala Ala Leu Gln Glu Lys Leu Cys Ala Thr Tyr Lys 130       140       150       160       170       180
CTGTGCCACCCCGAGGAGCTGGTGCTGCTCGGACACTCTCTGGGCATCCCCTGGGCTCCC
Leu Cys His Pro Glu Glu Leu Val Leu Leu Gly His Ser Leu Gly Ile Pro Trp Ala Pro 190       200       210       220       230       240
CTGAGCAGCTGCCCCAGCCAGGCCCTGCAGCTGGCAGGCTGCTTGAGCCAACTCCATAGC
Leu Ser Ser Cys Pro Ser Gln Ala Leu Gln Leu Ala Gly Cys Leu Ser Gln Leu His Ser 250       260       270       280       290       300
GGCCTTTTCCTCTACCAGGGGCTCCTGCAGGCCCTGGAAGGGATCTCCCCCGAGTTGGGT
Gly Leu Phe Leu Tyr Gln Gly Leu Leu Gln Ala Leu Glu Gly Ile Ser Pro Glu Leu Gly 310       320       330       340       350       360
CCCACCTTGGACACACTGCAGCTGGACGTCGCCGACTTTGCCACCACCATCTGGCAGCAG
Pro Thr Leu Asp Thr Leu Gln Leu Asp Val Ala Asp Phe Ala Thr Thr Ile Trp Gln Gln 370       380       390       400       410       420
ATGGAAGAACTGGGAATGGCCCCTGCCCTGCAGCCCACCCAGGGTGCCATGCCGGCCTTC
Met Glu Glu Leu Gly Met Ala Pro Ala Leu Gln Pro Thr Gln Gly Ala Met Pro Ala Phe 430       440       450       460       470       480
GCCTCTGCTTTCCAGCGCCGGGCAGGAGGGGTCCTAGTTGCCTCCCATCTGCAGAGCTTC
Ala Ser Ala Phe Gln Arg Arg Ala Gly Gly Val Leu Val Ala Ser His Leu Gln Ser Phe 490       500       510       520
CTGGAGGTGTCGTACCGCGTTCTACGCCACCTTGCCCAGCCCTGA
Leu Glu Val Ser Tyr Arg Val Leu Arg His Leu Ala Gln Pro ***
```

TABLE 4

```
       10       TC        30        40        50        60
GCACCAACATATCGCGCCTCGAGTCTACCACAGAGCTTCCTTTTAAAAAGCTTAGAGCAA
Ala Pro Thr Tyr Arg Ala Ser Ser Leu Pro Gln Ser Phe Leu Leu Lys Ser Leu Glu Gln 70        80        90        100·      110       120
GTGAGGAAGATCCAGGGCGATGGCGCAGCGCTCCAGGAGAAGCTGTGTGCCACCTACAAG
Val Arg Lys Ile Gln Gly Asp Gly Ala Ala Leu Gln Glu Lys Leu Cys Ala Thr Tyr Lys 130       140       150       160       170       180
CTGTGCCACCCCGAGGAGCTGGTGCTGCTCGGACACTCTCTGGGCATCCCCTGGGCTCCC
Leu Cys His Pro Glu Glu Leu Val Leu Leu Gly His Ser Leu Gly Ile Pro Trp Ala Pro 190       200       210       220       230       240
CTGAGCAGCTGCCCCAGCCAGGCCCTGCAGCTGGCAGGCTGCTTGAGCCAACTCCATAGC
Leu Ser Ser Cys Pro Ser Gln Ala Leu Gln Leu Ala Gly Cys Leu Ser Gln Leu His Ser 250       260       270       280       290       300
GGCCTTTTCCTCTACCAGGGGCTCCTGCAGGCCCTGGAAGGGATCTCCCCCGAGTTGGGT
Gly Leu Phe Leu Tyr Gln Gly Leu Leu Gln Ala Leu Glu Gly Ile Ser Pro Glu Leu Gly 310       320       330       340       350       360
CCCACCTTGGACACACTGCAGCTGGACGTCGCCGACTTTGCCACCACCATCTGGCAGCAG
Pro Thr Leu Asp Thr Leu Gln Leu Asp Val Ala Asp Phe Ala Thr Thr Ile Trp Gln Gln 370       380       390       400       410       420
ATGGAAGAACTGGGAATGGCCCCTGCCCTGCAGCCCACCCAGGGTGCCATGCCGGCCTTC
Met Glu Glu Leu Gly Met Ala Pro Ala Leu Gln Pro Thr Gln Gly Ala Met Pro Ala Phe 430       440       450       460       470       480
GCCTCTGCTTTCAATCGATCGGCAGGAGGGGTCCTAGTTGCCTCCCATCTGCAGAGCTTC
Ala Ser Ala Phe Asn Arg Ser Ala Gly Gly Val Leu Val Ala Ser His Leu Gln Ser Phe 490       500       510       520
CTGGAGGTGTCGTACCGCGTTCTACGCCACCTTGCCCAGCCCTGA
Leu Glu Val Ser Tyr Arg Val Leu Arg His Leu Ala Gln Pro ***
```

The hG-CSF, hG-CSF[ND28], hG-CSF[ND28N6] and hG-CSF[ND28N145] can be produced by constructing DNAs respectively coding for hG-CSF, hG-CSF[ND28], hG-CSF[ND28N6] and hG-CSF[ND28N145] by recombinant DNA techniques, inserting them into an appropriate expression vector, introducing the resulting recombinants into animal cells and causing expression thereof in said animal cells. In the case of hG-CSF[ND28N6] or hG-CSF[ND28N145] among the polypeptides thus obtained, a new carbohydrate chain (N-glycosylated carbohydrate chain) is added to about one third of the whole hG-CSF produced. Comparison in protease susceptibility between the newly or additionally glycosylated species and new glycosylation-free species of hG-CSF[ND28N6] or hG-CSF[ND28N145] has revealed that the newly glycosylated species is more resistant to protease. In the case of hG-CSF[ND28N6], it has also been found that the additionally glycosylated species is more stable against heat as compared with the species deprived of the new carbohydrate chain enzymatically. This finding has proved the efficacy of the invention. It has further been revealed that hG-CSF[ND28], when it is an expression product in animal cells, can have an additional O-glycosylated carbohydrate chain added thereto. In this case, too, the additionally O-glycosylated species is more resistant to protease.

(2) The case where the polypeptide or glycosylated polypeptide according to the invention is UK or t-PA:

Urokinase [UK] and streptokinase (SK) are currently in use as thrombolytic agents. These thrombolytic agents, however, have no affinity for fibrin, which is a thrombus component. Therefore, they must be administered in large quantities for effecting thrombolysis. Furthermore, they activate not only plasminogen adsorbed on thrombin but also plasminogen in blood, causing systemic hyperfibrinolysis and leading to a bleeding tendency. In contrast to these thrombolytic agents, tissue plasminogen activator (t-PA) and pro-urokinase (pro-UK) (inactive precursor to UK), which have affinity for fibrin, have lately attracted much attention.

t-PA, which has affinity for fibrin, is expected to be adsorbed specifically on thrombin and thereby dissolve thrombin efficiently, without causing systemic hyperfibrinolysis. There are two forms of t-PA, single-chain form and double-chain form. Plasmin converts the single-chain form to the double-chain form. While the double-chain form of t-PA is the active form, single-chain t-PA, too, can exhibit a fibrinolytic activity equivalent to that of double-chain t-PA when fibrin decomposition products are present. As far as the affinity for fibrin is concerned, it has been revealed that single-chain t-PA has greater affinity for fibrin [Tate et al.: Biochemistry, 26, 338 (1987)]. Therefore, it may be said that single-chain t-PA is higher in specificity to thrombin and is superior in this sense to double-chain t-PA.

In the case of UK, too, there are the single-chain form and the double-chain form. Plasmin converts inactive single-chain UK to active double-chain UK. This inactive single-chain UK is also called pro-UK. Where a protease named thrombin is present, this inactive single-chain UK, namely pro-UK, is converted to an inactive double-chain form of UK [Ichinose et al.: J. Biol, Chem., 261, 3486 (1986); Gurewich and Pannell: Blood, 69, 769 (1987)]. This thrombin susceptibility is a disadvantageous feature of pro-UK.

As mentioned above, the thrombolytic agents t-PA and pro-UK are readily converted to disadvantageous forms under the action of proteases, such as plasmin or thrombin. Reduction of their protease susceptibility by causing carbohydrate chain addition in the vicinity of their protease cleavage utilizing the method mentioned hereinabove, if attained, would expectedly give better thrombolytic enzymes. From such viewpoint, a DNA coding for pro-UK derivatives, UK-S1, having an Asn residue in lieu of the 164th amino acid Phe residue of mature pro-UK and having an N-glycosylated carbohydrate chain introduced thereinto on said Asn residue, UK-S3, having an Asn residue in lieu of the 153rd amino acid Leu residue of mature pro-UK and a Thr residue in lieu of the 155th amino acid Pro of mature pro-UK and having an N-glycosylated carbohydrate chain introduced thereinto on said Asn residue, were constructed.

The amino acid sequences of natural pro-UK, UK-S1 and UK-S3 used for illustrating the invention are shown in Table 5, Table 6 and Table 7, respectively.

TABLE 5

```
      10          20          30          40          50          60          70
ATGAGAGCCCTGCTGGCGCGCCTGCTTCTCTGCGTCCTGGTCGTGAGCGACTCCAAAGGCAGCAATGAACTTCAT
Met Arg Ala Leu Leu Ala Arg Leu Leu Leu Cys Val Leu Val Val Ser Asp Ser Lys Gly Ser Asn Glu Leu His 85          95         105         115         125         135         145
CAAGTTCCATCGAACTGTGACTGTCTAAATGGAGGAACATGTGTGTCCAACAAGTACTTCTCCAACATTCACTGG
Gln Val Pro Ser Asn Cys Asp Cys Leu Asn Gly Gly Thr Cys Val Ser Asn Lys Tyr Phe Ser Asn Ile His Trp 160         170         180         190         200         210         220
TGCAACTGCCCAAAGAAATTCGGAGGGCAGCACTGTGAAATAGATAAGTCAAAAACCTGCTATGAGGGGAATGGT
Cys Asn Cys Pro Lys Lys Phe Gly Gly Gln His Cys Glu Ile Asp Lys Ser Lys Thr Cys Tyr Glu Gly Asn Gly 235         245         255         265         275         285         295
CACTTTTACCGAGGAAAGGCCAGCACTGACACCATGGGCCGGCCTTGCCTGCCCTGGAACTCTGCCACTGTCCTT
His Phe Tyr Arg Gly Lys Ala Ser Thr Asp Thr Met Gly Arg Pro Cys Leu Pro Trp Asn Ser Ala Thr Val Leu 310         320         300         340         350         360         370
CAGCAAACGTACCATGCCCACAGATCTGATGCTCTTCAGCTGGGCCTGGGGAAACATAATTACTGCAGGAACCCA
Gln Gln Thr Tyr His Ala His Arg Ser Asp Ala Leu Gln Leu Gly Leu Gly Lys His Asn Tyr Cys Arg Asn Pro 385         395         405         415         425         435         445
GACAACCGGAGGCGACCCTGGTGCTATGTGCAGGTGGGCCTAAAGCCGCTTGTCCAAGAGTGCATGGTGCATGAC
Asp Asn Arg Arg Arg Pro Trp Cys Tyr Val Gln Val Gly Leu Lys Pro Leu Val Gln Glu Cys Met Val His Asp 460         470         480         490         500         510         520
TGCGCAGATGGAAAAAAGCCCTCCTCTCCTCCAGAAGAATTAAAATTTCAGTGTGGCCAAAAGACTCTGAGGCCC
Cys Ala Asp Gly Lys Lys Pro Ser Ser Pro Pro Glu Glu Leu Lys Phe Gln Cys Gly Gln Lys Thr Leu Arg Pro 535         545         555         565         575         585         595
CGCTTTAAGATTATTGGGGGAGAATTCACCACCATCGAGAACCAGCCCTGGTTTGCGGCCATCTACAGGAGGCAC
Arg Phe Lys Ile Ile Gly Gly Glu Phe Thr Thr Ile Glu Asn Gln Pro Trp Phe Ala Ala Ile Tyr Arg Arg His 610         620         630         640         650         660         670
CGGGGGGGCTCTGTCACCTACGTGTGTGGAGGCAGCCTCATCAGCCCTTGCTGGGTGATCAGCGCCACACACTGC
Arg Gly Gly Ser Val Thr Tyr Val Cys Gly Gly Ser Leu Ile Ser Pro Cys Trp Val Ile Ser Ala Thr His Cys
```

TABLE 5-continued

```
        685           695           705           715           725           735           745
TTCATTGATTACCCAAAGAAGGAGGACTACATCGTCTACCTGGGTCGCTCAAGGCTTAACTCCAACACGCAAGGG
Phe Ile Asp Tyr Pro Lys Lys Glu Asp Tyr Ile Val Tyr Leu Gly Arg Ser Arg Leu Asn Ser Asn Thr Gln Gly 760           770           780           790           800           810           820
GAGATGAAGTTTGAGGTGGAAAAACCTCATCCTACACAAGGACTACAGCGCTGACACGCTTGCTCACCACAATGAC
Glu Met Lys Phe Glu Val Glu Asn Leu Ile Leu His Lys Asp Tyr Ser Ala Asp Thr Leu Ala His His Asn Asp 835           845           855           865           875           885           895
ATTGCCTTGCTGAAGATCCGTTCCAAGGAGGGCAGGTGTGCGCAGCCATCCCGGACTATACAGACCATCTGCCTG
Ile Ala Leu Leu Lys Ile Arg Ser Lys Glu Gly Arg Cys Ala Gln Pro Ser Arg Thr Ile Gln Thr Ile Cys Leu 910           920           930           940           950           960           970
CCTTCGATGTATAACGATCCCCAGTTTGGCACAAGCTGTGAGATCACTGGCTTTGGAAAAGAGAATTCTACCGAC
Pro Ser Met Tyr Asn Asp Pro Gln Phe Gly Thr Ser Cys Glu Ile Thr Gly Phe Gly Lys Glu Asn Ser Thr Asp 985           995           1005          1015          1025          1035          1045
TATCTCTATCCGGAGCAGCTGAAAATGACTGTTGTGAAGCTGATTTCCCACCGGGAGTGTCAGCAGCCCCACTAC
Tyr Leu Tyr Pro Glu Gln Leu Lys Met Thr Val Val Lys Leu Ile Ser His Arg Glu Cys Gln Gln Pro His Tyr 1060          1070          1080          1090          1100          1110          1120
TACGGCTCTGAAGTCACCACCAAAATGCTGTGTGCTGCTGACCCACAGTGGAAAACAGATTCCTGCCAGGGAGAC
Tyr Gly Ser Glu Val Thr Thr Lys Met Leu Cys Ala Ala Asp Pro Gln Trp Lys Thr Asp Ser Cys Gln Gly Asp 1135          1145          1155          1165          1175          1185          1195
TCAGGGGGACCCCTCGTCTGTTCCCTCCAAGGCCGCATGACTTTGACTGGAATTGTGAGCTGGGGCCGTGGATGT
Ser Gly Gly Pro Leu Val Cys Ser Leu Gln Gly Arg Met Thr Leu Thr Gly Ile Val Ser Trp Gly Arg Gly Cys 1210          1220          1230          1240          1250          1260          1270
GCCCTGAAGGACAAGCCAGGCGTCTACACGAGAGTCTCACACTTCTTACCCTGGATCCGCAGTCACACCAAGGAA
Ala Leu Lys Asp Lys Pro Gly Val Tyr Thr Arg Val Ser His Phe Leu Pro Trp Ile Arg Ser His Thr Lys Glu 1285          1295
GAGAATGGCCTGGCCCTCTGA
Glu Asn Gly Leu Ala Leu ***
```

TABLE 6

```
        10            20            30            40            50            60            70
AGCAATGAACTTCATCAAGTTCCATCGAACTGTGACTGTCTAAATGGAGGAACATGTGTGTCCAACAAGTACTTC
Ser Asn Glu Leu His Gln Val Pro Ser Asn Cys Asp Cys Leu Asn Gly Gly Thr Cys Val Ser Asn Lys Tyr Phe 85            95            105           115           125           135           145
TCCAACATTCACTGGTGCAACTGCCCAAAGAAATTCGGAGGGCAGCACTGTGAAATAGATAAGTCAAAAACCTGC
Ser Asn Ile His Trp Cys Asn Cys Pro Lys Lys Phe Gly Gly Gln His Cys Glu Ile Asp Lys Ser Lys Thr Cys 160           170           180           190           200           210           220
TATGAGGGGAATGGTCACTTTTACCGAGGAAAGGCCAGCACTGACACCATGGGCCGGCCCTGCCTGCCCTGGAAC
Tyr Glu Gly Asn Gly His Phe Tyr Arg Gly Lys Ala Ser Thr Asp Thr Met Gly Arg Pro Cys Leu Pro Trp Asn 235           245           255           265           275           285           295
TCTGCCACTGTCCTTCAGCAAACGTACCATGCCCACAGATCTGATGCTCTTCAGCTGGGCCTGGGGAAACATAAT
Ser Ala Thr Val Leu Gln Gln Thr Tyr His Ala His Arg Ser Asp Ala Leu Gln Leu Gly Leu Gly Lys His Asn 310           320           330           340           350           360           370
TACTGCAGGAACCCAGACAACCGGAGGCGACCCTGGTGCTATGTGCAGGTGGGCCTAAAGCCGCTTGTCCAAGAG
Tyr Cys Arg Asn Pro Asp Asn Arg Arg Arg Pro Trp Cys Tyr Val Gln Val Gly Leu Lys Pro Leu Val Gln Glu 385           395           405           415           425           435           445
TGCATGGTGCATGACTGCGCAGATGGAAAAAAGCCCTCCTCTCCTCCAGAAGAATTAAAATTTCAGTGTGGCCAA
Cys Met Val His Asp Cys Ala Asp Gly Lys Lys Pro Ser Ser Pro Pro Glu Glu Leu Lys Phe Gln Cys Gly Gln 460           470           480           490           500           510           520
AAGACTCTGAGGCCCCGCTTTAAGATTATTGGGGGAGAAAACACCACCATCGAGAACCAGCCCTGGTTTGCGGCC
Lys Thr Leu Arg Pro Arg Phe Lys Ile Ile Gly Gly Glu Asn Thr Thr Ile Glu Asn Gln Pro Trp Phe Ala Ala 535           545           555           565           575           585           595
ATCTACAGGAGGCACCGGGGGGGCTCTGTCACCTACGTGTGTGGAGGCAGCCTCATCAGCCCTTGCTGGGTGATC
Ile Tyr Arg Arg His Arg Gly Gly Ser Val Thr Tyr Val Cys Gly Gly Ser Leu Ile Ser Pro Cys Trp Val Ile 610           620           630           640           650           660           670
AGCGCCACACACTGCTTCATTGATTACCCAAAGAAGGAGGACTACATCGTCTACCTGGGTCGCTCAAGGCTTAAC
Ser Ala Thr His Cys Phe Ile Asp Tyr Pro Lys Lys Glu Asp Tyr Ile Val Tyr Leu Gly Arg Ser Arg Leu Asn 685           695           705           715           725           735           745
TCCAACACGCAAGGGGAGATGAAGTTTGAGGTGGAAAAACCTCATCCTACACAAGGACTACAGCGCTGACACGCTT
Ser Asn Thr Gln Gly Glu Met Lys Phe Glu Val Glu Asn Leu Ile Leu His Lys Asp Tyr Ser Ala Asp Thr Leu
```

TABLE 6-continued

```
       760         770         780        790         800          810        820
GCTCACCACAATGACATTGCCTTGCTGAAGATCCTGTCCAAGGAGGGCAGGTGTGCGCAGCCATCCCGGACTATA
Ala His His Asn Asp Ile Ala Leu Leu Lys Ile Arg Ser Lys Glu Gly Arg Cys Ala Gln Pro Ser Ser Thr Ile 835         845         855        865         875          885        895
CAGACCATCTGCCTGCCCTCGATGTATAACGATCCCCAGTTTGGCACAAGCTGTGAGATCACTGGCTTTGGAAAA
Gln Thr Ile Cys Leu Pro Ser Met Tyr Asn Asp Pro Gln Phe Gly Thr Ser Cys Glu Ile Thr Gly Phe Gly Lys 910         920    ·    930        940         950          960        970
GAGAATTCTACCGACTATCTCTATCCGGAGCAGCTGAAAATGACTGTTGTGAAGCTGATTTCCCACCGGGAGTGT
Glu Asn Ser Thr Asp Tyr Leu Tyr Pro Glu Gln Leu Lys Met Thr Val Val Lys Leu Ile Ser His Arg Glu Cys 985         995        1005        1015       1025         1035       1045
CAGCAGCCCCACTACTACGGCTCTGAAGTCACCACCAAAATGCTGTGTGCTGCTGACCCACAGTGGAAAACAGAT
Gln Gln Pro His Tyr Tyr Gly Ser Glu Val Thr Thr Lys Met Leu Cys Ala Ala Asp Pro Gln Trp Lys Thr Asp 1060        1070        1080        1090       1100         1110       1120
TCCTGCCAGGGAGACTCAGGGGGGACCCCTCGTCTGTTCCCTCCAAGGCCGCATGACTTTGACTGGAATTGTGAGC
Ser Cys Gln Gly Asp Ser Gly Gly Pro Leu Val Cys Ser Leu Gln Gly Arg Met Thr Leu Thr Gly Ile Val Ser 1135        1145        1155        1165       1175         1185       1195
TGGGGCCGTGGATGTGCCCTGAAGGACAAGCCAGGCGTCTACACGAGAGTCTCACACTTCTTACCCTGGATCCGC
Trp Gly Arg Gly Cys Ala Leu Lys Asp Lys Pro Gly Val Tyr Thr Arg Val Ser His Phe Leu Pro Trp Ile Arg 1210        1220        1230
AGTCACACCAAGGAAGAGAATGGCCTGGCCCTCTGA
Ser His Thr Lys Glu Glu Asn Gly Leu Ala Leu ***
```

In accordance with the invention, DNAs respectively coding for pro-UK, UK-S1 and UK-S3 are constructed using recombinant DNA techniques and inserted into an expression vector, each resulting recombinant expression vector is introduced into animal cells, and expression is caused. Comparison of pro-UK and UK-S1 and UK-S3 thus obtained has revealed that UK-S1 and UK-S3 are lower in thrombin susceptibility than the natural form pro-UK and that their stability in serum and heat stability are improved, proving the efficacy of the invention also in the case of UK.

When the polypeptide or glycosylated polypeptide according to the invention is hG-CSF, UK or t-PA, a cDNA obtained by causing reverse transcription of a messenger RNA coding for hG-CSF, UK or t-PA by using appropriate recombinant DNA techniques, a DNA coding for hG-CSF, UK or t-PA as obtained from a chromosomal DNA, a synthetic DNA coding for hG-CSF, UK or t-PA, or the like may be used as the DNA coding for hG-CSF, UK or t-PA.

The hG-CSF cDNA may be any DNA provided that it codes for hG-CSF. As a specific example, there may be mentioned pCSF2, which has been produced by the present inventors as described in Reference Example 4.

The hG-CSF cDNA in pCSF2 has been identified by the dideoxy sequencing method using M13 phage [J. Messing et al.: Gene, 19, 269 (1982)]. The hG-CSF cDNA in pCSF2 contains the whole mature protein portion although a part of the signal sequence is missing therein. The base sequence of this mature protein portion is shown in Table 1.

The human t-PA cDNA or human UK cDNA to be used may be any DNA provided that it codes for human t-PA or human UK. As typical examples, there may be mentioned the human t-PA cDNA in the plasmid ptPA7 and the human UK cDNA in the plasmid pUK1 or pUK11. ptPA7, pUK1 and pUK11 are the plasmids produced by the present inventors as described in Reference Examples 1, 2 and 3, respectively. The human UK cDNA in pUK 1 and that in pUK11 have been sequenced by the dideoxy method using M13 phage.

Neither of the human UK cDNAs in pUK1 and pUK11 codes for the complete pro-UK but the base sequence of each cDNA is in agreement of a part of the base sequence shown in Table 5.

An *Escherichia coli* strain harboring ptPA7 has been deposited, since Sep. 3, 1987, with the Fermentation Research Institute (FRI), Agency of Industrial Science and Technology, under the designation *Escherichia coli* EtPA7 (deposit number FERM BP-1467), an *Escherichia coli* strain harboring pUK1 under the designation *Escherichia coli* EUK1 (FERM BP-1463), and an *Escherichia coli* strain harboring pUK11 under the designation *Escherichia coli* EUK11 (FERM BP-1464) in accordance with the Budapest Treaty.

The plasmid to be used for insertion thereinto of a DNA coding for hG-CSF, UK or t-PA may be any plasmid provided that said DNA can be expressed in *Escherichia coli* or animal cells. Preferred for the expression of hG-CSF, UK or t-PA in *Escherichia coli* are plasmids which allow insertion of a foreign DNA thereinto at a site downstream from an appropriate promoter, such as a trp or lac promoter, and in which the distance between the Shin-Dalgarno sequence (hereinafter abbreviated as SD sequence) and the initiation codon (ATG) has been adjusted to an appropriate length, for example 6 to 18 bases. As preferred specific examples, there may be mentioned pKYP10 (JP-A-58-110600 or U.S. Pat. No. 4,686,191; the term "JP-A" as used herein means an "unexamined published Japanese patent application) and pTrS33 (Reference Example 5), each created by the present inventors.

The plasmid to to be used for the expression of a DNA coding for hG-CSF, UK or t-PA in animal cells may be any plasmid provided that said DNA can be expressed in animal cells. Preferred are those plasmids which allow insertion of a foreign DNA thereinto at a site downstream from an appropriate promoter, such as the SV10 early promoter or SV40 later promoter, and which have a poly(A) signal, splicing signal and so forth.

As preferred specific examples of the plasmid, there may be mentioned pAGE103 [Minagami et al.: J. Biochem., 101, 1307–1310 (1987)], pSE1PA1-9A and pSE1-

PA1SE1dhfr1-9A (Reference Example 9), each created by the present inventors.

An *Escherichia coli* strain harboring pAGE103 has been deposited since Mar. 23, 1987 with the Fermentation Research Institute under the designation *Escherichia coli* EAGE103 (FERM BP-1312) in accordance with the Budapest Treaty. As a plasmid containing the dihydrofolate reductase (hereinafter abbreviated as dhfr) gene as a selective marker, there may be mentioned pSV2-dhfr [S. Subramani et al.: Mol. Cell. Biol., 1, 854 (1981)].

The recombination between the DNA coding for the novel polypeptide or glycosylated polypeptide of hG-CSF, UK or t-PA and the vector DNA can be carried out by ordinary recombinant DNA techniques of digesting both DNA with restriction enzymes and conducting ligation using T4 DNA ligase. The ligation may also be carried out following filling in of the ends of the DNA fragments obtained by digestion with restriction enzymes using DNA polymerase I Klenow fragment or T4 DNA polymerase, or following paring off of the cohesive ends of such fragments using T4 DNA polymerase, or using a DNA linker.

The following describes several cases in which recombinant plasmids with a DNA coding for a novel polypeptide or glycosylated polypeptide of hG-CSF or UK being incorporated therein are constructed using pCSF2 as the hG-CSF cDNA-containing plasmid or pUK1 and pUK11 as the pro-UK cDNA-containing plasmids and, if necessary, using a chemically synthesized linker or applying site-directed mutagenesis.

First, an illustration is given of a case in which a recombinant plasmid, pAS28, is constructed for the expression of the hG-CSF derivative hG-CSF[ND28] (cf. Reference Example 16) in animal cells.

Figure 5:
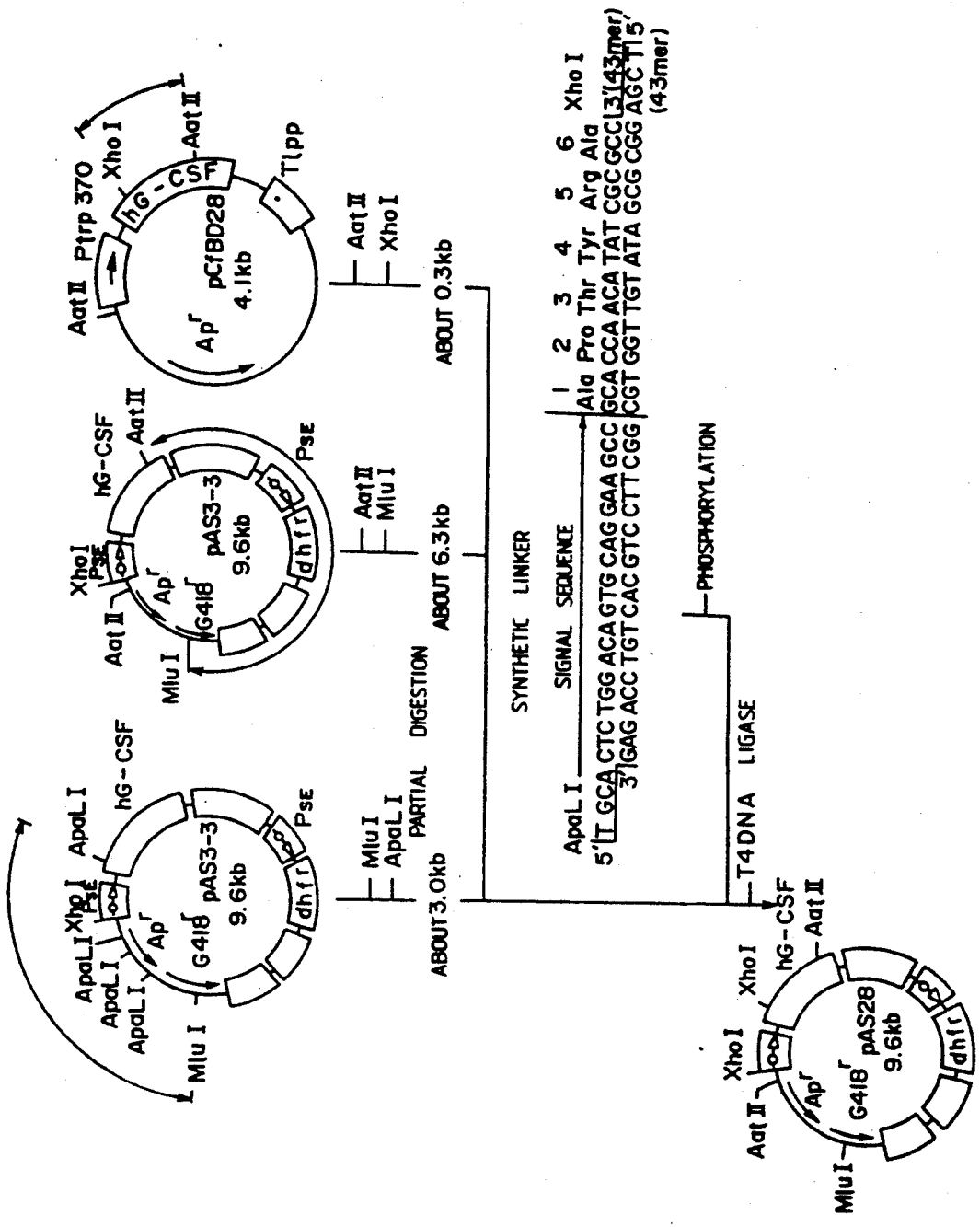
FIG. 5 shows the construction scheme for the plasmid pAS28.

As shown in FIG. 5, pAS3-3 (Reference Example 10) is cleaved with MluI and ApaLI and a DNA fragment about 3.0 kb in size is purified. Separately, the same plasmid is cleaved with AatII and MluI and a DNA fragment about 6.3 kb in size is purified. Further, separately, pCfBD28 (cf. Reference Example 16) is cleaved with AatII and XhoI and a DNA fragment about 0.3 kb in size is purified. These three DNA fragments and the synthetic DNA shown in FIG. 5 are ligated together using T4 DNA ligase to give pAS28.

Then, another illustration is given of a case in which a recombinant plasmid, pASN6, coding for a novel hG-CSF polypeptide, which is a modification of hG-CSF[ND28] and has an N-glycosylated carbohydrate chain addition site on the 6th (from the N terminus of hG-CSF[ND28]) amino acid residue, is constructed.

Figure 6:
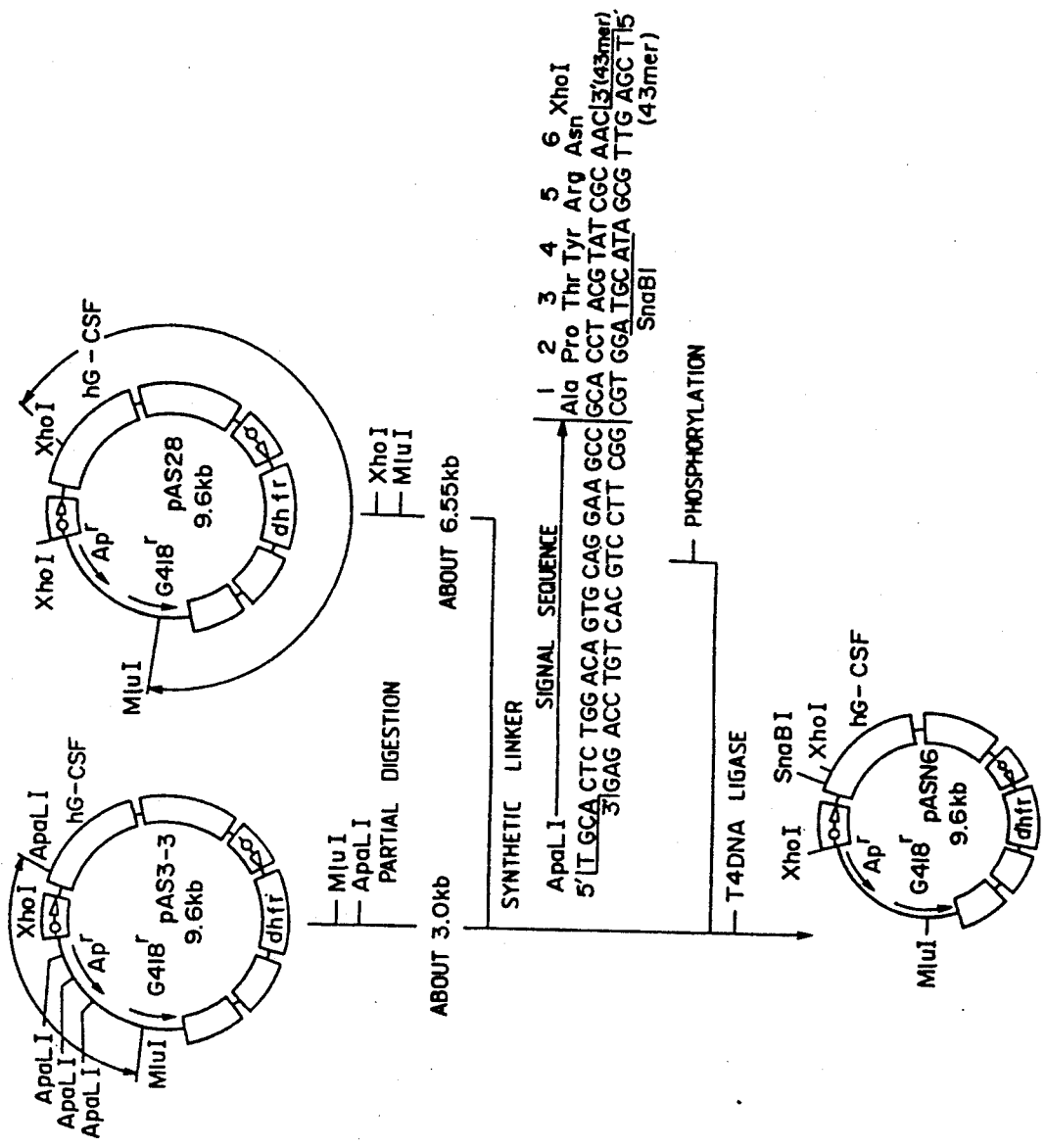
FIG. 6 shows the construction scheme for the plasmid pASN6.

As shown in FIG. 6, pAS3-3 is cleaved with MluI and ApaLI and a DNA fragment about 3.0 kb in size is purified. Separately, pAS28 is cleaved with XhoI and MluI and a DNA fragment about 6.55 kb in size is purified. These two DNA fragments and the synthetic DNA shown in FIG. 6 are ligated together in the presence of T4 DNA ligase to give pASN6.

Now, another illustration is given of a case in which a recombinant plasmid, pASN145, coding for a novel hG-CSF polypeptide which is a modification of hG-CSF[ND28] and has a N-glycosylated carbohydrate chain addition site on the 145th (from the N terminus of hG-CSF[ND28]) amino acid residue is constructed.

Figure 7:
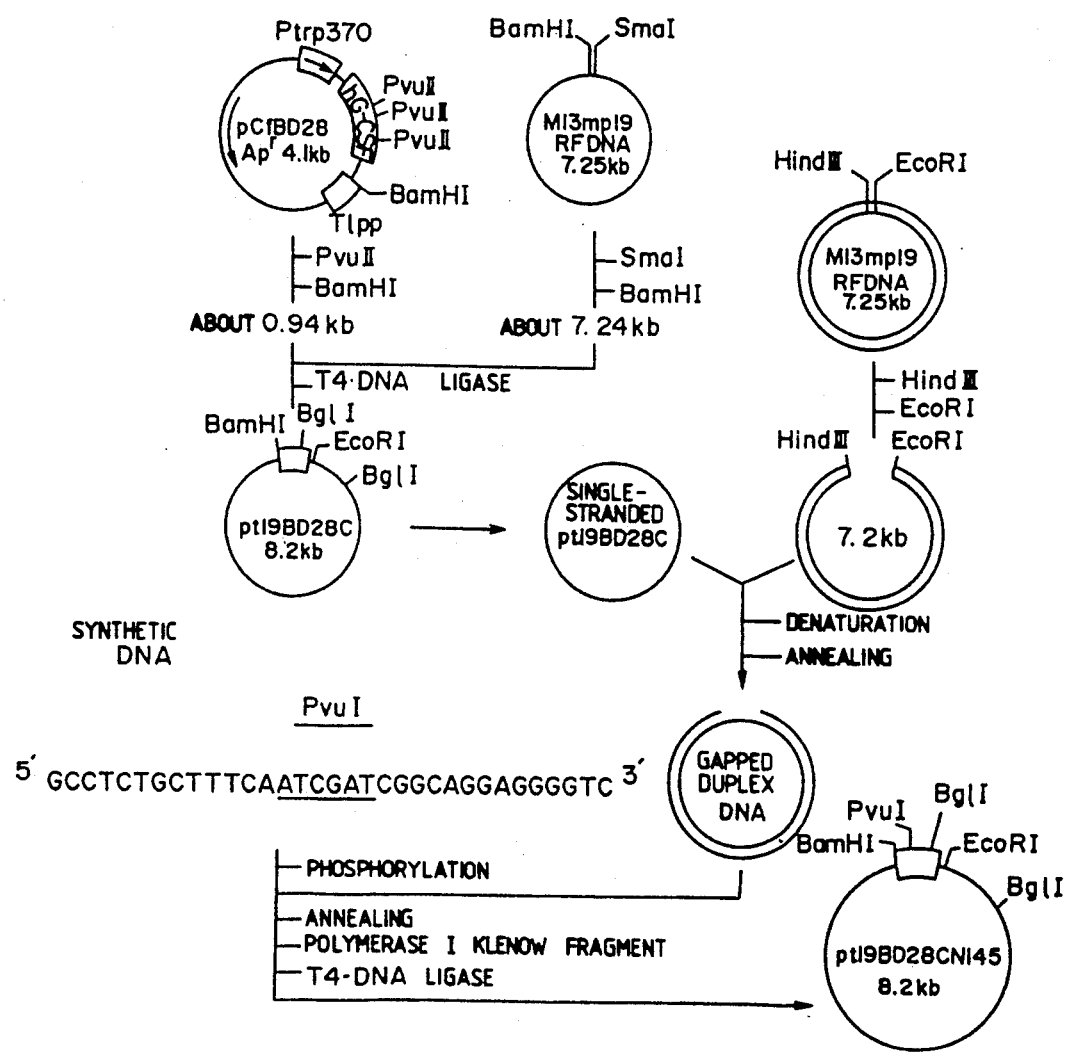
FIG. 7(1) shows the construction scheme for the plasmid pt19BD28CN145.
Figure 7:
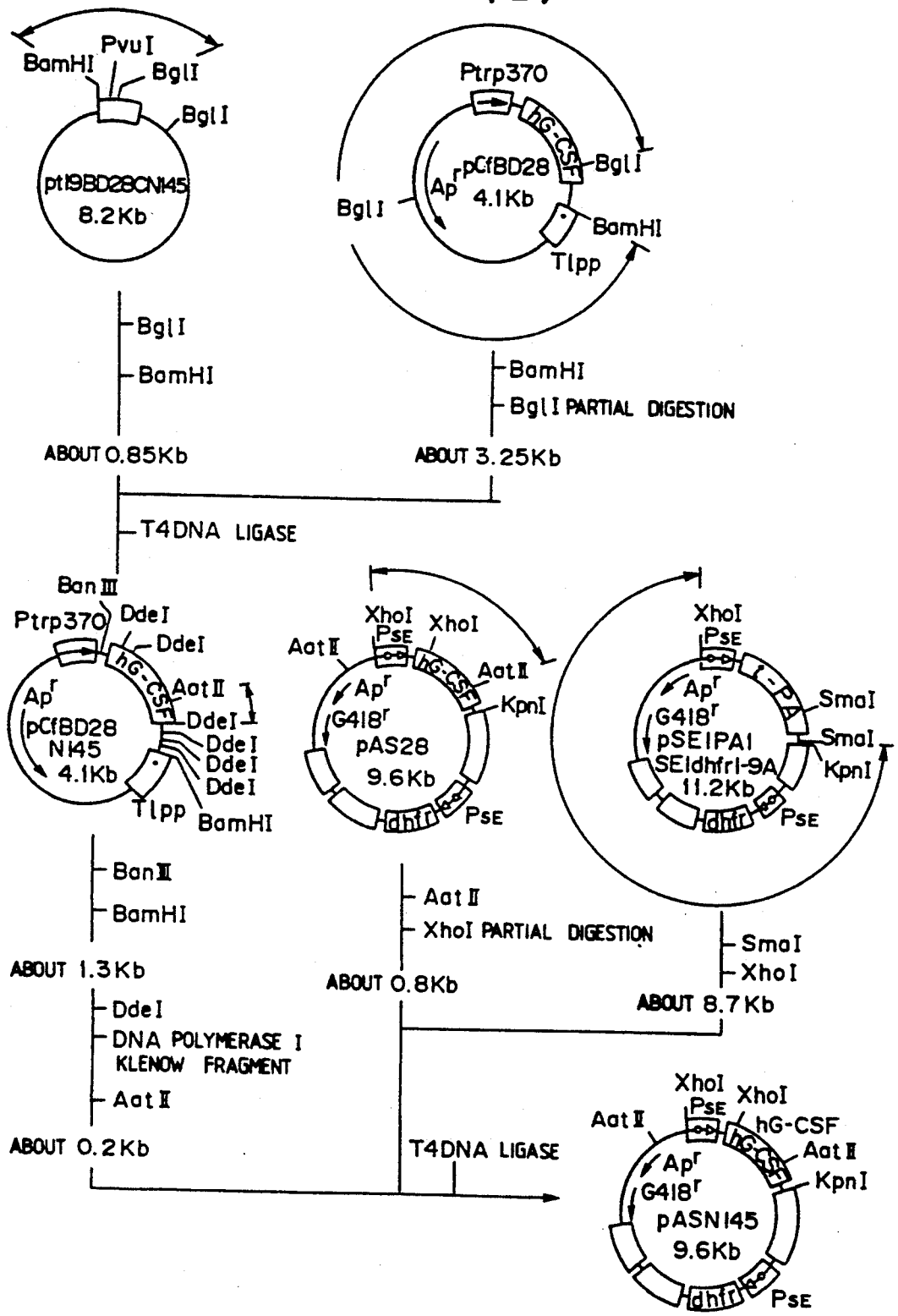

The construction of pASN145 is carried out using site-directed mutagenesis. As shown in FIG. 7-(1), pCfBD28 is cleaved with PvuII and BamHI and a DNA fragment about 0.94 kb in size is purified. Separately, the M13 phage vector M13mp19 RF DNA is cleaved with SmaI and BamHI and a DNA fragment about 7.24 kb in size is purified. The thus-obtained two DNA fragments are ligated together in the presence of T4 DNA ligase to give pt19BD28C. Then, this pt19BD28C is used to transfect *Escherichia coli* JM105. Single-stranded pt19BD28C is obtained from the phage obtained above. As also shown in FIG. 7-(1), the M13mp19 RF DNA is cleaved with HindIII and EcoRI and a DNA fragment about 7.2 kb in size is purified. This DNA fragment (about 7.2 kb) and the single-stranded pt19BD28C obtained above are mixed together and subjected to denaturing treatment, followed by annealing. The thus-formed gapped duplex DNA is purified. After annealing of this gapped duplex DNA with the synthetic DNA shown in FIG. 7-(1), the annealing product is circularized using the Klenow fragment and T4 DNA ligase. The resulting circular DNA is used to transfect *Escherichia coli* JM105 to give pt19BD28CN145 with site-directed mutagenesis introduced therein.

Then, as shown in FIG. 7-(2), pt19BD28CN145 is cleaved with BglI and BamHI and a DNA fragment about 0.85 kb in size is purified. Separately, pCfBD28 is cleaved with BamHI and BglI and a DNA fragment about 3.25 kb in size is purified. The two DNA fragments thus obtained are ligated together in the presence of T4 DNA ligase to give pCfBD28N145.

Then, as also shown in FIG. 7-(2), pCfBD28N145 is cleaved with BanIII and BamHI and a DNA fragment about 1.3 kb in size is purified. The thus-obtained DNA fragment (about 1.3 kb) is cleaved with DdeI, treated with DNA polymerase Klenow fragment for filling in the cohesive ends and then further cleaved with AatII, and a DNA fragment about 0.2 kb in size is purified. Separately, pAS28 is cleaved with AatII an XhoI and a DNA fragment about 0.8 kb in size is purified. Further, separately, pSE1PA1SE1dhfr1-9A (Reference Example 9) is cleaved with SmaI and XhoI and a DNA fragment about 8.7 kb in size is purified. The thus-obtained three DNA fragments (about 0.2 kb, about 0.8 kb and about 8.7 kb in size) are ligated together in the presence of T4 DNA ligase to give pASN145.

Then, description is given of a case where a recombinant plasmid, pSE1UKS1-1d, is constructed for the expression in animal cells of the UK derivative UK-S1 having an N-glycosylated carbohyrate chain added thereto in the vicinity of the thrombin cleavage site.

Figure 9:
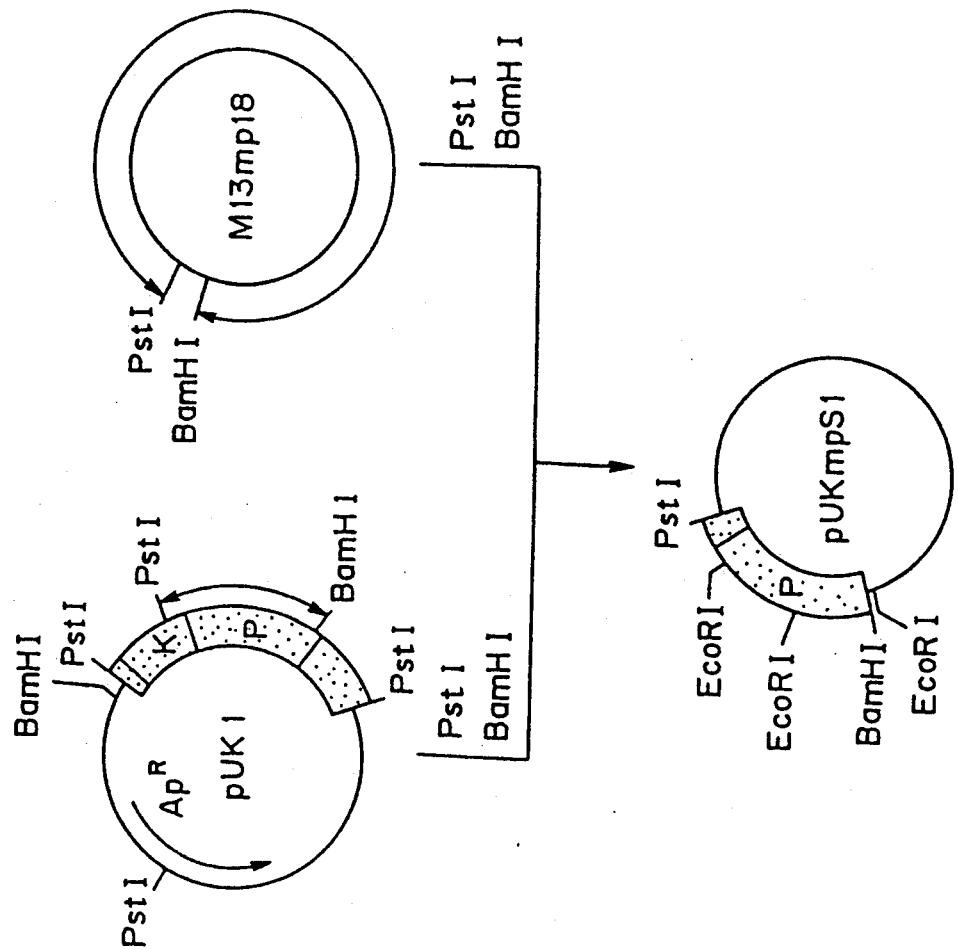
FIG. 9 shows the construction scheme for single-strand pUKmpS1.
Figure 8:
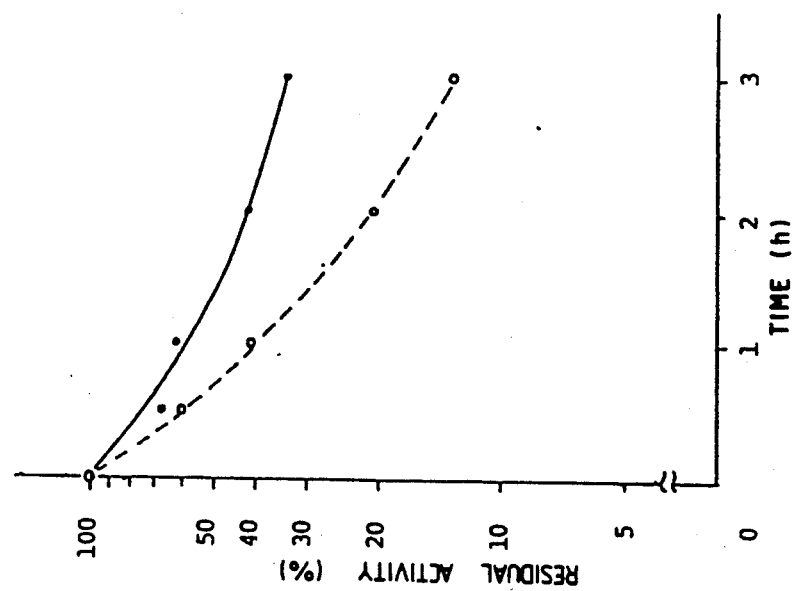

As shown in FIG. 9, pUK1 (Reference Example 2) is cleaved with PstI and BamHI and a DNA fragment 890 bp in size is purified. Separately, the M13mp18 RF DNA [Yanisch-Perron et al.: Gene, 33, 103 (1985)] is cleaved with PstI and BamHI and a DNA fragment about 7.2 kb is purified. Both the DNA fragments thus obtained are ligated together in the presence of T4 DNA ligase to give a plasmid, pUKmpS1, with a part of the UK cDNA subcloned in the M13mp18 vector.

Figure 10:
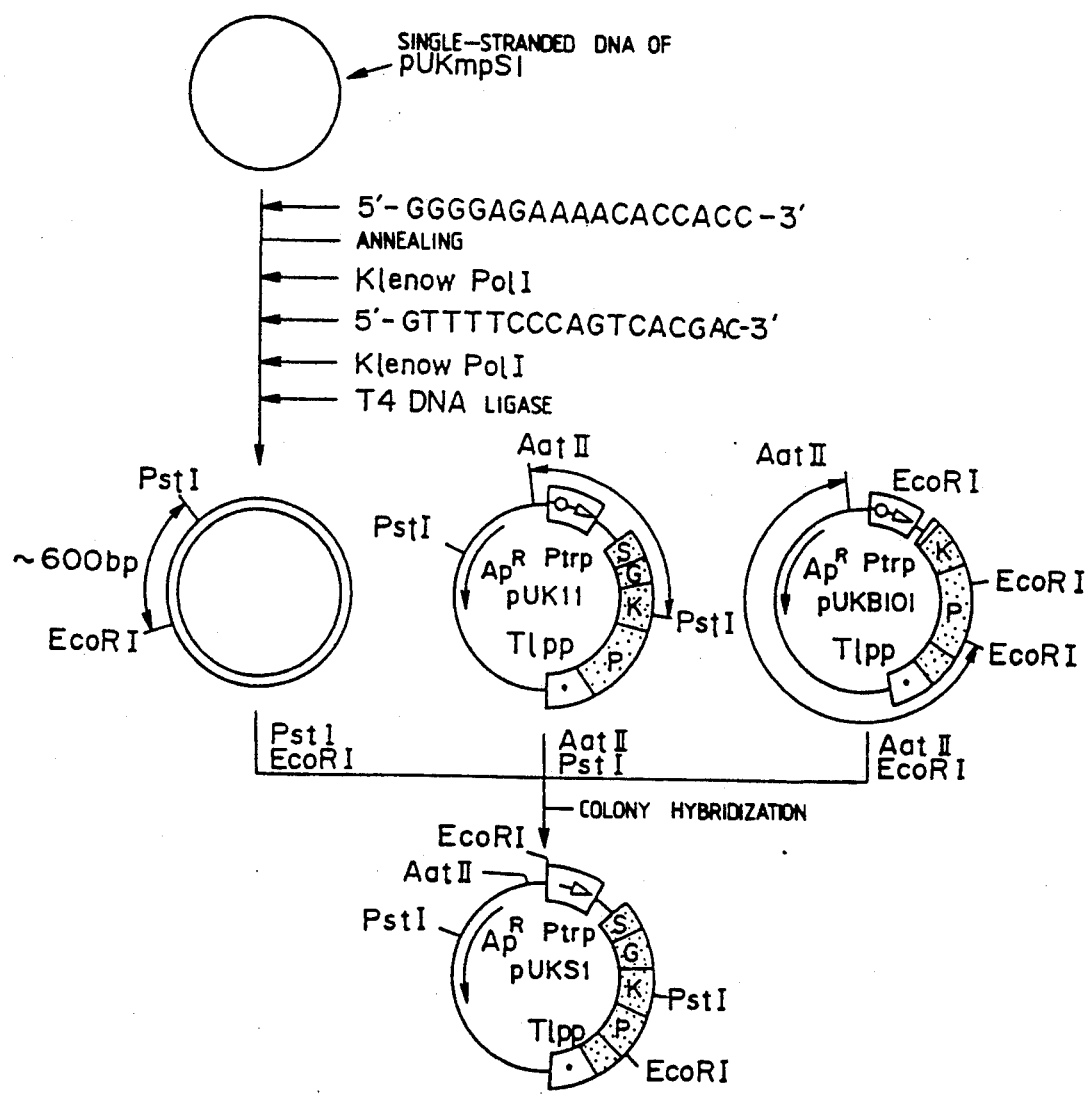
FIG. 10 shows the construction scheme for the plasmid pUKS1.

The single-stranded pUKmpS1 DNA is prepared in the conventional manner and then, as shown in FIG. 10, its base sequence is modified so that an N-glycosylated carbohydrate chain can be added onto the 164th (in UK) amino acid residue. Thus, using the synthetic DNA 5'-GGGGAGAAAACACCACC-3' for substituting Asn for Phe-164 and the synthetic DNA 5'-GTTTTCCCAGTCACGAC-3' for determining the DNA base sequence of M13mp18 as primers, the single-strand pUKmpS1 DNA is converted to the double-stranded DNA in the presence of *Escherichia coli* DNA polymerase I Klenow fragment and at the same time mutation is introduced into the desired site. The thus-obtained mutant double-stranded DNA is cleaved with PstI and EcoRI and a DNA fragment about 600 bp in size is purified. Separately, UK cDNA-containing pUK11 (Reference Example 3) is cleaved with AatII and PstI and a DNA fragment about 1.0 kb in size is purified. Further, separately, pUKB101 (Reference Example 12) with a KpnI site introduced therein on the 3' terminal side of the UK cDNA is cleaved with AatII and EcoRI and a DNA fragment about 2.9 kb in size is purified. The thus-obtained three DNA fragments are ligated together in the presence of T4 DNA ligase to give recombinant plasmid, pUKS1, coding for the UK derivative UK-S1.

Figure 11:
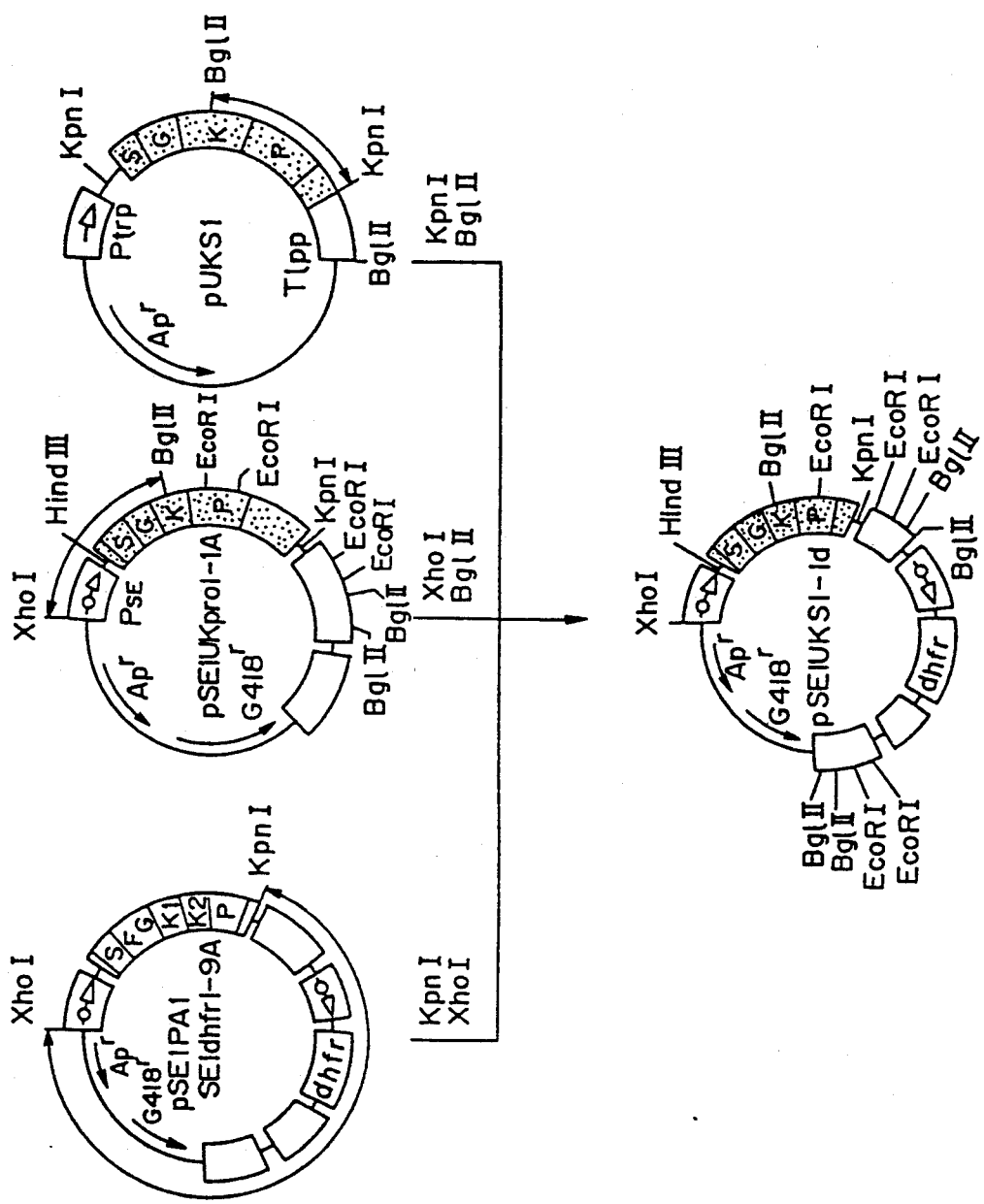
FIG. 11 shows the construction scheme for the plasmid pSElUKS1-1d.

Subsequently, as shown in FIG. 11, the expression vector for a foreign gene containing the dhfr gene for gene amplification pSE1PA1SEldhfr1-9A (Reference Example 9) is cleaved with KpnI and XhoI and a DNA fragment about 8.6 kb in size is purified. Separately, the recombinant plasmid for UK expression pSE1UKprol-1A (Reference Example 13) is cleaved with XhoI and BglII and a DNA fragment about 0.75 kb is size is purified. Further, separately, pUKS1coding for UK-S1 is cleaved with KpnI and BglII and a DNA fragment about 1.15 kb in size is purified. The thus-obtained three DNA fragments are ligated together using T4 DNA ligase to give a recombinant plasmid, pSE1UKS1-1d, allowing UK-S1 expression.

Recombinant plasmid pSEUKS3 coding for UK-S3 can be produced by similar method for obtaining pSE-1UKS1-1d.

The reaction conditions for use in the above-mentioned recombination techniques are generally as follows.

The DNA digestion reaction with an restriction enzyme or enzymes is generally carried out in a reaction mixture containing 0.1 to 20 µg of DNA, 2 to 200 mM (preferably 10 to 40 mM) Tris-HCl (pH 6.0 to 9.5, preferably pH 7.0 to 8.0), 0 to 200 mM NaCl and 2 to 20 mM (preferably 5 to 10 mM) MgCl$_2$ in the presence of 0.1 to 100 units (preferably 1 to 3 units per microgram of DNA) of each restriction enzyme at 20° to 70° C. (the optimal temperature varying depending on the kind of restriction enzyme) for 15 minutes to 24 hours. The reaction is terminated generally by heating at 55° to 75° C. for 5 to 30 minutes. It is also possible to inactivate the restriction enzymes used by means of phenol, diethyl pyrocarbonate or the like reagent.

The DNA fragments resulting from restriction enzyme digestion or the gapped duplex DNA can be purified by low melting point agarose gel electrophoresis (hereinafter referred to as "LGT method" for short) [L. Wieslander: Analytical Biochemistry, 98, 305 (1979)] or by the agarose gel freezing-thawing method (hereinafter abbreviated as "AFT method"). The AFT method comprises adding an equal volume of TE buffer [10 mM Tris-HCl (pH 7.5), 1 mM EDTA] and 2 volumes of phenol (saturated with TE buffer) to a slice of DNA fragment-containing agarose gel (0.7 to 1.5%), achieving admixture, repeating a freezing (−70° C.)-thawing (65° C.) cycle two times, centrifuging, separating the resulting upper aqueous solution layer and recovering the DNA fragment by precipitation with ethanol. The DNA fragments can also be eluted and purified from agarose gel or polyacrylamide gel by using an Atto model Maxfield AE-3241 DNA fragment recoverer. The latter method is hereinafter referred to as "electroelution method".

The ligation of DNA fragments is conducted in a reaction medium containing 2 to 200 mM (preferably 10 to 40 mM) Tris-HCl (pH 6.1 to 9.5, preferably pH 7.0 to 8.0), 2 to 20 mM (preferably 5 to 10 mM) MgCl$_2$, 0.1 to 10 mM (preferably 0.5 to 2.0 mM) ATP and 1 to 50 mM (preferably 5 to 10 mM) dithiothreitol (hereinafter sometimes referred to as "DTT") in the presence of 1° to 1,000 units of T4 DNA ligase at 1 to 37° C. (preferably 3° to 20° C.) for 15 minutes to 72 hours (preferably 2 to 20 hours).

The recombinant plasmid DNA resulting from the ligation reaction is introduced into *Escherichia coli* using the transformation method of Cohen et al. [S. N. Cohen et al.: Proc. Natl. Acad. Sci. USA, 69, 2110 (1972)] or the transformation method of Hanahan [J. Mol. Biol., 166, 557 (1983)], as necessary.

The recombinant M13 phage RF DNA resulting from the ligation reaction is introudced into *Escherichia coli* JM105 [J. Messing et al.: Gene, 33, 103 (1985)] using the known transfection method [Y. Kuchino et al.: Tanpakushitsu, Kakusan, Koso, 29, 294 (1984)] as necessary.

DNA isolation from *Escherichia coli* harboring any recombinant plasmid DNA or recombinant M13 phage RF DNA is performed by the method of Birnboim et al. [H. C. Birnboim et al.: Nucleic Acids Res., 7, 1513 (1979)], for instance.

Single-strand DNA isolation from the recombinant M13 phage is performed by the known method [Y. Kuchino et al.: Tanpakushitsu, Kakusan, Koso, 29, 294 (1984)].

The deoxyolignucleotides to be used in the practice of the invention can be synthesized by solid-phase synthesis by the phosphoric amidite method [S. L. Beaucage et al.: Tetrahedron Lett., 22, 1859 (1981); L. J. BcBrie et al.: ibid , 24, 245 (1983)] using an Applied Biosystems model 380A DNA synthesizer (Applied Biosystems Inc., Foster City, Calif. 94404). For ligating any of the deoxyolignucleotides thus synthesized to another DNA fragment, about 20 picomoles of the deoxyolignucleotide is 5'-phosphorylated in 20 µl of T4 kinase buffer [50 mM Tris-HCl (pH 7.6), 10 mM MgCl$_2$, 5 mM DTT, 0.1 mM EDTA, 0.5 mM ATP] in the presence of 5 units of T4 DNA kinase. For use as a probe for hybridization, the deoxyolignucleotide is radiolabeled at the 5' end by using 20 to 50 µCi of [Y-$^{32}$P]ATP (3,000 Ci/mmol; Amersham, Arlington Heights, II) in place of 0.5 mM ATP in the above-mentioned T4 kinase buffer.

Structural analysis of plasmid DNAs is performed by digesting each plasmid with 1 to 10 different restriction enzymes and then checking cleavage sites by agarose gel electrophoresis or polyacrylamide gel electrophoresis. Determination of the base sequence of a DNA, if necessary, can be made by the dideoxy sequencing method using M13 phage.

The polypeptide or glycosylated polypeptide according to the invention can be produced using *Escherichia coli* or animal cells as hosts. Examples of the host *E. coli* include the strain K-12, NY49, HB101 and C600SF8. Examples of the host aminal cells include a Chinese hamster ovary (CHO) cell and a Namalwa cell.

The novel hG-CSF polypeptide of the present invention is produced using Escherichia coli as the host in the following manner.

*Escherichia coli* K-12 MM294 [Backman K., et al., Proc. Natl. Acad. Sci. USA., 73, 4174 (1976)] is transformed with a plasmid (e.g. pCfBD28N145) and an *Escherichia coli* strain harboring pCfBD28N145 is selected from among the ampicillin-resistant (Ap$^r$; hereinafter the same shall apply) colonies obtained. The pCfBD28N145-bearing *Escherichia coli* strain is cultivated in a medium, whereby the novel hG-CSF polypeptide is produced in the culture.

The medium to be used here may be either a synthetic one or a nature-derived one provided that it is suited for the growth of *Escherichia coli* and the production of the novel hG-CSF polypeptide.

Thus, usable as the carbon source are glucose, fructose, lactose, glycerol, mannitol, sorbitol and the like. Usable nitrogen sources are $NH_4Cl$, $(NH_4)_2SO_4$, casamino acids, yeast extract, polypeptone, meat extract, Bacto-tryptone, corn steep liquor and the like. Usable as other nutrient sources are $K_2HPO_4$, $KH_2PO_4$, NaCl, $MgSO_4$, vitamin B1, $MgCl_2$, etc.

The cultivation is carried out at pH 5.5 to 8.5, at a temperature of 18° to 40° C., with aeration and stirring. After 5 to 90 hours of cultivation, the accumulation of the novel hG-CSF polypeptide in cultured cells becomes substantial. Cells are then harvested from the culture and disrupted by sonication, and the cell detritus mass is recovered by centrifugation. The novel hG-CSF polypeptide can be extracted from the cell detritus mass, followed by purification, solubilization and renaturation, by the method of Marston et al. [F. A. O. Marston et al.: BIO/TECHNOLOGY, 2, 800 (1984)] or by the method of Pennica et al. [Nature, 301, 214 (1983)] or by the method of Winkler et al. [BIO/TECHNOLOGY, 3, 990 (1985)].

Now, mention is made of method of producing a novel hG-CSF polypeptide or a novel glycosylated hG-CSF polypeptide using animal cells as hosts.

The host to be used for the expression of a novel hG-CSF polypeptide or a novel glycosylated hG-CSF polypeptide may be any animal cell line provided that it allows expression of said polypeptide or glycosylated polypeptide. As preferred specific animal cells, there may be mentioned, among others, dhfr-deficient CHO cells [G. Urlaub and L. A. Chasin: Proc. Natl. Acad. Sci. USA, 77, 4216 (1980)].

In the following, mention is made of case where a novel hG-CSF polypeptide or novel glycosylated hG-CSF polypeptide is produced using pASN6 as the plasmid for the expression of the novel hG-CSF and dhfr-deficient CHO cells as the hosts.

The plasmid pASN6 is introduced into dhfr-deficient CHO cells, for example by the calcium phosphate method [Graham and Van der Eb: Virology, 52, 546 (1978)]. A transformant harboring pASN6 can be selected, for example by using MEM ALPHA medium (ribonucleic acid- and deoxyribonucleic acid-free; Gibco-Oriental) containing G418 and dialyzed fetal calf serum. It is also possible to select a transformant strain in which the novel hG-CSF polypetide gene has been amplified from among transformants by using methotrexate. The transformant strain thus obtained is grown in a medium, whereby the novel hG-CSF polypeptide or novel glycosylated hG-CSF polypeptide is formed in the culture.

The medium to be used is, for example, HAM F10 medium or HAM F12 medium (Flow Laboratories), Dulbecco's MEM medium or RPMI-1640 medium (Nissui Pharmaceutical) or MEM ALPHA medium, each supplemented with a serum (e.g. fetal bovine serum), or a mixed medium composed of two or more of these. As necessary, glutamine (0.5 to 5 mM), an antibiotic [penicillin (25 U/ml), streptomycin (25 μg/ml), G418 (0.3 mg/ml), etc.], sodium bicarbonate (0.01%), and/or the like may be added to the medium each in an appropriate amount.

For the cultivation, various types of culture bottle, dish, roller bottle, spinner flask, jar fermenter and other vessels can be used. The cultivation is generally carried out at a seed cell density of $5 \times 10^4$ to $1 \times 10^6$ cells/ml and at a temperature of 30° to 40° C. In 2 to 10 days of cultivation, the substance of the invention is secreted for the most part extracellularly.

Cells are removed from the culture by centrifugation and the novel hG-CSF polypeptide or novel glycosylated polypeptide is extracted from the supernatant obtained by centrigugation.

While, in the above, methods of producing the novel polypeptide or novel glycosylated polypeptide using *Escherichia coli* or animal cells as the host cells have been mentioned, novel derivatives of UK or any other proteins can be produced in the same manner.

The activity measurement of the hG-CSF derivatives obtained in the above manner is performed as follows.

Bone marrow cells are taken aseptically from the femur of male C3H/He mice (8 to 12 weeks of age; Shizuoka Laboratory Animal Center) and suspended in α-minimum essential medium (Flow Laboratories; hereinafter abbreviated as "α-MEM medium") supplemented with 10% fetal bovine serum (FBS). This cell suspension (1.5 ml; about $5 \times 10^7$ cells) is applied to a nylon wool (Wako Pure Chemical Industries' Nylon Fiber 146-04231)-packed column (0.3 g) for immersion and then reaction is carried out in a 5% $CO_2$ incubator at 37° C. for 90 minutes. Then α-MEM medium warmed to 37° C. is passed through the column and bone marrow cells unadsorbable on nylon wool are recovered as an eluate fraction. These cells are washed once with α-MEM medium and adjusted to a predetermined concentration.

Then, the bone marrow hematopoietic stem cell colony forming potential is measured by the method of Okabe et al. [T. Okabe et al.: Cancer Research, 44, 4503-4506 (1986)]. Thus, 0.2 ml of the bone marrow cell suspension ($2 \times 10^6$ cells/ml) prepared as described above is added to a mixture of 0.2 ml of α-MEM, 0.4 ml of FBS and 0.2 ml of each sample after two serial dilutions. Thereto is added an equal volume (1.0 ml) of a 0.6% solution of agar (Difco, Agar purified #0560-01) maintained at 42° C. and the resulting mixture is distributed in 0.5-ml portions into wells of a 24-well multidish (Nunc, #143982) ($5 \times 10^4$ cells/well, n=3). After 7 days of cultivation in a 5% $CO_2$ incubator at 37° C., colonies consisting of 40 or more cells are counted under a microscope (Olympus, ×40) After colony counting, each colony is taken out onto a slide glass, fixed with an acetone-formalin mixture for 30 seconds and then subjected to esterase double staining by the method of Kubota et al. [K. Kubota et al.: Exp. Hematology, 8, 339-344 (1980)] for identification of the colony.

The potency of each sample is calculated based on the result of counting for the sample after two serial dilutions as obtained in the colony forming test, as follows. The activity giving a value half the maximum colony count value found with intact G-CSf used as a standard is defined as 50 units. The activity calculated to this scale is multiplied by 20 considering the dilution factor for each sample and for expressing the activity on the per-milliliter basis. The product obtained is reported as the potency (in units). The specific activity is expressed in terms of potency per unit weight (mg) of protein, namely in units/mg.

The hG-CSF protein content is determined by enzyme-linked immunosorbent assay ELISA) using anti-hG-CSF monoclonal antibody. In this assay, standard hG-CSF produced in *Escherichia coli* and purified and assayed by the Lowry method is used as a standard substance. The anti-hG-CSF monoclonal antibody is prepared by the method of Hanai et al. [Cancer Res., 46, 4438 (1986)]. The t-PA or UK activity can be determined by fibrin plate assay [Granelli-Piperno and Reich: J. Exp. Med., 148, 223 (1978)].

In the following examples, the cases where the polypeptide or glycosylated polypeptide according to the invention is an hG-CSF or UK are mentioned. Examples 1 to 5 are illustrative of the case in which the polypeptide or glycosylated polypeptide according to the invention is an hG-CSF and Examples 6 to 8 are illustrative of the case in which said polypeptide or glycosylated polypeptide is a UK.

Example 1

Construction of recombinant plasmid pAS28 for expression of hG-CSF derivative hG-CSF[ND28] (cf. Reference Example 16) in animal cells (cf. FIG. 5):

A 2 μg portion of pAS3-3 obtained in Reference Example 10 was dissolved in 20 μl of 10 mM Tris-HCl buffer (pH 7.5) containing 7 mM MgCl₂, 6mM 2-mercaptoethanol and 150 mM NaCl (hereinafter such buffer will be referred to as "Y-150 buffer" for short), 10 units of the restriction enzyme MluI (Takara Shuzo; hereinafter, unless otherwise specified, all the restriction enzymes used were obtained from Takara Shuzo) was added, and digestion was carried out at 37° C. for 2 hours. Then, 5 units of ApaLI was added and partial digestion was further effected at 37° C. for 10 minutes. About 0.5 μg of a DNA fragment about 3.0 kb in size was purified and recovered from the digestion reaction mixture by the LGT method.

Separately, 2 μg of the same plasmid was dissolved in 20 μl of 10 mM Tris-HCl buffer (pH 7.5) containing 7 mM MgCl₂, 6 mM 2-mercaptoethanol and 50 mM KCl (hereinafter such buffer will be referred to as "K-50 buffer" for short), 10 units of the restriction enzyme AatII (Toyobo) was added, and digestion was carried out at 37° C. for 2 hours. Then, NaCl was added to an NaCl concentration of 100 mM, then 10 units of MluI was added, and reaction was further carried out at 37° C. for 2 hours. About 1 μg of a DNA fragment about 6.3 kb in size was purified and recovered by the LGT method.

Separately, 2 μg of pCfBD28 (cf. Reference Example 16) was dissolved in 20 μl of K-50 buffer, 10 units of the restriction enzyme AatII (Toyobo) was added, and digestion was carried out at 37° C. for 2 hours. Then, NaCl was added to an NaCl concentration of 50 mM, 10 units of XhoI was added, and digestion was carried out at 37° C. for 2 hours. About 0.1 μg of a DNA fragment about 0.3 kb in size was purified and recovered from the reaction mixture by the LGT method.

Further, separately, for the purpose of substituting Ala for the N-terminal amino acid Thr of mature hG-CSF, Thr for the third amino acid Leu, Tyr for the fourth amino acid Gly and Arg for the fifth amino acid Pro, the following DNA linker was synthesized:

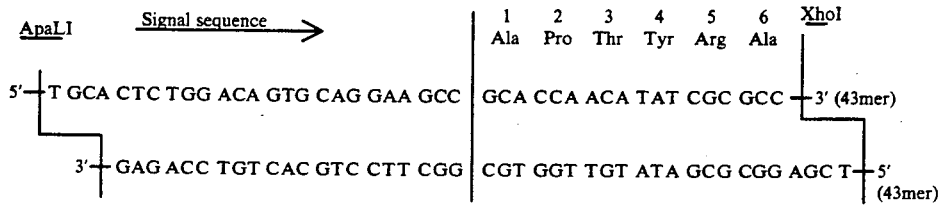

First, the two single-strand 43-mer DNAs were synthesized using an Applied Biosystems model 380A DNA synthesizer. Then, 20 picomoles each of the synthesized DNAs (two 43-mers) were dissolved in 40 μl of 50 mM Tris-HCl buffer (pH 7.5) containing 10 mM MgCl₂, 5 mM dithiothreitol, 0.1 mM EDTA and 1 mM ATP (hereinafter such buffer will be referred to as "T4 kinase buffer" for short), 30 units of T4 polynucleotide kinase (Takara Shuzo; hereinafter the same shall apply) was added, and phosphorylation was carried out at 37° C. for 60 minutes.

A 0.5 μg portion of the pAS3-3-derived MluI-ApaLI fragment (about 3.0 kb), 1.0 μg of the pAS3-3-derived AatII-MluI fragment (about 6.3 kb) and 0.1 μg of the pCfBD28-derived AatII-XhoI fragment (about 0.3 kb) were dissolved in 25 μl of 20 mM Tris-HCl buffer (pH 7.6) containing 10 mM MgCl₂, 10 mM dithiothreitol and 1 mM ATP (hereinafter such buffer will be referred to as "T4 ligase buffer" for short) and about 1 picomole of the above DNA linker was added to the solution. After further addition of 400 units of T4 DNA ligase (Takara Shuzo; hereinafter the same shall apply) to the solution, ligation was carried out at 4° C. for 18 hours.

The recombinant plasmid mixture obtained was used to transform *Escherichia coli* HB101 [Bolivar et al.: Gene, 2, 75 (1977)] by the method of Cohen et al. [S. N. Cohen et al.: Proc. Natl. Acad. Sci. USA, 69, 2110 (1972)] (hereinafter it is this method that was used for transforming *Escherichia coli* strains) and ampicillin (Ap)-resistant strains were obtained. A plasmid DNA was isolated from one of these transformant strains by the known method [H. C. Birnboim et al.: Nucleic Acids Res., 7, 1513 (1979)] (hereinafter it is this method that was used for isolating plasmid DNAs).

The structure of the plasmid obtained was confirmed by restriction enzyme digestion and by sequencing by the dideoxy method using M13 phage, this plasmid was named pAS28 (cf. FIG. 5). A microorganism harboring the plasmid pAS28 has been deposited since Sep. 24, 1988 with the Fermentation Research Institute, Agency of Industrial Science and Technology (FRI) under the designation *Escherichia coli* EAS28 (deposit number FERM BP-2069) in accordance with the Budapest Treaty. The polypeptide (hG-CSF derivative) encoded by the plasmid is distinguished from mature hG-CSF by the following amino acid residue substitutions:

| Position of amino acid substitution (amino acid of hG-CSF) | Plasmid pAS28 |
| --- | --- |
| First (Thr) | Ala |
| Third (Leu) | Thr |
| Fourth (Gly) | Tyr |
| Fifth (Pro) | Arg |
| Seventeenth (Cys) | Ser |

The polypeptide (hG-CSF derivative) encoded by pAS28 is hereinafter referred to as "hG-CSF[ND28]".

EXAMPLE 2

Construction of recombinant plasmid pASN6 (cf FIG. 6) coding for novel hG-CSF polypeptide allowing addition of N-glycosylated carbohydrate chain on 6th (from N terminus) amino acid residue of hG-CSF[ND28] (cf. Reference Example 16):

A 2 μg portion of pAS3-3 obtained in Reference Example 10 was dissolved in 20 μl of Y-150 buffer, 10 units of the restriction enzyme MluI was added, and digestion was carried out at 37° C. for 2 hours. Then, 5 units of ApaLI was added and partial digestion was further conducted at 37° C. for 10 minutes. About 0.5 μg of a DNA fragment about 3.0 kb in size was purified and recovered from the reaction mixture by the LGT method.

Separately, 2 μg of pAS28 obtained in Example 1 was dissolved in 20 μl of Y-150 buffer, 10 units each of the restriction enzymes XhoI and MluI were added, and digestion was carried out at 37° C. for 2 hours. A DNA fragment (1.0 μg) about 6.55 kb in size was purified and recovered from the reaction mixture by the LGT method.

Further, separately, for the purpose of substituting Asn for the 6th (from N terminus) amino acid Ala of hG-CSF[ND28] encoded by pAS28 of Example 1 for the formation of a site of addition of an N-glycosylated carbohydrate chain, the following DNA linker was synthesized. Since the following DNA linker was so designed that an SnaB1 cleavage site could additionally occur therein, incorporation of said linker could be confirmed by cleavage with the restriction enzyme SnaB1.

tion. After further addition of 400 units of T4 DNA ligase to the solution, ligation was carried out at 4° C. for 18 hours.

The recombinant plasmid-containing ligation reaction mixture was used to transform Escherichia coli HB101 by the method of Cohen et al. (vide supra) and Ap-resistant strains were obtained. A plasmid DNA was separated and purified from one of these transformant strains by the known method. The structure of said plasmid DNA was confirmed by restriction enzyme digestion and by the dideoxy sequencing method using M13 phage. This plasmid was named pASN6. A microorganism harboring the plasmid pASN6 has been deposited since Sep. 24, 1988 with the Fermentation Research Institute under the designation Escherichia coli EASN6 (deposit number FERM BP-2070) in accordance with the Budapest Treaty. The polypeptide (hG-CSF derivative) encoded by the plasmid is distinguished from mature hG-CSF by the following amino acid residue substitutions:

| Position of amino acid substitution (amino acid of hG-CSF) | Plasmid pASN6 |
| --- | --- |
| First (Thr) | Ala |
| Third (Leu) | Thr |
| Fourth (Gly) | Tyr |
| Fifth (Pro) | Arg |
| Sixth (Ala) | Asn |
| Seventeenth (Cys) | Ser |

The polypeptide (hG-CSF derivative) encoded by pASN6 is hereinafter referred to as "hG-CSF [ND28N6]".

EXAMPLE 3

Construction of recombinant plasmid pASN145 [cf. FIG. 7(1) and FIG. 7(2)] coding for novel hG-CSF polypeptide allowing addition of N-glycosylated carbohydrate chain on 145th (from N terminus) amino acid residue of hG-CSF[ND28] (cf. Reference Example 16):

(a) Construction of single-strand template DNA (single-strand pt19BD28C):

A 3 μg portion of pCfBD28 (cf. Reference Example 16) was dissolved in 20 μl of 10 mM Tris-HCl buffer

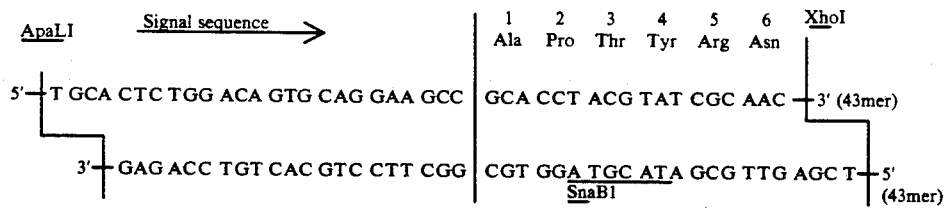

The single-strand DNAs (two 43-mers) were synthesized using an Applied Biosystems model 380A DNA synthesizer.

Twenty picomoles each of the DNAs (two 43-mers) synthesized were dissolved in 40 μl of T4 kinase buffer, 30 units of T4 polynucleotide kinase was added, and phosphorylation was carried out at 37° C. for 60 minutes.

A 0.5 μg portion of the pAS3-3-derived MluI-ApaLI fragment (about 3.0 kb) and 1 μg of the pAS28-derived XhoI-MluI fragment (about 6.55 kb), respectively obtained as described above, were dissolved in a total volume of 30 μl of T4 ligase buffer and about 1 picomole of the above DNA linker was added to the solu- (pH 7.5) containing 7 mM MgCl$_2$ and 6 mM 2-mercaptoethanol (such buffer is hereinafter referred to as "Y-0 buffer" for short), 10 units of the restriction enzyme PvuII was added, and digestion was carried out at 37° C. for 2 hours. Then, NaCl was added to an NaCl concentration of 100 mM, 10 units of BamHI was added, and reaction was carried out at 37° C. for 2 hours.

About 0.5 μg of a DNA fragment (PvuII-BamHI fragment) about 0.94 kb in size and coding for the C-terminal portion of hG-CSF[ND28] was obtained from the reaction mixture by the LGT method.

Separately, 1 μg of the M13 phage vector M13mp19RF DNA (Takara Shuzo) was dissolved in a total volume of 50 μl of Y-0 buffer, 10 units of the restriction enzyme SmaI was added, and digestion was carried out at 37° C. for 2 hours. Then, NaCl was added to an NaCl concentration of 100 mM, 10 units of the restriction enzyme BamHI was added, and digestion was carried out at 37° C. for 2 hours. About 0.8 μg of a DNA fragment (SmaI-BamHI fragment) about 7.24 kb in size was obtained from the reaction mixture by the LGT method.

A 0.2 μg portion of the PvuII-BamHI fragment (about 0.94 kb) and 0.05 μg of the SmaI-BamHI fragment (about 7.24 kb), respectively obtained as described above, were dissolved in 50 μl of T4 ligase buffer, 400 units of T4 DNA ligase was added to the solution, and ligation was carried out at 12° C. for 16 hours.

Then, the above ligation reaction mixture was used to transfect *Escerichia coli* JM105 by the known method [Messing et al.: Methods in Enzymology, 101, 20 (1983)] and recombinant phages were obtained. A recombinant 13 phage RF DNA was recovered from cultured cells of one recombinant phage-infected *Escherichia coli* JM105 strain by the same method as the plasmid DNA recovering method. The structure of this RF DNA [named pt19BD28C] was confirmed by cleavage with BamHI, EcoRI and BglI, followed by polyacrylamide gel electrophoresis. The single-strand pt19BD28C DNA was recovered from the recombinant phage by the above-mentioned known method and used as a template.

(b) Construction of gapped duplex DNA:

A 3-μg portion of the M13mp19 RF DNA (Takara Shuzo) was dissolved in 30 μl of 10 mM Tris-HCl buffer (pH 7.5) containing 7 mM MgCl₂, 6 mM 2-mercaptoethanol and 100 mM NaCl (hereinafter such buffer is referred to as "Y-100 buffer" for short), 10 units each of the restriction enzymes EcoRI and HindIII, and digestion was carried out at 37° C. for 2 hours. About 2.5 μg of a DNA fragment (EcoRI-HindIII fragment) about 7.2 kb in size was obtained from the digestion reaction mixture by the LGT method.

A 2-μg portion of this mp19 RF DNA-derived EcoRI-HindIII fragment (about 7.2 kb) and 1 μg of the single-strand template DNA pt19BD28C were dissolved in 27 μl of 50 mM Tris-HCl buffer (pH 7.8) containing 7 mM MgCl₂ and 6 mM 2-mercaptoethanol (hereinafter such buffer is referred to as "Klenow buffer" for short) and the solution was boiled at 100° C. for 6 minutes for causing DNA denaturation and then allowed to stand at 65° C. for 10 minutes, at 37° C. for 40 minutes, at 4° C. for 40 minutes and, finally, on ice for 10 minutes for causing annealing, whereby a gapped duplex DNA with only the hG-CSF gene portion in the template being single-stranded was formed. The gapped duplex DNA formed was recovered by the LGT method.

(c) Mutagenesis (construction of pt19BD28CN145):

For the purpose of substituting Asn for the 145th (from the N terminus) amino acid Gln and Ser for the 147th amino acid Arg of hG-CSF[ND28] encoded by pAS28 obtained in Example 1 so that an N-glycosylated carbohydrate chain addition site could be formed, the following single-strand DNA was synthesized. Since the single-strand DNA was designed such that a PvuI site should newly occur therein, mutagenesis could be confirmed by cleavage with the restriction enzyme PvuI.

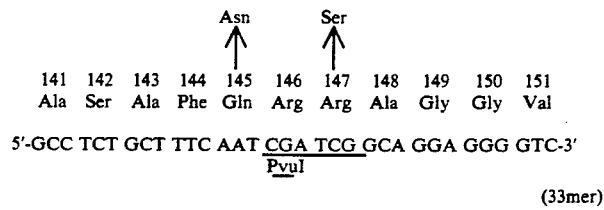

(33mer)

The single-strand DNA was synthesized using an Applied Biosystems model 380A DNA synthesizer. A 1-μg portion of the single-strand DNA synthesized was dissolved in 50 μl of T4 kinase buffer, 30 units of T4 polynucleotide kinase was added, and phosphorylation was carried out at 37° C. for 60 minutes.

Then, 0.2 μg of this phosphorylated single-strand DNA and 0.1 μg of the gapped duplex DNA obtained as described in the preceding section were dissolved in 34 μl of 6.5 mM Tris-HCl buffer (pH 7.5) containing 8 mM MgCl₂, 1 mM 2-mercaptoethanol and 100 mM NaCl, the solution was allowed to stand at 65° C. for 60 minutes and then at room temperature for 30 minutes for annealing of the single-strand DNA with the gapped duplex DNA.

To the solution were added dATP, dTTP, dCTP and dGTP each to a concentration of 0.5 mM. After further addition of 1.5 units of DNA polymerase I Klenow fragment and 400 units of T4 DNA ligase, chain extension was effected at 4° C. for 16 hours.

The resultant reaction mixture was used to transfect *Escherichia coli* JM105 and mutant phages were obtained. RF DNAs were recovered from mutant phage-infected *Escherichia coli* JM105 strains and examined for their structure by restriction enzyme cleavage and by sequencing by the dideoxy method using M13 phage. The desired mutant RF DNA was named pt19BD28CN145.

(d) Construction of pCfBD28N145 [cf. FIG. 7-(2)]

A 3-μg portion of pt19BD28CN145 obtained as described in the preceding section was dissolved in 50 μl of Y-100 buffer, 10 units each of the restriction enzymes BglI (Boehringer Mannheim) and BamHI were added, and digestion was carried out at 37° C. for 2 hours. From the reaction mixture, there was obtained by the LGT method 0.4 μg of a DNA fragment (BglI-BamHI fragment) about 0.85 kb in size and containing the mutation site introduced as described in the preceding section.

Separately, 2 μg of pCfBD28 (cf. Reference Example 16) was dissolved in 50 μl of Y-100 buffer, 10 units of the restriction enzyme BamHI was added, and digestion was carried out at 37° C. for 2 hours. Then, 5 units of the restriction enzyme BglI was added and partial digestion was further effected at 37° C. for 10 minutes. From the reaction mixture, there was obtained by the LGT method 0.5 μg of a DNA fragment (BamHI-BglI fragment) about 3.25 kb in size.

In 60 μl of T4 ligase buffer were dissolved 0.4 μg of the pt19BD28CN145-derived BglI-BamHI fragment (about 0.85 kb) and 0.5 μg of the pCfBD28-derived BglI-BamHI fragment (about 3.25 kb), respectively obtained as described above, and, after addition of 400 units of T4 DNA ligase, ligation was carried out at 12° C. for 16 hours.

The ligation reaction mixture was used to transform *Escherichia coli* HB101 and Ap-resistant strains were obtained. Plasmid DNAs were isolated from the transformants and analyzed for their structure by cleavage with restriction enzymes. The plasmid DNA having the desired structure was named pCfBD28N145.

(e) Construction of pASN145

In 50 μl of Y-100 buffer was dissolved 5 μg of pCfBD28N145 obtained as described in the preceding section and, after addition of 10 units each of the restriction enzymes BanIII (Toyobo) and BamHI, digestion was carried out at 37° C. for 2 hours. A DNA fragment (BanIII-BamHI fragment; 1 μg about 1.3 kb in size was obtained from the reaction mixture by the LGT method. This 1.3 kb DNA fragment (1 μg) was dissolved in 50 μl of Y-100 buffer, 10 units of the restriction enzyme DdeI (Toyobo) was added, and digestion was carried out at 37° C. for 2 hours. DNA was recovered by ethanol precipitation following exatraction with a mixture of equal volumes of phenol and chloroform (hereinafter referred to as "phenol-chloroform extraction") and dissolved in 30 μl of Klenow buffer, 2 units of DNA polymerase I Klenow fragment was added, and reaction was carried out at 37° C. for 1 hour. After 10-minute treatment at 68° C. for inactivating the DNA polymerase I Klenow fragment, DNA was recovered by ethanol precipitation. The DNA recovered was dissolved in 20 μl of K-50 buffer, 10 units of the restriction enzyme AatII (Toyobo) was added, and digestion was carried out at 37° C. for 2 hours. About 0.1 μg of a DNA fragment [DdeI (blunt end)-AatII fragment] about 0.2 kb in size was obtained from the reaction mixture by the LGT method.

Separately, 2 μg of pAS28 obtained in Example 1 was dissolved in 20 μl of K-50 buffer, 10 units of the restriction enzyme AatII (Toyobo) was added, and digestion was conducted at 37° C. for 2 hours. Thereafter, 5 units of the restriction enzyme XhoI was added and partial digestion was further effected at 37° C. for 10 minutes. About 0.1 μg of a DNA fragment AatII-XhoI fragment) about 0.8 kb in size was obtained from the reaction mixture by the LGT method.

Separately, 2 μg of pSE1PA1SE1dhfr1-9A obtained in Reference Example 9 was dissolved in 20 μl of Y-0 buffer, 10 units of the restriction enzyme SmaI was added, and digestion was carried out at 37° C. for 2 hours. Then, NaCl was added to a final NaCl concentration of 100 mM, 10 units of the restriction enzyme XhoI was added, and digestion was further conducted at 37° C. for 2 hours. About 1 μg of a DNA fragment (SmaI-XhoI fragment) about 8.7 kb in size was obtained from the reaction mixture by the LGT method.

About 0.1 μg of the pCfBD28N145-derived DdeI (blunt end)-AatII fragment (about 0.2 kb), about 0.1 μg of the pAS28-derived AatII-XhoI fragment (about 0.8 kb) and about 1 μg of the pSE1PA1SE1dhfr1-9A-derived SmaI-XhoI fragment (about 8.7 kb), respectively obtained as described above, were dissolved in 30 μl of T4 DNA ligase buffer, 400 units of T4 DNA ligase was added, and ligation was carried out at 4° C. for 18 hours. The ligation reaction mixture was used to transform *Escherichia coli* HB101 and Ap-resistant strains were obtained. Plasmids were isolated from the transformants and analyzed for their structure by cleavage with restriction enzymes and, as a result, a plasmid DNA having the desired structure, pASN145, was obtained. A microorganism harboring the plasmid pASN145 has been deposited, since Sep. 24, 1988, with the Fermentation Research Institute under the designation *Escherichia coli* EASN145 (deposit number FERM BP-2071) in accordance with the Budapest Treaty. The polypeptide (hG-CSF derivative) encoded by the plasmid is distinguished from mature hG-CSF by the following amino acid residue substitutions:

| Position of amino acid substitution (amino acid in hG-CSF) | Plasmid pASN145 |
| --- | --- |
| First (Thr) | Ala |
| Third (Leu) | Thr |
| Fourth (Gly) | Tyr |
| Fifth (Pro) | Arg |
| 17th (Cys) | Ser |
| 145th (Gln) | Asn |
| 147th (Arg) | Ser |

The polypeptide (hG-CSF derivative) encoded by pASN145 is hereinafter referred to as "hG-CSF[ND28N145]".

EXAMPLE 4

Production of hG-CSF[ND28], hG-CSF[ND28N6], hG-CSF[ND28N145] and hG-CSF in animal cells:

(1) Production of hG-CSF[ND28] in animal cells harboring pAS28:

pAS28 obtained in Example 1 was introduced into dhfr-deficient CHO cells by the calcium phosphate method. Thus, 5 ml of MEM ALPHA medium (containing ribonucleic acid and deoxyribonucleic acid; Gibco-Oriental) supplemented with 10% FCS and 1/50 volume of 7.5% NaHCO$_3$ solution (Flow Laboratories) [hereinafter such medium is referred to as "MEMα (nonselective medium)" for short] was inoculated with such cells at an inoculum size of 1×10$^5$ cells/ml [a dish 6 cm in diameter (made by LUX) being used for culture; hereinafter LUX dishes being used for culturing purposes] and cultured in a CO$_2$ incubator at 37° C. for 1 day. Separately, 10 μg of pAS28 was dissolved in 450 μl of 10 mM Tris-HCl (pH 7.5). To this solution was added 500 μl of a solution containing 280 mM NaCl, 1.5 mM Na$_2$HPO$_4$ and 50 mM HEPES (N-2-hydroxyethylpiperazine-N'-2-ethanesulfonic acid) (pH 7.1), followed by shaking. Furthermore, 50 μl of 2.5M CaCl$_2$ was added and, after shaking, the mixed solution was allowed to stand at room temperature for 5 minutes. The whole DNA solution was added to dhfr-deficient CHO cells prepared from the above-mentioned culture by discarding the medium, adding a fresh 10-ml portion of MEMα (nonselective medium) and incubating for 1 hour. The resultant mixture was incubated for 8 hours. Cells were then washed with PBS, 5 ml of MEMα (nonselective medium) was added, and incubation was continued for 16 hours. Cells were washed with PBS [8 g liter NaCl, 0.2 g/liter KCl, 1.15 g/liter Na$_2$HPO$_4$ (anhydrous), 0.2 g/liter KH$_2$PO$_4$], 3 ml of a solution containing 0 05% trypsin and 0.02% EDTA (ethylenediaminetetraacetic acid) was added and, after removal of the excess solution, the cells were incubated at 37° C. for 5 minutes [trypsin treatment]. MEM ALPHA medium (ribonucleic aicd- and deoxyribonucleic acid-free) supplemented with 10% dialyzed FCS (Gibco-Oriental), 1/50 volume 7.5% NaHCO$_3$, 1/100 volume 100×nonessential amino acid solution and 0.3 mg/ml G418 (Gibco-Oriental) [hereinafter such medium is referred to as "MEMα (selective medium)" for short] was added and, after causing the cells to be suspended well in said medium, the cells were cultured in a $CO_2$ incubator at 37° C. for 5 days using a dish 10 cm in diameter. The cells were washed with PBS, then MEMα (selective medium) was added, and incubation was continues for 5 days. After the same procedure was followed, incubation was further continued for 5 days. The cells were washed with PBS, then treated with trypsin, suspended in 10 ml of MEMα (selective medium) by adding the medium, and cultured in a $CO_2$ incubator at 37° C. for 3 to 7 days using a dish 6 cm in diameter. Colonies that had appeared were treated with trypsin and then inoculated into a dish, 10 cm in diameter, to a concentration of $5 \times 10^4$ cells/ml using 10 ml of MEMα (selective medium) containing 50 nM methotrexate (hereinafter referred to as "MTX" for short). Medium exchange was made three times at 5-day intervals using the above-mentioned medium. MTX-resistant colonies that had appeared were monoclonally separated and each cultured until confluence using a dish 6 cm in diameter. Thereafter, the medium was replaced with FCS-free MEMα (selective medium) and, after further 2 days of incubation, the production of hG-CSF[ND28] in the culture fluid was examined. The production was highest in clone No. 22, namely 10 μg hG-CSF[ND28] per $10^6$ cells/2 days. This clone was cultured in a Falcon 3027 roller bottle containing 100 ml of MEMα (selective medium) containing 50 nM MTX. After the culture cells became confluent, incubation was continued for 3 days using the above-mentioned FCS-free medium. This 100-ml culture fluid was used in Example 5.

(2) Production of hG-CSF[ND28N6] by animal cells harboring pASN6:

Cell lines capable of producing hG-CSF[ND28N6] were obtained following the procedure mentioned above and using pASN6 obtained in Example 2 and the dhfr-deficient CHO cell line. Among them, clone No. 16 showed the highest production of 7 μg/$10^6$ cells/2 days. This clone was cultured in a Falcon 3027 roller bottle containing 100 ml of MEMα (selective medium) containing 50 nM MTX and, after confluency was attained, cultivation was continued for 3 days using the above-mentioned FCS-free medium. This 100-ml culture fluid was used in Example 5.

(3) Production of hG-CSF[ND28N145] by animal cells harboring pASN145:

Cell lines capable of producing hG-CSF[ND28N145] were obtained following the procedure mentioned above and using pASN145 obtained in Example 3 and the dhfr-deficient CHO cell line. Among them, clone No. 9 showed the highest production of 7 μg/$10^6$ cells/2 days. This clone was cultured in a Falcon 3027 roller bottle containing 100 ml of MEMα (selective medium) containing 50 nM MTX and, after the culture cells became confluent, cultivation was continued for 3 days using the above-mentioned FCS-free medium. This 100-m culture fluid was used in Example 5.

(4) Production of hG-CSF by animal cells harboring pAS3-3:

Cell lines capable of producing hG-CSF were obtained following the procedure mentioned above and using pAS3-3 obtained in Reference Example 10 and the dhfr-deficient CHO cell line. Among them, clone No. 5 showed the highest production of 10 μg/$10^6$ cells/2 days. This clone was cultured in a Falcon 3027 roller bottle containing 100 ml of MEMα (selective medium) containing 50 nM MTX and, after the culture cells became confluent, cultivation was continued for 3 days using the above-mentioned FCS-free medium. The 100-ml culture fluid thus obtained was used in Example 5 as a sample containing natural hG-CSF.

EXAMPLE 5

Investigations of carbohydrate chain-introduced hG-CSF derivatives hG-CSF[ND28], hG-CSF[ND28N6] and hG-CSF[ND28N145] as to protease resistance and of hG-CSF[ND28N6] as to thermal stability:

(1) Confirmation of carbohydrate chain addition

Figure 8:
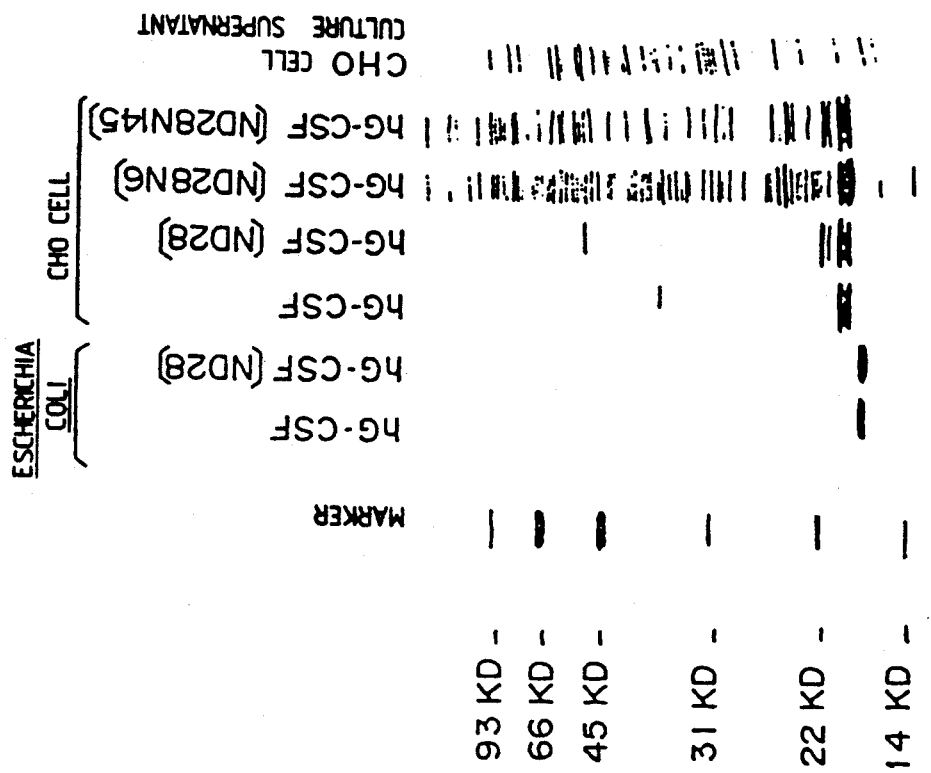
FIG. 8(1) shows the electrophorogram obtained by subjecting hG-CSF and hG-CSF[ND28] each purified following production in *Escherichia coli* as well as hG-CSF, hG-CSF[ND28], hG-CSF[ND28N6] and hG-CSF[ND28N145] each produced in CHO cells to SDS-polyacrylamide electrophoresis followed by silver staining.
Figure 8:
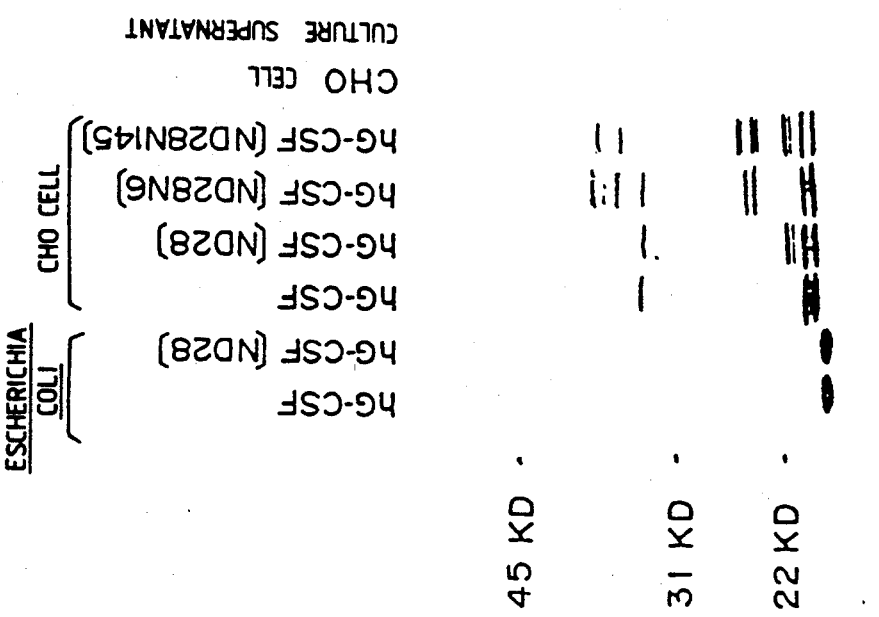
Figure 8:
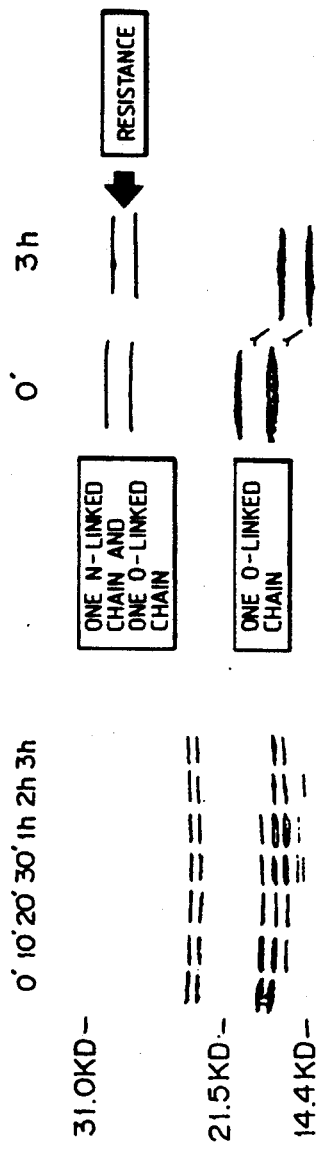
Figure 8:
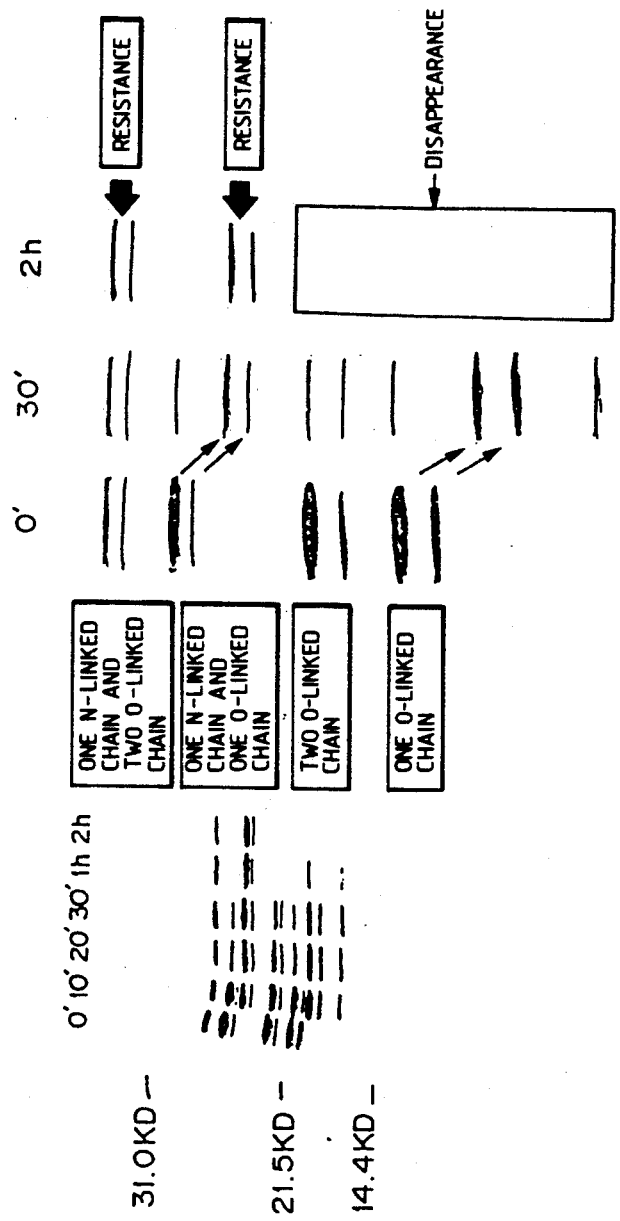

From the serum-free culture fluid obtained in Example 4 and containing natural hG-CSF, hG-CSF[ND28], hG-CSF[ND28N6] or hG-CSF[ND28N145], cells were completely removed by centrifugation. A 15-μl portion of each sample was subjected to SDS-polyacrylamide gel electrophoresis [Laemmli: Nature, 227, 680 (1970)]. A plasmid DNA-free CHO cell culture suspernatant and hG-CSF and hG-CSF[ND28] (cf. Reference Example 16) produced in *Escherichia coli* and purified were also subjected to SDS-polyacrylamide gel electrophoresis. The patterns obtained by silver staining (using Wako Pure Chemical Industries' silver staining kit) following electrophoresis are shown in FIG. 8-(1). FIG. 8-(2), on the other hand shows the results of enzyme-labeled antibody staining [K. Tabe: Saibo Kogaku (Cell Technology), 2, 1061 (1983)] using an anti-hG-CSF monoclonal antibody following transfer of the proteins on the same gel to a nitrocellulose membrane. The anti-hG-CSF monoclonal antibody was prepared by the method of Hanai et al. [Cancer Res., 46, 4438 (1986)].

It is known that natural hG-CSF or hG-CSF produced in CHO cells is glycosylated through addition of one O-glycosylated carbohydrate chain to the 133rd (from the N terminus) amino acid Thr residue. It is also known that the carbohydrate chain involved in said addition includes two species, one containing one sialic acid residue and the other containing two sialic acid residues [Oeda et al.: J. Biochem., 103, 544 (1988)]. In the present study, too, hG-CSF produced in CHO cells was found to have one O-glycosylated carbohydrate chain added thereto. As the carbohydrate chain added, there were found two kinds, one containing one sialic acid residue and the other containing two sialic acid residues. The two bands seen in FIG. 8-(1) or FIG. 8-(2) for hG-CSF reflect the difference in the number of sialic acid residues.

On the contrary, it was found that hG-CSF[ND28] produced in CHO cells was composed of two species, one having one O-glycosylated carbohydrate chain and the other having two such carbohydrate chains. In the case of hG-CSF[ND28N6] and hG-CSF[ND28N145] differing from hG-CSF[ND28] by having one newly introduced N-glycosylation site, about one third of the whole amount of hG-CSF produced had an N-glycosylated carbohydrate chain added thereto. In the case of hG-CSF[ND28N145], as in the case of hG-CSF[ND28], a species having an additional O-glycosylated carbohydrate chain added thereto was also present. Therefore, hG-CSF[ND28N145] included four polypeptide species differing in the kind and/or number of carbohydrate chains added: namely one having one O-glycosylated carbohydrate chain, like the natural type; one having two O-glycosylated carbohydrate chains; one having one O-glycosylated carbohydrate chain and one N-glycosylated carbohydrate chain; and one having two O-glycosylated carbohydrate chains and one N-glycosylated carbohydrate chains. On the other hand, hG-CSF[ND28N6] showed almost no new O-glycosylated carbohydrate chain addition.

The N-glycosylated carbohydrate chain addition was confirmed by treatment with N-glycanase (Seikagaku Kogyo), an enzyme cleaving the bond between N-glycosylated carbohydrate chain and polypeptide. The O-glycosylated carbohydrate chain addition was confirmed by using O-glycanase (Seikagaku Kogyo) and sialidase (Seikagaku Kogyo). FIG. 8-(3) is a schematic representation of FIG. 8-(2) and indicates the kind(s) and number of carbohydrate chains for each band.

(2) Protease resistance investigation

As mentioned in the preceding section, hG-CSF[ND28], hG-CSF[ND28N6] and hG-CSF[ND28N145] produced in CHO cells each included a species having an additional carbohydrate chain or chains added thereto and a species having no additional carbohydrate chain. Therefore, chymotrypsin was directly added to the culture supernatant containing both species (one having a new carbohydrate chain or chains and one having no such additional carbohydrate chain) obtained as described in the preceding section and the effects of the presence and absence of such additional carbohydrate chain or chains on protease resistance were compared. Thus, 2 μl of 0.5 mg/ml chymotrypsin (Sigma) was added to 450 μl of each of the above-mentioned culture supernatants containing hG-CSF[ND28], hG-CSF[ND28N6] and hG-CSF[ND28N145], respectively. Each mixture was incubated at 37° C. After the lapse of 10, 20, 30, 60, 120 and 180 minutes following chymotrypsin addition, samples were taken from the mixture each time in an amount of 60 μl and the reaction was terminated by adding 20 μl of SDS-polyacrylamide gel electrophoresis buffer [0.25M Tris-HCl (pH 6.8), 8% sodium lauryl sulfate (SDS), 40% glycerol and 0.004% bromphenol blue]. A sample containing no chymotrypsin was also prepared with each supernatant and this was used as a sample after the lapse of 0 (zero minute following chymotrypsin addition.

A 20-μl portion of each sample was subjected to SDS-polyacrylamide gel electrophoresis, then polypeptides were transferred to a nitrocellulose membrane, and enzyme-labeled antibody staining was performed in the same manner as described in the preceding section. As a result, it was found that all the newly glycosylated hG-CSF[ND28], hG-CSF[ND28N6] and hG-CSFND28N145] species were resistant to chymotrypsin as compared with the species having no additional carbohydrate chain.

In the case of hG-CSF[ND28], the species having two O-glycosylated carbohydrate chains was more resistant to chymotrypsin than the species (natural type) having one such chain [FIG. 8-(4)]. In the case of hG-CSF[ND28N6], the species having an additional N-glycosylated carbohydrate chain was more resistant to said enzyme than the species having no such carbohydrate chain [FIG. 8-(5)]. In the case of hG-CSF[ND28N145] comprising four kinds of polypeptide, namely the species having one O-glycosylated carbohydrate chain (natural type), that having an additional O-glycosylated carbohydrate chain, that having an additional N-glycosylated carbohydrate chain and that having both additional carbohydrate chains, those having an additional N-glycosylated carbohydrate chain were more resistant than others. The species having an additional O-glycosylated carbohydrate chain as well as an additional N-glycosylated carbohydrate chain was the most resistant [FIG. 8-(6)].

(3) Thermal stability investigation

A 5-ml portion of the hG-CSF[ND28N6] -containing, serum-free, culture supernatant obtained in Example 4-(2) was concentrated to 500 μl using a Molcut-10 membrane (Millipore). A 100-μl portion of the concentrate was applied to a Superose 12 column (Pharmacia) (1 cm×30 cm) and the N-glycosylated hG-CSF[ND28N6] species was isolated. For chromatography, 0.1M Tris-HCl buffer (pH 8.0) containing 0.2M NaCl and 1 mM EDTA was used. The buffer was passed through the column at a flow rate of 0.5 ml/minute. Three repetitions of the above chromatography gave about 1.5 ml of a solution containing the N-glycosylated hG-CSF[ND28N6] species (hG-CSF concentration about 1.7 μg/ml). To 350 μl of this solution were added 3.5 μl of 1% Tween 20 and 1 μl (0.25 unit) of N-glycanase (Seikagaku Kogyo), and the N-glycosylated carbohydrate chain was eliminated by conducting the reaction at 37° C. for 17.5 hours. An untreated control was also prepared by adding 1 μl of sterilized water in lieu of N-glycanase and subjected to the same reaction procedure. After the reaction period, a portion of each reaction mixture was subjected to SDS-polyacrylamide gel electrophoresis, followed by silver staining. It was thus confirmed that the N-glycosylated carbohydrate chain had been eliminated in the N-glycanase-treated sample.

Immediately after completion of the above reaction, both reaction mixtures were used in a comparative thermal stability test at 56° C. Thus, 60 μl of each reaction mixture was maintaind at 56° C. After 0, 30, 120, 240 and 360 minutes, sampling (10 μl per sampling) was made and hG-CSF activity measurement was performed by colony forming ability testing using mouse bone marrow hematopoietic stem cells. The results obtained are shown in FIG. 8-(7). In the figure, the activity is shown in terms of residual activity with the activity after 17.5 hours of incubation at 37° C. being taken as 100%. The activity after 17.5 hours of incubation at 37° C. was 48.1% for the N-glycanase-treated sample and 66.8% in the control when the activity before incubation was taken as 100%.

As shown in FIG. 8-(7), it was found that the N-glycosylated hG-CSF[ND28N6] species (control) was more stable against heat than the hG-CSF[ND28N6] species from which the N-glycosylated carbohydrate chain had been eliminated (N-glycanase treatment).

EXAMPLE 6

Construction of UK-S1 expression plasmid pSE1UKS1-1d:

(1) Construction of single-strand template DNA (single-strand pUKmpS1):

About 3 μg of pUK1 obtained in Reference Example 2 was dissolved in 30 μl of Y-100 buffer, 10 units each of the restriction enzymes PstI and BamHI were added, and digestion was carried out at 37° C. for 2 hours. After a 10-minute heat treatment at 65° C., a 890-bp PstI-BamHI fragment was purified by the AFT method [BioTechniques, 2, 66–67 (1984)].

Separately, about 1 μg of the M13mp18 RF DNA (M13 phage vector; Takara Shuzo) was dissolved in a total volume of 30 μl of Y-100 buffer, 10 units each of the restriction enzymes PstI and BamHI were added, and digestion was performed at 37° C. for 2 hours. After 10-minute heat treatment at 65° C., a DNA fragment about 7.2 kb was purified by the AFT method.

The thus-obtained pUK1-derived 890-bp DNA fragment and M13mp18 RF DNA-derived 7.2-kb DNA fragment were dissolved in a total volume of 20 μl of T4 ligase buffer, 300 units of T4 DNA ligase was added, and ligation was carried out at 4° C. for 18 hours.

Then, the above ligation reaction mixture was used to transfect Escherichia coli JM105 by the known method [Messing et al.: Methods in Enzymology, 101, 20 (1983)] and recombinant phages were obtained. Escherichia coli JM 105 was infected with one of the recombinant phages by the known method (vide supra) and cultured. A single-strand phage DNA was recovered from culture fluid. A double-stranded phage DNA was also recovered from cultured cells according to the plasmid DNA recovering method. The structure of this double-stranded phage DNA (pUKmpS1) was confirmed by digestion with restriction enzymes (cf. FIG. 9).

(2) Induction of mutation in UK cDNA using oligonucleotide:

[A] Preparation of synthetic DNA for mutagenesis and phosphorylation:

For the purpose of producing a UK derivative containing Asn in lieu of the 164th amino acid Phe residue of UK and having a carbohydrate chain added hereinafter said UK derivative is referred to as "UK-S1" for short), the 17-base synthetic DNA 5'-GGGGAGAAAACACCACC-3' was synthesized using an Applied Biosystems model 380A DNA synthesizer.

Then, 25 picomoles of the thus-obtained synthetic DNA was 5'-phosphorylated by carrying out the reaction in 10 μl of 50 mM Tris-HCl buffer (pH 7.6) containing 10 mM MgCl$_2$, 5 m DTT, 0.1 mM EDTA and 0.5 mM ATP in the presence of 5 units of T4 DNA kinase (Takara Shuzo) at 37° C. for 30 minutes.

[B] Site-directed mutagenesis using two oligonucleotide primers:

A mixed solution composed of 6.5 μl of a solution containing the single-strand recombinant phage DNA obtained as described above [containing about 2 μg of DNA), 1 μl of 10 times concentrated polymerase buffer [containing 500 mM Tris-HCl (pH 7.8), 70 mM MgCl$_2$, 60 mM 2-mercaptoethanol, 0.25 mM dATP, 0.25 mM dCTP, 0.25 mM dGTP and 0.25 mM dTTP] and 2 μl (2.5 picomoles) of the synthetic DNA for mutagenesis obtained as described above was allowed to stand at 65° C. for 5 minutes, at 55° C. for 5 minutes, at 37° C. for 10 minutes and then at 25° C. for 10 minutes, then 3 units of Escherichia coli polymerase I Klenow fragment (hereinafter abbreviated as "Klenow fragment") (Takara Shuzo) was added, and reaction was carried out at 25° C. for 30 minutes. Then 1 μl of 10 times concentrated polymerase buffer, 6 μl of 0.5 picomole/μl M13 primer M4 [Takara Shuzo) and 3 units of the Klenow fragment were added to the reaction mixture. After 10 minutes of reaction at 37° C. and 40 minutes of reaction at 25° C., 2 μl of 10 mM ATP and 300 units of T4 DNA ligase were added and ligation was carried out at 11° C. for 18 hours. After the reaction mixture was subjected to phenolchloroform extraction, a DNA fragment was recovered by ethanol precipitation. This DNA fragment was dissolved in a total volume of 30 μl of Y-100 buffer, 12 units of EcoRI and 12 units of PstI were added, and digestion was carried out at 37° C. for 2 hours. After 10-minute heat treatment at 65° C., a PstI-EcoRI fragment about 600 bp in size was purified by the AFT method.

[C] Insertion of mutant DNA fragment into vector

About 3 μg of the pUK11 plasmid DNA obtained in Reference Example 3 was dissolved in 30 μl of Y-50 buffer, 10 units of AatII (Toyobo) and 8 units of PstI were added, and digestion was carried out at 37° C. for 2 hours. After 10-minute heat treatment at 65° C., an AatII-PstI fragment about 1.0 kb in size was purified by the AFT method. Separately, about 3 μg of the pUKB101 plasmid DNA obtained in Reference Example 12 was dissolved in 30 μl of Y-50 buffer, 10 units of AatII and 10 units of EcoRI were added, and digestion was carried out at 37° C. for 2 hours. After 10-minute heat treatment at 65° C., an AatII-EcoRI fragment about 2.9 kb in size was purified by the AFT method.

The thus-obtained pUK11-derived AatII-PstI fragment (about 0.05 μg), pUKB101-derived AatII-EcoRI fragment (about 0.1 μg) and mutant 600 bp PstI-EcoRI fragment were dissolved in 20 μl of T4 ligase buffer, 300 units of T4 DNA ligase was added, and ligation was carried out at 4° C. for 18 hours.

The recombinant plasmid mixture obtained was used to transform Escherichia coli C600 SF8 [Proc. Natl. Acad. Sci. USA, 72, 3416 (1975)] and Ap-resistant strains were obtained. From among these transformants, a recombinant plasmid, pUKS1, capable of hybridizing with a probe prepared by labeling the synthetic DNA for mutagenesis (mentioned above) with $^{32}$P at the 5' end was isolated by the colony hybridization method. Structural analysis by restriction enzyme digestion and sequencing by the dideoxy method using M13 phage confirmed that pUKS1 had the desired structure (cf. FIG. 10).

(3) Construction of UK-S1 expression plasmid pSE1UKS1-1d:

About 2 μg of the pSE1PA1SE1dhfr1-9A plasmid DNA obtained in Reference Example 9 was dissolved in 30 μl of Y-0 buffer, 10 units of KpnI was added, and digestion was carried out at 37° C. for 2 hours. Then, 1.5 μl of 2M NaCl and 10 units of XhoI were added and digestion was effected at 37° C. for 1 hour. After 10-minute heat treatment at 65° C., a DNA fragment about 8.6 kb in size was purified by the AFT method. Separately, about 3 μg of the pSE1UKpro1-1A plasmid DNA obtained in Reference Example 13 was dissolved in 30 μl of Y-100 buffer, 12 units of BglII and 12 units of XhoI were added, and digestion was carried out at 37° C. for 2 hours. After 10-minute heat treatment at 65° C., a DNA fragment about 0.75 kb in size was purified by the AFT method. Further, separately, about 3 μg of the pUKS1 plasmid DNA obtained as described above was dissolved in 30 μl of Y-0 buffer, 15 units of KpnI was added, and digestion was conducted at 37° C. for 2 hours. Then, 1.5 μl of 2M NaCl and 12 units of BglII were added and digestion was further carried out at 37° C. for 1 hour. After 10-minute heat treatment at 65° C., a DNA fragment about 1.15 kb in size was purified by the AFT method.

The thus-obtained pSE1PA1SE1dhfr1-9A-derived DNA fragment (about 8.6 kb; about 0.1 μg), pSE1UKpro1-1A-derived DNA fragment (about 0.75 kb; about 0.02 μg) and pUKS1-derived DNA fragment (about 1.15 kb; about 0.02 μg) were dissolved in a total volume of 20 μl of T4 ligase buffer, 100 units of T4 DNA ligase was added, and ligation was carried out at 4° C. for 18 hours.

The recombinant plasmid mixture obtained was used to transform *Escherichia coli* MM294 and Ap-resistant strains were obtained. A plasmid DNA, pSE1UKS1-1d, was isolated from one of the transformants. As a result of structural analysis by restriction enzyme digestion, it was confirmed that pSE1UKS1-1d had the desired structure (cf. FIG. 11).

A microorganism harboring the plasmid pSE1UKS1-1d has been deposited since Sep. 24, 1988 with the Fermentation Research Institute under the designation *Escherichia coli* EUKS1-1d (deposit number FERM BP-2072) in accordance with the Budapest Treaty.

EXAMPLE 7

Production of UK-S1 and pro-UK polypeptides in animal cells:

(1) Production of UK-S1 polypeptide by CHO cells harboring pSE1UKS1-1d:

pSE1UKS1-1d obtained in Example 6 was introduced into dhfr-deficient CHO cells according to the calcium phosphate method. Thus, 5 ml of MEMα (nonselective medium) supplemented with 1/10 volume FCS and 1/50 volume 7.5% $NaHCO_3$ (Flow Laboratories) was inoculated with said cells at an inoculum size of $1 \times 10^5$ cells/ml and, using a LUX dish (6 cm in diameter), cultivation was Conducted in a $CO_2$ incubator at 37° C. for 1 day. Separately, 10 μg of the pSE1UKS1-1d DNA was dissolved in 450 μl of 10 mM Tris-HCl (pH 7.5). To the solution was added 500 μl of 50 mM HEPES (N-2-hydroxyethylpiperazine-N'-2-ethanesulfonic acid) buffer (pH 7.1) containing 280 mM NaCl and 1.5 mM Na followed by further addition of 50 μl of 2.5M $CaCl_2$. The resultant mixture was allowed to stand at room temperature for 5 minutes. The whole amount of this DNA solution was added to dhfr-deficient CHO cells prepared from the above culture by discarding the medium, adding 10 ml of fresh MEMα (nonselective medium) and culturing further for 1 hour. Incubation was then performed for 8 hours. Cells were washed with PBS, 5 ml of MEMα (nonselective medium) was added and cultivation was carried out for 16 hours. Cells were washed with PBS [8 g/liter NaCl, 0.2 g/liter KCl, 1.15 g/liter $Na_2HPO_4$ (anhydrous), 0.2 g/liter $KH_2PO_4$], 3 ml of a solution containing 0.05% trypsin and 0.2% EDTA [ethylenediaminetetraacetic acid) was added and, after discarding the excess solution, incubation was carried out at 37° C. for 5 minutes (trypsin treatment). MEMα (selective medium) supplemented with 10% dialyzed FCS (Gibco-Oriental), 1/50 volume 7.5% $NaHCO_3$, 1/100 volume 100 × nonessential amino acid solution and 0.3 mg/ml G418 (Gibco-Oriental) was added and, after attaining sufficient suspension of cells, cultivation was carried out in a $CO_2$ incubator at 37° C. for 5 days using a dish 10 cm in diameter. Cells were washed with PBS, MEMα (selective medium) was added, and cultivation was continued for 5 days. Following the same procedure, further cultivation was conducted for 5 days. Cells were washed with PBS, then treated with trypsin, suspended in 10 ml of MEMα (selective medium) and cultivated in a $CO_2$ incubator at 37° C. for 3 to 7 days using a dish 6 cm in diameter. Colonies that had appeared were treated with trypsin and inoculated into a dish (10 cm in diameter) using 10 ml of MEMα (selective medium) containing 50 nM MTX to a cell concentration of $5 \times 10^4$ cells/ml. Medium exchange was made three times at 5-day intervals using the medium mentioned above. MTX-resistant colonies that had appeared were monoclonally isolated and respectively cultured until confluence using dishes 6 cm in diameter. After medium substitution with 5 ml of MEMα (selective medium) containing 50 nM MTX, cultivation was conducted for 1 day and each culture fluid was examined for UK-S1 activity by the fibrin plate assay method [Granelli-Piperno and Reich: J. Exp. Med., 148, 233 (1978)]. Clone No. 12 showed the highest activity and the yield of UK-S1 amounted to 5 μg/$10^6$ cells/day. This clone was cultured in a Falcon 3027 roller bottle containing 100 ml of MEMα (selective medium) containing 50 nM MTX. After confluence was attained, cultivation was continued for 3 days using the same medium as the above-mentioned one except that it was FCS-free and contained 10 KIU/ml aprotinin (Boehringer Mannheim). The resultant culture fluid (100 ml) was used in Example 8.

(2) Production of pro-UK polypeptide by animal cells harboring pSE1UKpro1-1A:

Using the recombinant plasmid pSE1UKpro1-1A obtained in Reference Example 13 together with pSV2-dhfr [Subramani et al., Mol. Cell Biol., 1, 854 (1981)] and dhfr-deficient CHO cells and following the procedure mentioned above, pro-UK-producing cell lines were obtained. Among them, clone No. 5 showed the highest activity and the pro-UK production by said clone amounted to 3 μg/$10^6$ cells/day. This clone was cultured in a Falcon 3027 roller bottle containing 100 ml of MEMα (selective medium) containing 50 nM MTX. After confluence was achieved, cultivation was continued for 3 days using the same medium as the above-mentioned one except that it was free of FCS and contained 10 KIU/ml aprotinin (Boehringer Mannheim). This 100-ml culture fluid was used in Example 8.

EXAMPLE 8

Comparison in thrombin sensitivity between natural pro-UK and carbohydrate chain-added modification UK-S1:

(1) Purification of pro-UK and UK-S1 from CHO cell culture fluids:

To the 100-ml serum-free culture fluid obtained in Example 7 and containing natural pro-UK or the carbohydrate chain-added modification UK-S1 was added 5 ml of zinc (Zn) chelate-Sepharose (Pharmacia Fine Chemicals) equilibrated with 50 mM phosphate buffer (pH 7.5) containing 0.05% Tween 80 and 0.05% $NaN_3$ (hereinafter such buffer is referred to as "PBS-TA" for short). The mixture was stirred gently at 4° C. for 1 hour. The mixture was packed into an Econo column (Bio-Rad).

Each column was washed with 10 bed volumes of PBS-TA containing 10 KIU/ml aprotinin and the elution was carried out with PBS-TA containing 10 KIU/ml aprotinin and 50 mM imidazole. Eluate fractions were examined for the presence of urokinase protein by the above-mentioned fibrin plate assay method and urokinase protein-containing fractions were pooled. To the pooled solution was added 5 ml of SP-Sephadex C50 (Pharmacia Fine Chemicals) equilibrated with PBS-TA. The resulting mixture was stirred gently at 4° C. for 1 hour and then pakced into a minicolumn (Seikagaku Kogyo's Sepacol Mini). The column was washed with 10 bed volumes of PBS-TA and then eluted with 3 bed volumes of PBS-TA containing 500 mM NaCl.

Immediately thereafter, 1 ml of benzamidine-Sepharose 6B (Pharmacia Fine Chemicals) equilibrated with PBS-TA was added to the eluate. The mixture was stirred gently at 4° C. for 1 hour and then packed into a minicolumn (Seikagaku Kogyo's Sepacol Mini) and the effluent fraction was collected. This fraction contained natural single-chain pro-UK or single-chain UK-S1.

That UK-S1 contained a new N-glycosylated carbohydrate chain was confirmed by the fact that upon analysis by SDS-polyacrylamide gel electrophoresis, UK-S1 showed a greater molecular weight as compared with natural pro-UK and the fact that treatment of natural pro-UK and UK-S1 with N-glycanase resulted in decreases in molecular weight in both cases, giving products almost equal in molecular weight.

(2) Test of purified natural pro-UK and UK-S1 for thrombin sensitivity:

The solution containing natural pro-UK or UK-S1 as obtained as described above was diluted with PBS-TA containing 300 mM NaCl to adjust the urokinase activity to 1,000 IU/ml as determined by the fibrin plate assay method. To 216 $\mu$l of the dilution was added 36 $\mu$l of 24 $\mu$M human thrombin and the mixture was incubated at 37° C. The human thrombin used was a product of Sigma. The human thrombin was used after addition of 100 IU of aprotinin to 298 IU of thrombin, followed by 1-hour reaction at 37° C. After the lapse of 15, 30, 60 and 120 minutes following thrombin addition, sampling was made (63 $\mu$l per sampling). The reaction was terminated by adding 9 $\mu$l of 24 $\mu$m thrombin inhibitor ("Thromstop"; American Diagnostica). A sample was also prepared by adding the thrombin inhibitor immediately after thrombin addition (this was regarded as a sample after the lapse of 0 (zero) minute following thrombin addition). In a control group, incubation was performed at 37° C. without addition of thrombin.

Then, 22.5 $\mu$l of each sample was subjected to SDS-polyacrylamide gel electrophoresis [Laemmli: Nature, 227, 680 (1970)] and whether the single chain urokinase (or derivative) was converted to the double chain form. As a result, it was found that the proportion of the double chain form was smaller in UK-S1 as compared with natural pro-UK (cf. FIG. 12). This result indicate that UK-S1 is less sensitive to thrombin.

Furthermore, for confirming the above result, S-2444 amidolytic activity measurement was made. Thus, each of the above samples was diluted 5 times with TNT buffer [0.5M Tris-HCl (pH 7.4), 0.38M NaCl, 0.1% Tween 80], 50 $\mu$l of 10 $\mu$m human plasmin was added to 50 $\mu$l of the dilution, and the mixture was incubated at 37° C. for 30 minutes. The human plasmin used was a product of Boehringer Mannheim. Then, 50 $\mu$l of the chromogenic substrate S-2444 (1.2 mM; Kabi Vitrum) was added and, after further 90 minutes of reaction at 37° C., the absorbance at 405 nm was measured and the amidolytic activity was calculated. The results thus obtained are shown in FIG. 13.

Figure 13:
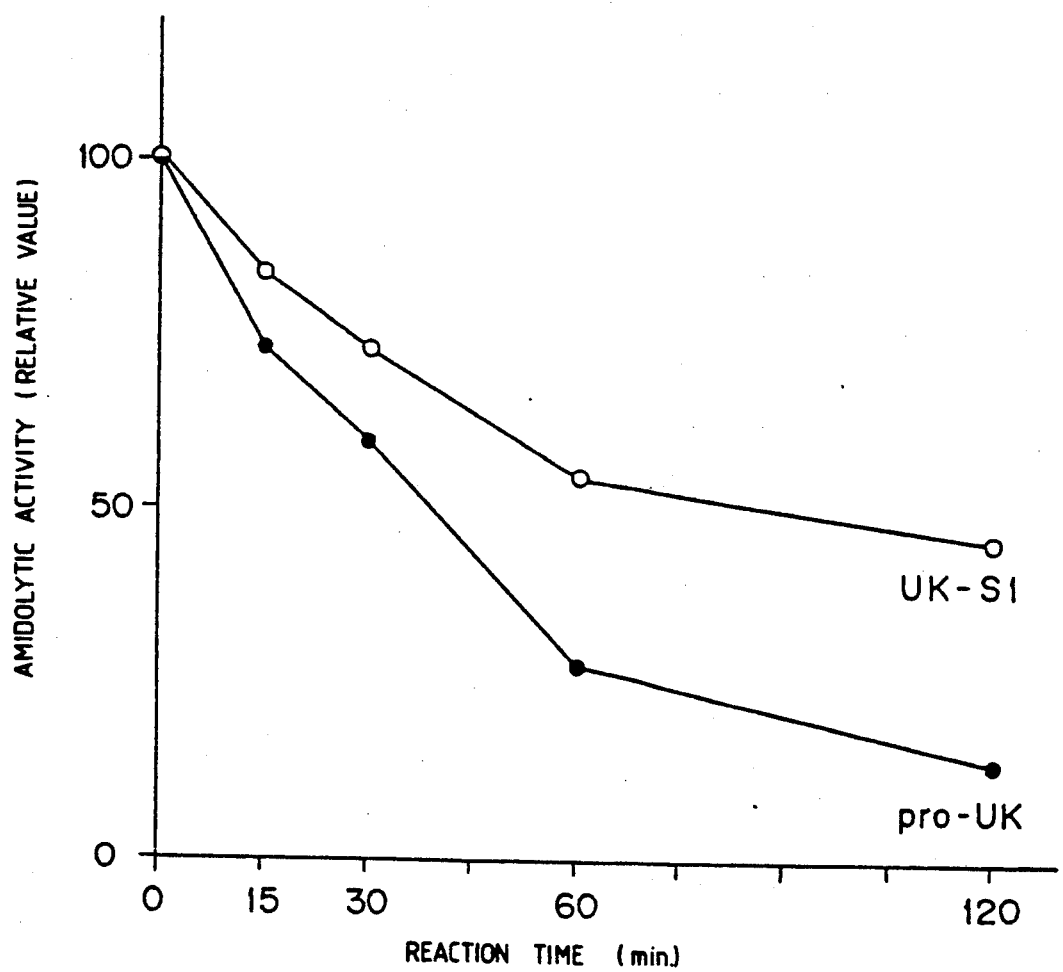
FIG. 13 graphically shows the result of comparison of naturally occurring pro-UK and the UK derivative UK-S1 with respect to thrombin sensitivity as expressed in terms of amidolytic activity.

As shown in FIG. 13, it was found that UK-S1 has lower sensitivity to thrombin as compared with natural pro-UK.

EXAMPLE 9

In vivo evaluation of natural pro-UK and carbohydrate chain-added UK-S1

(1) Constant infusion experiment:

Male beagle dogs (weighing 5.5–11.5 kg) aged 4–6 months were used. The animals were anesthetized with pentobarbital sodium, 39 mg/kg i.v., and underwent artificial respiration with room air. Natural pro-UK or the carbohydrate chain-added UK-S1 obtained in Example 8 was administered by constant infusion for 30 minutes (2,000 U/kg/min) into the femoral vein. Blood was collected from the femoral artery before administration (0 min) and after 15, 30, 45, 60 and 90 minutes after initiation of administration. The blood samples collected were immediately centrifuged and the plasma samples obtained were stored frozen at −20° C. until assayed. Using the plasma samples obtained, three systemic fibrinolytic factors, namely, $\alpha_2$-plasmin inhibitor, plasminogen and fibrinogen, were determined as follows.

One volume of 3.8% citric acid was added to 9 volumes of each whole blood sample, the mixture was centrifuged at 3,000 rpm for 10 minutes and the supernatant was used as a sample for assaying the above three factors. For assaying $\alpha_2$-plasmin inhibitor and plasminogen, PPACK (D-phenylalanyl-L-prolyl-L-arginine chloromethyl ketone, CALBIOCHEM ® Lot No. 86042, Hoechst) was added to the plasma sample to give a final concentration of 12.5 $\mu$M and, for assaying fibrinogen, 250 U/ml of aprotinin (Trasylol ®, Bayer) was added to the plasma sample.

Measurements were performed using an Olympus model AU510 autoanalyzer. The reagents used were ALP Autocolor Sankyo ® (Sankyo) for assaying $\alpha_2$-plasmin inhibitor and plasminogen, and Fibrinogen Reagent ® (International Reagent) for assaying fibrinogen.

Figure 45:
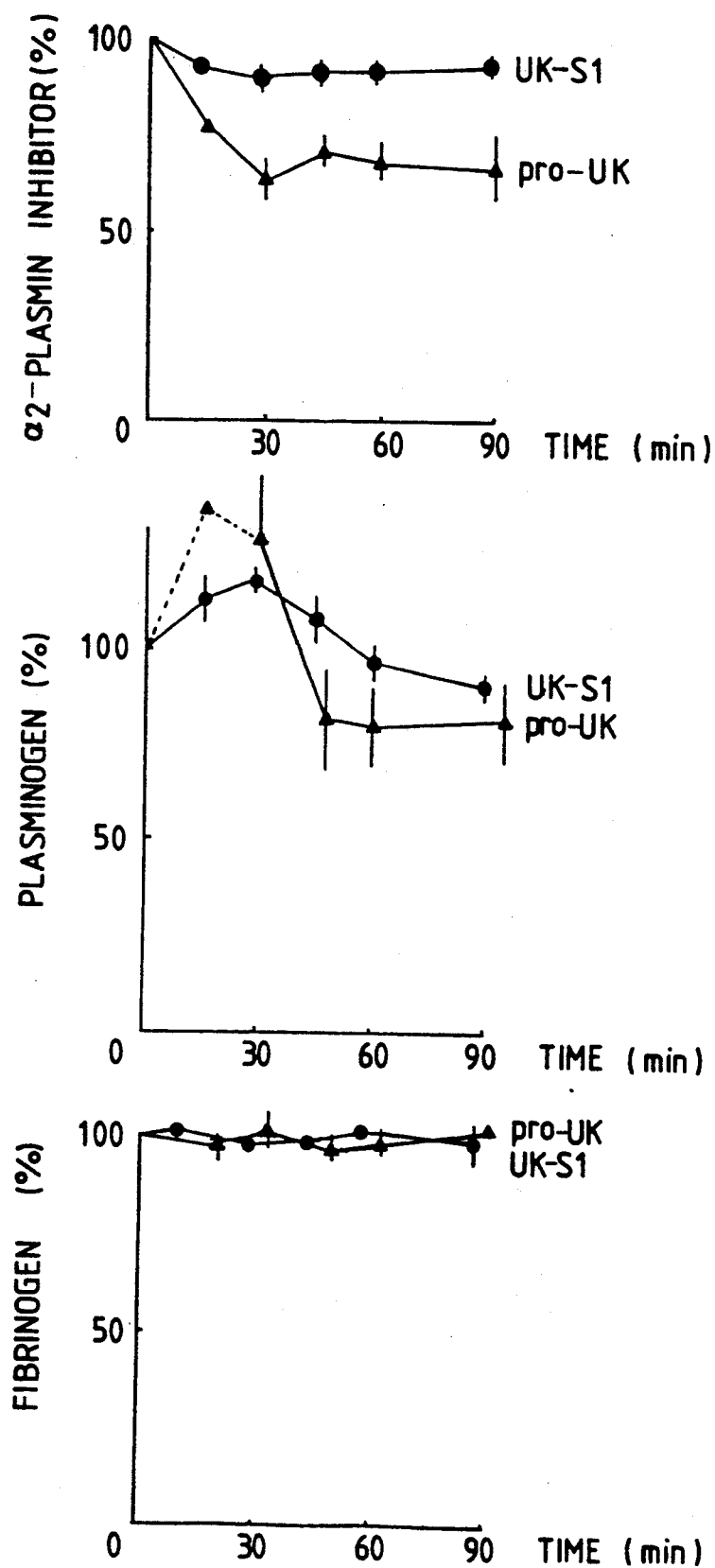
FIG. 45 illustrates the changes with time in whole-body fibrinolytic system factor levels during continuous infusion of natural pro-UK and of the carbohydrate chain-added UK-S1.

It was found that the carbohydrate chain-added UK-S1, like natural pro-UK, scarcely activated systemic fibrinolytic system (cf. FIG. 45). Sandwitch immunoenzyme assay using antibody against urokinase revealed that the plasma elimination half-life of the carbohydrate chain-added UK-S1 was 24.2 minutes, whereas that of natural pro-UK was 12.0 minutes, showing a prolongation of elimination half-life. The area under the plasma concentration-time curve (AUC) for the carbohydrate chain-added UK-S1 was about 3.6 times larger than that for natural pro-UK [cf. Table 8-(A)].

(2) Rapid bolus intravenous injection experiment:

Male and female mongrel dogs (weighing 4.6–13.0 kg) were used. The femoral artery of each dog prepared in the same manner as above was exposed in a length of about 5 cm and electromagnet flowmeter was fixed to the most proximal site. The distal and proximal ends of a portion (about 1 cm) of the artery containing the bifurcation were ligated to make a small portion free of blood flow where thrombus was prepared by infusing 0.2–0.4 ml of 1,000 U/ml of thrombin (Green Cross) from the bifurcation. Thrombus formation and lysis were determined by increase or decrease of blood flow, respectively. The animal was left untreated for at least 1 hour (1–1.5 hours) after thrombus formation to ascertain that spontaneous recanalization did not occur. Natural pro-UK or the carbohydrate chain-added UK-S1 (0.6 mg/kg) was administered by bolus intravenous injection over 3 minutes and blood samples were collected before administration (0 minutes) and 15, 30, 45, 60, 90 and 120 minutes after initiation of administration.

Recanalization was not observed in 2 dogs to which natural pro-UK was administered, while recanalization was observed in all three dogs treated with the carbohydrate chain-added UK-S1.

Figure 46:
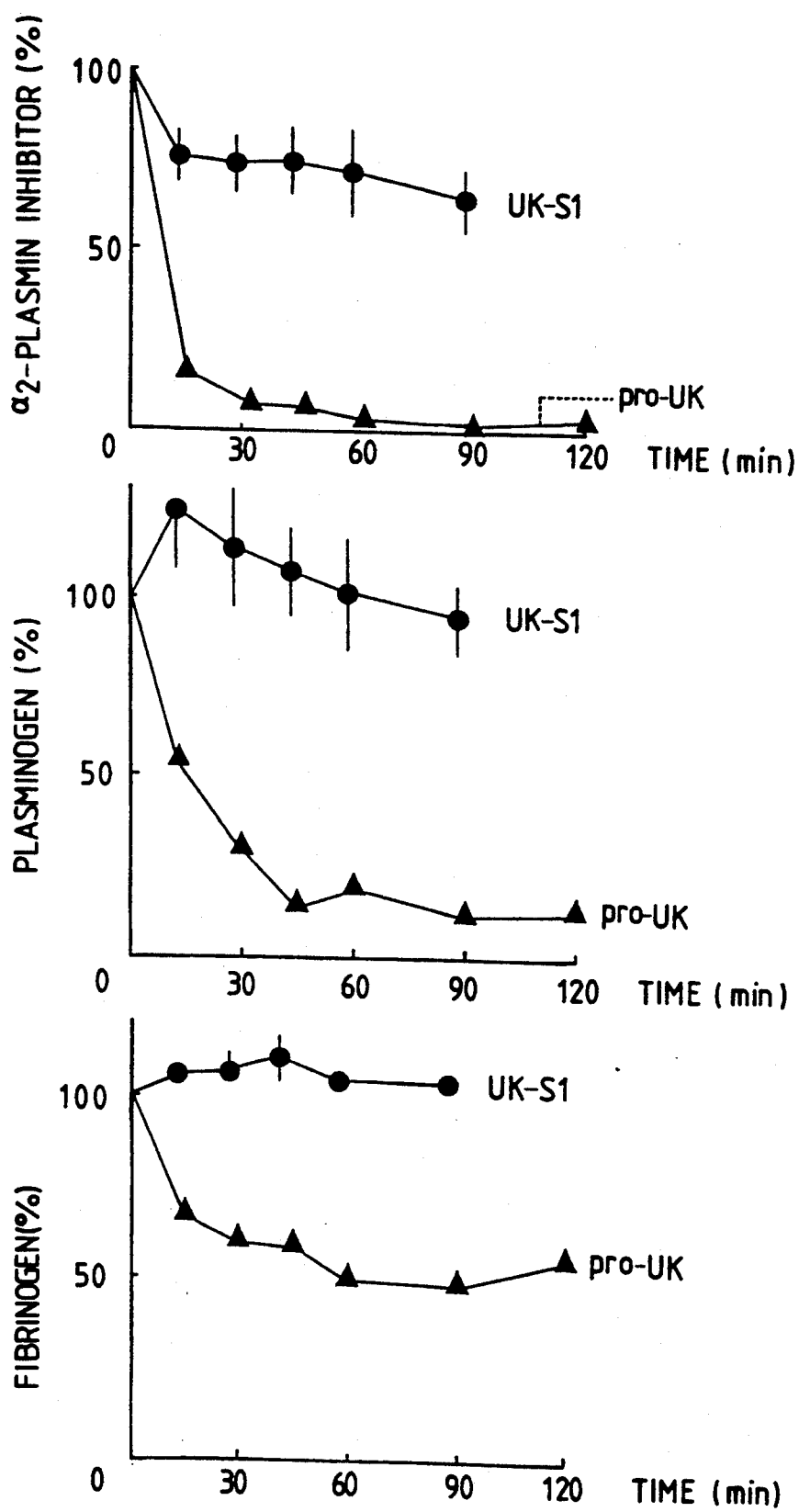
FIG. 46 illustrates the changes with time in whole-body fibrinolytic system factor levels following rapid bolus intravenous administration of natural pro-UK and of the carbohydrate chain-added UK-S1.

With natural pro-UK, systemic fibrinolytic factors tended to be activated, while with the carbohydrate chain-added UK-S1, as in infusion, no activation of systemic fibrinolytic factors was found (cf. FIG. 46).

At the same time, the plasma level of natural pro-UK and that of the carbohydrate chain-added UK-S1 were determined. The elimination half-life of the carbohydrate chain-added UK-S1 was 48.1 minutes, while that of natural pro-UK was 30.3 minutes, showing a prolongation of the elimination half-life of the former. The AUC for UK-S1 was about 5.6 times larger than that for natural pro-UK.

TABLE 8

Blood half-life data for natural pro-UK and carbohydrate chain-added UK-S1

| | T½ (min) | AUC (μg · min/ml) |
|---|---|---|
| (A) Continuous infusion (beagle dogs) | | |
| Pro-UK | 12.0 ± 1.9 | 60.2 ± 13.4 |
| UK-S1 | 24.2 ± 10.0 | 214 ± 57.6 |
| (B) Rapid bolus intravenous injection (mongrel dogs) | | |
| Pro-UK | 30.3 ± 8.9 | 98.8 ± 38.1 |
| UK-S1 | 48.1 ± 2.0 | 555 ± 118 |

EXAMPLE 10

Construction of recombinant plasmid pUKS3 coding for carbohydrate chain-added UK-S3:

In 30 μl of Y-100 buffer was dissolved about 2 μg of the pUKS1 plasmid DNA obtained in Example 6-(2)-(c), 16 units of CfrI and 10 units of HindIII were added to the solution, and digestion was effected at 37° C. for 2 hours. After 10-minute heat treatment at 65° C., a DNA fragment about 0.75 kb in size was purified by the AFT method. Separately, about 2 μg of the phPA2 plasmid DNA obtained in Reference Example 20 was dissolved in 30 μl of Y-100 buffer, 10 units of HindIII and 1 unit of EcoRI were added, and digestion was carried out at 37° C. for 2 hours. After 10-minute heat treatment at 65° C., a DNA fragment about 3.4 kb in size was purified by the AFT method. The following two synthetic DNAs (43-mer and 43-mer) were synthesized and phosphorylated at the 5' ends as described in Example 1:

5'-GGCCAA AAG ACT ATT CGA ACG CGT
ITT AAG ATT AIT GGG GGA G-3'

3'-TT TTC TGA TAA GCT TGC GCA AAA
TTC TAA TAA CCC CCT CTTAA-5'

Figure 47:
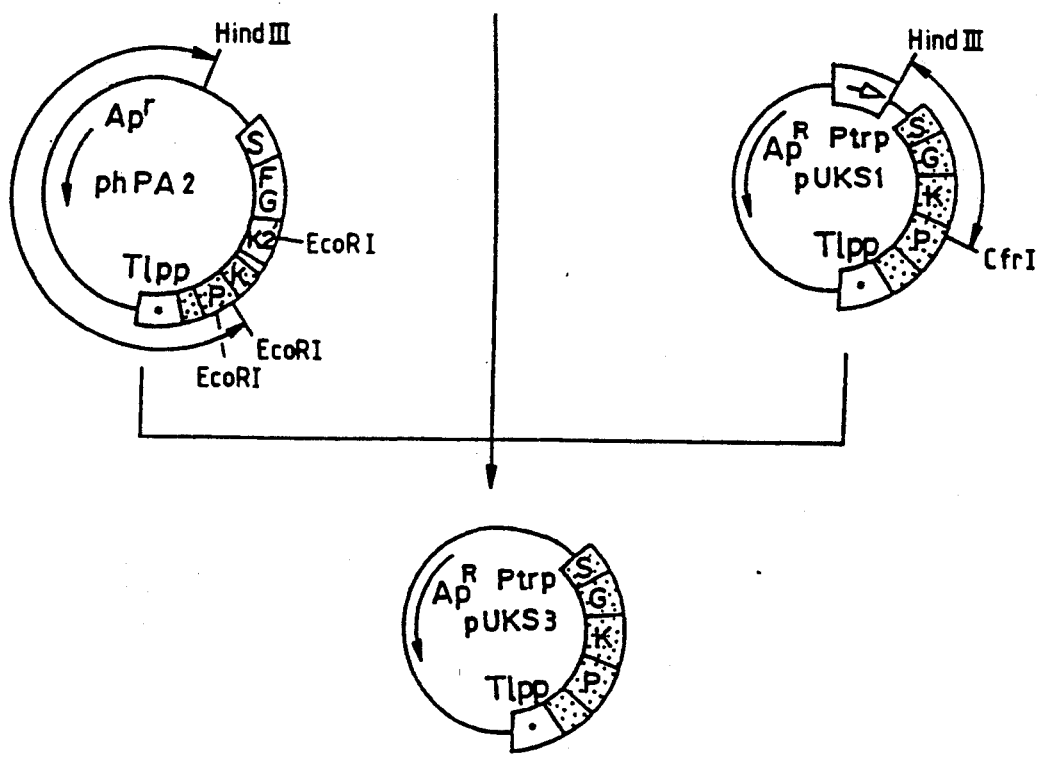
FIG. 47 shows the construction scheme for the plasmid pUKS3.

The thus-prepared pUKS1-derived DNA fragment (about 0.75 kb; about 0.1 μg), phPA2-derived DNA fragment (about 3.4 kb; about 0.1 μg) and two 5'-phosphorylated synthetic DNAs (1 picomole each) were dissolved in a total of 20 μl of T4 ligase buffer, 300 units of T4 ligase was added, and ligation was carried out at 4° C. for 18 hours. The recombinant plasmid mixture thus obtained was used to transform Escherichia coli MM294 to give Ap-resistant transformant strains. The plasmid DNA was isolated from each transformant and subjected to structural analysis by restriction enzyme digestion and to base sequence determination by the M13 dideoxy sequencing method. A plasmid DNA having the desired structure and including the base substitutions of the 153th Leu with Asn and the 155th Pro with Thr was named pUKS3 (cf. FIG. 47). The amino acid sequence of UK-S3 obtained herein is shown in Table 7.

TABLE 7

```
    10         20         30         40         50         60         70
AGCAATGAACTTCATCAAGTTCCATCGAACTGTGACTGTCTAAATGGAGGAACATGTGTGTCCAACAAGTACTTC
Ser Asn Glu Leu His Gln Val Pro Ser Asn Cys Asp Cys Leu Asn Gly Gly Thr Cys Val Ser Asn Lys Tyr Phe 85         95        105        115        125        135        145
TCCAACATTCACTGGTGCAACTGCCCAAAGAAATTCGGAGGGCAGCACTGTGAAATAGATAAGTCAAAAACCTGC
Ser Asn Ile His Trp Cys Asn Cys Pro Lys Lys Phe Gly Gly Gln His Cys Glu Ile Asp Lys Ser Lys Thr Cys 160        170        180        190        200        210        220
TATGAGGGGAATGGTCACTTTTTACCGAGGAAAGGCCAGCACTGACACCATGGGCCGGCCCTGCCTGCCCTGGAAC
Tyr Glu Gly Asn Gly His Phe Tyr Arg Gly Lys Ala Ser Thr Asp Thr Met Gly Arg Pro Cys Leu Pro Trp Asn 235        245        255        265        275        285        295
TCTGCCACTGTCCTTCAGCAAACGTACCATGCCCACAGATCTGATGCTCTTCAGCTGGGCCTGGGGAAACATAAT
Ser Ala Thr Val Leu Gln Gln Thr Tyr His Ala His Arg Ser Asp Ala Leu Gln Leu Gly Leu Gly Lys His Asn 310        320        330        340        350        360        370
TACTGCAGGAACCCAGACAACCGGAGGCGACCCTGGTGCTATGTGCAGGTGGGCCTAAAGCCGCTTGTCCAAGAG
Tyr Cys Arg Asn Pro Asp Asn Arg Arg Pro Trp Cys Tyr Val Gln Val Gly Leu Lys Pro Leu Val Gln Glu 385        395        405        415        425        435        445
TGCATGGTGCATGACTGCGCAGATGGAAAAAAGCCCTCCTCTCCTCCAGAAGAATTAAAATTTCAGTGTGGCCAA
Cys Met Val His Asp Cys Ala Asp Gly Lys Lys Pro Ser Ser Pro Pro Glu Glu Leu Lys Phe Gln Cys Gly Gln 460        470        480        490        500        510        520
AAGACTAATCGAACGCGTTTTAAGATTATTGGGGGAGAATTCACCACCATCGAGAACCAGCCCTGGTTTGCGGCC
Lys Thr Asn Arg Thr Arg Phe Lys Ile Ile Gly Gly Glu Phe Thr Thr Ile Glu Asn Gln Pro Trp Phe Ala Ala 535        545        555        565        575        585        595
ATCTACAGGAGGCACCGGGGGGGCTCTGTCACCTACGTGTGTGGAGGCAGCCTCATCAGCCCTTGCTGGGTGATC
Ile Tyr Arg Arg His Arg Gly Gly Ser Val Thr Tyr Val Cys Gly Gly Ser Leu Ile Ser Pro Cys Trp Val ILe 610        620        630        640        650        660        670
AGCGCCACACACTGCTTCATTGATTACCCAAAGAAGGAGGACTACATCGTCTACCTGGGTCGCTCAAGGCTTAAC
Ser Ala Thr His Cys Phe Ile Asp Tyr Pro Lys Lys Glu Asp Tyr Ile Val Tyr Leu Gly Arg Ser Arg Leu Asn 685        695        705        715        725        735        745
TCCAACACGCAAGGGGAGATGAAGTTTGAGGTGGAAAACCTCATCCTACACAAGGACTACAGCGCTGACACGCTT
Ser Asn Thr Gln Gly Glu Met Lys Phe Glu Val Glu Asn Leu Ile Leu His Lys Asp Tyr Ser Ala Asp Thr Leu 760        770        780        790        800        810        820
GCTCACCACAATGACATTGCCTTGCTGAAGATCCGTTCCAAGGAGGGCAGGTGTGCGCAGCCATCCCGGACTATA
Ala His His Asn Asp Ile Ala Leu Leu Lys Ile Arg Ser Lys Glu Gly Arg Cys Ala Gln Pro Ser Arg Thr Ile
```

TABLE 7-continued

```
           835         845         855         865         875         885         895
CAGACCATCTGCCTGCCCTCGATGTATAACGATCCCCAGTTTGGCACAAGCTGTGAGATCACTGGCTTTGGGAAAA
Gln Thr Ile Cys Leu Pro Ser Met Tyr Asn Asp Pro Gln Phe Gly Thr Ser Cys Glu Ile Thr Gly Phe Gly Lys 910         920         930         940         950         960         970
GAGAATTCTACCGACTATCTCTATCCGGAGCAGCTGAAATGACTGTTGTGAAGCTGATTTCCCACCGGGAGTGT
Glu Asn Ser Thr Asp Tyr Leu Tyr Pro Glu Gln Leu Lys MetThr Val Val Lys Leu Ile Ser His Arg Glu Cys 985         995        1005        1015        1025        1035        1045
CAGCAGCCCCACTACTACGGCTCTGAAGTCACCACCAAAATGCTGTGTGCTGCTGACCCACAGTGGAAAACAGAT
Gln Gln Pro His Tyr Tyr Gly Ser Glu Val Thr Thr Lys Met Leu Cys ALAAla Asp Pro Gln Trp Lys Thr Asp 1060       1070       1080       1090       1100       1110       1120
TCCTGCCAGGGAGACTCAGGGGGACCCCTCGTCTGTTCCCTCCAAGGCCGCATGACTTTGACTGGAATTGTGAGC
Ser Cys Gln Gly Asp Ser Gly Gly Pro Leu Val Cys Ser Leu Gln Gly Arg Met Thr Leu Thr Gly Ile Val Ser 1135       1145       1155       1165       1175       1185       1195
TGGGGCCGTGGATGTGCCCTGAAGGACAAGCCAGGCGTCTACACGAGAGTCTCACACTTCTTACCCTGGATCCGC
Trp Gly Arg Gly Cys Ala Leu Lys Asp Lys Pro Gly Val Tyr Thr Arg Val Ser His Phe Leu Pro Trp Ile Arg 1210       1220       1230
AGTCACACCAAAGGAAGAGAATGGCCTGGCCCTCTGA
Ser His Thr Lys  Glu Glu Asn Gly Leu Ala Leu ***
```

EXAMPLE 11

Construction of UK-S3 expression plasmid pSEUKS3:

About 2 μg of the pSE1PA1SE1dhfr1-9A plasmid DNA obtained in Reference Example 9 was dissolved in 30 μl of Y-0 buffer, 10 units of KpnI was added, and digestion was carried out at 37° C. for 2 hours. Then, 1.5 μl of 2M NaCl and 10 units of XhoI were added, and digestion was further performed at 37° C. for 1 hour. After 10-minute heat treatment at 65° C., a DNA fragment about 8.6 kb in size was purified by the AFT method. Separately, about 3 μg of the pSE1UKpro1-1A plasmid DNA was dissolved in 30 μl of Y-100 buffer, 12 units of BglII and 12 units of XhoI were added, and digestion was carried out at 37° C. for 2 hours. After 10-minute heat treatment at 65° C., a DNA fragment about 0.75 kb in size was purified by the AFT method. Further, separately, about 3 μg of the pUKS3 plasmid DNA obtained in Example 10 was dissolved in 30 μl of Y-0 buffer, 15 units of KpnI was added, and digestion was carried out at 37° C. for 2 hours. Then, 1.5 μl of 2M NaCl and 12 units of BglII were added, and digestion was further carried out at 37° C. for 1 hour. After 10-minute heat treatment at 65° C., a DNA fragment about 1.15 kb in size was purified by the AFT method.

The thus-obtained pSE1PA1SE1dhfr1-9A-derived DNA fragment (about 8.6 kb; about 0.1 μg), pSE1UKpro1-1A derived DNA fragment (about 0.75 kb; about 0.02 μg) and pUKS3-derived DNA fragment (about 1.15 kb; about 0.02 μg) were dissolved in a total of 20 μl of T4 ligase buffer, 100 units of T4 DNA ligase was added, and ligation was carried out at 4° C. for 18 hours.

Figure 48:
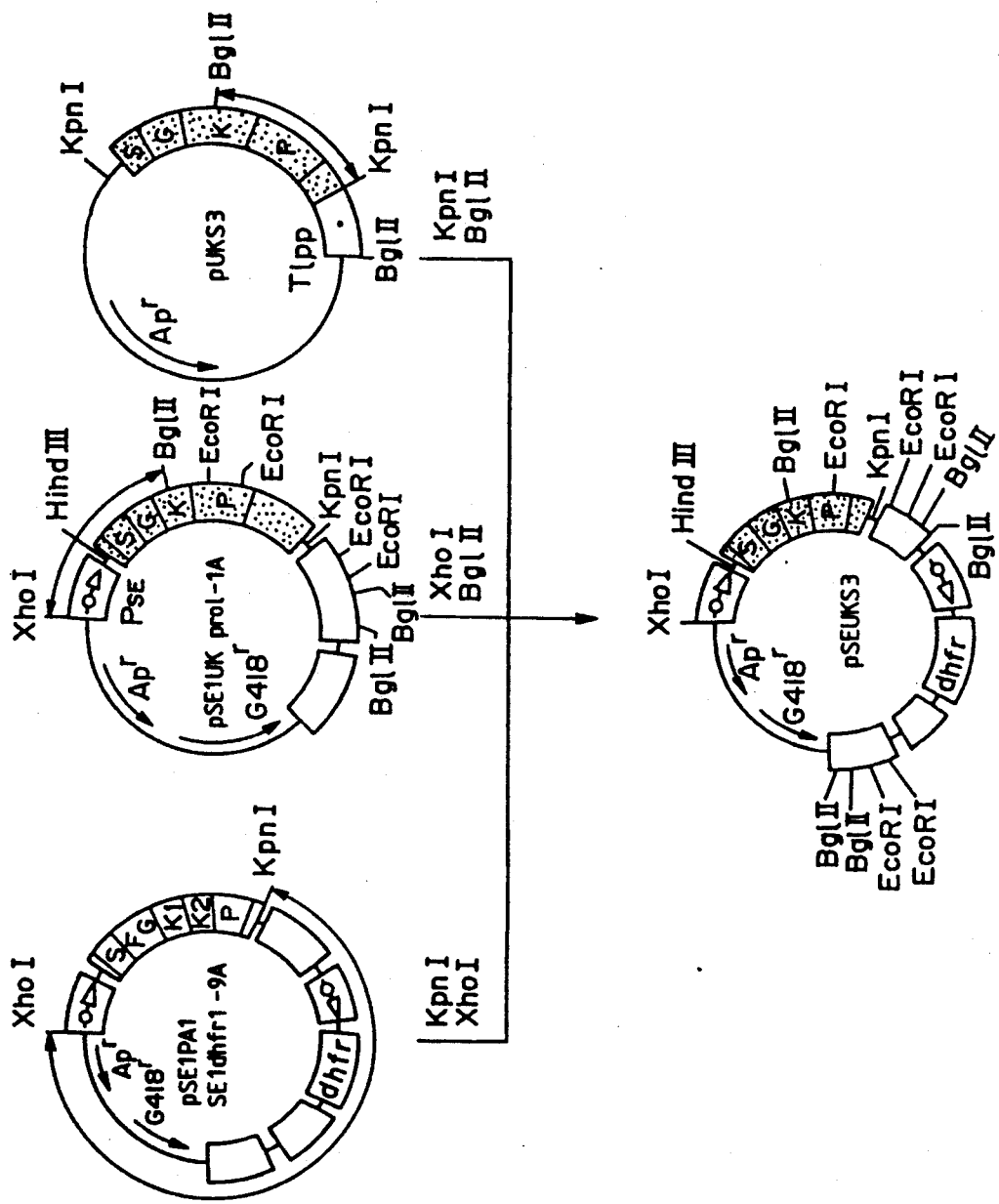
FIG. 48 shows the construction scheme for the plasmid pSEUKS3.

The recombinant plasmid mixture thus obtained was used to transform *Escherichia coli* MM294 to give Ap-resistant transformants. Upon structural analysis by restriction enzyme digestion, the plasmid DNA pSEUKS3 isolated from one of the transformants was found to have the desired structure (cf. FIG. 48).

An *Escherichia coli* strain harboring the plasmid pSEUKS3 has been deposited, since Jun. 15, 1989, with the Fermentation Research Institute under the designation *Escherichia coli* ESEUKS3 and deposit number FERM BP-2478 under the Budapest Treaty.

EXAMPLE 12

Production of UK-S3 polypeptide by animal cells carrying pSEUKS3

UK-S3-producing cell lines were obtained using the recombinant plasmid pSEUKS3 obtained in Example 11 and dhfr-deficient CHO cells and following the procedure mentioned above. Among them, clone No. 13 had the highest activity and produced UK-S3 at a rate of 3 μg/106 cells/day. This clone was cultured in a Falcon 3027 roller bottle containing 100 ml of MEMα (selective medium) containing 50 nM MTX. After confluence was achieved, cultivation was continued for 3 days using the same medium as the above-mentioned one except that it was free of FCS but contained 10 KIU/ml aprotinin (Boehringer Mannheim) to thereby obtain 100-ml culture fluid.

EXAMPLE 13

Figure 49:
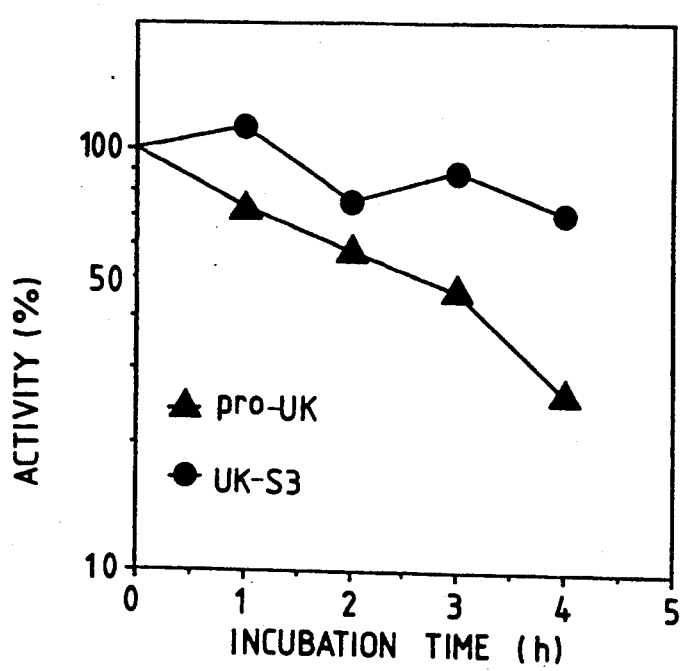
FIG. 49 graphically illustrates the time courses of thermal deactivation at 70° C. of natural pro-UK and the carbohydrate chain-added modification UK-S3.

Heat stability testing of carbohydrate chain-added UK-S3:

The carbohydrate chain-added UK-S3 was purified from the CHO cell culture fluid in the same manner as in Example 8-(1). The purified natural pro-UK and carbohydrate chain-added UK-S3 were each dissolved in 50 mM phosphate buffer (pH 7.5) containing 200 mM arginine, 100 mM NaCl, 0.01% Tween 80 and 0.05% sodium azide to give a concentration of 10 μg/ml and each solution was incubated at 70° C. Samples were collected before incubation and 1, 2, 3 and 4 hours. after initiation of incubation, cooled on ice and immediately assayed for residual activity by the fibrin plate method (cf. FIG. 49).

It was found that the carbohydrate chain-added UK-S3 was more stable against heat than natural pro-UK.

REFERENCE EXAMPLE 1

Construction of plasmid ptPA7 carrying human t-PA cDNA:

(1) Preparation of poly(A) RNA from Detroit 562 cells:

A poly(A)-containing RNA was prepared from the human laryngeal cancer cell line Detroit 562 by the guanidine thiocyanate-lithium chloride method [Cathala et al.: DNA, 2, 329 (1983)].

Thus, human laryngeal cancer Detroit 562 cells [Peterson, W. D., Jr. et al.: Proc. Soc. Exp. Biol. Med., 136, 1187 (1971)] were grown in 50 ml of MEM medium (Nissui Pharmaceutical) containing 10% fetal bovine serum, 1/100 volume of 100×nonessential amino acid solution (Flow Laboratories), 1 mM sodium pyruvate and 0.1% lactoalbumin hydrolyzate (Gibco-Oriental) in each of six tissue culture flasks (Corning; 150 cm$^2$). After incubation at 37° C. until confluency, cells were washed with PBS, then phorbol myristate acetate (PMA) was added in a concentration of 100 ng/ml, 30 ml of the same medium as mentioned above except that it was free from fetal bovine serum was added, and incubation was continued at 37° C. for 24 hours. Cells were then treated with 10 ml of a solution containing 0.05% trypsin and 0.02% EDTA to give a cell suspension. A total of $1\times10^8$ cells were obtained from the six tissue culture flasks. The cells were harvested from the cell suspension by centrifugation (1,100×g, 4° C., 10 minutes), washed with 80 ml of phosphate buffer, and solubilized in 10 ml of a solution containing 5M guanidine thiocyanate, 10 mM EDTA, 50 mM Tris-HCl (pH 7) and 8% (v/v) 2-mercaptoethanol by using a vortex mixer. This solubilization product was transferred to a centrifuge tube, 80 ml of 4M LiCl was added and, after stirring, the mixture was allowed to stand at 4° C. for 20 hours. The mixture was centrifuged at 9,000 rpm for 90 minutes using a Hitachi RPR 10 rotor and RNA was recovered as a precipitate. The RNA precipitate was suspended in 50 ml of a solution containing 4M urea and 2M lithium chloride, the suspension was centrifuged at 9,000 rpm for 60 minutes by means of a Hitachi RPR 10 rotor and RNA was again recovered as a precipitate. The RNA precipitate was dissolved in 10 ml of a solution containing 0.1% sodium lauryl sulfate, 1 mM EDTA and 10 mM Tris-HCl (pH 7.5) and, after phenol-chloroform extraction, RNA was recovered by ethanol precipitation. The RNA obtained (about 2.5 mg) was dissolved in 1 ml of a solution containing 10 mM Tris-HCl (pH 8.0) and 1 mM EDTA. The solution was incubated at 65° C. for 5 minutes and 0.1 ml of 5M NaCl was then added. The mixture was subjected to oligo(dT)-cellulose column (P-L Biochemicals) chromatography (column volume 0.5 ml). Poly(A)-containing mRNA adsorbed was eluted with a solution containing 10 mM Tris-HCl (pH 7.5) and 1 mM EDTA to give about 90 μg of poly(A)-containing mRNA.

(2) cDNA synthesis and insertion of said DNA into vector:

A cDNA was synthesized and a recombinant plasmid with the same inserted therein was constructed by the Okayama-Berg method [Mol. Cell. Biol., 2, 161 (1982)]. This process is outlined in FIG. 14.

Thus, 400 μg of pCDV1 [Okayama & Berg: Mol. Cell. Biol., 3, 280 (1983)] was added to 300 μl of a solution containing 10 mM Tris-HCl (pH 7.5), 6 mM MgCl$_2$ and 10 mM NaCl and, after further addition of 500 units of KpnI, the plasmid was cleaved at its KpnI site by 6 hours of reaction at 37° C. After phenol-chloroform extraction, DNA was recovered by ethanol precipitation. About 200 μg of the KpnI-cleaved DNA was added to 200 μl of a solution prepared by adding dTTP in a concentration of 0.25 mM to a buffer (hereinafter, TdT buffer) containing 40 mM sodium cacodylate, 30 mM Tris-HCl (pH 6.8), 1 mM CaCl$_2$ and 0.1 mM dithiothreitol (hereinafter, DTT). After further addition of 81 units of terminal deoxynucleotidyl transferase (hereinafter, TdT) (P-L Biochemicals), the mixture was incubated at 37° C. for 11 minutes, whereby an approximately 67-mer poly(dT) chain was added to the KpnI cleavage site 3' terminus of pCDV1. Ethanol precipitation from the solution following phenol-chloroform extraction gave about 100 μg of poly(dT) chain-added pCDV1 DNA. This DNA was added to 150 μl of 10 mM Tris-HCl (pH 7.5) containing 6 mM MgCl$_2$ and 100 mM NaCl and, after further addition of 360 units of EcoRI, the mixture was incubated at 37° C. for 2 hours. After treatment of the reaction mixture by the LGT method, a DNA fragment, 3.1 kb in length, was recovered. Thus was obtained about 60 μg of poly(dT) chain-added pCDV1. This DNA was dissolved in 500 μl of 10 mM Tris-HCl (pH 8.0) containing 1 mM EDTA, the solution was incubated at 65° C. for 5 minutes and then cooled with ice, and 50 μl of 5M NaCl was added. The mixture was subjected to oligo(dA)-cellulose column (Collaborative Research) chromatography. Fragments sufficient in (dT) chain length were adsorbed on the column. They were eluted with 10 mM Tris-HCl (pH 8.0) containing 1 mM EDTA to give 27 μg of poly(dT) chain-added pCDV1 (hereinafter briefly referred to as "vector primer").

Then, a linker DNA was prepared.

About 14 μg of pL1 [Okayama & Berg: Mol. Cell. Biol., 3, 280 (1983)] was added to 200 μl of 10 mM Tris-HCl buffer (pH 7.5) containing 6 mM MgCl$_2$ and 50 mM NaCl and, after further addition of 50 units of PstI, the mixture was incubated at 37° C. for 4 hours for cleavage of the pL1 DNA at its PstI site. After phenol-chloroform extraction of the reaction mixture, about 13 μg of PstI-cleaved pL1 DNA was recovered by ethanol precipitation. This DNA (about 13 μg) was added to 50 μl of TdT buffer containing dGTP in a final concentration of 0.25 mM and, after further addition of 54 units of TdT (P-L Biochemicals), the mixture was incubated at 37° C. for 13 minutes, whereby an oligo(dG) chain (about 14-mer) was added to pL1 at its PstI cleavage site 3' terminus. Following phenol-chloroform extraction, DNA was recovered by ethanol precipitation. This DNA was added to 100 μl of 10 mM Tris-HCl buffer (pH 7.5) containing 6 mM MgCl$_2$ and 60 mM NaCl and, after further addition of 80 units of HindIII, the mixture was incubated at 37° C. for 3 hours for cleavage of the Pl1 DNA at the HindIII site. The reaction mixture was fractionated by agarose gel electrophoresis and a DNA fragment of about 0.5 kb was recovered by the DEAE paper method [Dretzen et al.: Anal. Biochem., 112, 295 (1981)]. Thus was obtained an oligo(dG) chain-added linker DNA (hereinafter briefly referred to as "linker DNA").

About 4 μg of the poly(A) RNA and about 1.4 μg of the vector primer, each prepared as mentioned above, were dissolved in 22.3 μl of a solution containing 50 mM Tris-HCl (pH 8.3), 8 mM MgCl$_2$, 30 mM KCl, 0.3 mM DTT, 2 mM each dNTP (dATP, dTTP, dGTP and dCTP) and 10 units of ribonuclease inhibitor (P-L Biochemicals) and, after addition of 10 units of reverse transcriptase (Seikagaku Kogyo), the mixture was incubated at 41° C. for 90 minutes for synthesis of a DNA complementary to the mRNA. The reaction mixture was subjected to phenol-chloroform extraction and then to ethanol precipitation, whereby the vector primer DNA with an RNA-DNA double strand added thereto was recovered. This DNA was dissolved in 20 μl of TdT buffer containing 66 μM dCTP and 0.2 μg of poly(A) and, after addition of 14 units of TdT P-L Biochemicals), the mixture was incubated at 37° C. for 2 minutes for addition of an oligo(dC) chain (20-mer) to the cDNA 3' terminus. The reaction mixture was subjected to phenol-chloroform extraction and then to ethanol precipitation, whereby the cDNA-vector primer DNA with the (dC) chain added was recovered. This DNA was dissolved in 400 μl of 10 mM Tris-HCl (pH 7.5) containing 6 mM MgCl$_2$ and 60 mM NaCl, 20 units of HindIII was added, and the mixture was incubated at 37° C. for 2 hours for cleavage at the HindIII site. The reaction mixture was subjecred to phenol-chloroform extraction and then to ethanol precipitation, whereby 0.5 picomole of a (dC) chain-added cDNA-vector primer DNA was obtained. A 0.2 picomole portion of this DNA and 0.4 picomole of the above-mentioned linker DNA were dissolved in 100 μl of 10 mM Tris-HCl (pH 7.5) containing 0.1M NaCl and 1 mM EDTA and the solution was incubated at 65° C. for 10 minutes, then at 42° C. for 25 minutes and further at 0° C. for 30 minutes. The solution was made up to 1,000 μl so that the resultant solution contained 20 mM Tris-HCl (pH 7.5), 4 mM MgCl$_2$, 10 mM (NH 0.1M KCl and 0.1 mM β-NAD. To the solution was added 25 units of *Escherichia coli* DNA ligase (New England BioLabs). The mixture was incubated at 11° C. for 18 hours. After addition of each dNTP (40 μM) and β-NAD (to a final concentration of 0.15 mM), followed by addition of 10 units of *Escherichia coli* DNA ligase, 20 units of *Escherichia coli* DNA polymerase I (P-L Biochemicals) and 10 units of *Escherichia coli* ribonuclease H (P-L Biochemicals), the resultant solution was incubated at 12° C. for 1 hour and then at 25° C. for 1 hour. The above reaction procedure caused cyclization of the cDNA-containing DNA and substitution of DNA for the RNA portion of the RNA-DNA double strand, giving a recombinant plasmid having a completely double-stranded DNA structure.

(3) Selection of human t-PA cDNA-containing recombinant DNA:

Then, colony hybridization was performed and the t-PA cDNA was selected as a clone capable of associating with a $^{32}$P-labeled synthetic DNA identical in base sequence with the base sequence of a part of the t-PA signal peptide region of human t-PA cDNA [Pennica et al.: Nature, 301, 214 (1983)], namely $^{32}$P-labeled 5'-ATGGATGCAAT-GAAGAGAGGGCTCTGCTGT-3', which was used as a probe, in the following manner.

First, the recombinant plasmid obtained in (2) was used to tranform *Escherichia coli* C600 SF8 [Cameron: Proc. Natl. Acad, Sci. USA, 72, 3416 (1975)] by the method of Hanahan [J. Mol. Biol., 166, 557 (1983)]. About 10,000 colonies obtained were immobilized on nitrocellulose filters by the method of Hanahan and Meselson [Methods in Enzymology, 100, 333 (1983)]. Prehybridization on each filter was performed in a solution containing 6×NET [1×NET=150 mM NaCl, 15 mM Tris-HCl (pH 7.5), 1 mM EDTA], 10×Denhardt solution and 100 μg/ml of fragmented *Escherichia coli* chromosome DNA at 65° C. for 4 hours or longer. The above-mentioned $^{32}$P-labeled probe was added to this prehybridization solution and allowed to associate with DNA on the filter (65° C., 16 hours or longer). Then, the filter was washed twice with 6×SSC (1×SSC =150 mM NaCl, 15 mM sodium citrate) (room temperature, 5 minutes/washing), then washed with a solution containing 2×SSC and 0.1% SDS at 65° C. for 30 minutes, further washed with a solution containing 2×SSC and 0.1% SDS at 65° C. for 15 minutes and, finally, washed twice with 6×SSC at room temperature (5 minutes/washing). The filter was air-dried and then subjected to autoradiography for positive clone identification. The base sequence of the cDNA of a plasmid, ptPA7, carried by one positive clone thus identified was determined by the dideoxy sequencing method using M13 phage and found to code for t-PA in complete agreement with the amino acid sequence of t-PA as reported by Pennica et al. [Nature, 301, 214 (1983)] except for the substitution of GAT and ACC for the codon (GAC) for the 95th amino acid (asparagine) and the codon (ACA) for the 512th amino acid (threonine), respectively, in mature t-PA.

This bacterial strain has been deposited with the Fermentation Research Institute as *Escherichia coli* EtPA7 under the deposit number FERM BP-1467 in accordance with the Budapest Treaty.

REFERENCE EXAMPLE 2

Construction of human pro-UK cDNA-containing plasmid pUK1:

The Detroit 562 cell cDNA library built up in Reference Example 1 was screened by the colony hybridization method and a human pro-UK cDNA clone was isolated. Thus, the recombinant plasmid obtained in Reference Example 1 was used to transform *Escherichia coli* C600 SF8 [Cameron: Proc. Natl. Acad. Sci. USA, 72, 3416 (1975)] by the method of Hanahan [J. Mol. Biol., 166, 557 (1983)]. About 30,000 colonies obtained were immobilized on nitrocellulose filters by the method of Hanahan and Meselson [Methods in Enzymology, 100, 333 (1983)]. Prehybridization on each filter was performed in a solution containing 6×NET, 10×Denhardt solution and 100 μg/ml of fragmented *Escherichia coli* chromosome DNA at 65° C. for 4 hours or longer.

Then, a $^{32}$P-labeled probe derived from a 41-base synthetic DNA identical in base sequence with a portion of the kringle region of human pro-UK cDNA [Holmes et al.: Bio/Technology, 3, 923 (1985)], namely 5'-GGGAATGGTCACTTTTACCGAGGAAAGG-CCAGCACTGACAC-3' (corresponding to the underlined base sequence shown in FIG. 5 for the human pro-UK cDNA isolated by the present inventors), was added to the above-mentioned prehybridization solution and allowed to associate with DNA on the filter (65° C., 16 hours or longer). Then, the filter was washed twice with 6×SSC (room temperature, 5 minutes/washing), then washed with a solution containing 1×SSC and 0.1% SDS at 57° C. for 30 minutes, further washed with a solution containing 1×SSC and 0.1% SDS at 57° C. for 15 minutes and, finally, washed twice with 6×SSC (room temperature, 5 minutes/washing). The filter was air-dried and then subjected to autoradiography for positive clone identification. The base sequence of the cDNA of a plasmid, pUK1, carried by one positive clone thus identified was determined by the dideoxy sequencing method using M13 phage (Table 5). As a result, it was found that the cDNA of pUK1 codes for that part of the pro-UK translation region which is downstream from the 41st (according to the numbering of amino acid residues of pro-UK as shown in Table 5) amino acid (Cys) residue of Pro-UK, together with the 3'-nontranslation region. The amino acid sequence of pro-UK encoded by the cDNA of pUK1 was in agreement with that reported by Holmes et al. [Bio/Technology, 3, 923 (1985)] except for the third base of each of the codons for the following four amino acids:
254th amino acid Asn: AAC→AAT;
340th amino acid Leu: CTA→CTG;
345th amino acid Pro: CCC→CCA; and
346th amino acid Gln: CAA→CAG.

This bacterial strain has been deposited with the Fermentation Research Institute as *Escherichia coli* EUK1 under the deposit number FERM BP-1463.

REFERENCE EXAMPLE 3

Construction of human pro-UK cDNA-containing plasmid pUK11:

Since the pro-UK cDNA encoded by the plasmid pUK1 obtained in Reference Example 2 does not contain the pro-UK signal region and growth factor domain region, a cDNA containing these regions was cloned following the procedure shown below.

First, a vector, pCCK2, for use in cloning the cDNA was constructed in the following manner.

(1) Construction of recombinant plasmid pCCK1:

The *Escherichia coli* HB101 strain harboring the plasmid pRC19, containing a rat brain cholecystokinin (CCK) precursor cDNA, constructed by Kuwano et al. [J. Biochem., 96, 923-926 (1984)] was grown and the pRC19 DNA was prepared from cultured cells by the conventional method. About 3 μg of the pRC19 DNA obtained was dissolved in 30 μl of Y-50 buffer, 1 unit of PvuII was added, and digestion was conducted at 37° C. for 1 hour. This digestion reaction resulted in partial digestion of the DNA with PvuII. After 10-minute heat treatment at 65° C., a DNA fragment about 530 bp in size was purified by the AFT method. Separately, about 1 μg of the plasmid DNA pUC19 constructed by Norrander et al. [Norrander, J. et al.: Gene, 26, 101 (1983); the pUC19 plasmid DNA is available from Takara Shuzo] was dissolved in 30 μl of Y-0 buffer containing 20 mM KCl, 16 units of SmaI was added, and digestion was carried out at 30° C. for 2 hours. After 10-minute heat treatment at 65° C., a DNA fragment about 2.7 kb in size was purified by the AFT method.

The thus-obtained, pRC19-derived 530-bp DNA fragment (about 0.01 μg) and pUC19-derived 2.7 kb DNA fragment (about 0.05 μg) were dissolved in 20 μl of T4 ligase buffer and, after addition of 200 units of T4 DNA ligase, ligation was conducted at 4° C. for 18 hours.

Figure 15:
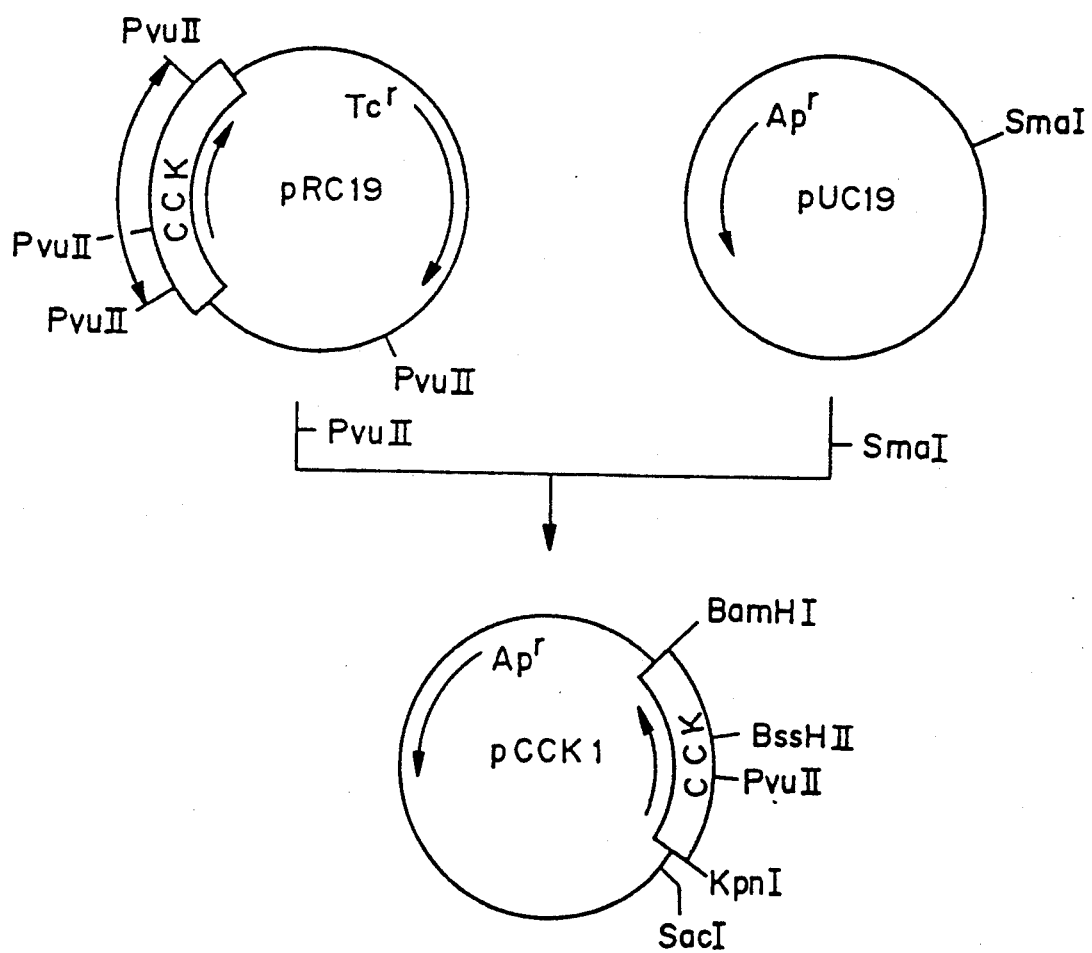
FIG. 15 shows the construction scheme for the plasmid pCCK1.

The recombinant plasmid mixture obtained was used to transform *Escherichia coli* MM294 to give Ap-resistant strains. The plasmid DNA isolated from one of the transformants was named pCCK1 and structural analysis with restriction enzymes confirmed that the DNA had the desired structure (cf. FIG. 15).

(2) Construction of recombinant plasmid pCCK2:

About 2 μg of the pCCK1 plasmid obtained in the above manner was dissolved in 30 μl of Y-0 buffer, 12 units of SacI was added, and digestion was conducted at 37° C. for 2 hours. Further, 1.5 μl of 2M NaCl and 10 units of BamHI were added and digestion was performed at 37° C. for 2 hours. After 10-minute heat treatment at 65° C., a DNA fragment about 0.55 kb in size was purified by the AFT method. Separately, about 2 μg of the pTrS33 plasmid obtained in Reference Example 5 was subjected to the same reaction as mentioned above and the resulting SacI-BamHI fragment about 2.85 kb in size was purified by the AFT method.

The thus-obtained, pCCK1-derived 0.55 kb DNA fragment (about 0.02 μg) and pTrS33-derived 2.85 kb DNA fragment (about 0.1 μg) were dissolved in 20 μl of T4 ligase buffer, 50 units of T4 DNA ligase was added, and ligation was conducted at 4° C. for 18 hours.

Figure 16:
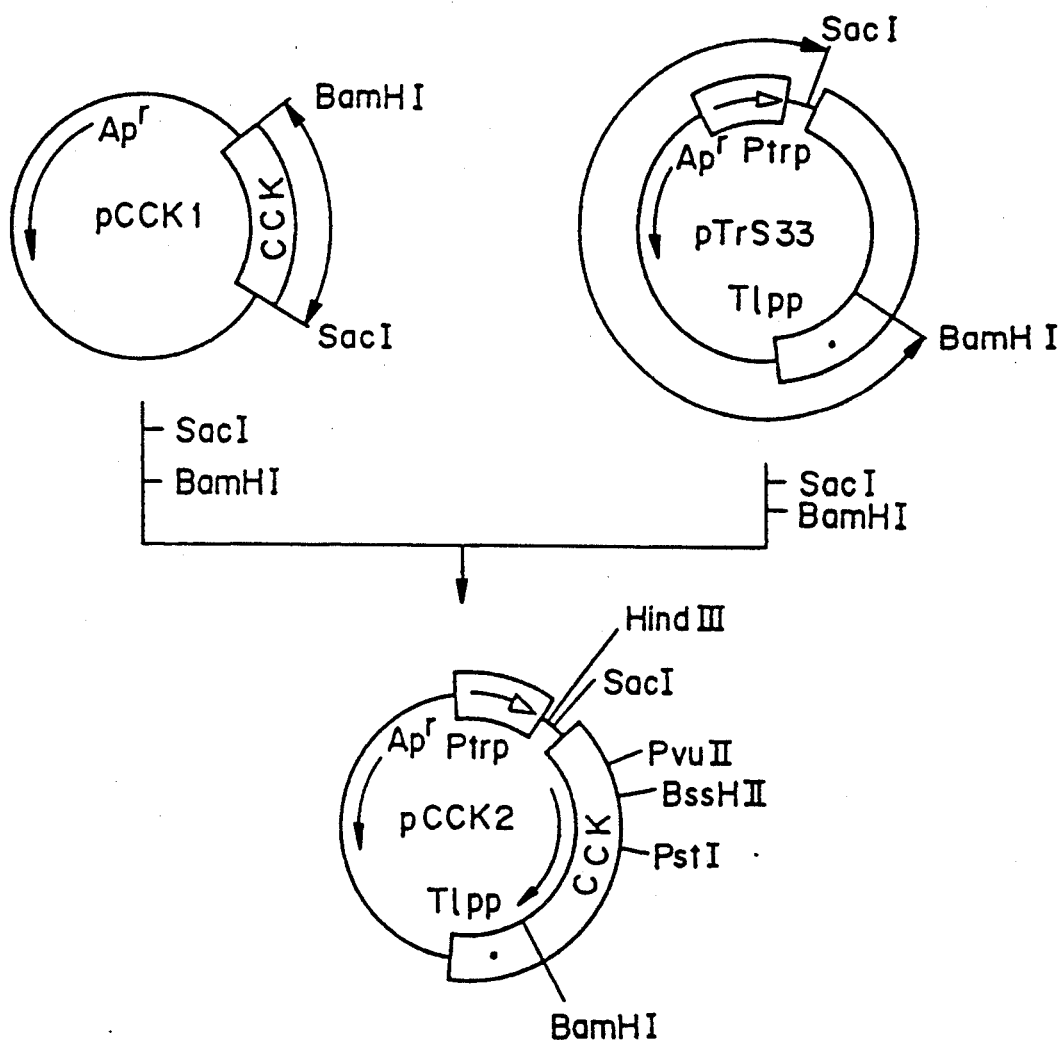
FIG. 16 shows the construction scheme for the plasmid pCCK2.

The recombinant plasmid mixture obtained was used to transform *Eacherichia coli* MM294 and Ap-resistant strains were obtained. A plasmid DNA, pCCK2, was isolated from one of these transformant strains and subjected to structural analysis with restriction enzymes, whereby it was confirmed that said plasmid DNA had the desired structure (cf. FIG. 16).

(3) Isolation of plasmid pUK11 carrying human pro-UK cDNA:

About 8 μg of the Detroit 562 cell-derived poly(A) RNA (mRNA) prepared in Reference Example 1 [dissolved in 7 μl of 10 mM Tris-HCl (pH 7.5) containing 0.5 mM EDTA] was heated at 65° C. for 10 minutes and then cooled rapidly on ice. This solution was adjusted to a final volume of 80 μl such that the final solution contained 50 mM Tris-HCl (pH 8.3), 8 mM MgCl₂, 30 mM KCl, 5 mM DTT, 1 mM each dNTP (dATP, dTTP, dGTP, dCTP), 10 units of ribonuclease inhibitor (P-L Biochemicals) and 5 μg/ml oligo(dT)₁₂₋₁₈ (Collaborative). The resultant solution was incubated at 41° C. for 15 minutes. Then, 20 units of reverse transcriptase (Seikagaku Kogyo) was added and incubation was performed at 41° C. for 90 minutes for the synthesis of a cDNA complementary to the mRNA. The reaction mixture was subjected to phenol-chloroform extraction and then to ethanol precipitation. The precipitate was dissolved in 40 μl of 0.3M NaOH and the solution was allowed to stand at 37° C. for 15 minutes for hydrolyzing the mRNA. After neutralization by addition of 10 μl of 1M Tris-HCl (pH 7.5) and 40 μl of 0.3 N HCl, the resultant single-strand cDNA was recovered by ethanol precipitation and dissolved in 28.5 μl of H₂O.

The solution was adjusted to a final volume of 40 μl such that the final solution contained 50 mM Tris-HCl (pH 8.3), 8 mM MgCl₂, 30 mM KCl, 5 mM DTT, 1 mM each dNTP (dATP, dTTP, dGTP, dCTP) and 2.5 μg/ml synthetic DNA primer CATGAGAGCCCTGCTGG (in agreement with the base sequence of a part of the human pro-UK signal peptide region). The resultant solution was incubated at 65° C. for 10 minutes and then at 41° C. for 30 minutes. Then, 10 units of reverse transcriptase was added and incubation was conducted at 41° C. for 60 minutes for converting the single-strand cDNA to the corresponding double-stranded cDNA. The reaction mixture was subjected to phenol-chloroform extraction and then to ethanol precipitation. The precipitate was dissolved in 30 μl of Y-0 buffer containing 25 mM NaCl, then 25 units of BssHII (New England BioLabs) was added, and digestion was carried out at 50° C. for 2 hours. Then, 1.25 μl of 2M NaCl and 12 units of BamHI was added and further digestion was conducted at 37° C. for 2 hours. After 10-minute heat treatment at 65° C., a mixture of cDNA fragments about 1.1 to 1.4 kb in size was purified by the AFT method.

Separately, about 2 μg of the pCCK2 plasmid DNA obtained as mentioned above was cleaved with BssHII and BamHI in the same manner as mentioned above and a BssHII-BamHI fragment about 2.9 kb in size was purified by the AFT method.

The thus-obtained 1.1-1.4 kb cDNA fragment mixture (about 0.02 μg) and pCCK2-derived 2.9 kb DNA fragment (about 0.05 μg) were dissolved in 20 μl of T4 ligase buffer, 200 units of T4 DNA ligase was added, and ligation was effected at 4° C. for 18 hours.

Figure 17:
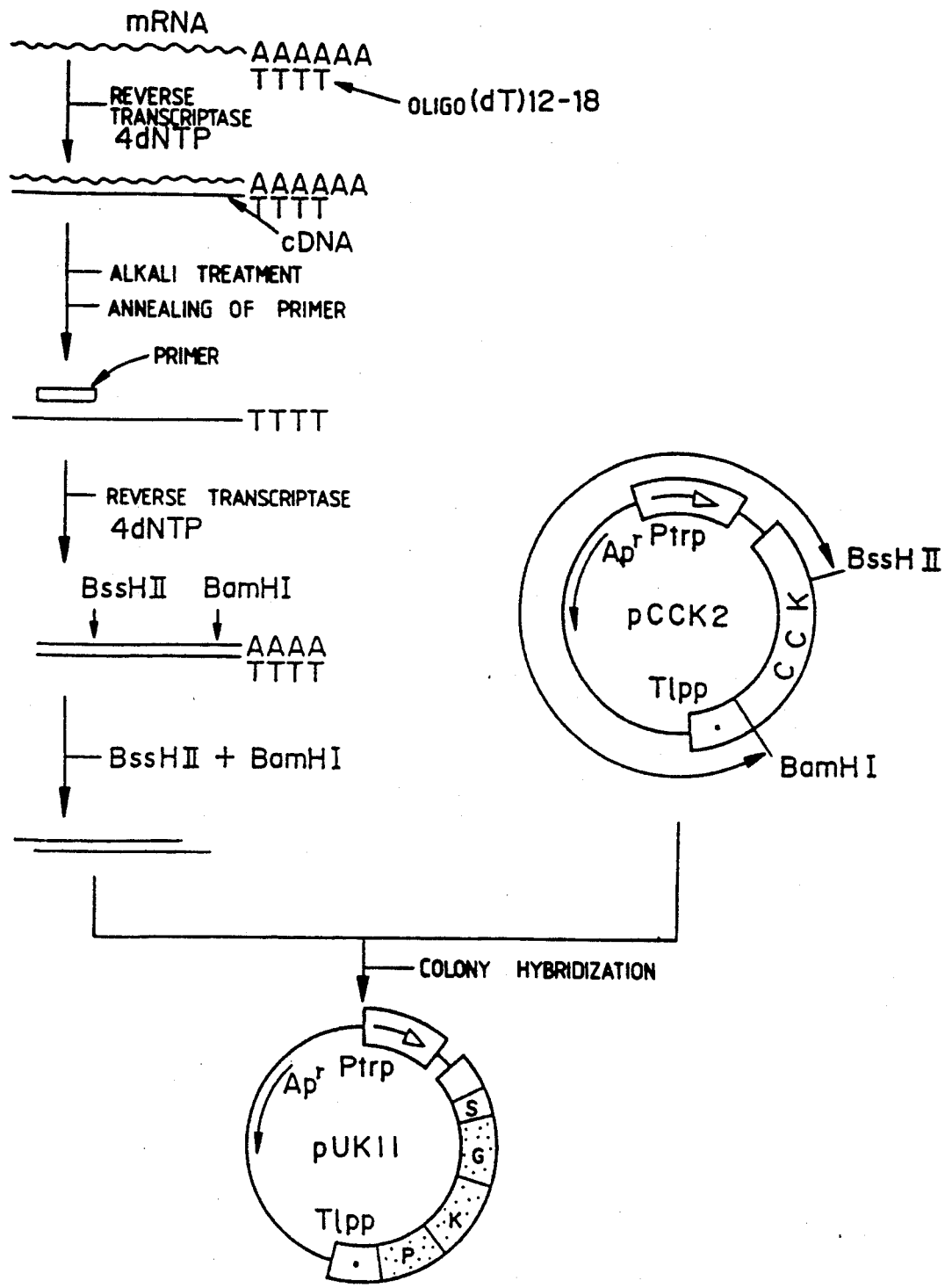
FIG. 17 shows the construction scheme for the plasmid pUK11 carrying the human pro-UK cDNA.

The recombinant plasmid mixture obtained was used to transform *Escherichia coli* C600 SF8. Among about 25,000 Ap-resistant strains obtained, about 1,000 positive clones capable of associating with the same probe as used in isolating the pro-UK cDNA in Reference Example 2 were isolated by the colony hybridization method. The hybridization and filter washing conditions were the same as those employed in Reference Example 2. A plasmid, pUK11 (cf. FIG. 17), harbored by one positive clone thus obtained was isolated and the base sequences of its pro-UK signal peptide, growth factor domain and kringle domain regions were determined by the dideoxy sequencing method using M13 phage. This base sequences were in agreement with those reported by Holmes et al. [Bio/Technology, 3, 923 (1985)].

REFERENCE EXAMPLE 4

Construction of hG-CSF cDNA-carrying plasmids pCSF1-2 and pCSF2:

(1) Preparation of poly(A) RNA from normal human peripheral blood macrophages:

Leukocytes obtained from normal human peripheral blood by centrifugation were cultured in a plastic bottle, adherent cells, i.e. macrophages, were isolated by removing nonadherent cells by washing, and a poly(A)-containing RNA was prepared from these macrophages by the guanidine thiocyanate-lithium chloride method [Cathala et al.: DNA, 2, 329 (1983)], as mentioned below.

Normal human peripheral blood (400 ml) was centrifuged at 1,800 rpm for 20 minutes using a Hitachi RPR10 rotor. The blood cells sedimented were suspended in 50 ml of phosphate-buffered saline [8 g/liter NaCl, 0.2 g/liter KCl, 1.15 g/liter anhydrous $Na_2HPO_4$ and 0.2 g/liter $KH_2PO_4$ (pH 7.2); hereinafter referred to as "PBS"]. A 25-ml portion of this suspension was layered on 25 ml of lymphocyte separating solution (Bionetics) and centrifugation was performed at 1,800 rpm for 30 minutes using a Hitachi RPR10 rotor. The middle leukocyte layer was recovered, and the leukocytes were washed with an equal volume of PBS (1,500 rpm, 10 minutes, Hitachi RPR10 rotor), suspended in 20 ml of RPMI 1640 medium (Nissui Pharmaceutical) containing 5% fetal bovine serum and cultured in a flask for tissue culture (Corning). After 1.5 hours of cultivation at 37° C., the culture supernatant was removed together with nonadherent cells. After addition of a fresh 20-ml portion of the same medium and *Escherichia coli* -derived lipopolysaccharide (LPS) (to a concentration of 0.3 mg/ml), further cultivation was carried out at 37° C. for 4 hours. Then, cells were collected from the culture fluid by centrifugation (1,100×g, 4° C., 10 minutes), washed with 80 ml of PBS and solubilized in 10 ml of 50 mM Tris-HCl (pH 7) containing 5 guanidine thiocyanate, 10 mM EDTA and 8% (v/v) 2-mercaptoethanol by means of a vortex mixer. The solubilization product was transferred to a centrifuge tube, 80 ml of 4M LiCl was added, and the mixture was stirred and then allowed to stand at 4° C. for 20 hours. RNA was recovered as a sediment by 90-minute centrifugation at 9,000 rpm using a Hitachi RPR10 rotor. The RNA sediment was suspended in 50 ml of a solution containing 4M urea and 2M lithium chloride and RNA was again recovered by centrifugation (9,000 rpm, 60 minutes, Hitachi RPR10 rotor).

The RNA sediment was dissolved in 10 ml of 10 mM Tris-HCl (pH 7.5) containing 0.1% sodium lauryl sulfate and 1 mM EDTA and, after phenol-chloroform extraction, RNA was recovered by ethanol precipitation. The RNA obtained (about 0.8 mg) was dissolved in 1 ml of Tris-HCl (pH 8.0) containing 1 mM EDTA. After 5-minute incubation at 65° C., 0.1 ml of 5M NaCl was added. The mixture was subjected to chromatography on an oligo(dT)-cellulose column (P-L Biochemicals) (column volume 0.5 ml). Elution of adsorbed, poly(A)-containing mRNA with 10 mM Tris-HCl (pH 7.5) containing 1 mM EDTA gave about 30 µg of poly(A)-containing mRNA.

Figure 14:
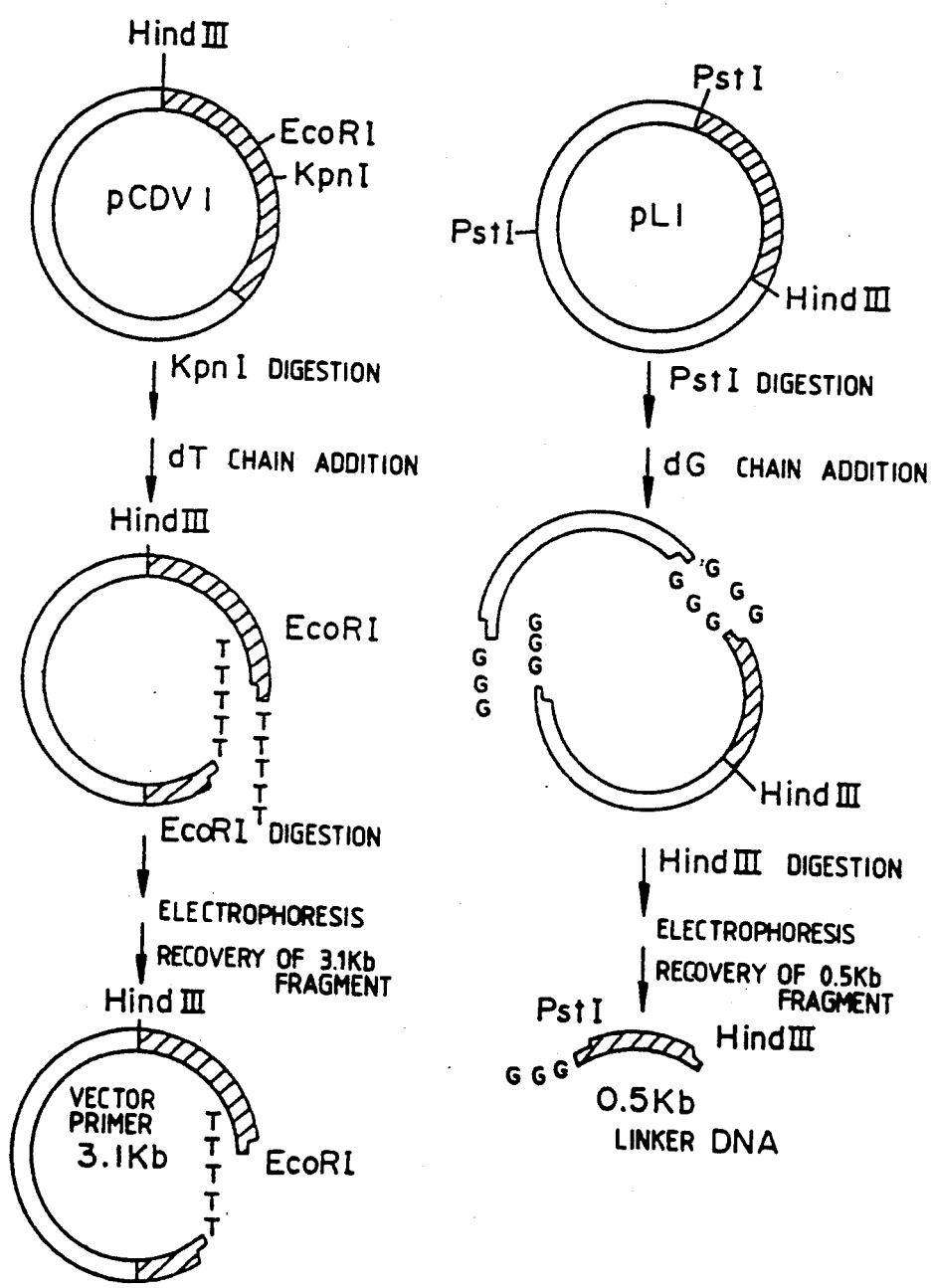
FIG. 14(1) and FIG. 14(2) show the process for synthesizing a cDNA by the Okayama-Berg method and the construction scheme for a recombinant plasmid containing said cDNA, respectively.
Figure 14:
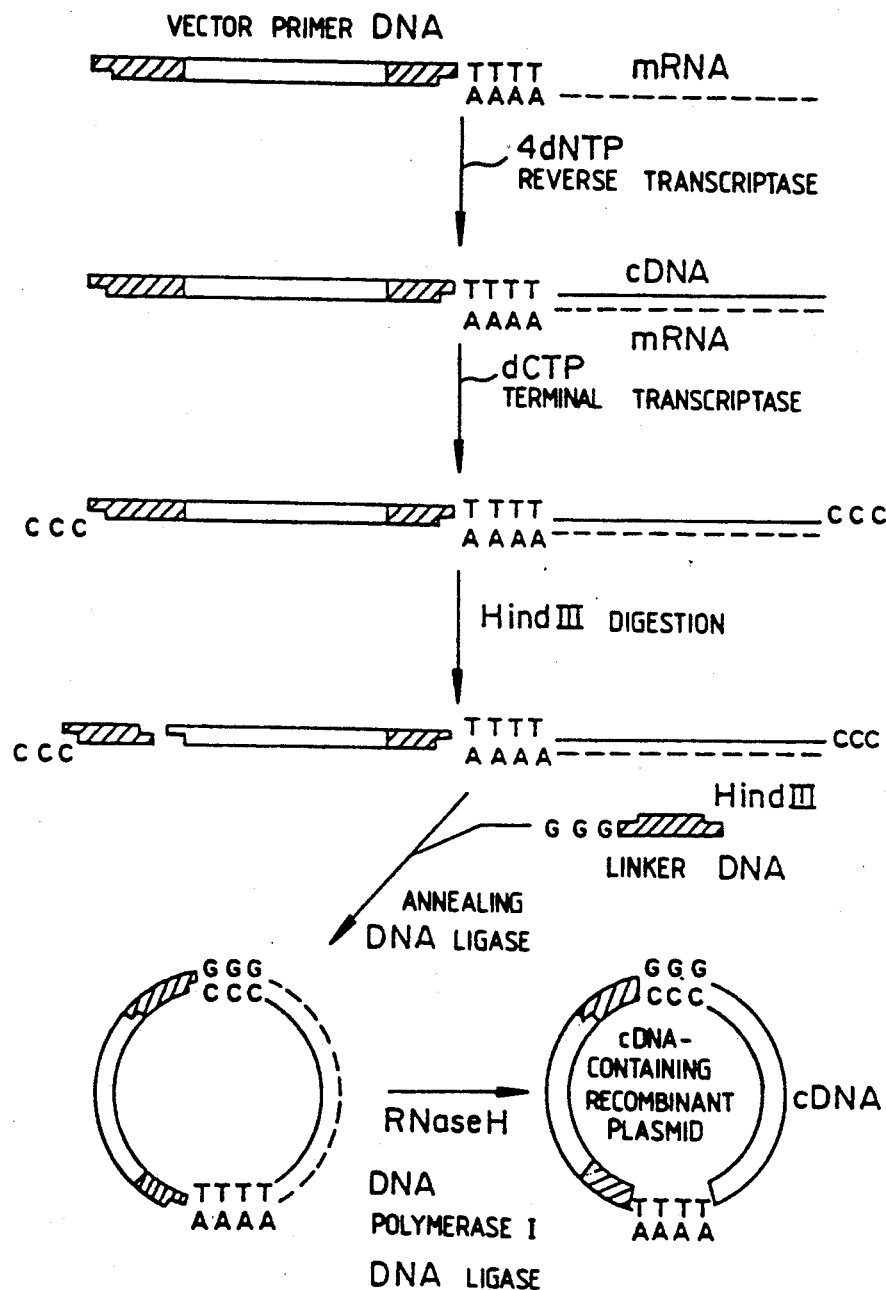

(2) Synthesis of cDNA and insertion of the cDNA into vector:

Following the Okayama-Berg method [Mol. Cell. Biol., 2, 161 (1982)], cDNA synthesis was performed and a plasmid was constructed with the synthesized cDNA inserted therein. The processes therefor are schematically illustrated in FIG. 14.

About 3 µg of the poly(A) RNA prepared as mentioned above and about 1.4 µg of the vector primer were dissolved in 22.3 µl of 50 mM Tris-HCl (pH 8.3) containing 8 mM $MgCl_2$, 30 mM KCl, 0.3 mM DTT, 2 mM each dNTP (dATP, dTTP, dGTP, dCTP) and 10 units of ribonuclease inhibitor (P-L Biochemicals) and, after addition of 10 units of reverse transcriptase, incubation was carried out at 41° C. for 90 minutes for the synthesis of DNA complementary to the mRNA. The reaction mixture was subjected to phenol-chloroform extraction and then to ethanol precipitation, whereby the vector primer DNA with an RNA-DNA double strand added thereto was recovered. This DNA was dissolved in 20 µl of TdT buffer containing 66 µM dCTP and 0.2 µg of poly(A) and, after addition of 14 units of TdT (P-L Biochemicals), incubation was conducted at 37° C. for 2 minutes for addition of an oligo(dC) chain (about 20-mer) to the 3′ terminus of the cDNA. The reaction mixture was subjected to phenol-chloroform extraction and then to ethanol precipitation, whereby the cDNA-vector primer DNA with the (dC) chain added thereto was recovered. This DNA was dissolved in 400 µl of 10 mM Tris-HCl (pH 7.5) containing 6 mM $MgCl_2$ and 60 mM NaCl and, after addition of 20 units of HindIII, incubation was performed at 37° C. for 2 hours for cleavage at the HindIII site. The reaction mixture was subjected to phenolchloroform extraction and then to ethanol precipitation to give 0.5 picomole of a (dC) chain-added cDNA-vector primer DNA. A 0.2-picomole portion of the DNA and 0.4 picomole of the above-mentioned linker DNA were dissolved in 100 µl of 10 mM Tris-HCl pH 7.5) containing 0.1M NaCl and 1 mM EDTA and the solution was incubated at 65° C. for 10 minutes, then at 42° C. for 25 minutes and finally at 0° C. for 30 minutes. The reaction mixture was adjusted to a final volume of 1,000 µl such that the final solution contained 20 mM Tris-HCl (pH 7.5), 4 mM $MgCl_2$, 10 mM $(NH_4)_2 SO_4$, 0.1M KCl and 0.1 mM β-NAD. To this reaction mixture was added 25 units of *Escherichia coli*-derived DNA ligase (New England BioLabs). Incubation was conducted at 11° C. for 18 hours. The reaction mixture was supplemented with each dNTP (40 µM) and β-NAD (to a final concentration of 0.15 mM) and, after addition of 10 units of *Escherichia coli*-derived DNA ligase, 20 units of *Escherichia coli*-derived DNA polymerase I (P-L Biochemicals) and 10 units of *Escherichia coli*-derived ribonuclease H (P-L Biochemicals), incubation was carried out at 12° C. for 1 hour and then at 25° C. for 1 hour. The reactions mentioned above resulted in circularization of the cDNA-containing recombinant DNA and DNA substitution for the RNA portion of the RNA-DNA double strand to give a completely double-stranded recombinant plasmid.

(3) Selection of hG-CSF cDNA-containing recombinant DNA:

The recombinant plasmid obtained as described above in (2) was used to transform *Escherichia coli* C600 SF8 by the method of Scott et al. [K. Shigesada: Saibo Kogaku (Cell Technology), 2, 616 (1983)]. About 9,200 colonies obtained were fixed on nitrocellulose filters. Two strains capable of strongly hybridizing at 60° C. with the $^{32}$P-labeled probe prepared by labeling of a synthetic 27-base DNA 5'-ACCCCCCTGGGCCCTGCCAGCTCCCTG-3' corresponding to the N-terminal nine amino acids of the mature hG-CSF protein isolated by Nagata et al. [Nature, 319, 415 (1986)] were selected by the Grunstein-Hogness method [Proc. Natl. Acad. Sci. USA, 72, 3961 (1975)]. The whole base sequence of the cDNA in the plasmids pCSF1-2 and pCSF2 harbored by these strains was determined by the dideoxy sequencing method using M13 phage. As a result, the cDNA contained in pCSF1-2 and pCSF2 was found to be one coding for hG-CSF. A microorganism harboring the plasmid pCSF1-2 and a microorganism harboring the plasmid pCSF2 have been deposited with the Fermentation Research Institute under the designations of *Escherichia coli* ECSF1-2 (deposit number FERM BP-1220) and *Escherichia coli* ECSF2 (deposit number FERM BP-2073) in accordance with the Budapest Treaty.

REFERENCE EXAMPLE 5

Figure 18:
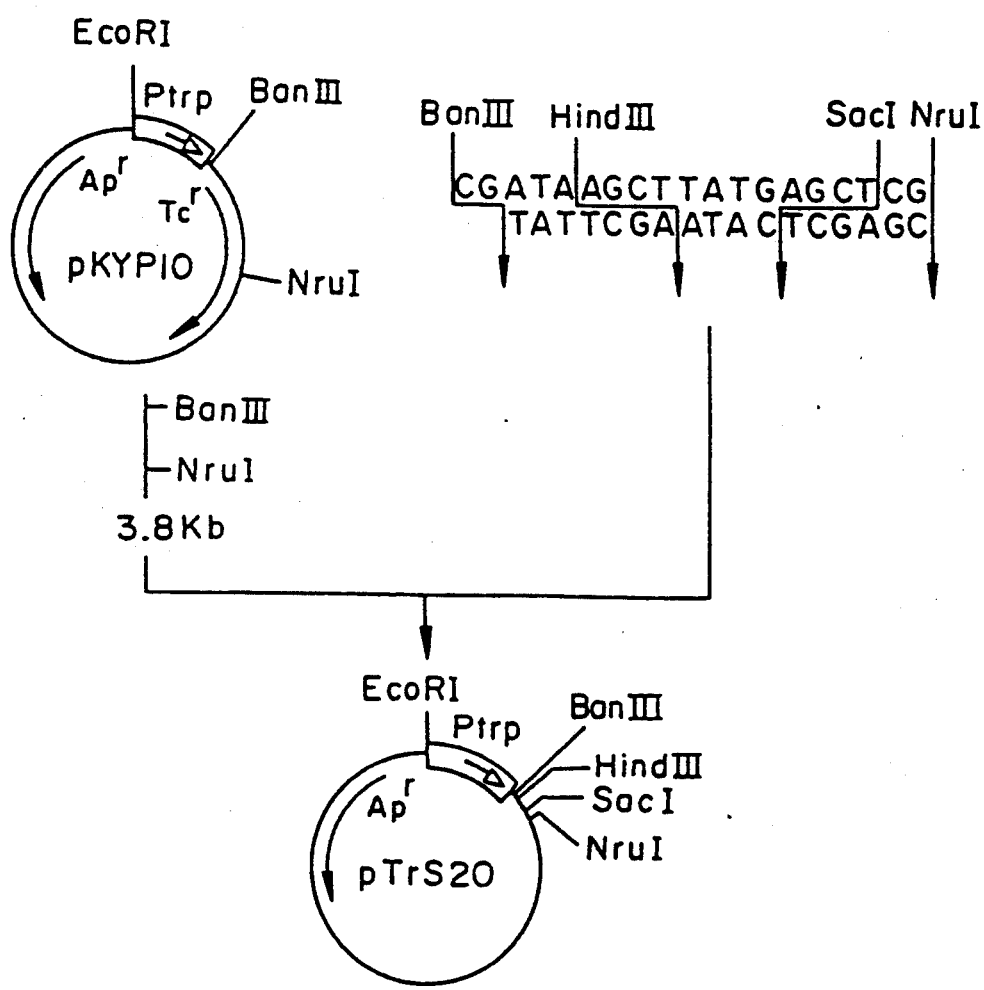
FIG. 18 shows the construction scheme for the plasmid pTrS20.

Construction of recombinant plasmid pTrS33:

(1) Construction of ATG vector pTrS20:

An ATG vector, pTrS20, containing the SD sequence and ATG initiation codon separated from each other by 14 bases and having a SacI site immediately behind the ATG codon was constructed by the process shown in FIG. 18.

First, 3 μg of pKYP10 prepared by the method described in JP-A-58-110600 or U.S. Pat. No. 4,686,191 was dissolved in 30 μl of Y-100 buffer, 6 units each of the restriction enzymes BanIII and NruI (new England BioLabs) were added, and cleavage was effected at 37° C. for 3 hours. About 0.5 μg of a Ptrp-containing DNA fragment about 3.8 kb in size (BanIII-NruI fragment) was recovered from the reaction mixture by the LGT method.

Separately, for providing an ATG initiation codon downstream from Ptrp, the following DNA linker was synthesized by the phosphotriester method:

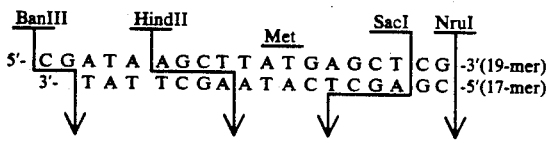

The synthetic 19-mer and 17-mer DNAs (each 10 picomoles) were dissolved in a total volume of 20 μl of 50 mM Tris-HCl (pH 7.5) containing 10 mM MgCl$_2$, 5 mM dithiothreitol, 0.1 mM EDTA and 1 mM ATP, 3 units of T4 polynucleotide kinase (Takara Shuzo) was added, and phosphorylation was carried out at 37° C. for 60 minutes.

Then 0.1 μg of the pKYP-10-derived BanIII-NruI fragment (about 3.8 kb) obtained as described above and about 0.5 picomole of the above DNA linker were dissolved in 20 μl of T4 ligase buffer, 2 units of T4 DNA ligase was further added, and ligation was performed at 4° C. for 18 hours.

The thus-obtained recombinant plasmid mixture was used to transform *Escherichia coli* HB101 [Bolivar et al.: Gene, 2, 75 (1977)] and Ap$^r$ colonies were obtained. One of these colonies was cultured and the plasmid DNA was recovered from cultured cells. The structure of the plasmid obtained was confirmed by agarose gel electrophoresis following cleavage with the restriction enzymes EcoRI, BanIII, HindIII, SacI and NruI. This plasmid was named pTrS20 (FIG. 18). The base sequence in the vicinity of the BanIII and HindIII sites of pTrS20 was confirmed by the dideoxy sequencing method using M13 phage to be as folows:

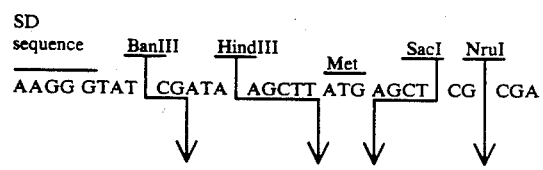

(2) Construction of pTrS33:

About 3 μg of the pTrs20 plasmid DNA obtained as mentioned above was dissolved in 30 μl of Y-0 buffer, 12 units of SacI was added, and digestion was carried out at 37° C. for 2 hours. Then, 1.5 μl of 2M NaCl and 10 units of PstI were further added and digestion was effected at 37° C. for 2 hours. After 10-minute heat treatment at 65° C., a DNA fragment about 1.15 kb in size was purified by the AFT method. Separately, 2 μg of pKYP26 prepared by the method described in JP-A-62-48699 corresponding to U.S. patent application No. 896,734 or EP-A-0 214 555 [a pKYP26-carrying strain of *Escherichia coli* has been deposited with the Fermentation Research Institute under the designation *Escherichia coli* IKYP26 (deposit number FERM BP-863) in accordance with the Budapest Treaty] was dissolved in 30 μl of Y-100 buffer, 8 units of PstI and 10 units of BamHI were added, and digestion was effected at 37° C. for 2 hours. After 10-minute heat treatment at 65° C., a DNA fragment about 1.7 kb in size was purified by the AFT method. Further, separately, 2 μg of the M13mp18RF DNA [Norrander, J. et al.: Gene, 26, 101 (1983); the M13mp18RF DNA was obtained from Takara Shuzo] was dissolved in 30 μl of Y-0 buffer, 10 units of SacI was added, and digestion was conducted at 37° C. for 2 hours. After addition of 1.5 μl of 1M NaCl and 10 units of ClaI, digestion was further carried out at 37° C. for 2 hours. After 10-minute heat treatment at 65° C., a DNA fragment about 0.65 kb in size was purified by the AFT method. Separately from these, the two synthetic DNAs (43 bases and 45 bases) shown below were synthesized using an Applied Biosystems model 380A DNA synthesizer and individually subjected to 5'-phosphorylation by the method mentioned above.

(43 bases)
5'-CGATAAGCTTATGATATCCAACGTCGACGACGGCGTCGAACCATGGCCG-3'
3'-TATTCGAATACTATAGGTTGCAGCTGCTGCCGCAGCTTGGTACCGGCCTAG-5'
(45 bases)

The thus-obtained pTrS20-derived 1.15 kb DNA fragment (about 0.1 μg), pKYP26-derived 1.7 kb DNA fragment (about 0.1 μg), M13mp18-derived 0.65 kb DNA fragment (about 0.05 μg) and 5'-phosphorylated synthetic DNAs (each 1 picomole) were dissolved in 20 μl of T4 ligase buffer, 50 units of T4 DNA ligase was added, and ligation was carried out at 4° C. for 18 hours.

Figure 19:
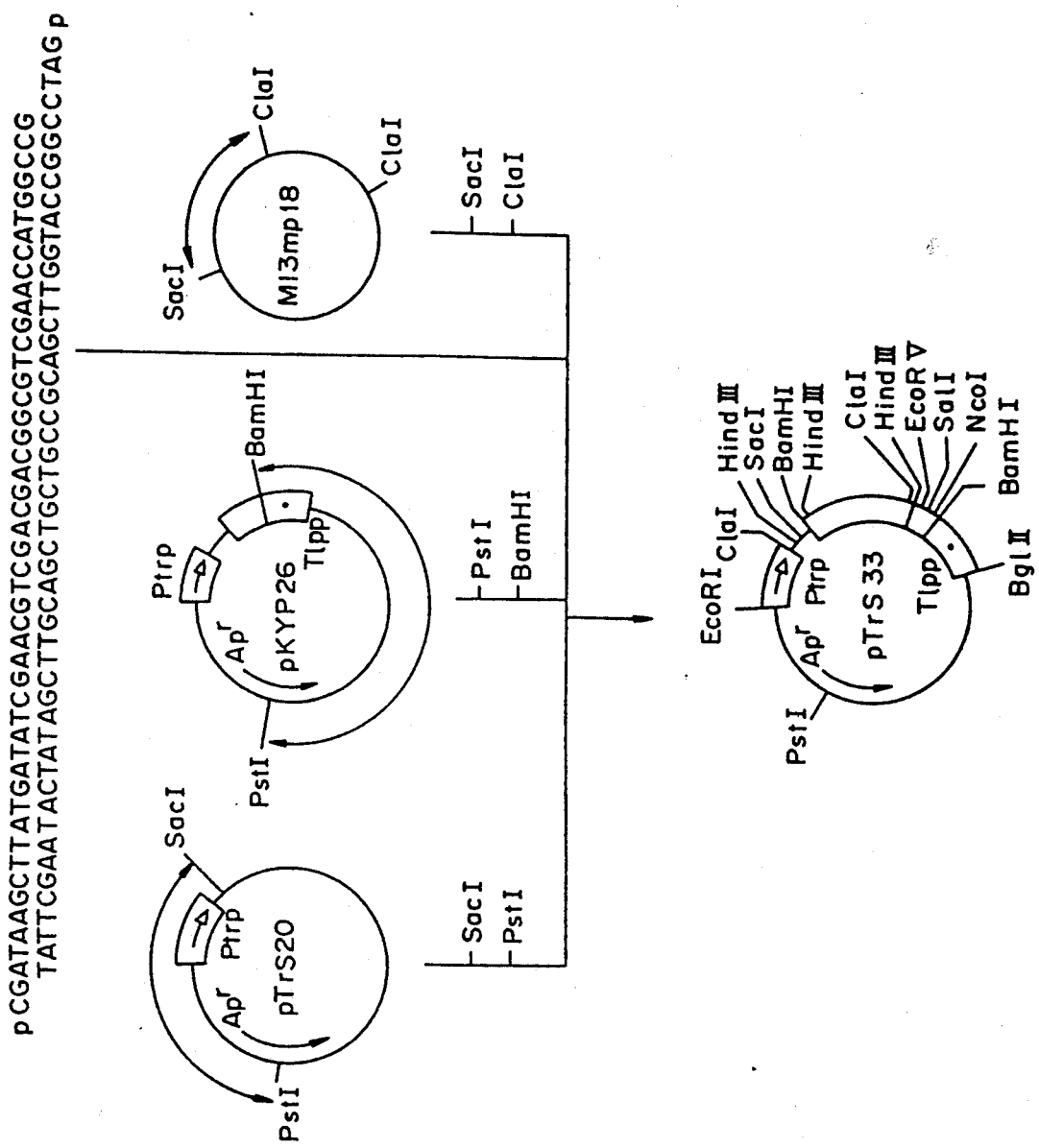
FIG. 19 shows the construction scheme for the plasmid pTrS33.

The thus-obtained recombinant plasmid mixture was used to transform *Escherichia coli* MM294. The plasmid pTrS33 was isolated from one of the Ap-resistant transformant strains obtained. Structural analysis by restriction enzyme digestion and sequencing by the dideoxy method confirmed that pTrS33 had the desired structure (cf. FIG. 19).

REFERENCE EXAMPLE 6

Figure 20:
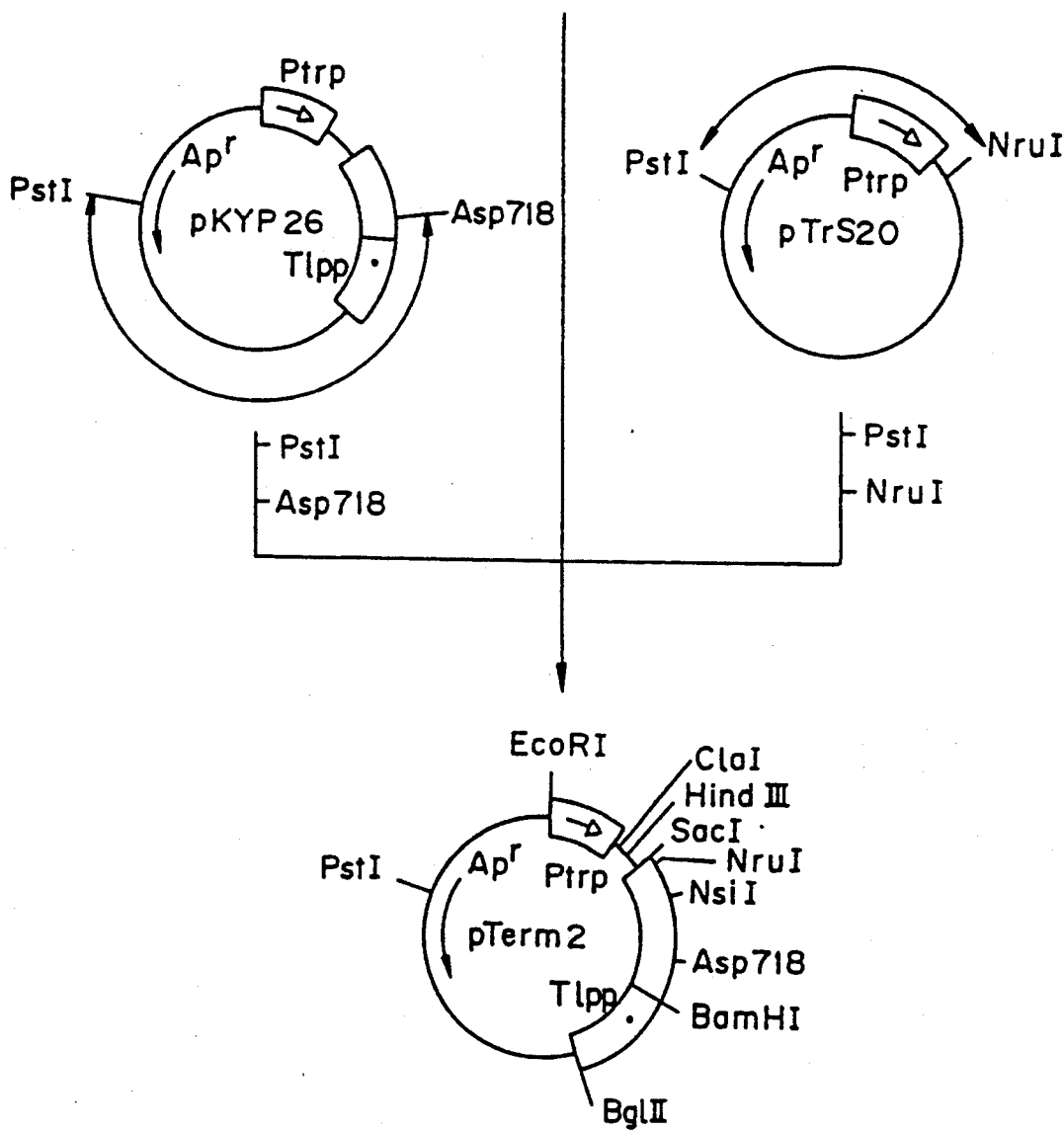
FIG. 20 shows the construction scheme for the plasmid pTerm2.

Construction of plasmid pTerm2:

About 2 μg of the pKYP26 plasmid DNA (JP-A-62-48699) was dissolved in 30 μl of 10 mM Tris-HCl (pH 8.0) containing 75 mM NaCl, 7 mM $MgCl_2$ and 6 mM 2-mercaptoethanol, 16 units of Asp718 (Boehringer Mannheim) and 10 units of PstI were added, and digestion was effected at 37° C. for 2 hours. After 10-minute heat treatment at 65° C., a DNA fragment about 1.7 kb in size was purified by the AFT method. Separately, about 2 μg of the pTrS20 plasmid DNA obtained as described in Reference Example 5-(1) was dissolved in 30 μl of Y-100 buffer, 8 units of PstI and 10 units of NruI (Boehringer Mannheim) were added, and digestion was carried out at 37° C. for 2 hours. After 10-minute heat treatment at 65° C., a DNA fragment about 1.5 kb in size was purified by the AFT method. Further, separately, the two synthetic DNAs (19 bases and 23 bases) shown in FIG. 20 were synthesized using an Applied Biosystems model 380A DNA synthesizer and individually subjected to 5'-phosphorylation by the method mentioned above.

The thus-obtained pKYP26-derived 1.7Kb DNA fragment (about 0.1 μg), pTrS20-derived 1.15 Kb DNA fragment and two 5'-phosphorylated synthetic DNAs (each 1 picomole) were dissolved in 20 μl of T4 ligase buffer, 50 units of T4 DNA ligase was added, and ligation was carried out at 4° C. for 18 hours.

The recombinant plasmid mixture obtained was used to transform *Escherichia coli* MM294 to give Ap-resistant strains. The plasmid DNA isolated from one of the transformants and named pTerm2 was examined by structural analysis by restriction enzyme digestion and by sequencing by the dideoxy method. It was confirmed that pTerm2 had the desired structure (cf. FIG. 20).

REFERENCE EXAMPLE 7

Construction of recombinant plasmid pTSF10:

From cultured cells of *Escherichia coli* C600 SF8 harboring the human t-PA cDNA-containing plasmid ptPA7 obtained in Reference Example 1, there was prepared the ptPA7 DNA by the conventional method. About 2 μg of the ptPA7 DNA obtained was dissolved in 30 μl of Y-100 buffer, 8 units of the restriction enzyme BglII was added, and digestion was effected at 37° C. for 2 hours. After 10-minute heat treatment at 65° C., a DNA fragment about 2.0 kb in size was purified by the AFT method. Separately, about 2 μg of the pTrS33 DNA (Reference Example 5) was dissolved in 30 μl of Y-100 buffer, 10 units of the restriction enzyme BamHI was added, and digestion was carried out at 37° C. for 2 hours. After 10-minute heat treatment at 65° C., a DNA fragment about 2.8 kb in size was purified by the AFT method.

The thus-obtained ptPA7-derived 2.0 kb DNA fragment (about 0.1 μg) and pTrS33-derived 2.8 kb DNA fragment (about 0.1 μg) were dissolved in a total volume of 20 μl of T4 ligase buffer, 50 units of T4 DNA ligase was added, and ligation was carried out at 4° C. for 18 hours.

Figure 21:
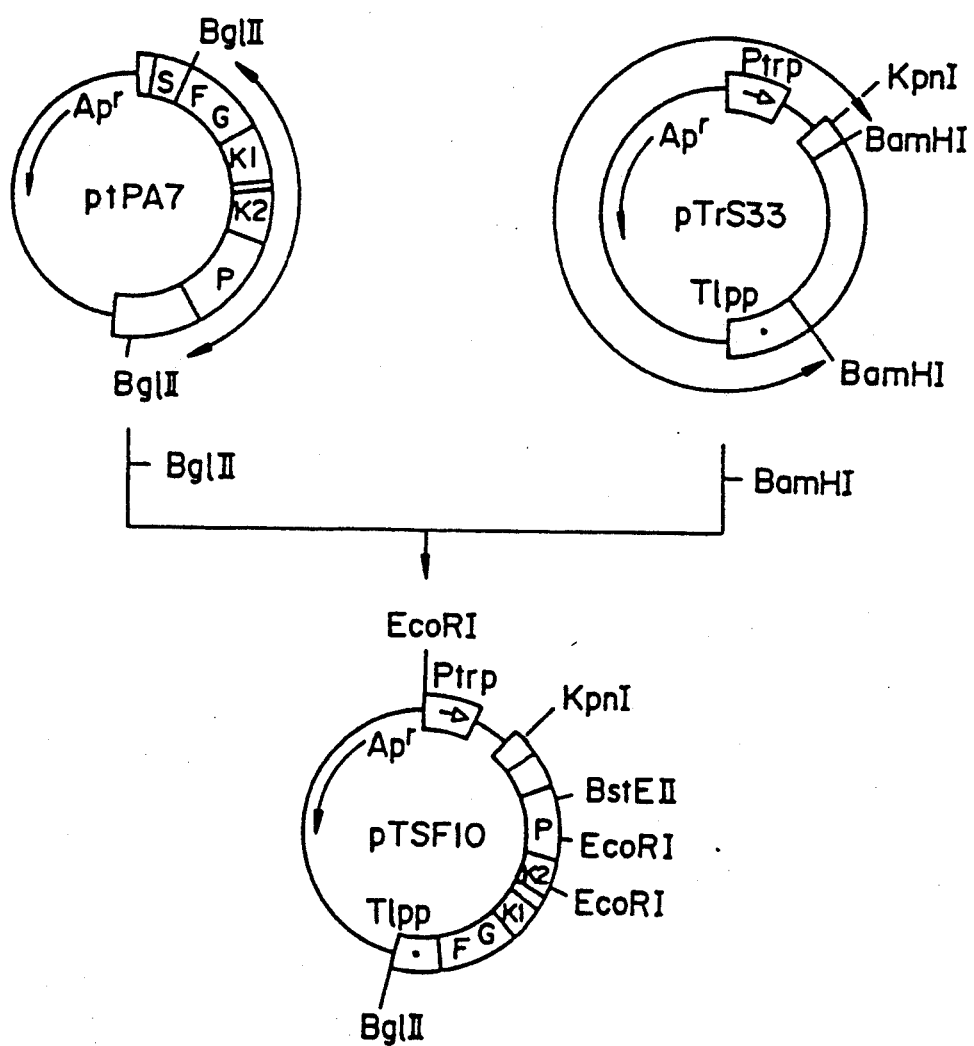
FIG. 21 shows the construction scheme for the plasmid pTSF10.

The recombinant plasmid mixture obtained was used to transform *Escherichia coli* MM294 to give Ap-resistant strains. The plasmid DNA isolated from one of the transformants was named pTSF10 and subjected to structural analysis by restriction enzyme digestion. It was confirmed that this plasmid had the desired structure (cf. FIG. 21).

REFERENCE EXAMPLE 8

Construction of recombinant plasmid pTA4:

About 3 μg of the pTSF10 plasmid DNA obtained in Reference Example 7 was dissolved in 30 μl of Y-0 buffer, 12 units of the restriction enzyme KpnI was added, and digestion was effected at 37° C. for 2 hours. Then, 1.5 μl of 3M NaCl and 12 units of the restriction enzyme BstEII (New England BioLabs) were added, and digestion was further conducted at 60° C. for 2 hours. Thereafter, a DNA fragment about 0.3 kb in size was purified by the AFT method.

Separately, *Escherichia coli* IGHA2 (deposited with the Fermentation Research Institute under the deposit number FERM BP-400) was cultured and the pGHA2 plasmid DNA (JP-A-60-221091, U.S. patent application No. 681,292 or EP-A-0 152 613) was prepared from cultured cells by the conventional method. About 2 μg of the pGHA2 DNA obtained was dissolved in 30 μl of Y-100 buffer, 8 units of PstI and 8 units of BglII were added, and digestion was effected at 37° C. for 2 hours. After 10-minute heat treatment at 65° C., a DNA fragment about 0.75 kb in size was purified by the AFT method.

Separately, about 3 μg of the ptPA7 DNA (Reference Example 1) was dissolved in 30 μl of Y-150 buffer, 10 units of BglII was added, and digestion was effected at 37° C. for 2 hours. Then, 12 units of BstEII was added and digestion was further conducted at 60° C. for 2 hours, followed by purification of a DNA fragment about 1.55 kb in size using the AFT method.

Further, separately, about 2 μg of the pTerm2 DNA obtained in Reference Example 6 was dissolved in 30 μl of Y-0 buffer, 12 units of KpnI was added, and digestion was carried out at 37° C. for 2 hours. Then, 1.5 μl of 2M NaCl and 8 units of PstI were added and digestion was further effected at 37° C. for 2 hours, followed by purification of a DNA fragment about 1.7 kb in size using the AFT method.

The thus-obtained four DNA fragments (0.03 μg of the pTSF10-derived fragment, 0.05 μg of the pGHA2-derived fragment, 0.1 μg of the ptPA7-derived fragment and 0.1 µg of the pTerm2-derived fragment) were dissolved in 20 µl of T4 ligase buffer, 200 units of T4 DNA ligase was added, and ligation was carried out at 4° C. for 18 hours.

Figure 22:
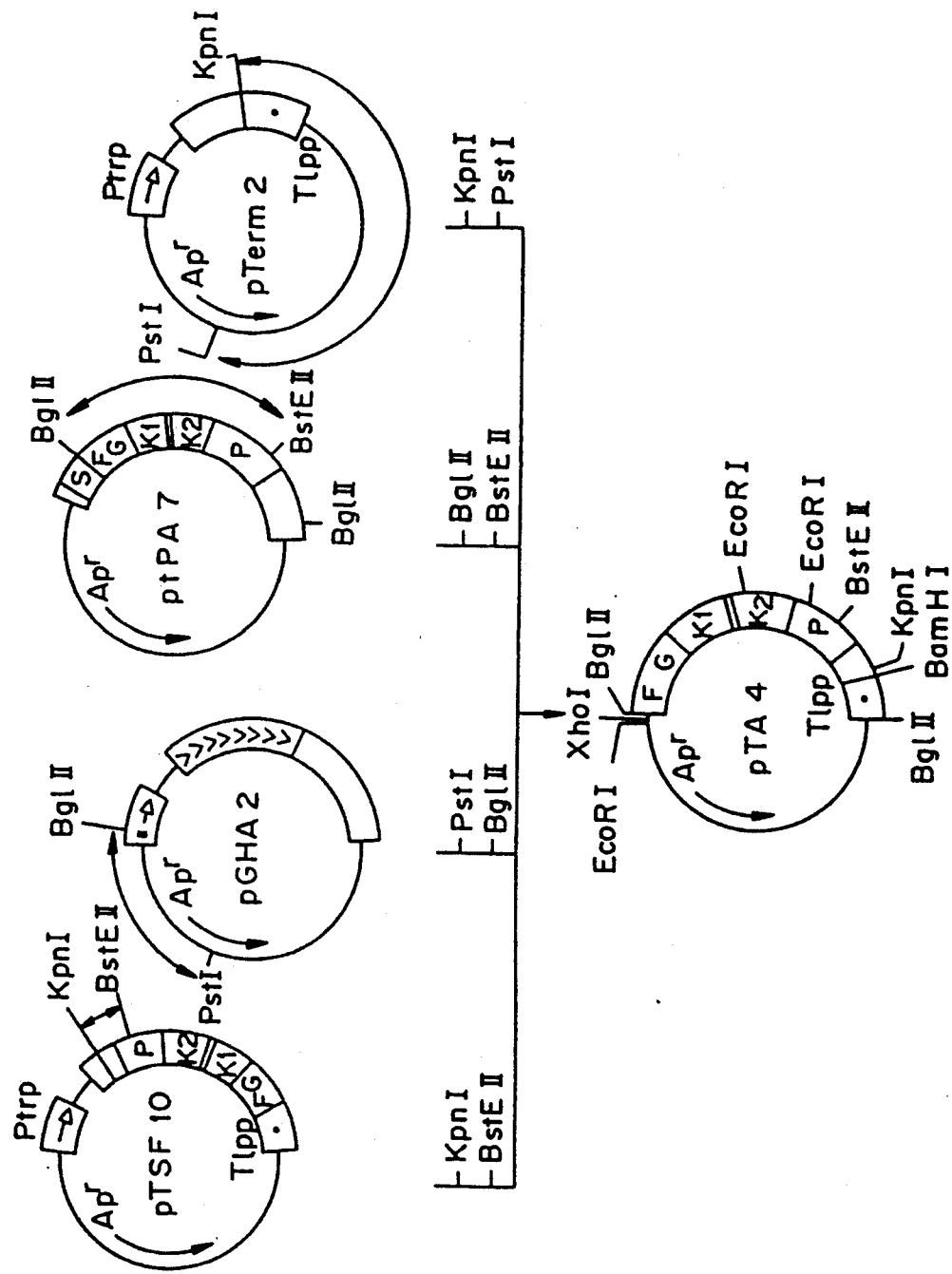
FIG. 22 shows the construction scheme for the plasmid pTA4.

The recombinant plasmid mixture obtained was used to transform *Escherichia coli* MM294 to give Ap-resistant strains. The plasmid DNA isolated from one of these transformants was named pTA4 and subjected to structural analysis by restriction enzyme digestion. It was confirmed that pTA4 had the desired structure (cf. FIG. 22).

REFERENCE EXAMPLE 9

Construction of t-PA expression plasmid pSE1PA1-SE1dhfr1-9A:

(1) Construction of recombinant plasmid pAGE105M: *Escherichia coli* HB101 harboring the plasmid pAGE28 constructed by the present inventors [Mizukami et al.: J. Biochem., 101, 1307–1310 (1987)] was cultured and the pAGE28 DNA was prepared from cultured cells by the conventional method. About 2 µg of the pAGE28 DNA obtained was dissolved in 30 µl of Y-100 buffer, 8 units of XhoI and 12 units of ScaI were added, and digestion was effected at 37° C. for 2 hours. After 10-minute heat treatment at 65° C., a DNA fragment about 2.8 kb in size was purified by the AFT method. Separately, *Escherichia coli* HB101 harboring the plasmid pAGE103 constructed by the present inventors [Mizukami et al.: J. Biochem., 101, 1307–1310 (1987); FERM BP-1312] was cultured and the pAGE103 DNA was prepared from cultured cells by the conventional method. About 3µg of the pAGE103 DNA obtained was dissolved in 30 µl of Y-100 buffer, 10 units of EcoRI was added, and digestion was conducted at 37° C. for 2 hours. A DNA fragment was recovered by ethanol precipitation following phenolchloroform extraction. This DNA fragment was dissolved in a total volume of 40 µl of polymerase buffer, 6 units of the Klenow fragment was added, and reaction was carried out at 15° C. for 1 hour, whereby the EcoRI cohesive ends were converted to blunt ends. The reaction was terminated by phenolchloroform extraction, the DNA fragment was recovered by ethanol precipitation. This DNA fragment was dissolved in 30 µl of Y-100 buffer, 12 units of XhoI was added, and digestion was performed at 37° C. for 2 hours. After 10-minute heat treatment at 65° C., a DNA fragment about 0.4 kb in size was purified by the AFT method. Furthermore, *Escherichia coli* HB101 harboring the plasmid pKCR constructed by O'Hara et al. [Proc. Natl. Acad. Sci. USA, 78, 1527 (1981)] was cultured and the pKCR DNA was prepared from cultured cells by the conventional method. About 2 µg of the pKCR DNA obtained was dissolved in 30 µl of Y-150 buffer, 12 units of BamHI and 16 units of SalI were added, and digestion was carried out at 37° C. for 2 hours. After phenolchloroform extraction, a DNA fragment was recovered by ethanol precipitation. This DNA fragment was dissolved in a total volume of 40 µl of polymerase buffer, 6 units of the Klenow fragment was added, and reaction was carried out at 15° C. for 1 hour, whereby the BamHI cohesive end and SalI cohesive end were converted each to a blunt end. After 10-minute heat treatment at 65° C., a DNA fragment about 1.85 kb in size was purified by the AFT method.

The thus-obtained pAGE28-derived 2.8 kb DNA fragment (about 0.05 µg), pAGE103-derived 0.4 kb DNA fragment (about 0.03 µg) and pKCR-derived 1.85 kb DNA fragment (about 0.2 µg) were dissolved in 20 µl of T4 ligase buffer, 300 units of T4 DNA ligase was added, and ligation was carried out at 4° C. for 18 hours.

Figure 23:
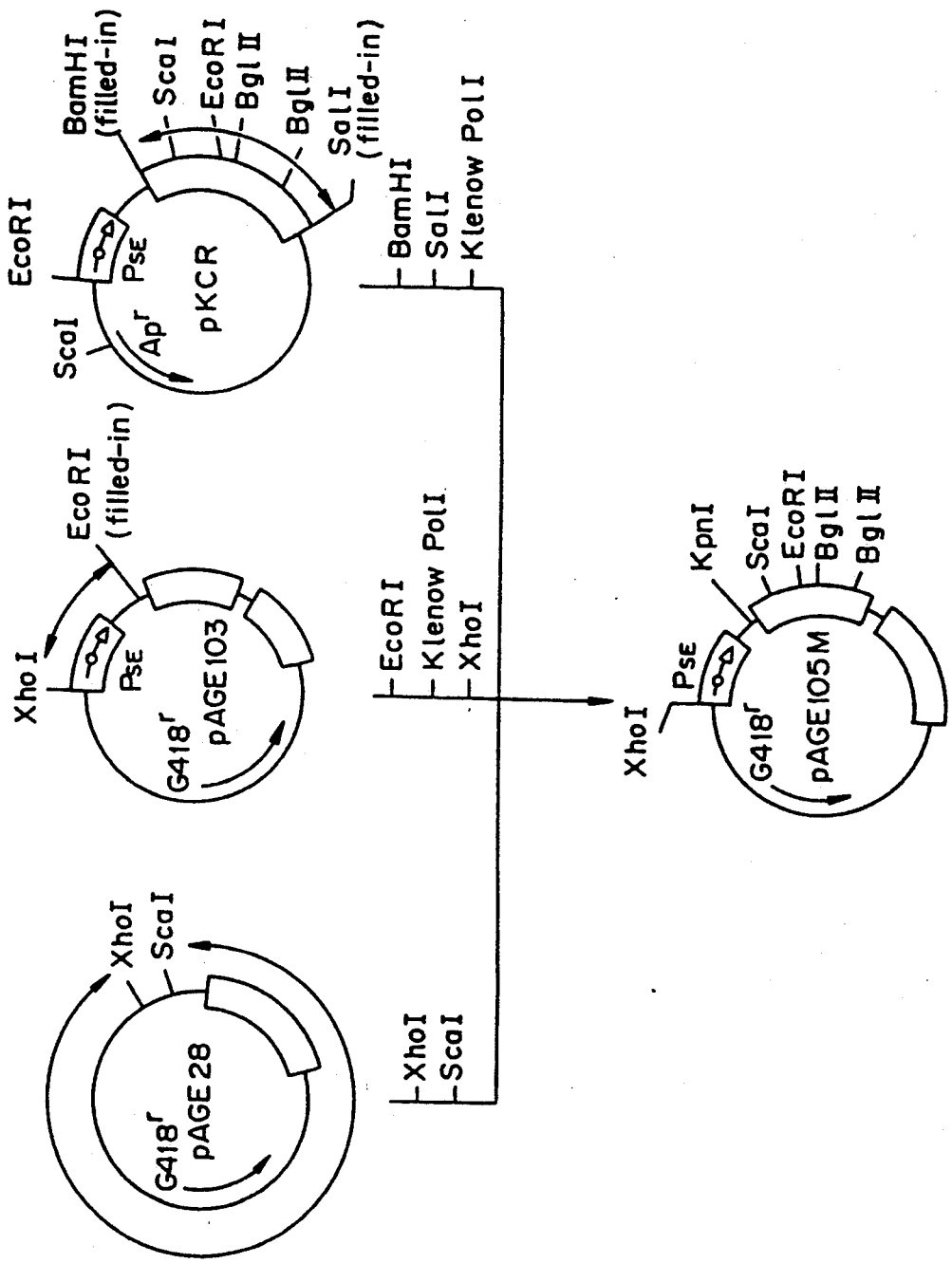
FIG. 23 shows the construction scheme for the plasmid pAGE105M.

The thus-obtained recombinant plasmid mixture was used to transform *Escherichia coli* MM294 and kanamycin (hereinafter briefly referred to as Km)-resistant strains. The plasmid isolated from one of these transformant strains was named pAGE105M and subjected to structural analysis by restriction enzyme digestion. It was confirmed that pAGE105M had the desired structure (cf. FIG. 23).

(2) Construction of recombinant plasmid pAGE106: About 2 µg of the pAGE105M DNA obtained as described above was dissolved in 30 µl of Y-100 buffer, 12 units of ScaI was added, and digestion was carried out at 37° C. for 2 hours. After 10-minute heat treatment at 65° C., a DNA fragment about 5.0 kb in size was purified by the AFT method. Separately, a 5'-phosphorylated EcoRI linker was prepared in the same manner as in Example 1.

The thus-obtained pAGE105M-derived 5.0 kb DNA fragment (about 0.1 µg) and 1 picomole of the 5'-phosphorylated EcoRI linker were dissolved in 20 µl of T4 ligase buffer, 100 units of T4 DNA ligase was added, and ligation was carried out at 4° C. for 18 hours.

Figure 24:
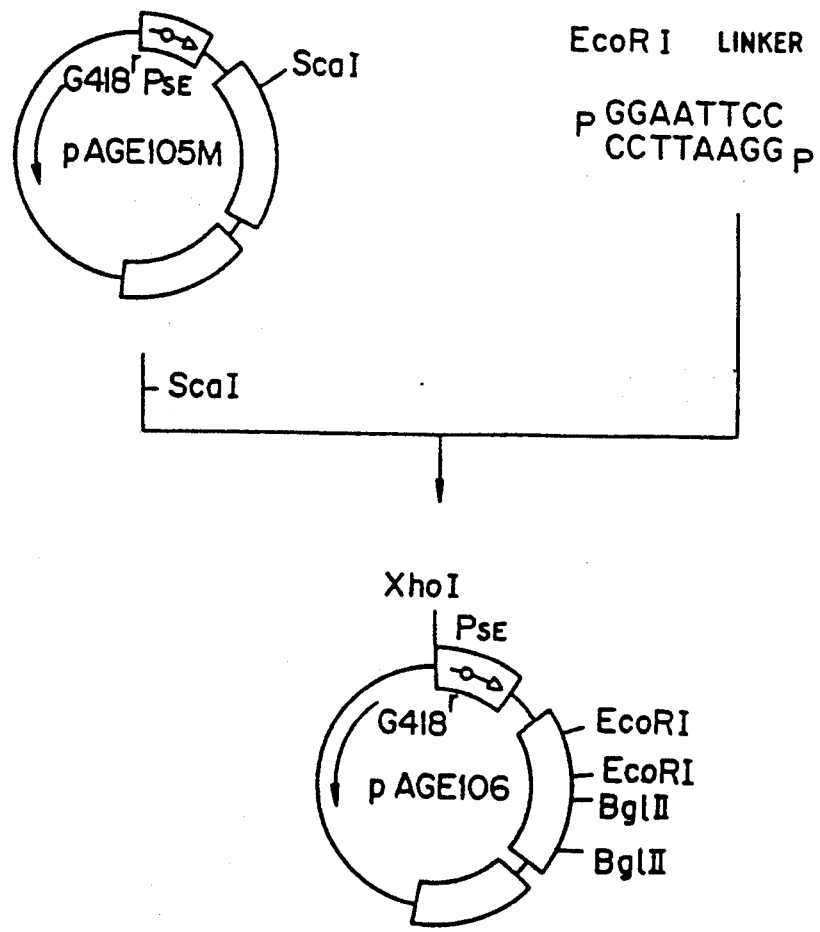
FIG. 24 shows the construction scheme for the plasmid pAGE106.

The recombinant plasmid mixture obtained was used to transform *Escherichia coli* MM294 and Km-resistant strains were obtained. The plasmid DNA isolated from one of these transformant strains was named pAGE106. Structural analysis by restriction enzyme digestion confirmed that pAGE106 had the desired structure (cf. FIG. 24).

(3) Construction of t-PA expression plasmid pSE1-PA1-5:

About 2 µg of the pAGE106 DNA obtained as described above was dissolved in 30 µl of Y-0 buffer, 12 units of KpnI was added, and digestion was conducted at 37° C. for 2 hours. Then, 1.5 µl of 2 M NaCl and 10 units of BamHI were added and digestion was further carried out at 37° C. for 2 hours. After 10-minute heat treatment at 65° C., a DNA fragment about 5.0 kb in size was purified by the AFT method. Separately, about 3 µg of the ptPA7 plasmid DNA obtained in Reference Example 1 was dissolved in 30 µl of Y-0 buffer containing 75 mM NaCl, 12 units of FokI and 12 units of EcoRI were added, and digestion was effected at 37° C. for 2 hours. After 10-minute heat treatment at 65° C., a DNA fragment about 0.7 kb in size was purified by the AFT method. Furthermore, the following two synthetic DNAs (21 bases and 21 bases) were synthesized using an Applied Biosystems model 380A DNA synthesizer and individually 5'-phosphorylated by the method mentioned in Example 1.

5'-GATCCATGGATGCAATGAAGA-3' (21 bases)

3'-GTACCTACGTTACTTCTCTCC-5' (21 bases)

The thus-obtained pAGE106-derived 5.0 kb DNA fragment (about 0.1 µg) and ptPA7-derived 0.7 kb DNA fragment (about 0.1 µg) as well as the pTA4-derived 1.4 kb EcoRI-KpnI fragment (about 0.05 µg) prepared in Reference Example 8 and the two 5'-phosphorylated synthetic DNAs obtained as described above (each 1 picomole) were dissolved in 20 µl of T4 ligase buffer, 50 units of T4 DNA ligase was added, and ligation was carried out at 4° C. for 18 hours.

Figure 25:
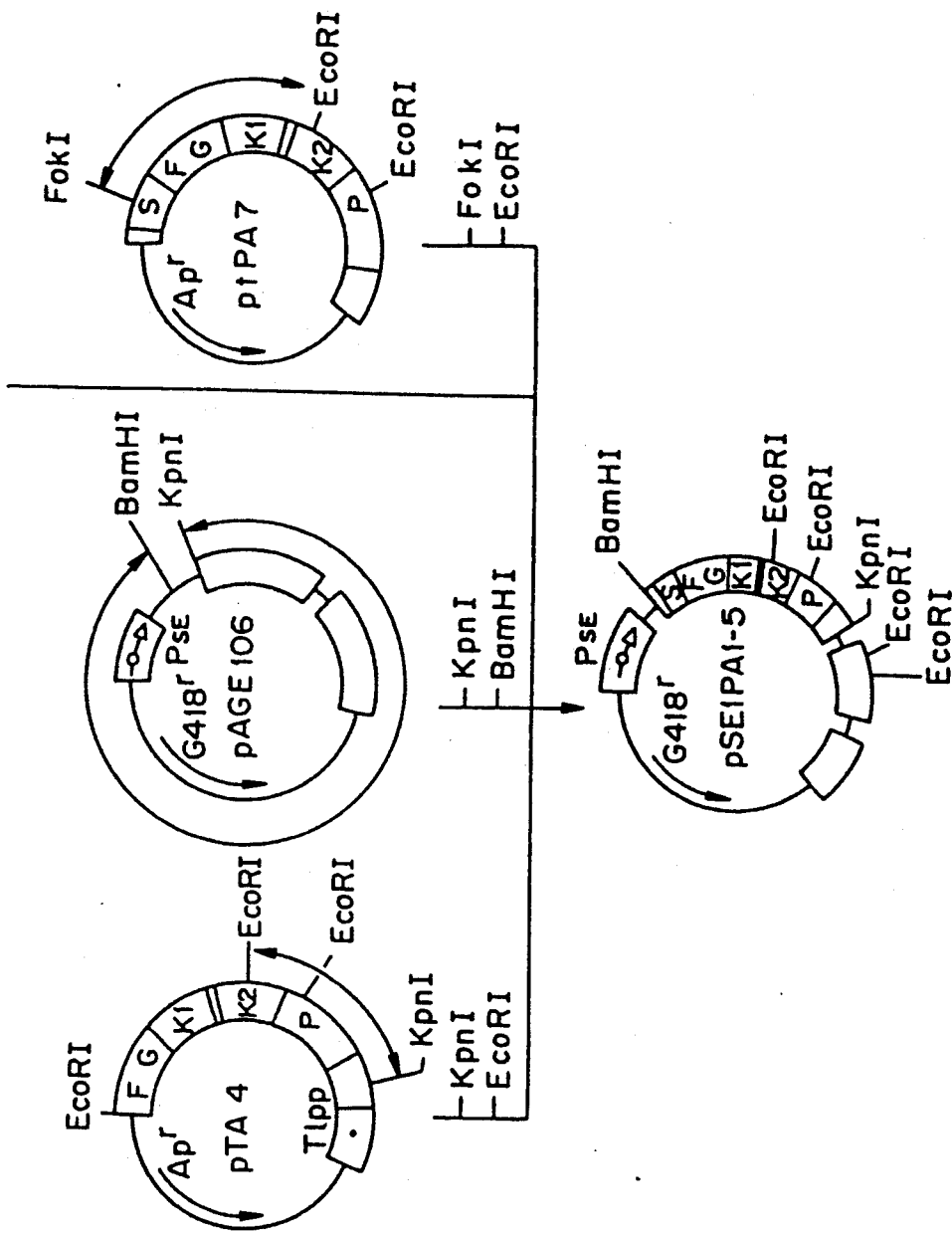
FIG. 25 shows the construction scheme for the plasmid pSE1PA1-5.

The recombinant plasmid mixture obtained was used to transform *Escherichia coli* MM294 and Km-resistant strains were obtained. The plasmid DNA isolated from one of these transformant strains was named pSE1PA1-5. Structural analysis by restriction enzyme digestion as well as sequencing by the dideoxy method using M13 phage confirmed that pSE1PA11-5 had the desired structure (cf. FIG. 25).

(4) Construction of t-PA expression plasmid pSE1-PA1-9:

About 2 μg of the pSE1PA1-5 DNA obtained as described above was dissolved in 30 μl of Y-0 buffer, 12 units of KpnI was added, and digestion was carried out at 37° C. for 2 hours. Then, after addition of 1.5 μl of 2M NaCl and 8 units of HindIII, further digestion was carried out at 37° C. for 2 hours. After 10-minute heat treatment at 65° C., a DNA fragment about 5.0 kb in size was purified by the AFT method. Separately, about 2 μg of the pSE1PA1-5 DNA was dissolved in 30 μl of Y-0 buffer, 12 units of KpnI was added, and digestion was effected at 37° C. for 2 hours. Then, 1.0 μl of 2M NaCl and 10 units of NcoI were added and further digestion was effected at 37° C. for 2 hours. After 10-minute heat treatment at 65° C., a DNA fragment about 4.9 kb in size was purified by the AFT method. Furthermore, the following four synthetic DNAs (47 bases, 49 bases, 49 bases and 47 bases; these synthetic DNAs constitute a part of 5'-nontranslational region of the t-PA cDNA) were synthesized using an Applied Biosystems model 380A DNA synthesizer and individually 5'-phosphorylated in the same manner as mentioned in Example 1.

digestion with DraI. After 10-minute heat treatment at 65° C., two DNA fragments, namely a HindIII-DraI fragment about 1.55 kb in size and a DraI-HindIII fragment about 1.1 kb in size, were purified by the AFT method. Separately, 20 picomoles of a HindIII linker (CAAGCTTG; Collaborative Research) was 5'-phosphorylated by the method mentioned in Example 1.

The thus-obtained pUC19-derived 1.55 kb DNA fragment (0.03 μg) and 1.1 kb DNA fragment (0.03 μg) were dissolved, together with 1 picomole of the 5'-phosphorylated HindIII linker, in 20 μl of T4 ligase buffer, 50 units of T4 DNA ligase was added, and ligation was carried out at 4° C. for 18 hours.

Figure 27:
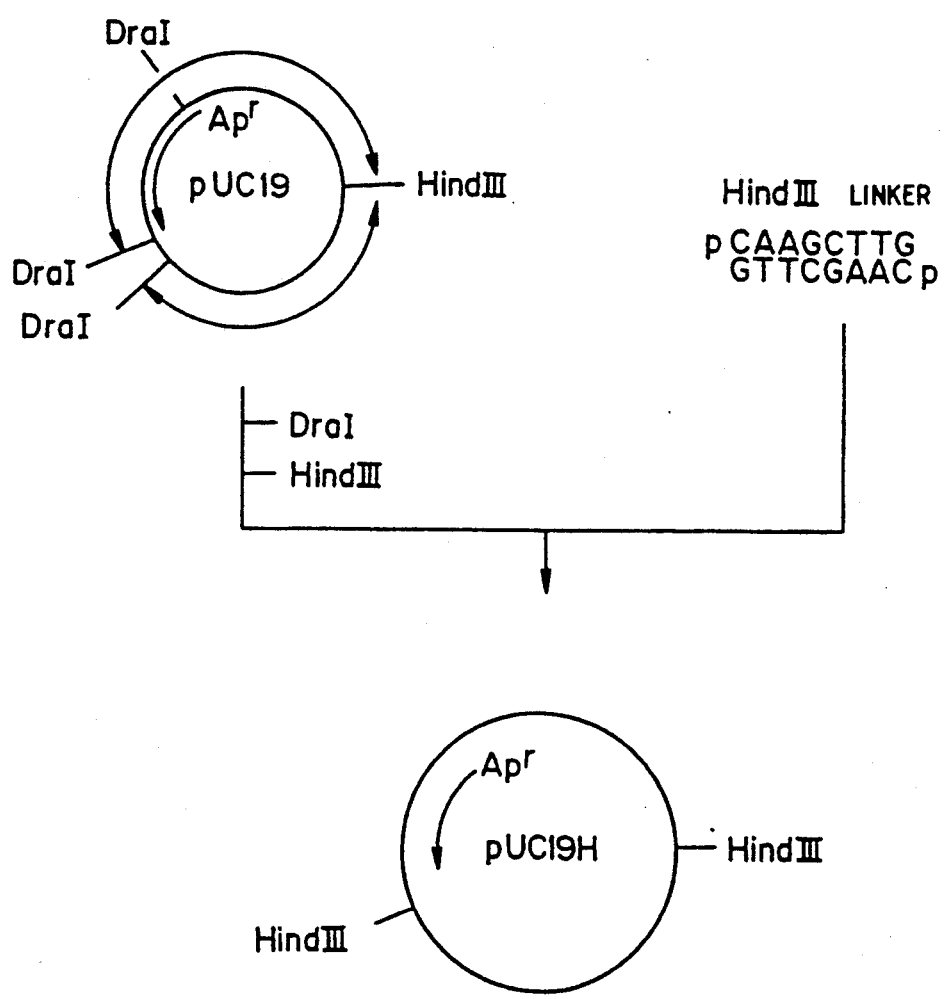
FIG. 27 shows the construction scheme for the plasmid pUC19H.

The recombinant plasmid mixture obtained was used to transform *Escherichia coli* MM294 and Ap-resistant strains were obtained. The plasmid DNA isolated from one of these transformants was named pUC19H. Structural analysis by restriction enzyme digestion confirmed that pUC19H had the desired structure (cf. FIG. 27).

(6) Construction of recombinant plasmid pSE1PA1-9A (insertion of Ap resistance gene into pSE1PA1-9):

About 2 μg of the pUC19H plasmid DNA obtained as described above was dissolved in 30 μl of Y-50 buffer, 8 units of HindIII and 8 units of PvuII were added, and digestion was conducted at 37° C. for 2 hours. Following phenol-chloroform exatraction, a DNA fragment was recovered by ethanol precipitation. This DNA fragment was dissolved in a total volume of 40 μl of polymerase buffer, 6 units of the Klenow fragment was added, and reaction was carried out at 15° C. for 1 hour for conversion of the HindIII cohesive end to a blunt end. After 10-minute heat treatment at 65° C., a

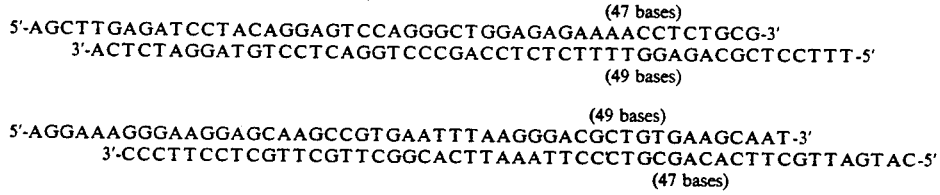

(47 bases)
5'-AGCTTGAGATCCTACAGGAGTCCAGGGCTGGAGAGAAAACCTCTGCG-3'
3'-ACTCTAGGATGTCCTCAGGTCCCGACCTCTCTTTTGGAGACGCTCCTTT-5'
(49 bases)

(49 bases)
5'-AGGAAAGGGAAGGAGCAAGCCGTGAATTTAAGGGACGCTGTGAAGCAAT-3'
3'-CCCTTCCTCGTTCGTTCGGCACTTAAATTCCCTGCGACACTTCGTTAGTAC-5'
(47 bases)

The thus-obtained pSE1PA1-5-derived 5.0 kb DNA fragment (about 0.1 μg) and pSE1PA1-5-derived 4.9 kb DNA fragment (about 0.1 μg) as well as the four 5'-phosphorylated synthetic DNAs (each 1 picomole) were dissolved in 20 μl of T4 ligase buffer, 50 units of T4 DNA ligase was added, and ligation was carried out at 4° C. for 18 hours.

The recombinant plasmid mixture obtained was used to transform *Escherichia coli* MM294 to give Km-resistant strains. The plasmid DNA isolated from one of these transformant strains was named pSE1PA1-9. Structural analysis by restriction enzyme digestion and sequencing by the dideoxy method using M13 phage confirmed that pSE1PA1-9 had the desired structure (cf. FIG. 26).

(5) Construction of recombinant plasmid pUC19H (rendering Ap resistance gene portable):

*Escherichia coli* HB101 harboring the plasmid DNA pUC19 constructed by Norrander et al. [Norrander, J. et al.: Gene, 26, 101 (1983); the pUC19 plasmid DNA is available from Takara Shuzo] was cultured and the pUC19 DNA was prepared from cultured cells by the conventional method. About 2 μg of the pUC19 DNA obtained was dissolved in 30 μl of Y-50 buffer, 10 units of HindIII and 1 unit of DraI were added, and digestion was performed at 37° C. for 1 hour. This reaction resulted in complete digestion with HindIII and partial DNA fragment about 1.4 kb in size was purified by the AFT method. Separately, about 2 μg of the t-PA expression plasmid pSE1PA1-9 obtained as described above was dissolved in 30 μl of Y-150 buffer, 8 units of XhoI and 8 units of EcoRV were added, and digestion was effected at 37° C. for 2 hours. After 10-minute heat treatment at 65° C., a DNA fragment about 5.9 kb in size was purified by the AFT method. Further, separately, about 3 μg of the pAGE28 plasmid prepared as described above was dissolved in 30 μl of Y-150 buffer, 10 units of XhoI and 10 units of EcoRV were added, and digestion was carried out at 37° C. for 2 hours. After 10-minute heat treatment at 65° C., a DNA fragment about 0.85 kb in size was purified by the AFT method.

The thus-obtained pUC19H-derived 1.4 kb DNA fragment (about 0.1 μg), pSE1PA1-9-derived 5.9 kb DNA fragment (about 0.1 μg) and pAGE28-derived 0.85 kb DNA fragment (about 0.05 μg) were dissolved in 20 μl of T4 ligase buffer, 100 units of T4 DNA ligase was added, and ligation was carried out at 4° C. for 18 hours.

Figure 28:
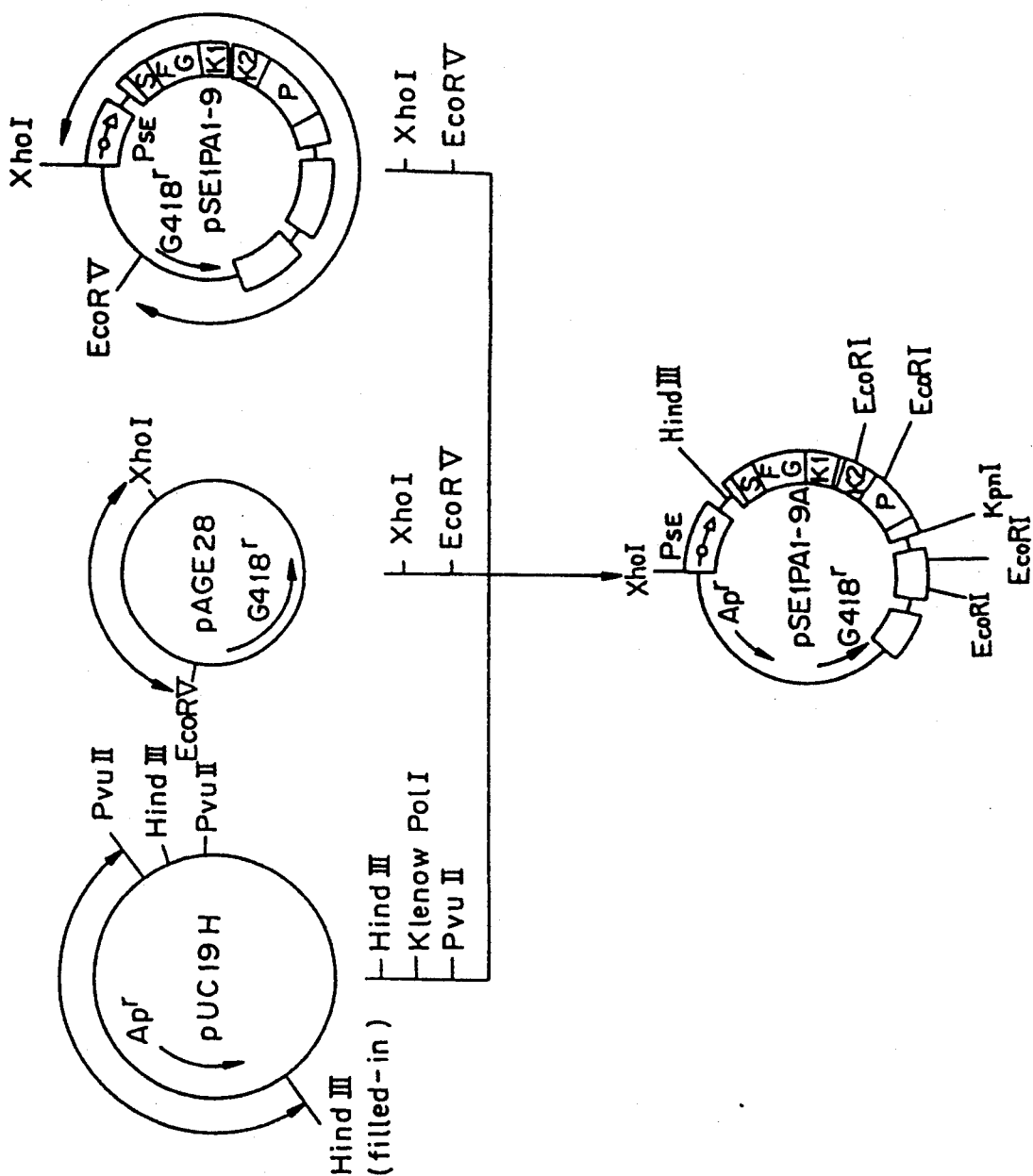
FIG. 28 shows the construction scheme for the plasmid pSE1PA1-9A.

The recombinant plasmid mixture obtained was used to transform *Escherichia coli* MM294 and strains resistant to both Ap and Km were obtained. The plasmid DNA isolated from one of these transformant strains was named pSE1PA1-9A. Structural analysis by restriction enzyme digestion confirmed that it had the desired structure (cf. FIG. 28).

A microorganism harboring the plasmid DNA pSE1-PA1-9A has been deposited, since Sep. 3, 1987, with the Fermentation Research Institute under the designation *Escherichia coli* EhPA1-9A (deposit number FERM BP-1460) in accordance with the Budapest Treaty.

(7) Construction of recombinant plasmid pSE1dhfr1A:

About 2 μg of the pAGE106 plasmid DNA obtained as described above was dissolved in 30 μl of Y-50 buffer, 12 units of Asp718 (Boehringer Mannheim), and digestion was effected at 37° C. for 2 hours. After phenolchloroform extraction, a DNA fragment was recovered by ethanol precipitation. This DNA fragment was dissolved in a total volume of 40 μl of polymerase buffer, 6 units of the Klenow fragment was added, and reaction was carried out at 15° C. for 1 hour for conversion of the Asp718 cohesive ends to blunt ends. Then, after phenol-chloroform extraction, the DNA fragment was recovered by ethanol precipitation and dissolved in a total volume of 30 μl of Y-150 buffer, 10 units of MluI was added, and digestion was effected at 37° C. for 2 hours. After 10-minute heat treatment at 65° C., a DNA fragment about 3.3 kb in size was purified by the AFT method.

Separately, about 3 μg of the pSV2dhfr plasmid DNA [Subramani et al.: Mol. Cell. Biol., 1, 854 (1981)] containing the dhfr gene was dissolved in 30 μl of Y-100 buffer, 12 units of BglII was added, and digestion was effected at 37° C. for 2 hours. After phenol-chloroform extraction, a DNA fragment was recovered by ethanol precipitation. This DNA fragment was dissolved in a total volume of 40 μl of polymerase buffer, 6 units of the Klenow fragment was added, and reaction was performd at 15° C. for 1 hour for converting the BglII cohesive ends to blunt ends. After phenol-chloroform extraction, the DNA fragment was recovered by ethanol precipitation and dissolved in a total volume of 30 μl of Y-100 buffer, 12 units of HindIII was added, and digestion was conducted at 37° C. for 2 hours. After 10-minute heat treatment at 65° C., a DNA fragment about 0.75 kb in size was purified by the AFT method. Further, separately, about 3 μg of the pSE1PA1-9A plasmid DNA obtained as described above was dissolved in 30 μl of Y-100 buffer, 12 units of HindIII was added, and digestion was carried out at 37° C. for 2 hours. Then, 1.5 μl of 1M NaCl and 12 units of MluI were added, and digestion was further conducted at 37° C. for 2 hours. After 10-minute heat treatment at 65° C., a DNA fragment about 2.9 kb in size was purified by the AFT method.

The thus-obtained pAGE106-derived DNA fragment (about 0.1 μg), pSV2dhfr-derived DNA fragment (about 0.03 μg) and pSE1PA1-9A-derived DNA fragment (about 0.1 μg) were dissolved in 20 μl of T4 ligase buffer, 100 units of T4 DNA ligase was added, and ligation was carried out at 4° C. for 18 hours.

Figure 29:
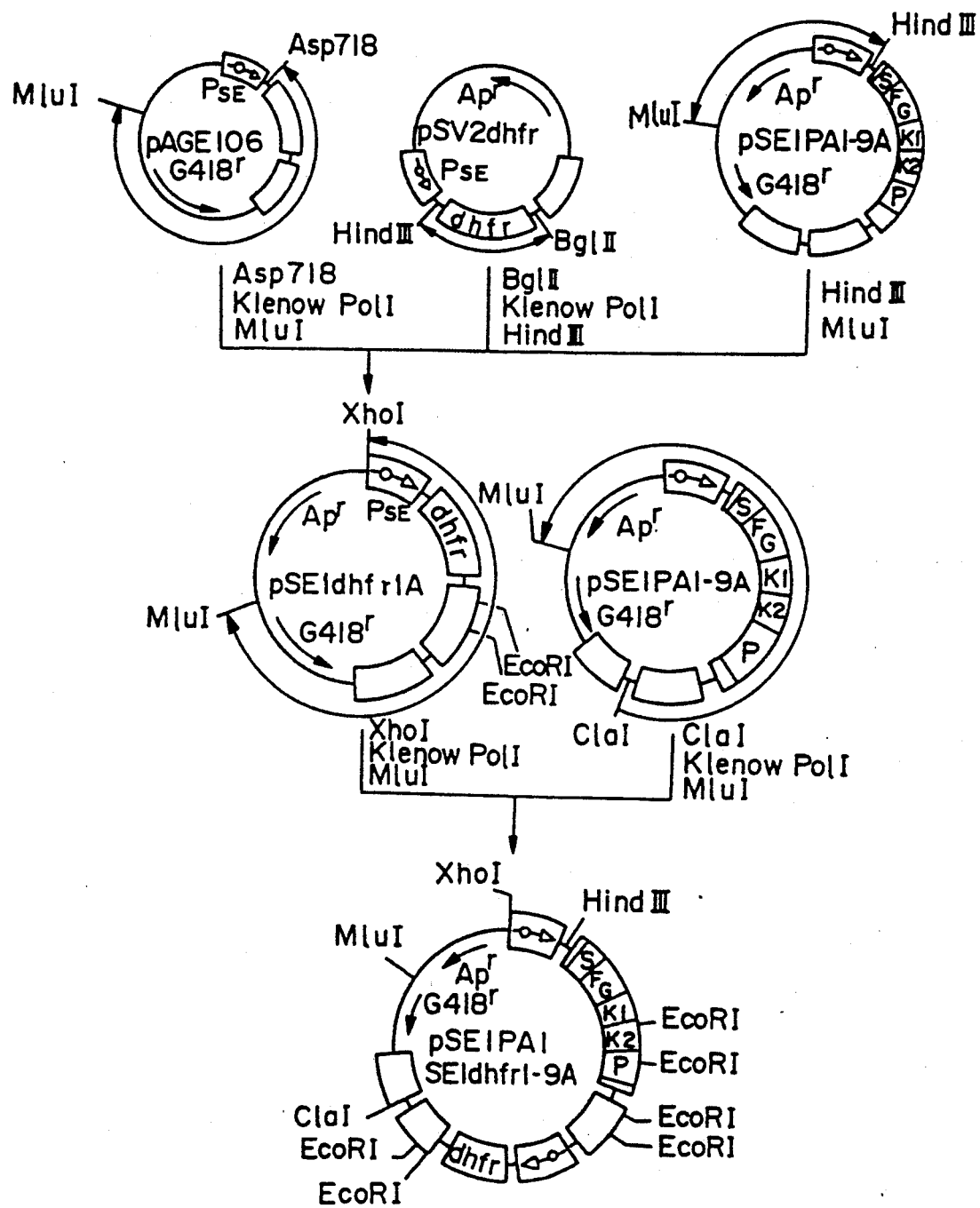
FIG. 29 shows the construction scheme for the plasmid pSE1PA1SE1dhfr1-9A.

The recombinant plasmid mixture obtained was used to transform *Escherichia coli* MM294 and Ap-resistant strains were obtained. The plasmid DNA isolated from one of these transformant strains was named pSE1dhfr1A. Structural analysis by restriction enzyme digestion confirmed that it had the desired structure (cf. FIG. 29).

(8) Construction of recombinant plasmid pSE1PA1-SE1dhfr1-9A:

About 3 μg of the pSE1dhfr1A plasmid DNA obtained as described above was dissolved in 30 μl of Y-100 buffer, 12 units of XhoI was added, and digestion was effected at 37° C. for 2 hours. After phenol-chloroform extraction, a DNA fragment was recovered by ethanol precipitation. This DNA fragment was dissolved in a total volume of 40 μl of polymerase buffer, 6 units of the Klenow fragment was added, and reaction was carried out at 15° C. for 1 hour, whereby the XhoI cohesive ends were converted to blunt ends. Then, after phenol-chloroform extraction, the DNA was recovered by ethanol precipitation and dissolved in a total volume of 30 μl of Y-150 buffer, 12 units of MluI was added, and digestion was performed at 37° C. for 2 hours. After 10 minute heat treatment at 65° C., a DNA fragment about 4.4 kb in size was purified by the AFT method.

Separately, about 3 μg of the pSE1PA1-9A plasmid DNA obtained as described above was dissolved in 30 μl of Y-50 buffer, 12 units of ClaI was added, and digestion was effected at 37° C. for 2 hours. After phenol-chloroform extraction, a DNA fragment was recovered by ethanl precipitation. This DNA fragment was dissolved in a total volume of 40 μl of polymerase buffer, 6 units of the Klenow fragment was added, and reaction was carried out at 15° C. for 1 hour, whereby the ClaI cohesive ends were rendered blunt. Then, after phenol-chloroform extraction, the DNA fragment was recovered by ethanol precipitation and dissolved in 30 μl of Y-150 buffer, 12 units of MluI was added, and digestion was conducted at 37° C. for 2 hours. After 10 minute heat treatment at 65° C., a DNA about 6.75 kb in size was purified by the AFT method.

The thus-obtained pSE1dhfr1A-derived DNA fragment (about 0.1 μg) and pSE1PA1-9A-derived DNA fragment (about 0.1 μg) were dissolved in 20 μl of T4 ligase buffer, 100 units of T4 DNA ligase was added, and ligation was carried out at 4° C. for 18 hours.

The recombinant plasmid mixture obtained was used to transform *Escherichia coli* MM294 and Ap-resistant strains were obtained. The plasmid DNA isolated from one of these transformant strains was named pSE1PA1-SE1dhfr1-9A. Structural analysis by restriction enzyme digestion confirmed that it had the desired structure (cf. FIG. 29).

REFERENCE EXAMPLE 10

Figure 30:
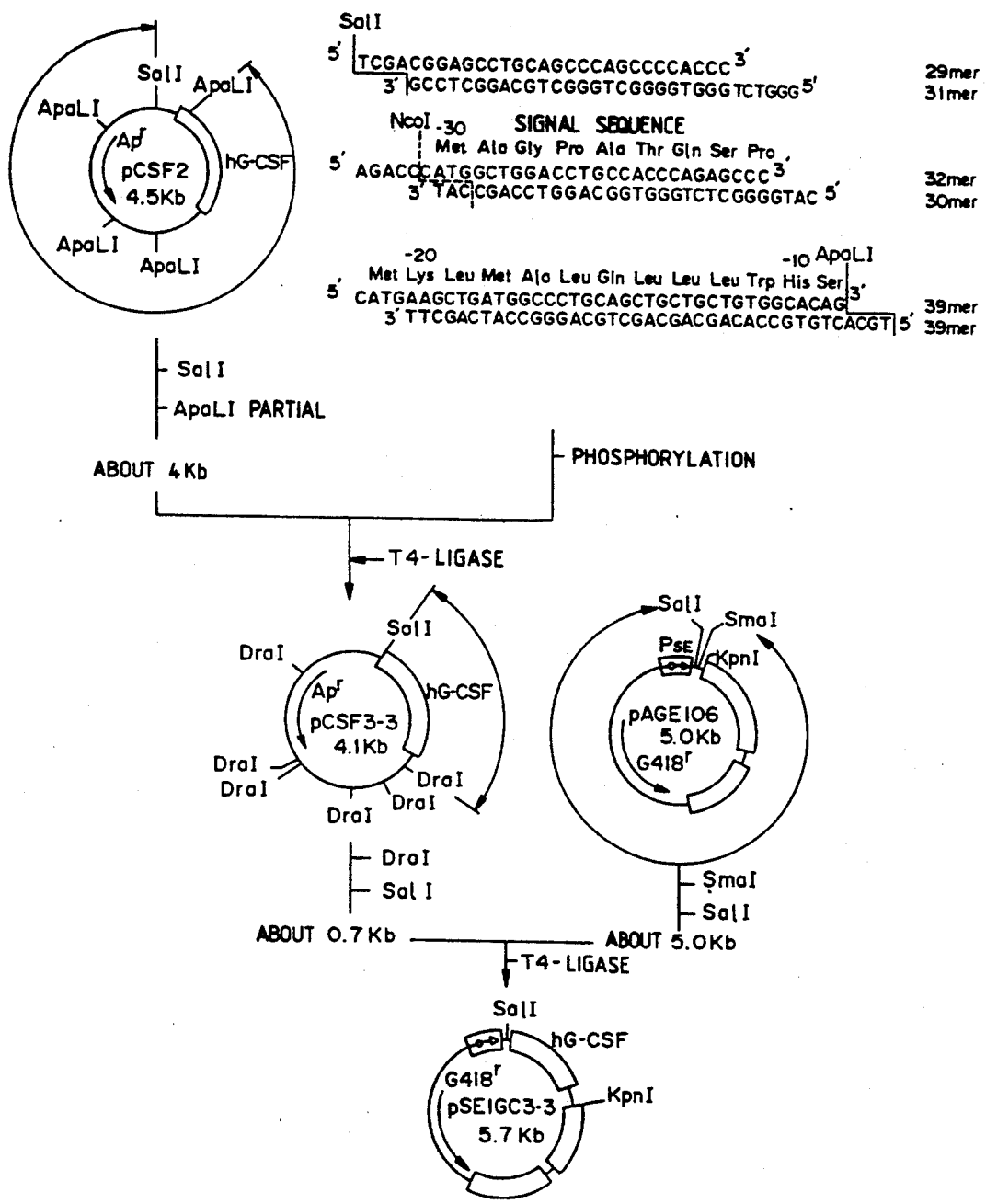
FIG. 30 shows the construction scheme for the plasmid pSE1GC3-3.
Figure 31:
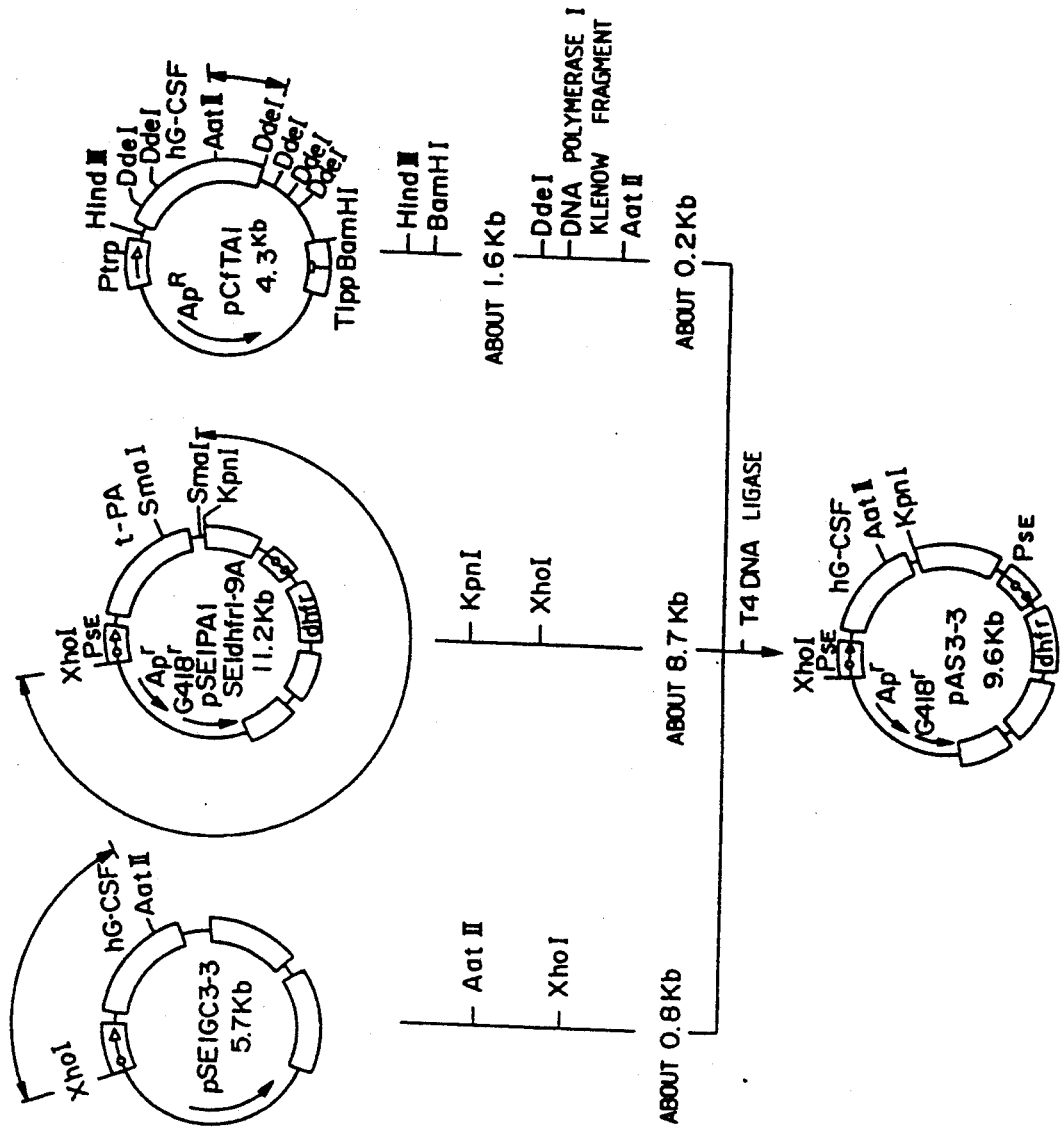
FIG. 31 shows the construction scheme for the plasmid pAS3-3.

Construction of hG-CSF expression plasmid pAS3-3: (Cf. FIG. 30 and FIG. 31)

(1) Consturction of recombinant plasmid pCSF3-3:

A 2-μg portion of pCSF2 obtained in Reference Example 4 was dissolved in 20 μl of Y-150 buffer, 10 units of the restriction enzyme SalI was added, and digestion was effected at 37° C. for 2 hours. Then, 5 units of the restriction enzyme ApaLI was added and partial cleavage was effected at 37° C. for 10 minutes. About 1.5 μg of a DNA fragment about 4.0 kb in size (SalI-ApaLI fragment) was isolated from the reaction mixture by the LGT method.

Separately, for preparing a cDNA containing the whole hG-CSF translation region, the following three DNA linkers were synthesized:

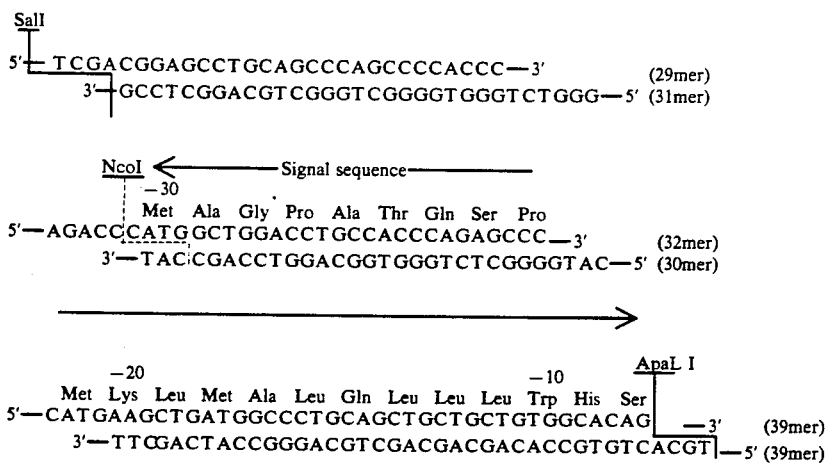

The above single-strand DNAs, namely the 29-mer, 31-mer, 32-mer, 30-mer and 39-mers (two kinds), were synthesized using an Applied Biosystems model 380A DNA synthesizer. The 29-mer and 31-mer complementary to each other (each 20 picomoles) were dissolved in 40 μl of T4 kinase buffer, 6 units of T4 polynucleotide kinase was added, and phosphorylation was effected at 37° C. for 60 minutes. The 32-mer and 30-mer complementary to each other as well as the two 39-mers complementary to each other were phosphorylated in the same manner.

The pCSF2-derived SalI-ApaLI fragment obtained as described above (about 4.0 kb; 0.1 μg) was dissolved in 30 μl of T4 DNA ligase buffer, the above three DNA linkers (each 2 picomoles) were added and, after further addition of 400 units of T4 DNA ligase, ligation was conducted at 4° C. for 18 hours.

The reaction mixture was used to transform Escherichia coli HB101 and Ap-resistant strains were obtained. The plasmid DNA isolated from one of the transformant strains was subjected to structural analysis by restriction enzyme cleavage. It was thus confirmed that the plasmid was the desired one, namely pCSF3-3.

(2) Construction of hG-CSF expression plasmid pSE1GC3-3:

pCSF3-3 (3 μg) obtained as described in the preceding section was dissolved in 40 μl of Y-0 buffer, 10 units of the restriction enzyme DraI was added, and digestion was conducted at 37° C. for 2 hours. NaCl was added to an NaCl concentration of 150 mM, 10 units of the restriction enzyme SalI was added, and cleavage was further effected at 37° C. for 2 hours. About 0.6 μg of a DNA fragment about 0.7 kb in size (DraI-SalI fragment) was isolated from the reaction mixture by the LGT method.

Separately, 2 μg of pAGE106 obtained in Reference Example 9 was dissolved in 30 μl of Y-0 buffer, 10 units of SmaI was added, and cleavage was effected at 37° C. for 2 hours. Then, NaCl was added to a final NaCl concentration of 150 mM and after further addition of 10 units of the restriction enzyme SalI, cleavage was carried out at 37° C. for 2 hours. About 1.5 μg of a DNA fragment about 5.0 kb in size (SmaI-SalI fragment) was recovered from the reaction mixture by the LGT method.

Then, about 0.6 μg of the pCSF3-3-derived DraI-SalI fragment [about 0.7 kb] and about 1.0 μg of the pAGE106-derived SmaI-SalI fragment (about 5.0 kb), each obtained as above, were dissolved in 25 μl of T4 DNA ligase buffer, 400 units of T4 DNA ligase was added, and ligation was carried out at 4° C. for 18 hours.

The reaction mixture thus obtained was used to transform Escherichia coli HB101 and Ap-resistant strains were obtained. The plasmid isolated from one of these transformants was subjected to structural analysis by restriction enzyme cleavage. As a result, it was confirmed that it was the desired plasmid DNA, namely pSE1GC3-3.

(3) Construction of hG-CSF expression plasmid pAS3-3:

pCfTA1 (5 μg; cf. Reference Example 15) was dissolved in 50 μl of Y-100 buffer, 10 units each of the restriction enzymes HindIII and BamHI were added, and digestion was conducted at 37° C. for 2 hours. From the reaction mixture was obtained 1 μg of a DNA fragment about 1.6 kb in size (HindIII-BamHI fragment) by the LGT method. This 1.6 kb DNA fragment [1 μg] was dissovled in 50 μl of Y-100 buffer, 10 units of the restriction enzyme DdeI (Toyobo) was added, and digestion was effected at 37° C. for 2 hours. After phenol-chloroform extraction, DNA was recovered by ethanol precipitation. It was dissolved in 30 μl of Klenow buffer, 2 units of DNA polymerase I Klenow fragment was added, and reaction was carried out at 37° C. for 1 hour. After inactivation of DNA polymerase I Klenow fragment by 10 minute heat treatment at 68° C., DNA was recovered by ethanol precipitation. The DNA recovered was dissolved in 20 μl of K-50 buffer, 10 units of the restriction enzyme AatII (Toyobo) was added, and cleavage was carried out at 37° C. for 2 hours. About 0.1 μg of a DNA fragment about 0.2 kb in size [DdeI (blunt end)-AatII fragment] was obtained from the reaction mixture by the LGT method.

Separately, 2 μg of pSE1GC3-3 obtained as described in the proceding section was dissolved in 20 μl of K-50 buffer, 10 units of the restriction enzyme AatII (Toyobo) was added, and digestion was performed at 37° C. for 2 hours. Then, 10 units of the restriction enzyme XhoI was added and digestion was further conducted at 37° C. for 2 hours. About 0.1 μg of a DNA fragment about 0.8 kb in size (AatII-XhoI fragment) was obtained from the reaction mixture by the LGT method.

Separately 2 μg of pSE1PA1SE1dhfr1-9A obtained in Reference Example 9 was dissolved in 20 μl of Y-0 buffer, 10 units of the restriction enzyme SmaI was added, and digestion was effected at 37° C. for 2 hours. Then, NaCl was added to an NaCl concentration of 100 mM, 10 units of the restrction enzyme XhoI was added, and digestion was further conducted at 37° C. for 2 hours. About 1 µg of a DNA fragment about 8.7 kb in size (SmaI-XhoI fragment) was obtained from the reaction mixture by the LGT method.

The pCfTA1-derived DdeI (blunt end)-AatII fragment (about 0.2 kb; about 0.1 µg), pSE1GC3-3-derived AatII-XhoI fragment (about 0.8 kb; about 0.1 µg) and pSE1PA1SE1dhfr1-9A-derived SmaI-XhoI fragment (about 8.7 kb; about 1 µg) respectively obtained in the above manner were dissolved in 30 µl of T4 DNA ligase buffer, 400 units of T4 DNA ligase was added, and ligation was carried out at 4° C. for 18 hours. The resultant reaction mixture was used to transform *Escherichia coli* HB101 and Ap-resistant strains were obtained. The plasmid isolated from one of these transformant strains was analyzed for its structure by restriction enzyme cleavage and, as a result, it was confirmed that it was the plasmid DNA having the desired structure, namely pAS3-3.

REFERENCE EXAMPLE 11

Construction of recombinant plasmid pUKA2:

The pUK1 DNA was prepared by a conventional method from *Escherichia coli* C600 SF8 harboring the human pro-UK cDNA-containing plasmid pUK1 obtained in Reference Example 2. About 2 µg of the pUK1 DNA obtained was dissolved in 30 µl of Y-100 buffer, 8 units of the restriction enzyme NcoI and 8 units of StuI were added, and digestion was carried out at 37° C. for 2 hours. After 10-minute heat treatment at 65° C., a DNA fragment about 1.2 kb in size was purified by the AFT method. Separately, about 2 µg of the pTrS33 plasmid DNA obtained in Reference Example 5 was dissolved in 30 µl of 10 mM Tris-HCl (pH 7.5)

containing 25 mM KCl, 7 mM MgCl2 and 6 mM 2-mercaptoethanol (hereinafter such buffer will be referred to as "K-25 buffer"), 16 units of the restriction enzyme SmaI was added, and digestion was performed at 30° C. for 2 hours. Then, 1.5 µl of 1M NaCl and 10 units of NcoI were added, and digestion was further conducted at 37° C. for 2 hours. After 10-minute heat treatment at 65° C., a DNA fragment about 2.85 kb in size was purified by the AFT method.

The thus-obtained pUK1-derived 1.2 kb DNA fragment (about 0.05 µg) and pTrS33-derived 2.85 kb DNA fragment (about 0.1 µg) were dissolved in a total volume of 20 µl of T4 ligase buffer, 100 units of T4 DNA ligase was added, and ligation was carried out at 4° C. for 18 hours.

The recombinant plasmid mixture obtained was used to transform *Escherichia coli* MM294 and Ap-resistant strains were obtained. The DNA isolated from one of these transformant strains was named pUKA2 and analyzed for its structure by restriction enzyme digestion and it was confirmed that pUKA2 had the desired structure (cf. FIG. 32).

REFERENCE EXAMPLE 12

Construction of recombinant plasmid pUKB101:

About 2 µg of the pUKA2 plasmid DNA obtained as described above was dissolved in 30 µl of Y-0 buffer, 12 units of the restriction enzyme KpnI was added, and digestion was carried out at 37° C. for 2 hours. Then, 1.5 µl of 2M NaCl and 10 units of NcoI were added, and digestion was further conducted at 37° C. for 2 hours.

After 10-minute heat treatment at 65° C., a DNA fragment about 1.2 kb in size was purified by the AFT method. Separately, about 2 µg of the pTrS33 plasmid DNA obtained in Reference Example 5 was dissolved in 30 µl of K-25 buffer, 16 units of SmaI was added, and digestion was performed at 30° C. for 2 hours. Then, 1.5 µl of 2M NaCl and 10 units of PstI were added, and digestion was further conducted at 37° C. for 2 hours. After 10-minute heat treatment at 65° C., a DNA fragment about 1.15 kb in size was purified by the AFT, method. Further, separately, about 2 µg of the pTerm2 plasmid DNA obtained in Reference Example 6 was dissolved in 30 µl of Y-0 buffer, 12 units of KpnI was added, and digestion was performed at 37° C. for 2 hours. Then, 1.5 µl of 2M NaCl and 10 units of PstI were added, and digestion was further carried out at 37° C. for 2 hours. After 10-minute heat treatment at 65° C., a DNA fragment about 1.7 kb in size was purified by the AFT method. In addition, the following two synthetic DNAs (41-mer and 45-mer) were synthesized using an Applied Biosystems model 380A DNA synthesizer.

5'-GGGAATGGTCACTTTTACCGAG-
GAAAGGCCAGCACTGACAC-3' (42 mer)

3'-CCCTTACCAGT-
GAAAATGGCTCCTTTCCGGTCGT-
GACTGTGGTAC-5' (45 mer)

These synthetic DNAs (20 picomoles each) were individually phosphorylated at the 5' end by carrying out phosphorylation in 20 µl of T4 kinase buffer in the presence of 5 units of T4 polynucleotide kinase at 37° C. for 30 minutes.

The thus-obtained pUKA2-derived 1.2 kb DN fragment (about 0.05 µg), pTrS33-derived 1.15 kb DNA fragment (about 0.05 µg), pTerm2-derived 1.7 kb DNA fragment (about 0.05 µg) and two 5'-phosphorylated synthetic DNAs (1 picomole each) were dissolved in a total volume of 20 µl of T4 ligase buffer, 300 units of T4 DNA ligase was added, and ligation was carried out at 4° C. for 18 hours.

Figure 33:
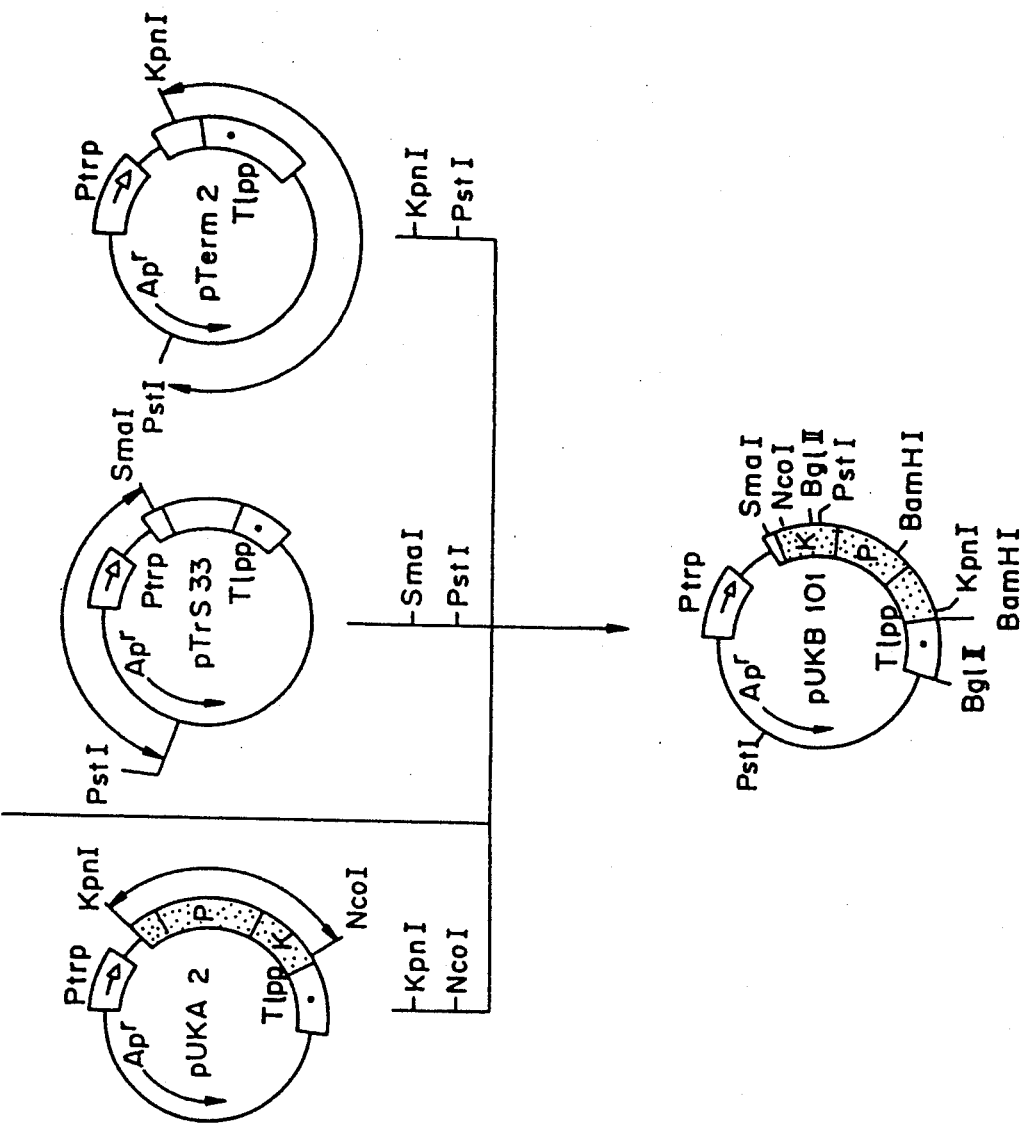
FIG. 33 shows the construction scheme for the plasmid pUKB101.

The recombinant plasmid mixture obtained was used to transform *Escherichia coli* MM294 and Ap-resistant strains were obtained. The plasmid DNA isolated from one of these transformants were named pUKB101. Structural analysis by restriction enzyme digestion and base sequence determination by the M13 dideoxy sequencing method confirmed that pUKB101 had the desired structure (cf. FIG. 33).

REFERENCE EXAMPLE 13

Construction of human pro-UK expression plasmid pSE1UKpro1-1A:

(1) Construction of recombinant plasmid pUKF2:

About 3 µg of the pUK11 plasmid DNA obtained in Reference Example 3 was dissolved in 30 µl of Y-100 buffer, 12 units of NcoI and 12 units of HindIII were added, and digestion was carried out at 37° C. for 2 hours. After 10-minute heat treatment at 65° C., a DNA fragment about 0.45 kb in size was purified by the AFT method. Separately, about 2 µg of the pUKA2 plasmid of Y-0 buffer, 10 units of KpnI was added, and digestion was effected at 37° C. for 2 hours. Then, 1.5 µl of 2M NaCl and 10 units of NcoI were added, and digestion was further conducted at 37° C. for 2 hours. After 10-minute heat treatment at 65° C., a DNA fragment about 1.2 kb in size was purified by the AFT method. Further, separately, about 2 µg of the pTerm2 plasmid DNA obtained in Reference Example 6 was dissolved in 30 μl of Y-0 buffer, 10 units of KpnI was added, and digestion was carried out at 37° C. for 2 hours. Then, 1.5 μl of 2M NaCl and 8 units of HindIII were added, and digestion was further performed at 37° C. for 2 hours. After 10-minute heat treatment at 65° C., a DNA fragment about 2.85 kb in size was purified by the AFT method.

The thus-obtained pUK11-derived 0.45 kb DNA fragment (about 0.02 μg), pUKA2-derived 1.2 kb DNA fragment (about 0.05 μg) and pTerm2-derived 2.85 kb fragment (about 0.05 μg) were dissolved in a total volume of 20 μl of T4 ligase buffer, 50 units of T4 DNA ligase was added, and ligation was effected at 4° C. for 18 hours.

Figure 34:
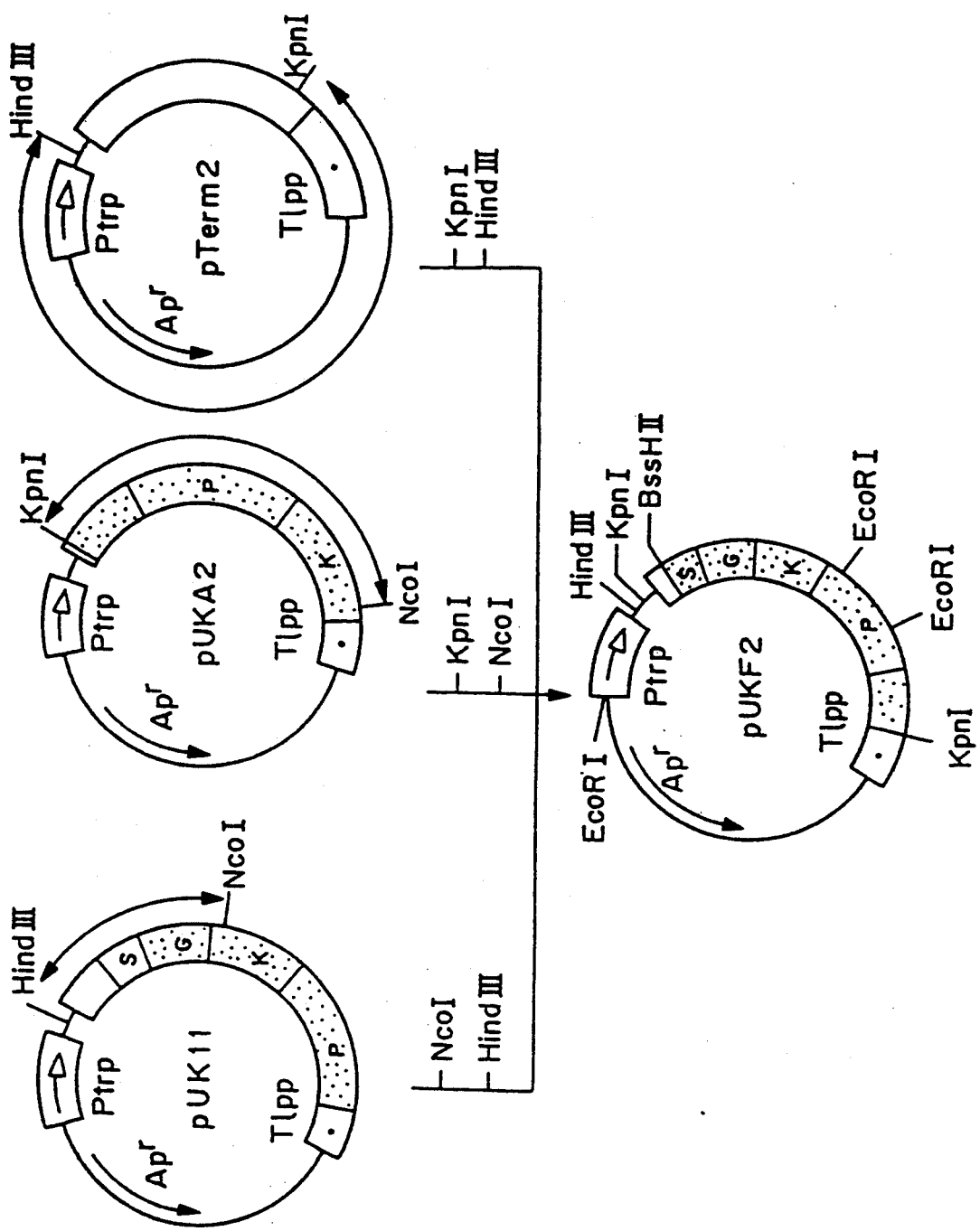
FIG. 34 shows the construction scheme for the plasmid pUKF2.

The recombinant plasmid mixture obtained was used to transform *Escherichia coli* MM294 and Ap-resistant strains were obtained. The plasmid DNA isolated from one of these transformants was named pUKF2. Structural analysis by restriction enzyme digestion confirmed that pUKF2 had the desired structure (cf. FIG. 34).

(2) Construction of recombinant plasmid pUKFpro:

About 2 μg of the pUKF2 plasmid DNA obtained in the above manner was dissolved in 30 μl of Y-0 buffer containing 25 mM NaCl, 10 units of BssHII (new England BioLabs) was added, and digestion was performed at 50° C. for 2 hours. Then, 1.0 μl of 2M NaCl and 10 units of HindIII were added and digestion was further conducted at 37° C. for 2 hours. After 10-minute heat treatment at 65° C., a DNA fragment about 4.3 kb in size was purified by the AFT method. Separately, the following six synthetic DNAs (39-mer, 41-mer, 41-mer, 39-mer, 17-mer, 17-mer) were synthesized and then phosphorylated at the 5' end in the same manner as mentioned above.

rately, about 3 μg of the pUKFpro plasmid DNA obtained as described above was dissolved in 30 μl of Y-0 buffer, 15 units of KpnI was added, and digestion was conducted at 37° C. for 2 hours. Then, 1.5 μl of 2M NaCl and 10 units of HindIII were added and digestion was further conducted at 37° C. for 2 hours. After 10-minute heat treatment at 65° C., a DNA fragment about 1.55 kb in size was purified by the AFT method.

The thus-obtained pSE1PA1-9A-derived 6.3 kb DNA fragment (about 0.1 μg) and pUKFpro-derived 1.55 kb DNA fragment (about 0.05 μg) were dissovled in a total volume of 20 μl of T4 ligase buffer, 100 units of T4 DNA ligase was added, and ligation was carried out at 4° C. for 18 hours.

The recombinant plasmid mixture obtained was used to transform *Escherichia coli* MM294 and Ap-resistant strains were obtained. The plasmid DNA isolated from one of these transformants was named pSE1UKpro1-1A. It was confirmed by structural analysis by restriction enzyme digestion that pSE1UKpro1-1A had the desired structure (cf. FIG. 36).

REFERENCE EXAMPLE 14

1) Isolation of human LT cDNA-containing plasmid pLT1

(1) Preparation of poly(A) RNA from LukII cells:

A poly(A)-containing RNA was prepared from the human lymphoblastoid cell line LukII by the guanidine thiocyanate-lithium chloride method [Cathala et al.: DNA, 2, 329 (1983)] in the following manner.

The human lymphoblastoid cell line LukII [Berish Y. Rubin et al.: Proc. Natl. Acad. Sci. USA, 82, 6637 (1985)] was inoculated into 1 liter of RPMI 1640 medium (Nissui Pharmaceutical) containing 5% fetal bo-

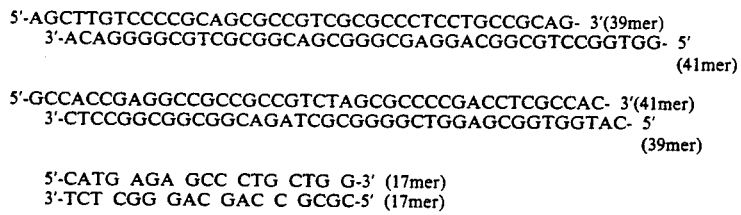

```
5'-AGCTTGTCCCCGCAGCGCCGTCGCGCCCTCCTGCCGCAG- 3'(39mer)
      3'-ACAGGGGCGTCGCGGCAGCGGGCGAGGACGGCGTCCGGTGG- 5'
                                                    (41mer)

5'-GCCACCGAGGCCGCCGCCGTCTAGCGCCCCGACCTCGCCAC- 3'(41mer)
   3'-CTCCGGCGGCGGCAGATCGCGGGGCTGGAGCGGTGGTAC- 5'
                                                (39mer)

5'-CATG AGA GCC CTG CTG G-3'  (17mer)
3'-TCT CGG GAC GAC C GCGC-5'  (17mer)
```

The thus-obtained pUKF2-derived 4.3 kb DNA fragment (about 0.1 μg) and six 5'-phosporylated synthetic DNAs (1 picomole each) were dissolved in a total volume of 20 μl of T4 ligase buffer, 300 units of T4 DNA ligase was added, and ligation was carried out at 4° C. for 18 hours.

Figure 35:
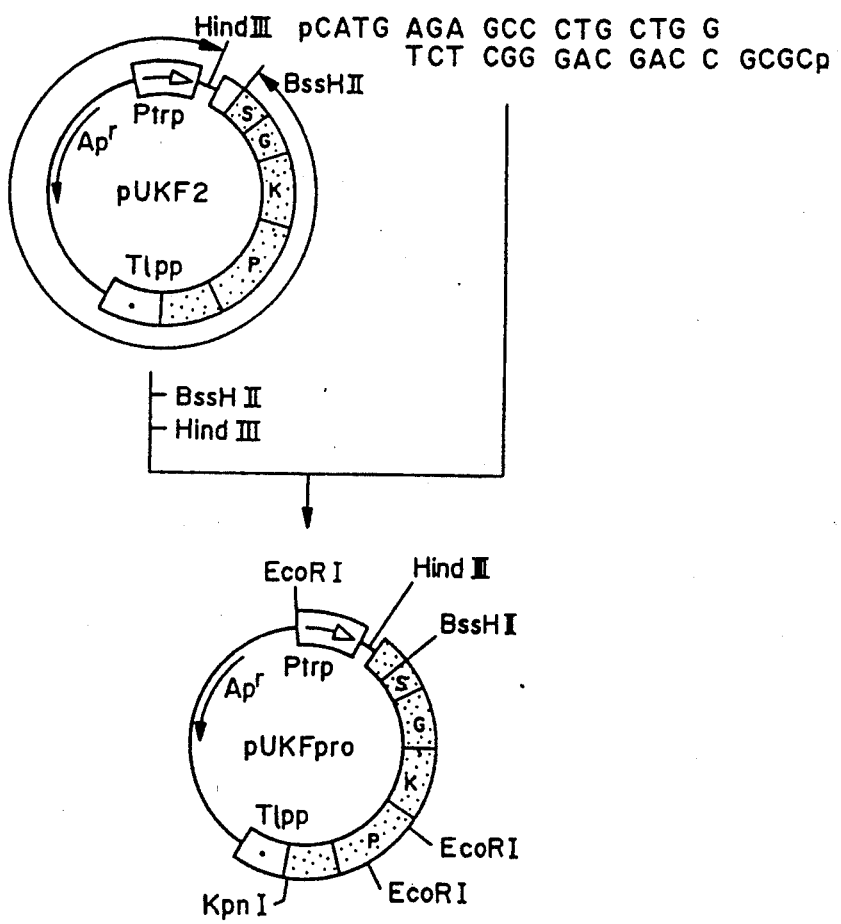
FIG. 35 shows the construction scheme for the plasmid pUKFpro.

The recombinant plasmid mixture obtained was used to transform *Escherichia coli* MM294 and Ap-resistant strains were obtained. The plasmid DNA isolated from one of these transformants was named pUKFpro. Structural analysis by restriction enzyme digestion as well as base sequnce determination by the M13 dideoxy sequencing method established that pUKFpro had the desired structure [cf. FIG. 35].

(3) Construction of recombinant plasmid pSE1UKpro1-1A:

About 2 μg of the pSE1PA1-9A plasmid DNA obtained in Reference Example 9 was dissolved in 30 μl of Y-0 buffer, 10 units of KpnI was added, and digestion was conducted at 37° C. for 2 hours. Then, 1.5 μl of 2M NaCl and 10 units of HindIII were added and digestion was further performed at 37° C. for 2 hours. After 10-minute heat treatment at 65° C., a DNA fragment about 6.3 kb in size was purified by the AFT method. Sepavine serum and 1 mM N-2-hydroxyethylpiperazine-N'-2-ethanesulfonic acid (HEPES) at an inoculum size of $8 \times 10^5$ cells/ml and grown therein using a spinner culture bottle. After growing at 37° C. for 48 hours, cells were collected by centrifugation, transferred to a fresh one-liter portion of RPMI 1640 medium containing 10 ng/ml phorbol myristate acetate (PMA), 5% fetal bovine serum and 1 mM HEPES, and further grown at 37° C. for 48 hours. Then, cells were collected from a portion (250 ml) of the resultant cell suspension by centrifugation (1,100×g, 4° C., 10 minutes), washed with 80 ml of phosphate buffer, and solubilized in 10 ml of 50 mM Tris-HCl (pH 7) containing 5M guanidine thiocyanate, 10 mM EDTA and 8% (v/v) 2-mercaptoethanol using a vortex mixer. The solubilization product was transferred to a centrifuge tube, 80 ml of 4M LiCl was added and, after stirring, the mixture was allowed to stand at 4° C. for 20 hours. After centrifugation (9,000 rpm, 90 minutes) using a Hitachi RPR10 rotor, there was recoverd RNA as a sediment. The RNA sediment was suspended in 50 ml of a solution containing 4M urea and 2M lithium chloride, the suspension was centrifuged at 9,000 rpm for 60 minutes on a Hitachi RPR10 rotor, and an RNA sediment was again recovered. The RNA sediment was dissolved in 10 ml of 10 mM Tris-HCl (pH 7.5) containing 0.1% sodium lauryl sulfate and 1 mM EDTA and, after phenol-chloroform extraction, recovered by ethanol precipitation. About 2.5 mg of the RNA obtained was dissolved in 1 ml of 10 mM Tris-HCl (pH 8.0) containing 1 mM EDTA. After 5 minutes of incubation at 65° C., 0.1 ml of 5M NaCl was added. The mixture was subjected to oligo(dT)-cellulose column (P-L Biochemicals) chromatography (column volume 0.5 ml). The poly(A)-containing mRNA adsorbed was eluted with 10 mM Tris-HCl (pH 7.5) containing 1 mM EDTA to give 100 $\mu$g of poly(A)-containing mRNA.

(2) cDNA synthesis and insertion into vector:

cDNA synthesis and construction of a recombinant plasmid with the same inserted therein were carried out following the Okayama-Berg method [Mol. Cell. Biol., 2, 161 (1982)]. The processes are schematically shown in FIG. 14.

About 2 $\mu$g of the poly(A) RNA prepared as described above and about 1.4 $\mu$g of the vector primer were dissolved in 22.3 $\mu$l of 50 mM Tris-HCl (pH 8.3) containing 8 mM MgCl$_2$, 30 mM KCl, 0.3 mM DTT, 2 mM each dNTP (dATP, dTTP, dGTP, dCTP) and 10 units of ribonuclease inhibitor (P-L Biochemicals), 10 units of reverse transcriptase (Seikagaku Kogyo) was added, and the mixture was incubated at 41° C. for 90 minutes for the synthesis of a DNA complementary to the mRNA. The reaction mixture was subjected to phenol-chloroform extraction and then the vector primer DNA with an RNA-DNA double strand added thereto was recovered by ethanol precipitation. This DNA was dissolved in 20 $\mu$l of TdT buffer containing 66 $\mu$M dCTP and 0.2 $\mu$g poly(A), 14 units of TdT (P-L Biochemicals) was added, and the mixture was incubated at 37° C. for 2 minutes for the addition of a 20-mer (dC) chain to the 3' end of cDNA. The reaction mixture was subjected to phenol-chlorofrom extraction and then the resultant (dC) chain-added cDNA-vector primer DNA was recovered by ethanol precipitation. This DNA was dissolved in 400 $\mu$l of 10 mM Tris-HCl (pH 7.5) containing 6 mM MgCl$_2$ and 60 mM NaCl, 20 units of HindIII was added, and the mixture was incubated at 37° C. for 2 hours for causing cleavage at the HindIII site. The reaction mixture was subjected to phenol-chloroform extraction and the subsequent ethanol precipitation gave 0.5 picomole of the resultant (dC) chain-added cDNA-vector primer DNA. This DNA (0.2 picomole) and 0.4 picomole of the above-mentioned linker DNA were dissolved in 100 $\mu$l of 10 mM Tris-HCl [pH 7.5) containing 0.1M NaCl and 1 mM EDTA and the solution was incubated at 65° C. for 10 minutes, then at 42° C. for 25 minutes and, finally, at 0° C. for 30 minutes. The reaction mixture was made up to a total volume of 100 $\mu$l while the composition was adjusted so that the final solution contained 20 mM Tris-HCl (pH 7.5), 4 mM MgCl$_2$, 10 mM (NH$_4$)$_2$SO$_4$, 0.1M KCl and 0.1 mM $\beta$-NAD. *Escherichia coli* DNA ligase (New England BioLabs; 25 units) was added to the solution and incubation was carried out at 11° C. for 18 hours. The reaction mixture was supplemented with dNTPs (each 40 $\mu$M) and $\beta$-NAD (to 0.15 mM), then 10 units of *Escherichia coli* DNA ligase, 20 units of *Escherichia coli* DNA polymerase I (P-L Biochemicals) and 10 units of *Escherichia coli* ribonuclease H (P-L Biochemicals) were added, and the mixture was incubated at 12° C. for 1 hour and then at 25° C. for 1 hour. The above reaction procedure resulted in cyclization of the cDNA-containing recombinant DNA and substitution of DNA for the RNA portion of the RNA-DNA double strand to give a completely double-stranded DNA recombinant plasmid.

(3) Selection of human LT cDNA-containing recombinant DNA:

The recombinant plasmid obtained in step (2) mentioned above was used to transform *Escherichia coli* C600 SF8 [Cameron: Proc. Natl. Acad. Sci. USA, 72, 3416 (1975)] by the method of Scott et al. [K. Shigesada: Saibo Kogaku, 2, 616 (1983)]. About 30,000 colonies obtained were immobilized on nitrocellulose filters. One strain capable of strongly hybridizing at 52° C., with the $^{32}$P-labeled 17-mer synthetic DNA probe coinciding in base sequence with a part of the 5'-nontranslational region of the human LT cDNA isolated by Genentech [Patrick W. Gray et al.: Nature, 312, 721 (1984)], namely $^{32}$P-labeled 5'-GATCCCCGGCCTGCCTG-3', was selected by the Grunstein-Hogness method [Proc. Natl. Acad. Sci. USA, 72, 3961 (1975)]. The whole base sequence of the cDNA of the plasmid pLT1 harbored by this strain was determined by the dideoxy sequencing method using M13 phage. As a result, it was revealed that the cDNA of pLT1 was one coding for human LT.

Figure 37:
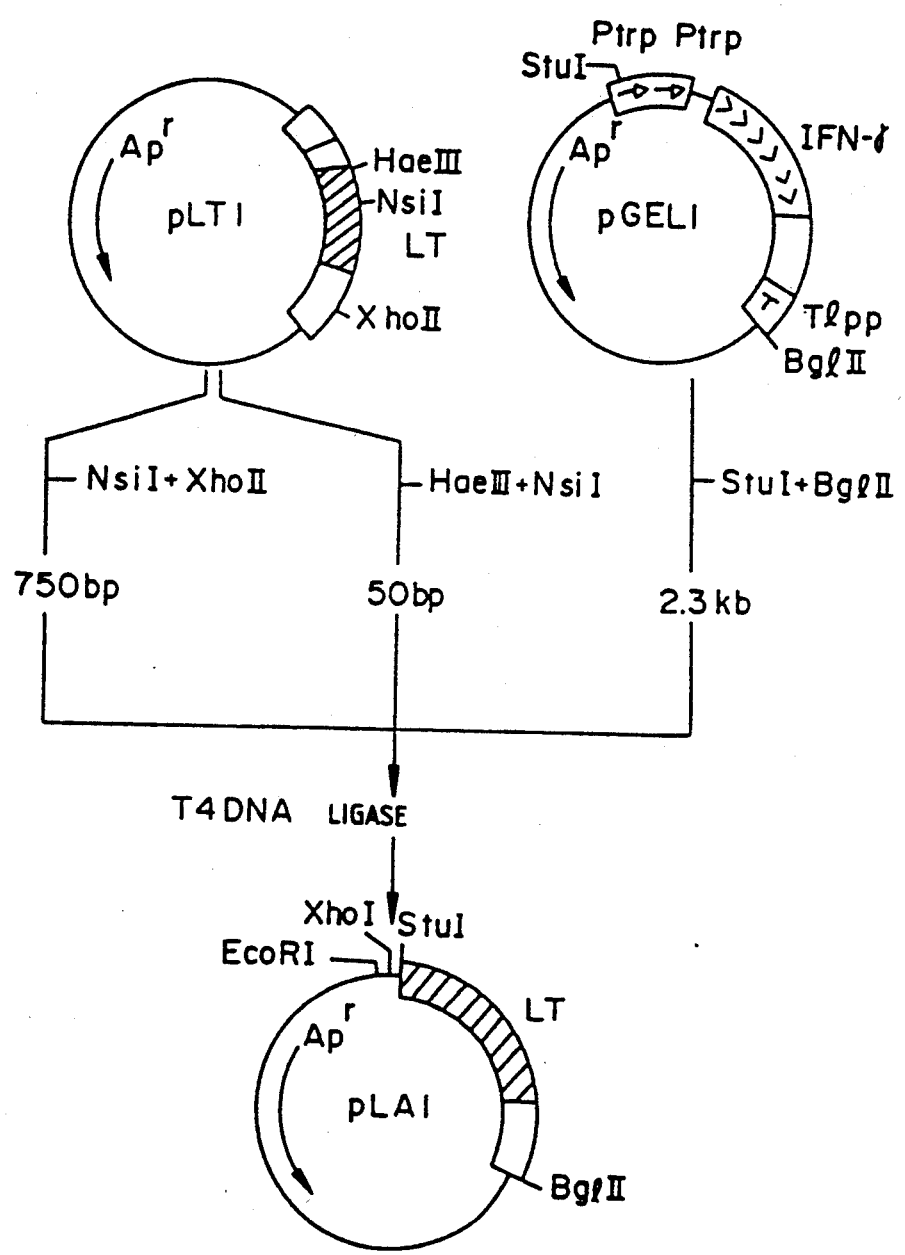
FIG. 37 shows the construction scheme for the plasmid pLA1.

2) Construction of recombinant plasmid pLA1 (cf. FIG. 37):

In a total volume of 50 $\mu$l of Y-0 buffer was dissolved 5 $\mu$g of pLT1 (4.7 kb) obtained by the method described in the preceding section, 10 units of the restriction enzyme XhoII (Boehringer Mannheim) was added, and digestion was carried out at 37° C. for 2 hours. Then, NaCl was added to a final concentration of 150 mM, 10 units of the restriction enzyme NsiI (New England BioLabs) was added, and digestion was further performed at 37° C. for 3 hours. About 0.3 $\mu$g of a DNA fragment (XhoII-NsiI fragment) about 750 bp in size and containing most of the human LT DNA was obtained from the reaction mixture by the LGT method.

Separately, 20 $\mu$g of pLT1 was dissolved in 200 $\mu$l of Y-50 buffer, 40 units of the restriction enzyme HaeIII was added, and cleavage was conducted at 37° C. for 2 hours. Then, NaCl was added to a final concentration of 150 mM, 40 units of NsiI was added, and cleavage was further conducted at 37° C. for 3 hours. About 40 ng of a DNA fragment (HaeIII-NsiI fragment) about 50 bp in size and containing the N-terminus portion of the human LT DNA was recovered from the reaction mixture by polyacrylamide gel electrophoresis.

Further, separately, 3 $\mu$g of pGEL1 (3.4 kb) [Sekine et al., Proc. Natl. Acad. Sci., USA, 82, 4306 (1985), FERM BP-629] was dissolved in a total volume of 30 $\mu$l of Y-100 buffer, 6 units each of the restriction enzymes StuI and BglII were added, and cleavage was effected at 37° C. for 3 hours.

About 1.0 $\mu$g of an Apr gene-containing DNA fragment about 2.3 kb in size (StuI-BglII fragment) was obtained from the reaction mixture by the LGT method.

Then, 0.2 $\mu$g of the pLT1-derived XhoII-NsiI fragment (about 750 bp), 20 ng of the pLT1-derived HaeIII-NsiI fragment (about 50 bp) and 0.6 $\mu$g of the pGEL1-derived StuI-BglII fragment (about 2.3 kb), respectively obtained as described above, were dissolved in a total volume of 20 $\mu$l of T4 ligase buffer, 2 units of T4 DNA ligase (Takara Shuzo) was further added to this mixed solution, and reaction was carried out at 4° C. for 18 hours.

The thus-obtained recombinant plasmid DNA was used to transform *Escherichia coli* KM430 by the method of Cohen at al. and Ap$^r$ colonies were obtained. The plasmid DNA isolated and purified from one of these transformant strains by the known method was subjected to structural analysis by cleaving this plasmid DNA with StuI and other restriction enzymes and, as a result, it was confirmed that it was the desired plasmid. This recombinant plasmid was named pLA1.

Figure 38:
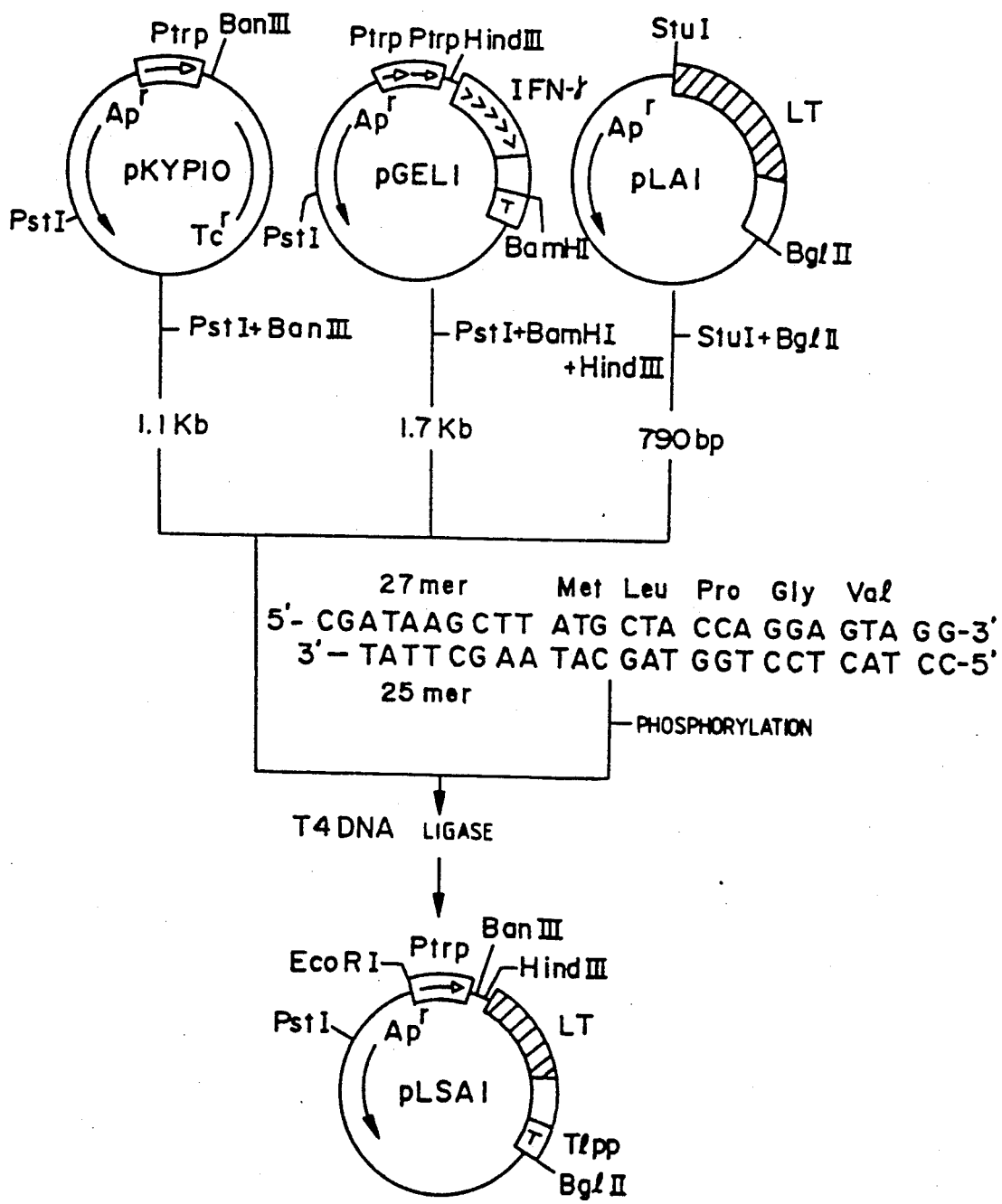
FIG. 38 shows the construction scheme for the plasmid pLSA1.

3) construction of LT expression plasmid pLSA1 (cf. FIG. 38):

*Escherichia coli* KM430 harboring pLA1 (3.1 kb) obtained as described in the preceding section was cultured and the pLA1 DNA was prepared from cultured cells by the conventional method. A 3 μg portion of the pLA1 DNA obtained was dissolved in 30 μl of Y-100 buffer, 3 units each of StuI and BglII were added, and cleavage was carried out at 37° C. for 3 hours. About 0.5 μg of a DNA fragment (StuI-BglII fragment) about 790 bp in size and containing most of the human LT gene was obtained from the reaction mixture by the LGT method.

Separately, 3 μg of pKYP10 prepared by the method described in JP-A-58-110600 or U.S. Pat. No. 4,686,191 was dissolved in 30 μl of Y-100 buffer, 6 units each of the restriction enzymes BanIII and PstI were added, and cleavage was carried out at 37° C. for 3 hours. About 0.6 μg of a DNA fragment (BanIII-PstI fragment) about 1.1 kb in size and containing the tryptophan promoter (Ptrp) was recovered from the reaction mixture by the LGT method. Further, separately, 2 μg of pGEL1 (3.4 kb) was dissolved in 20 μl of Y-100 buffer, 4 units each of the restriction enzymes HindIII, BamHI and PstI were added, and cleavage was effected at 37° C. for 3 hours. About 0.7 μg of a DNA fragment (PstI-BamHI fragment) about 1.7 kb in size and containing the lipoprotein gene-derived terminator was obtained from the reaction mixture by the LGT method.

Separately, in view of the necessity of providing that base sequence covering from the codon for the N-terminal Leu (CTA) to the second base (GG) of the codon for the fifth amino acid Gly (GGC) of the mature human LT polypeptide, the necessity of providing the initiation codon (ATG) necessary for expression and the necessity of adjusting the distance between the SD sequence and ATG downstream from Ptrp to an appropriate length within the range of 6 to 18 bp and for other reasons, the following DNA linker was synthesized;

and phosphorylation was carried out at 37° C. for 60 minutes.

Then, 0.3 μg of the pLA1-derived StuI-BglII (about 790 bp), 0.4 μg of the BanIII-PstI fragment (about 1.1 kb) of the expression vector pKYP10 and 0.6 μg of the pGEL1-derived PstI-BamHI fragment about 1.7 kb), respectively obtained as described above, were dissolved in 25 μl of T4 ligase buffer, about 1 picomole of the above DNA linker was added to the mixture and, after further addition of 6 units of T4 DNA ligase, ligation was effected at 4° C. for 18 hours.

The recombinant plasmid-containing reaction mixture was used to transform *Escherichia coli* KM430 and Ap$^r$ colonies were obtained. A plasmid DNA was recovered from cells obtained by culture of one of the colonies. The structure of the plasmid obtained was confirmed by cleavage with the restriction enzymes EcoRI, BanIII, PstI, HindIII and BglII, followed by agarose gel electrophoresis. This plasmid was named pLSA1. It was confirmed by the Maxam-Gilbert method [A. M. Maxam et al.: Proc. Natl. Acad. Sci. USA, 74, 560 (1977)] that, in the vicinity of the BanIII and HindIII sites, pLSA1 had the following base sequence:

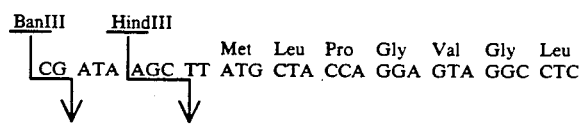

REFERENCE EXAMPLE 15

Construction of hG-CSF expression plasmid pCfTA1 (cf. FIG. 39):

The pCSF1-2 DNA obtained in Reference Example 4 (2 μg) was dissolved in a total volume of 20 μl of Y-100 buffer, 10 units each of the restriction enzymes ApaI (Boehringer Mannheim) and BamHI were added, and reaction was carried out at 37° C. for 4 hours. A 1.5 kb DNA fragment (0.4 μg) was purified and recovered from the reaction mixture by the LGT method.

Separately, 2 μg of the plamsid pLSA1 prepared by the method described in Reference Example 14 was dissolved in 20 μl of Y-100 buffer, 10 units each of the restriction enzymes BanIII (Toyobo) and BamHI were added, and reaction was carried out at 37° C. for 4 hours. A 2.8 kb DNA fragment (0.8 μg) was purified and recoverd from the reaction mixture by the LGT method.

Separately, in view of the necessity of providing the codons for the N-terminal first to fifth amino acids of the mature hG-CSF polypeptide [threonine$^1$ (ACA or ACT), proline$^2$ (CCA or CCT), leucine$^3$ (CTA), glycine$^4$ (GGC), proline$^5$ (CCC)] and the initiation codon

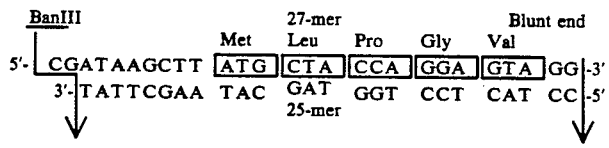

First, the single-strand 27-mer and 25-mer DNAs were synthesized by the ordinary triester method. The 27-mer and 25-mer (20 picomoles each) were dissolved in a total volume of 40 μl of T4 kinase buffer, 6 units of T4 polynucleotide kinase (Takara Shuzo) was added, (ATG) necessary for expression and the necessity of adjusting the distance between the SD sequence and ATG downstream from the tryptophan promoter (Ptrp) to an appropriate length within the range of 6 to 18 bp and for other reasons, the following DNA linker was synthesized:

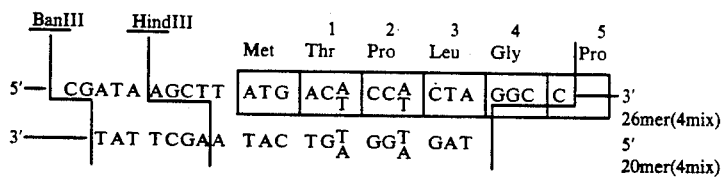

First, the single-strand 26-mer and 20-mer DNAs were synthesized by the ordinary triester method [R. Crea et al.: Proc. Natl. Acad. Sci. USA, 75, 5765 (1978)]. The 26-mer and 20-mer (2 μg each) were dissolved in T4 kinase buffer, 30 units of T4 polynucleotide kinase was added, and phosphorylation was carried out at 37° C. for 60 minutes.

The pCSF1-2-derived ApaI-BamHI fragment (1.5 kb; 0.4 μg) and pLSA1-derived BanIII-BamHI fragment (2.8 kb; 0.2 μg) obtained as described above were dissolved in 25 μl of T4 ligase buffer, 0.1 μg of the above DNA linker was added to the mixture and, after further addition of 6 units of T4 DNA ligase, ligation was carried out at 4° C. for 18 hours.

The recombinant plasmid mixture obtained was used to transform *Escherichia coli* HB101 [Bolivar et al: Gene, 2, 75 ( 1977)] by the method of Cohen et al. [S. N. Cohen et al. : Proc. Natl. Acd. Sci. USA, 69, 2110 (1972)] and Ap$^r$ colonies were obtained. A plasmid DNA was recoverd from cells obtained by growing one of the colonies. The structure of the plasmid obtained was confirmed by cleavage with BanIII, RsaI, PstI, HindIII and BglII, followed by agarose gel electrophoresis. This plasmid was named pCfTA1. It was confirmed by the dideoxy sequencing method using M13 phage that, in the vicinity of the BanIII and HindIII sites, pCfTA1 had the following base sequence:

REFERENCE EXAMPLE 16

Figure 40:
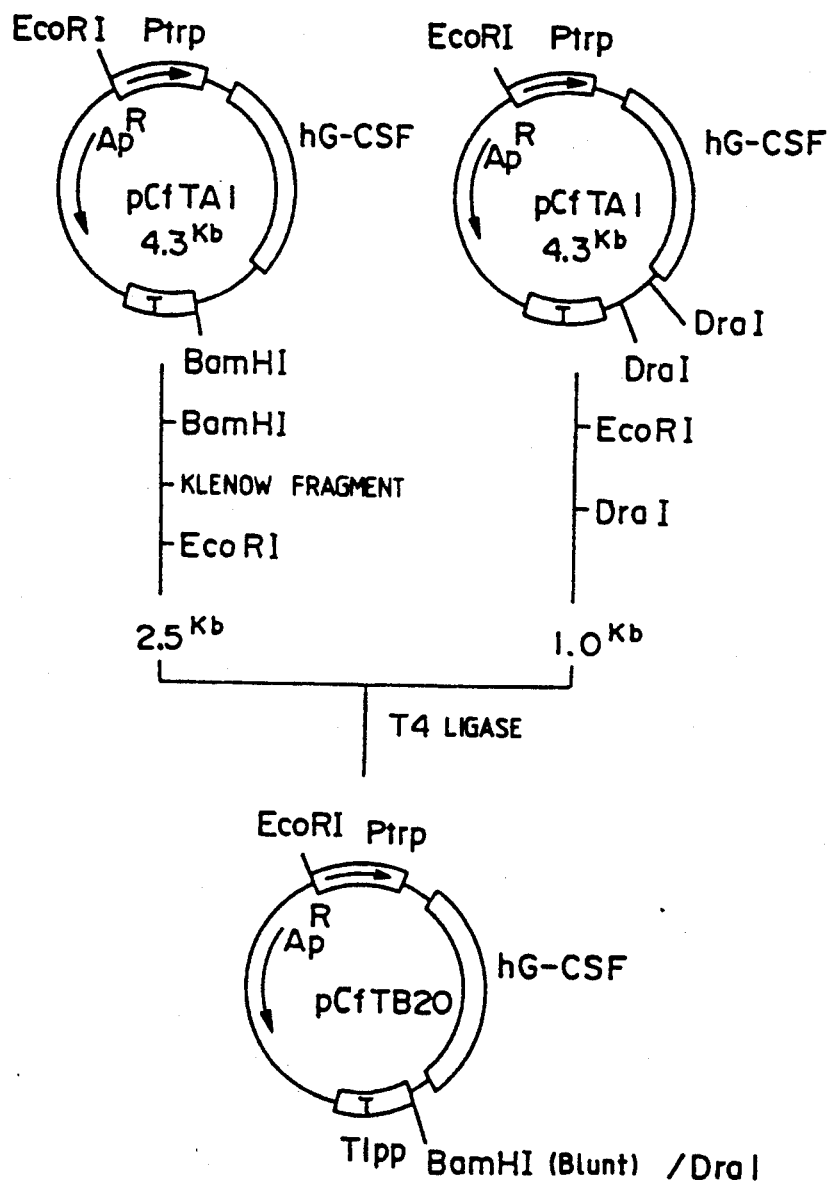
FIG. 40 shows the construction scheme for the plasmid pCfTB20.

Construction of pCfBD28:

(1) Construction of plasmid pCfTB20 lacking in part of 3'-nontranslational region of hG-CSF cDNA (cf. FIG. 40):

A 2 μg portion of the hG-CSF expression plasmid pCfTA1 (4.3 kb) obtained in Reference Example 15 was dissolved in 20 μl of Y-100 buffer, 4 units of the restriction enzyme BamHI was added, and digestion was effected at 37° C. for 4 hours. After phenol-chloroform extraction, 1.8 μg of a DNA fragment was recovered by ethanol precipitation. This DNA fragment was dissolved in 20 μl of Klenow buffer, dATP, dTTP, dCTP and dGTP were added each to a concentration of 1 mM and, after further addition of 4 units of DNA polymerase I Klenow fragment, reaction was carried out at room temperature for 1 hour for converting the cohesive ends to blunt ends. After phenol-chloroform extraction, 1.6 μg of the resultant DNA fragment was recovered by ethanol precipitation. This DNA fragment was dissolved in 20 μl of Y-100 buffer, 10 units of EcoRI was added, and cleavage was effected at 37° C. for 4 hours. From the reaction mixture was obtained by the LGT method 1 μg of a 2.5 kb DNA fragment (BamHI (blunt end)-EcoRI fragment).

Separately, 2 μg of pCfTA1 was dissolved in 20 μl of Y-100 buffer, 10 units of EcoRI was added, and cleavage was carried out at 37° C. for 4 hours. Then, NaCl was added to a final NaCl concentration of 150 mM, 10 units of DraI was added, and cleavage was further conducted at 37° C. for 4 hours. After confirmation of completness of digestion by agarose gel electrophoresis, 0.2 μg of an hG-CSF cDNA-containing 1.0 kb DNA fragment (EcoRI-DraI fragment) was purified and recovered by the LGT method.

The thus-obtained BamHI (blunt end)-EcoRI fragment (2.5 kb; 0.2 μg) and EcoRI-DraI fragment (1.0 kb; 0.2 μg) were dissolved in 25 μl of T4 ligase buffer, 6 units of T4 DNA ligase was added to the solution and ligation was carried out at 4° C. for 18 hours.

The recombinant plasmid mixture obtained was used to transform *Escherichia coli* HB101 and Ap$^r$ colonies were obtained. A plasmid DNA was recovered from cells obtained by cultivating one of the colonies. The structure of the plasmid obtained was confirmed by cleavage with HindIII and PstI, followed by agarose gel electrophoresis. This plasmid was named pCfTB20.

(2) Construction of plasmid pCfTL38 coding for polypeptide derived from hG-CSF by substitution of N-terminal amino acid (cf. FIG. 41):

A 3 μg portion of pCSF1-2 (4.5 kb) obtained by the procedure of Reference Example 4 was dissolved in 60 μl of Y-100 buffer, 8 units each of the restriction enzymes ApaI (Boehringer Mannheim) and BamHI were added, and cleavage was conducted at 37° C. for 3 hours. About 0.4 μg of a DNA fragment (ApaI-BamHI fragment) about 1.5 kb in size and containing most of the hG-CSF gene was recovered from the reaction mixture by the LGT method.

Separately, 2 μg of pGEL1 [Sekine et al.: Proc. Natl. Acad. Sci. USA, 82, 4306 (1985)] (obtained from a culture of *E. coli* IGEL1 FERM BP-629 by the conventional method) (3.4 kb) was dissolved in 40 μl of Y-100 buffer, 4 units each of the restriction enzymes HindIII, BamHI and PstI were added, and cleavage was carried out at 37° C. for 3 hours. About 0.5 μg of a DNA fragment (PstI-BamHI fragment) about 1.7 kb in size and containing the lipoprotein gene-derived terminator was obtained from the reaction mixture by the LGT method.

Separately, 3 μg of pKYP10 prepared by the method described in JP-A-58-110600 or U.S. Pat. No. 4,686,191 was dissolved in 60 μl of Y-100 buffer, 6 units each of the restriction enzymes BanIII (Toyobo) and PstI were added, and cleavage was effected at 37° C. for 3 hours. About 0.5 μg of a DNA fragment (BanIII-PstI fragment) about 1.1 kb in size and containing the tryptophan promoter (Ptrp) was obtained from the reaction mixture by the LGT method.

On the other hand, in view of the necessity of providing a codon for substituting Ser, Cys, Arg or Gly for the N-terminal amino acid Thr of mature hG-CSF and providing the initiation codon [ATG) necessary for expression and the necessity of adjusting the distance between the SD sequence and ATG downstream from Ptrp to an appropriate length within the range of 6 to 18 bp and for other reasons, the following DNA linker was synthesized:

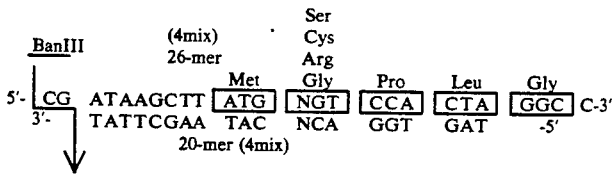

where N stands for any of the bases G, A, T and C.

First, the single-strand 26-mer and 20-mer DNAs were synthesized by the ordinary triester method. Twenty picomoles each of the 26-mer and 20-mer were dissolved in 40 μl of T4 kinase buffer, 6 units of T4 polynucleotide kinase was added, and phosphorylation was carried out at 37° C. for 60 minutes.

Then, 0.3 μg of the pCSF1-2-derived ApaI-BamHI fragment (about 1.5 kb), 0.2 μg of the pGEL1-derived PstI-BamHI fragment (about 1.7 kb) and 0.2 μg of the expression vector pKYP10-derived BanIII-PstI fragment (about 1.1 kb), respectively obtained as described above, were dissolved in a total volume of 30 μl of T4 ligase buffer, about 1 picomole of the above DNA linker was added to the solution and, after further addition of 6 units of T4 DNA ligase to the solution, ligation was performed at 4° C. for 18 hours.

Figure 41:
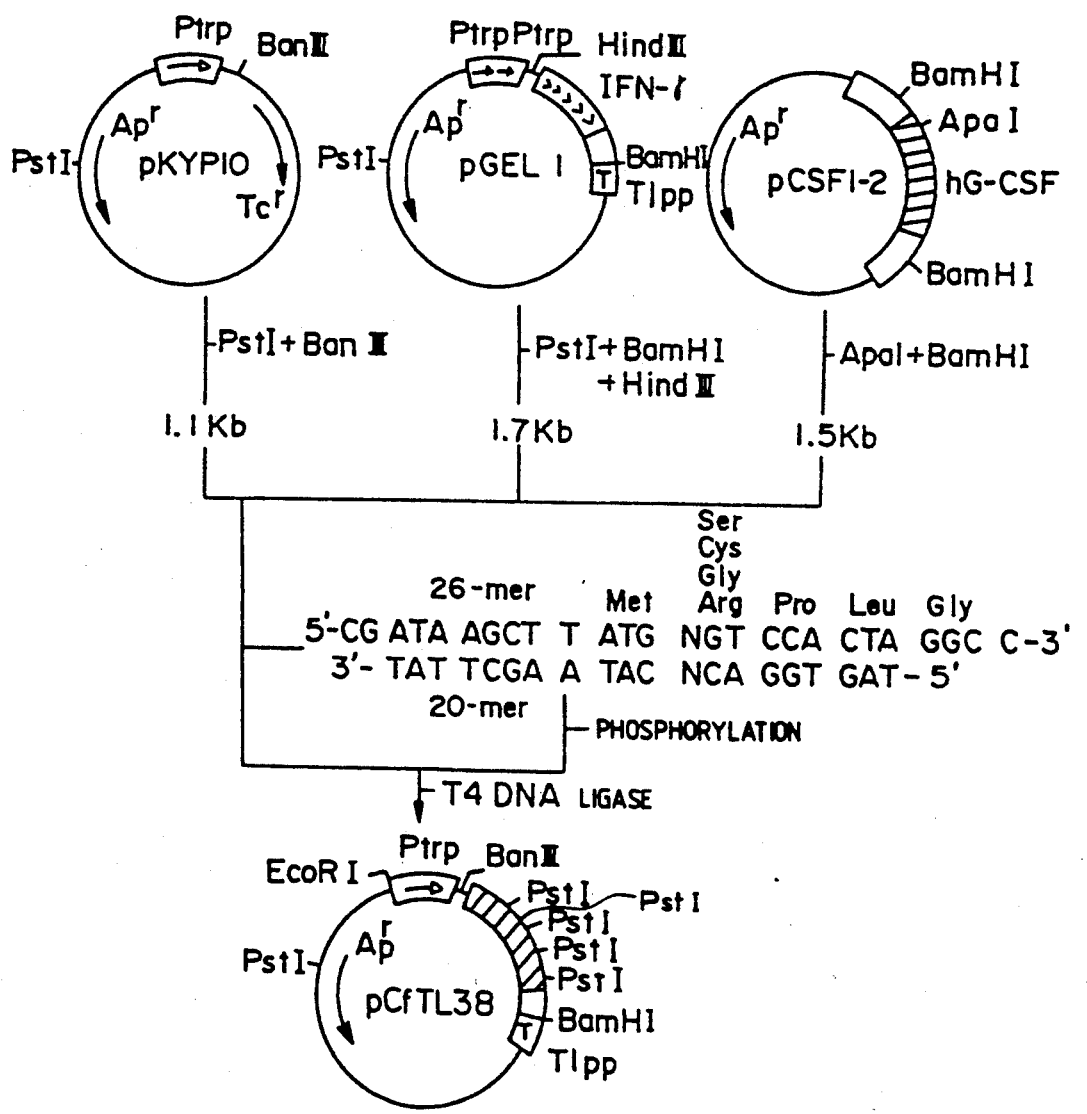
FIG. 41 shows the construction scheme for the plasmid pCfTL38.

The recombinant plasmid-containing reaction mixture was used to transform *Escherichia coli* C600 SF8 (FERM BP-1070) [Cameron et al.: Proc. Natl. Acad. Sci. USA, 72, 3416 (1975)] and Ap$^r$ colonies were obtained. A plasmid DNA was isolated and purified from one of the transformants by the known method. The structure of said plasmid DNA was confirmed by cleavage with PstI, EcoRI and BanIII, followed by polyacrylamide gel electrophoresis. This plasmid was named pCfTL38, as shown in FIG. 41. Sequencing by the dideoxy method using M13 phage confirmed that the sequence in the vicinity of the N terminus of the hG-CSF derivative gene in the above polasmid was as follows:

```
              Met Ser Pro Leu Gly Pro Ala
pCfTL38-ATG AGT CCA CTA GGC CCT GCC
```

Figure 42:
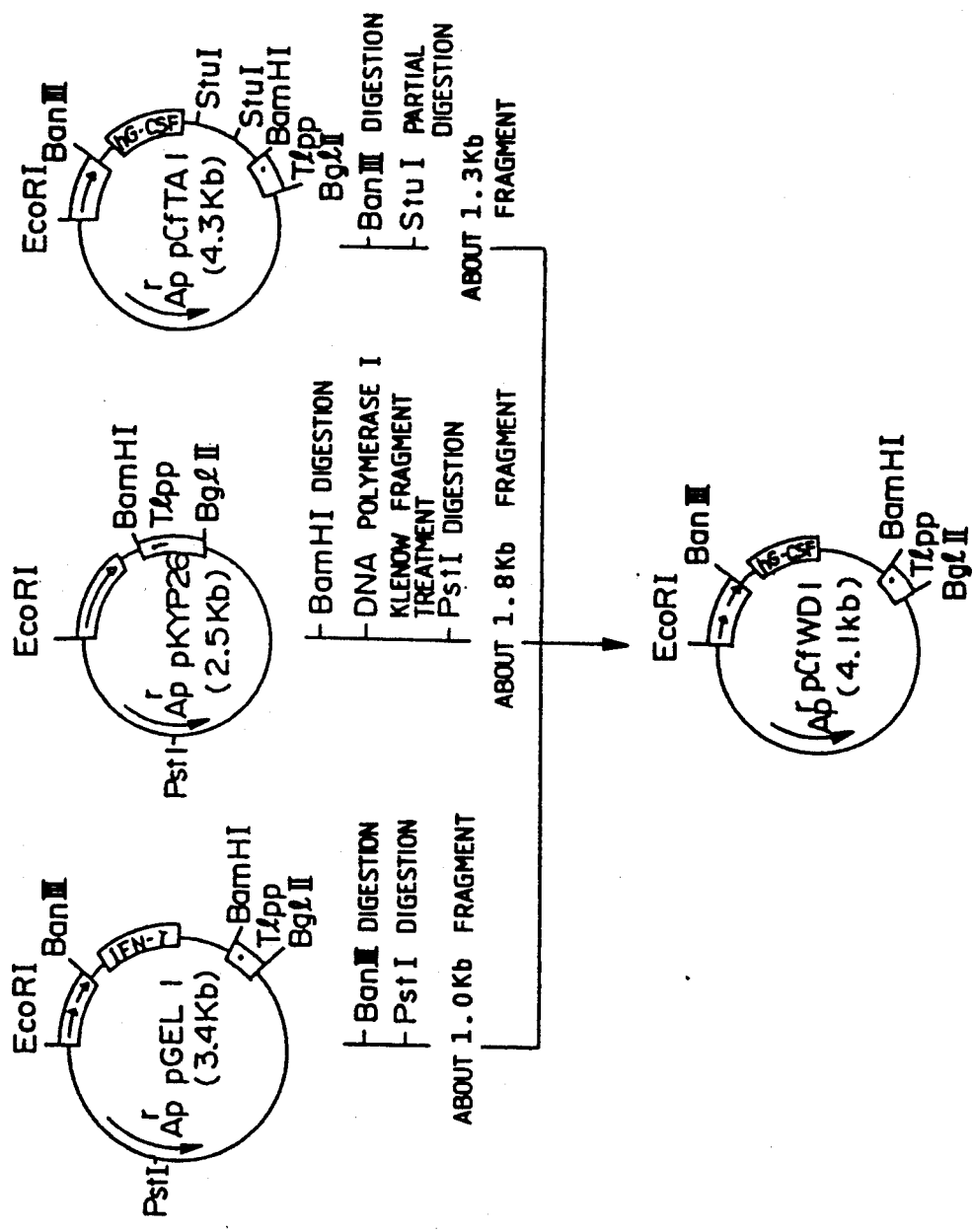
FIG. 42 shows the construction scheme for the plasmid pCfWD1.

(3) Construction of recombinant plasmid pCfWD1 (cf. FIG. 42):

A 5 μg portion of pCfTA1 obtained by the method described in Reference Example 15 was dissolved in 50 μl of Y-100 buffer, 10 units of the restriction enzyme StuI and 10 units of the restriction enzyme BanIII (Toyobo) were added, and digestion was carried out at 37° C. for 1 hour. About 0.5 μg of an hG-CSF cDNA-containing DNA fragment (BanIII-StuI fragment) about 1.3 kb in size was obtained from the reaction mixture by the LGT method. Separately, 3 μg of pKYP26 (FERM BP-863) produced by the method of Reference Example 2 was dissolved in 50 μl of Y-100 buffer, 6 units of BamHI was added, and digestion was carried out at 30° C. for 1 hour.

Thereto was added an equal volume of phenol saturated with 10 mM Tris-HCl (pH 7.5) containing 1 mM EDTA and, after vigorous stirring, the aqueous layer was collected by low-speed centrifugation (j,300 rpm, 10 minutes; hereinafter the same shall apply). An equal volume of chloroform was added to the aqueous layer, the mixture was stirred vigorously, and the aqueous layer was recovered again by low-speed centrifugation. One tenth volume of 3M sodium acetate was added, then 2.5 volumes of ethanol was added, and the resultant mixture was allowed to stand at −20° C. for 1 hour. The resultant precipitate was collected by centrifugation with cooling (4° C., 11,000 rpm, 10 minutes). This precipitate was dissolved in 30 μl of Klenow buffer, dATP, dTTP, dCTP and dGTP were added each to a concentration of 100 μM, 2 units of DNA polymerase I Klenow fragment was added, and reaction was carried out at 17° C. for 15 minutes. The DNA polymerase I Klenow fragment was inactivated by 10-minute heat treatment at 68° C., NaCl was then added to a final concentration of 100 mM and, after addition of 5 units of the restriction enzyme PstI, digestion was carried out at 37° C. for 1 hour. About 0.6 μg of an lpp terminator-containing DNA fragment [BamHI (blunt end)-PstI fragment] about 1.8 kb in size was obtained from the reaction mixture by the LGT method. Separately, 4 μg of pGEL1 was dissolved in 40 μl of Y-100 buffer, 10 units of the restriction enzyme BanIII (Toyobo) and 10 units of PstI were added, digestion was carried out at 37° C. for 1 hour, and 0.4 μg of a tryptophan promoter-containing DNA fragment (BanIII-PstI fragment) about 1 kb in size was obtained from the reaction mixture by the LGT method.

About 0.2 μg of the pCfTA1-derived BanIII-StuI fragment (about 1.3 kb), about 0.1 μg of the pKYP26-derived BamHI (blunt end)-PstI fragment (about 1.8 kb) and about 0.1 μg of the pGEL1-derived BanIII-PstI fragment (about 1 kb), respectively obtained as described above, were dissolved in 30 μl of T4 DNA ligase buffer, 4 units of T4 DNA ligase was added, and ligation was carried out at 4° C. for 18 hours.

The reaction mixture was used to transform *Escherichia coli* HB101 and Ap$^r$ colonies were obtained. A plasmid DNA was recovered from one of the colonies by the above-mentioned method of Birnboim et al. This was the plasmid pCfWD1 shown in FIG. 42.

Figure 43:
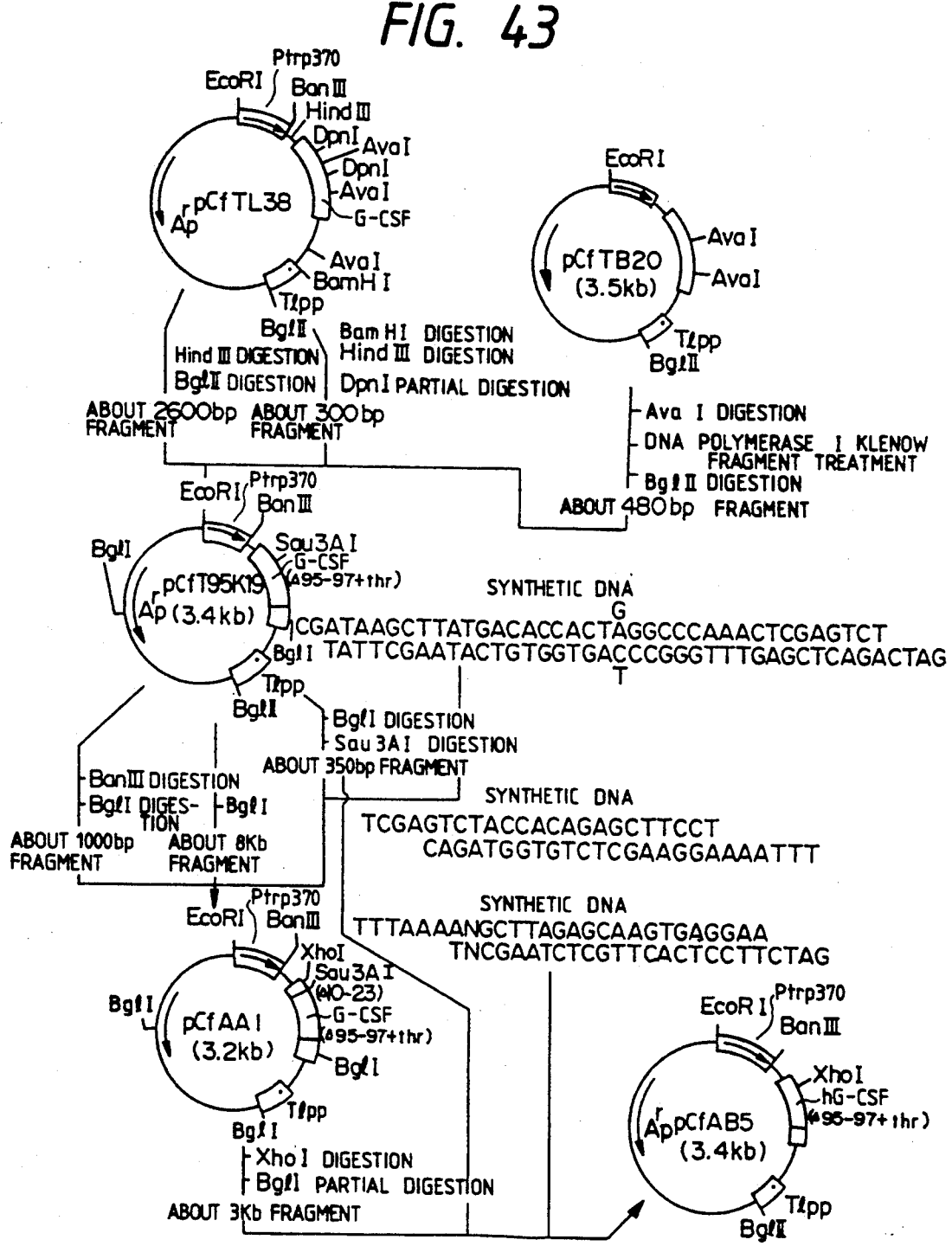
FIG. 43 shows the construction scheme for the plasmids pCfT95K19, pCfAA1 and pCfAB5.

(4) Construction of pCfT95K19 (cf. FIG. 43):

pCfTL38 (5 μg) as obtained in the above section (2) was dissolved in 50 μl of Y-100 buffer, 10 units each of the restriction enzymes HindIII and BglII were added, and digestion was carried out at 37° C. for 1 hour. About 0.7 μg of a tryptophan promoter-containing DNA fragment (HindIII-BglII fragment) about 2.6 kb in size was obtained from the reaction mixture by the LGT method. Separately, 100 μg of pCfTL38 was dissolved in 1.5 ml of Y-100 buffer, 80 units each of the restriction enzymes BamHI and HindIII were added, and digestion was carried out at 37° C. for 6 hours. An hG-CSF cDNA-containing DNA fragment was recovered from the reaction mixture by the LGT method and purified using ELUTIP ™-d (Schleicher & Schuell).

This DNA was dissolved in 90 µl of Y-150 buffer, 3 units of the restriction enzyme DpnI (Boehringer Mannheim) was added, and digestion was carried out at 37° C. for 15 minutes. About 1 µg of an hG-CSF cDNA-containing DNA fragment (HindIII-DpnI fragment) about 300 bp in size was obtained from the reaction mixture by polyacrylamide electrophoresis.

Separately, 10 µg of PCfTB20 obtained in the above section (1) was dissolved in 100 µl of Y-100 buffer, 10 units of the resriction enzyme AvaI was added, and digestion was carried out at 37° C. for 1 hour. After phenol-chloroform extraction, the resultant DNA was recovered by ethanol precipitation and dissolved in 30 µl of Klenow buffer, 2 units of DNA polymerase I Klenow fragment was added, and reaction was carried out at 17° C. for 30 minutes. The DNA polymerase I Klenow fragment was inactivated by 10-minute heat treatment at 68° C., NaCl was added to a final concentration of 100 mM and, after further addition of 10 units of the restriction enzyme BglII, digestion was carried out at 37° C. for 1 hour. About 0.3 µg of an lpp terminator portion-containing DNA fragment [AvaI (blunt end)-BglII fragment] about 480 bp in size was obtained from the reaction mixture by the LGT method.

About 0.1 µg of the pCfTL-38-derived HindIII-BglII fragment (about 2.6 kb), about 0.2 µg of the pCfTL38-derived HindIII-DpnI fragment (about 300 bp) and about 0.15 µg of the pCfTB20-derived AvaI (blunt end)-BglII fragment (about 480 bp), respectively obtained as described above, were dissolved in 30 µl of T4 DNA ligase buffer, 4 units of T4 DNA ligase was added, and ligation was carried out at 4° C. for 18 hours. The reaction mixture was used to transform *Escherichia coli* HB101 and Ap$^r$ colonies were obtained. A plasmid DNA was recovered from one of the colonies by the above-mentioned method of Birnboim et al. Thus was obtained pCfT95K19 shown in FIG. 43.

(5) Construction of pCfAA1 (cf. FIG. 43):

A 5 µg portion of pCfT95K19 obtained as described in the preceding section was dissolved in 50 µl of Y-100 buffer, 7 units of the restriction enzyme BanIII (Toyobo) and 2 units of BglI (Nippon Gene) were added, and digestion was carried out at 37° C. for 1 hour. About 0.6 µg of a tryptophan promoter portion-containing DNA fragment (BanIII-BglI fragment) about 1 kb in size and about 1 µg of an lpp terminator portion-containing DNA fragment (BqlI-BglI fragment) about 1.8 kb in size were obtained from the reaction mixture by the LGT method.

Separately, 15 µg of pCfT95K19 was dissolved in 150 µl of Y-100 buffer, 6 units of the restriction enzyme BglI (Nippon Gene) and 10 units of Sau3AI were added, and digestion was carried out at 37° C. for 1 hour. About 0.3 µg of an hG-CSF cDNA portion-containing DNA fragment (BglI-Sau3AI fragment) about 350 bp in size was obtained from the reaction mixture by polyacrylamide gel electrophoresis.

Further, separately, the following DNA linker was synthesized:

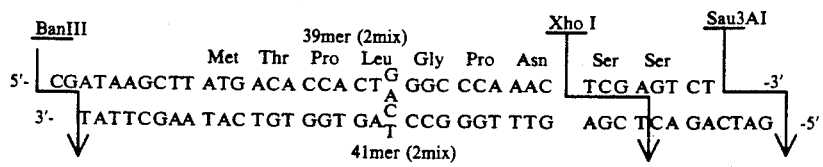

First, the single-strand 39-mer and 41-mer DNAs were synthesized by the ordinary triester method. Twenty picomoles each of the 39-mer and 41-mer were dissolved in a total volume of 40 µl of T4 kinase buffer, 6 units of T4 polynucleotide kinase (Takara Shuzo) was added, and phosphorylation was carried out at 37° C. for 60 minutes.

Then, 0.1 µg of the pCfT95K19-derived BanIII-BglI fragment (about 1 kb), 0.05 µg of the pCfT95K19-derived BglI-BglI fragment (about 1.8 kb) and 0.1 µg of the pCfT95K19-derived BglI-Sau3AI fragment (about 350 bp), respectively obtained as described above, were dissolved in 25 µl of T4 DNA ligase buffer and about 2 picomoles of the above DNA linker was added to the solution. Further, 6 units of T4 DNA ligase was added and ligation was carried out at 4° C. for 18 hours.

The reaction mixture was used to transform *Escherichia coli* HB101 and Ap$^r$ colonies were obtained. A plasmid DNA was recovered from one of these colonies by the above-mentioned method of Birnboim et al. Thus was obtained pCfAA1 shown in FIG. 43. Determination of the base sequence of the DNA linker portion of pCfAA1 by the above-mentioned dideoxy sequencing method revealed that the third base of the codon coding for the 4th amino acid Leu was A. In this pCfAA1, that DNA portion coding for the 10th amino acid Pro to the 23rd amino acid Lys (14 amino acids) of hG-CSF is missing. Furthermore, a mutation has been introduced therein so that Asn is encoded in lieu of the 6th amino acid Ala of hG-CSF and an XhoI site newly occurs.

(6) Construction of pCfAB5 (cf. FIG. 43):

A 3 µg portion of pCfAA1 obtained as described in the preceding section was dissolved in 30 µl of Y-100 buffer, 5 units of the restriction enzyme XhoI was added, and digestion was carried out at 37° C. for 1 hour. After confirmation of completeness of XhoI cleavage by means of agarose gel electrophoresis, 1 unit of the restriction enzyme BglI (Nippon Gene) was added, and digestion was performed at 37° C. for 25 minutes. About 1 µg of a tryptophan promoter portion- and lpp terminator portion-containing DNA fragment (XhoI-BglI fragment) about 3 kb in size was obtained from the reaction mixture by the LGT method. Separately, the following DNA linker was synthesized:

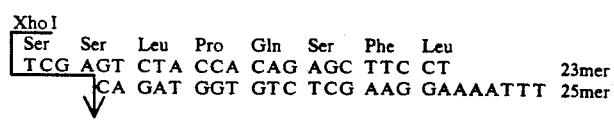

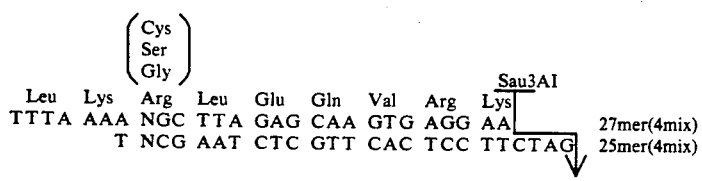

where N stands for G, A, T or C.

This linker DNA contains that DNA portion coding for the 10th amino acid Pro to the 23rd amino acid Lys of hG-CSF which was missing in the hG-CSF cDNA in pCfAA1.

First, the single-strand 27-mer, 25-mer (two kinds) and 23-mer DNAs were synthesized by the ordinary triester method. The 27-mer and the 25-mer complementary thereto as well as the 25-mer and the 23-mer complementary thereto were dissolved in a total volume of 40 μl of T4 kinase buffer each in an amount of 20 picomoles, 6 units of T4 polynucleotide kinase (Takara Shuzo) was added, and phosphorylation was carried out at 37° C. for 60 minutes.

Then, 0.1 μg of the pCfAA1-derived XhoI-BglI fragment (about 3 kb) obtained as described above and 0.1 μg of the pCfT95K19-derived BglI-Sau3AI fragment (about 350 bp) obtained as described in the preceding section were dissolved in 30 μl of T4 DNA ligase buffer, 2 picomoles each of the above-mentioned DNA linker components were added to the solution and, after further addition of 6 units of T4 DNA ligase, ligation was carried out at 4° C. for 18 hours.

The reaction mixture was used to transform *Escherichia coli* HB101 and Ap$^r$ colonies were obtained. A plasmid DNA was recovered from one of the colonies by the above-mentioned method of Birnboim et al. Thus was obtained pCfAB5 shown in FIG. 43. Determination of the base sequence of the DNA linker portion of pCfAB5 by the above-mentioned dideoxy sequencing method revealed that, in pCfAB5, the first base of the codon coding for the 17th amino acid was A and, hence, that the codon coded for Ser in lieu of the 17th amino acid Cys of mature hG-CSF.

Figure 44:
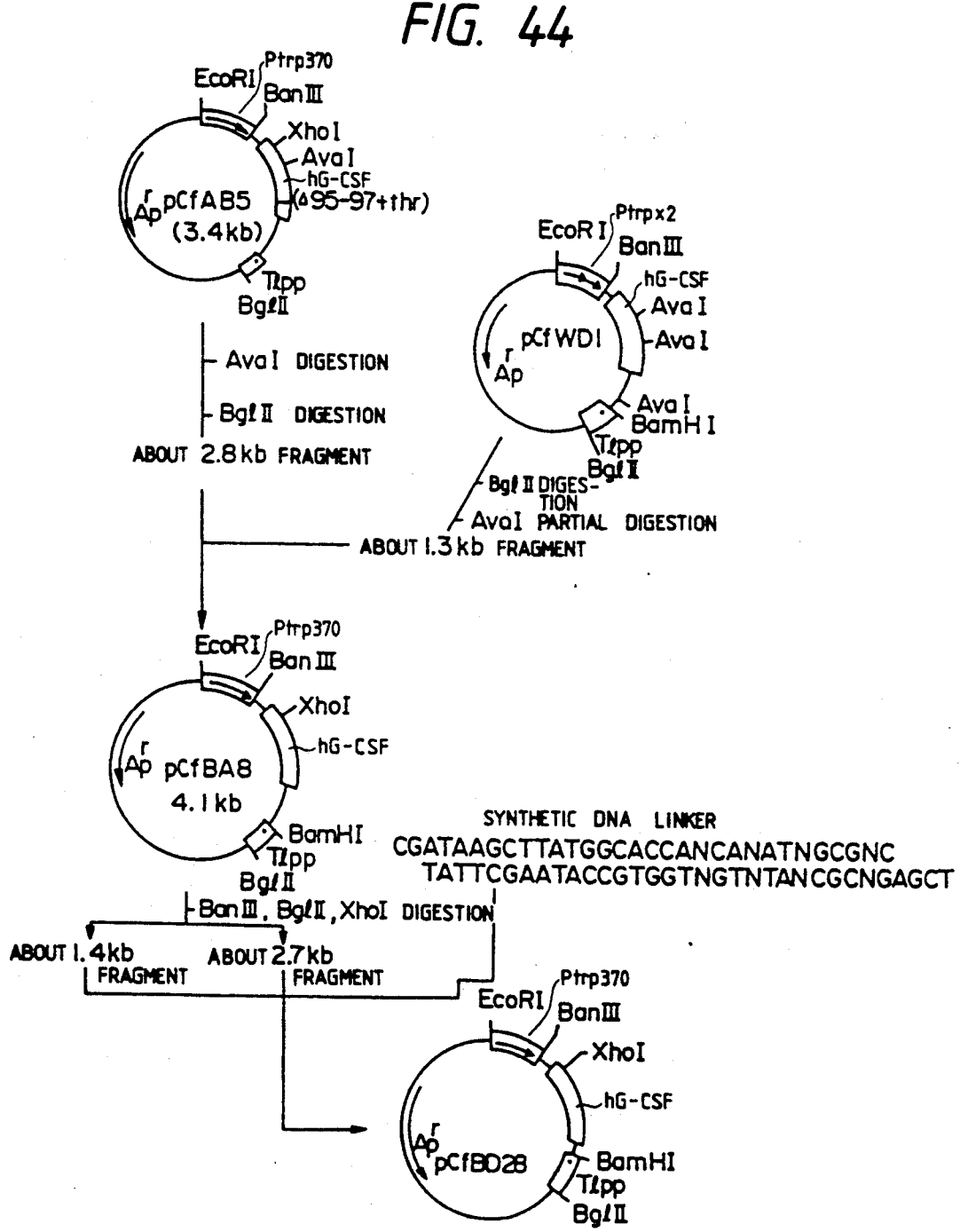
FIG. 44 shows the construction scheme for the plasmids pCfBA8 and pCfBD28.

(7) Construction of pCfBA8 (cf. FIG. 44):

A 3 μg portion of pCfAB5 obtained as described in the preceding section was dissolved in 40 μl of Y-100 buffer, 5 units each of the restriction enzymes AvaI and BglII were added, and digestion was conducted at 37° C. for 1 hour. About 1 μg of a tryptophan promoter portion- and lpp terminator portion-containing DNA fragment (AvaI-BglII fragment) about 2.8 kb in size was obtained from the reaction mixture by the LGT method.

Separately, 6 μg of pCfWD1 obtained in the above section (1) was dissolved in 50 μl of Y-100 buffer, 5 units of the restriction enzyme BglII was added, and digestion was performed at 37° C. for 1 hour. After confirmation of completeness of BglII cleavage by means of agarose gel electrophoresis, 3 units of the restriction enzyme AvaI was added and partial cleavage was effected at 37° C. for 20 minutes. From the reaction mixture, there was obtained by the LGT method 0.4 μg of a DNA fragment (BglII-AvaI fragment) about 1.3 kb in size and containing most of the hG-CSF cDNA.

Then, 0.1 μg of the pCfAB5-derived AvaI-BglII fragment (about 2.8 kb) and 0.3 μg of the pCfWD1-derived BglII-AvaI fragment (about 1.3 kb), respectively obtained as described above, were dissolved in 25 μl of T4 DNA ligase buffer, 3 units of T4 DNA ligase was added, and ligation was carried out at 4° C. for 18 hours.

The reaction mixture was used to transform *Escherichia coli* HB101 and Ap$^r$ colonies were obtained. A plasmid DNA was recovered from one of these colonies by the above-mentioned method of Birnboim et al. Thus was obtained pCfBA8 shown in FIG. 44.

The amino acid sequence of the hG-CSF derivative encoded by pCfBA8 contains Asn in lieu of the 6th amino acid Ala of mature hG-CSF and Ser in lieu of the 17th amino acid Cys.

(8) Construction of pCfBD28 (cf. FIG. 44):

First, the following DNA linker was synthesized:

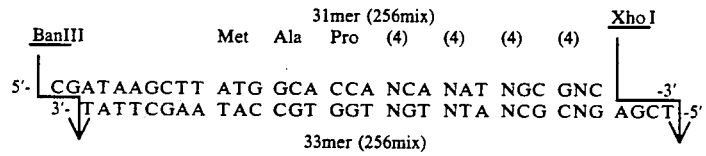

where N stands for any of G, A, T and C.

This DNA linker was obtained as a mixture of a total of 256 DNA linker species since the four bases represented by N in the coding strand each could be any of G, A, T and C. Thus, the linker designing was such that there were a total of 256 possibilities for the hG-CSF N-terminal amino acid sequence encoded by this DNA linker, namely four amino acids for each of the four relevant codons.

First, the single-strand 31-mer and 33-mer DNAs were synthesized by the ordinary triester method. The 31-mer and 33-mer (2 μg each) were dissolved in a total volume of 40 μl of T4 kinase buffer, 30 units of T4 polynucleotide kinase (Takara Shuzo) was added, and phosphorylation was carried out at 37° C. for 60 minutes.

Then, 0.1 μg of the pCfBA8-derived BanIII-BglII fragment (about 2.7 kb) and 0.1 μg of the pCfBA8-derived XhoI-BglII fragment (about 1.4 kb) were dissolved in 25 μl of T4 DNA ligase buffer and about 2 picomoles of the above DNA linker was added to the solution. After further addition of 6 units of T4 DNA ligase, ligation was carried out at 4° C. for 18 hours.

The recombinant plasmid mixture obtained was used to transform *Escherichia coli* HB101 and Ap$^r$ colonies were obtained. Plasmid recovery from one of the colonies gave pCfBD28. Determination of the base sequence of the DNA linker portion by the above-mentioned dideoxy sequencing method revealed that the base sequence on the N-terminal side of the hG-CSF derivative was as follows:

pCfBD28

```
Met Ala Pro Thr Tyr Arg Ala
ATG GCA CCA ACA TAT CGC GCC
```

The hG-CSF derivative encoded by pCfBD28 is distinguished from mature hG-CSF by the following amino acid residue substitutions:

| Position of amino acid substitution (amino acid of hG-CSF) | Plasmid pCfBD28 |
| --- | --- |
| First (Thr) | Ala |
| Third (Leu) | Thr |
| Fourth (Gly) | Tyr |
| Fifth (Pro) | Arg |
| Seventeenth (Cys) | Ser |

The hG-CSF derivative encoded by pCfBD28 was named hG-CSF[ND28]. A pCfBD28-carrying strain of Escherichia coli has been deposited with the Fermentation Research Institute under the designation Escherichia coli ECfBD28 (deposit number FERM BP-1479) in accordance with the Budapest Treaty.

REFERENCE EXAMPLE 17

Construction of recombinant plasmid pTkSR18:

(1) Construction of recombinant plasmid pTkSJ1:

About 2 µg of the pTA4 plasmid DNA obtained in Reference Example 8 was dissolved in 30 µl of Y-0 buffer, 10 units of EcoRI and 30 units of BbeI were added, and digestion was carried out at 37° C. for 2 hours. After 10-minute heat treatment at 65° C., a BbeI-EcoRI fragment about 2.8 kb in size was purified by the AFT method. Separately, about 3 µg of the pTA4 DNA was dissolved in 30 µl of Y-0 buffer, 12 units of KpnI was added, and digestion was effected at 37° C. for 2 hours. Then, 1.5 µl of 2M NaCl and 1 unit of EcoRI were added and digestion was further carried out at 37° C. for 1 hour. As a result of this serial digestion, the DNA was completely digested with KpnI and partially digested with EcoRI. After 10-minute heat treatment at 65° C., an EcoRI-KpnI fragment about 1.4 kb in size was purified by the AFT method. Further, separately, the following two synthetic DNAs (16-mer and 24-mer) were synthesized using Applied Biosystems model 380 A DNA synthesizer and respectively 5'-phosphorylated in the same manner as mentioned above:

5'-CTCCTGCCTCCCATGG-3'

3'-CGCGGAGGACGGAGGGTACCTTAA-5'

The thus-obtained pTA4-derived BbeI-EcoRI fragment (about 2.8 kb; about 0.1 µg), pTA4-derived EcoRI-KpnI fragment (about 1.4 kb; about 0.05 µg) and two 5'-phosphorylated synthetic DNAs (1 picomole each) were dissolved in 20 µl of T4 ligase buffer, 50 units of T4 DNA ligase was added, and ligation was carried out at 4° C. for 18 hours.

Figure 50:
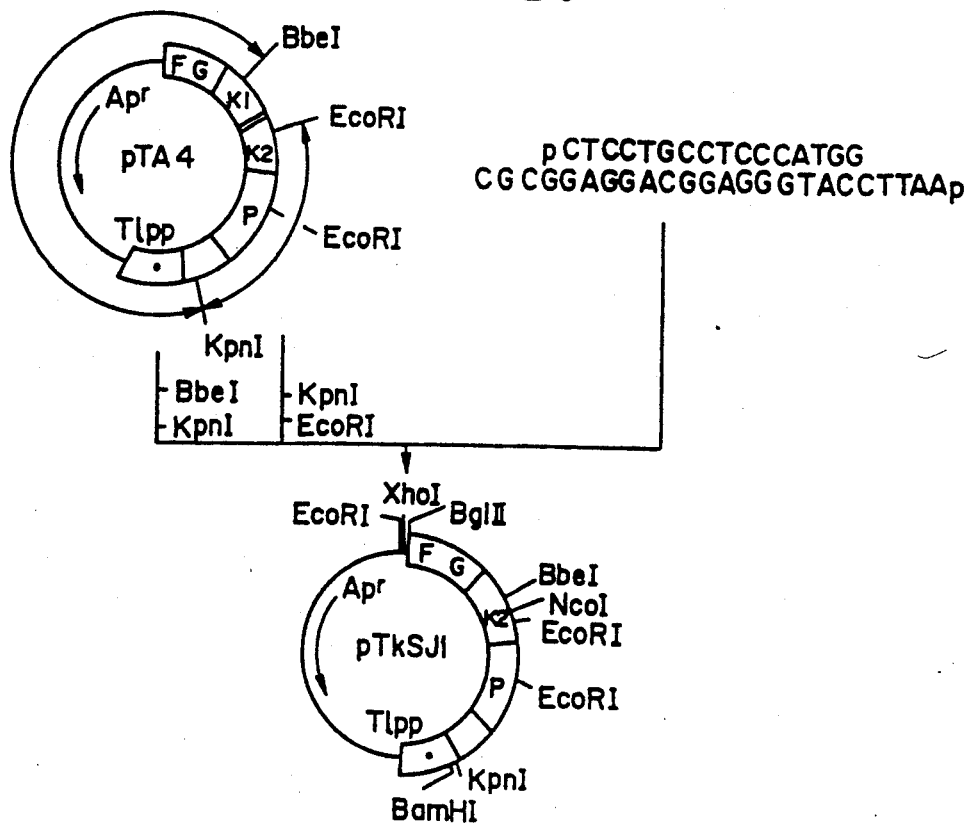
FIG. 50 shows the construction scheme for the plasmid pTkSJ1.

The recombinant plasmid mixture thus obtained was used to transform Escherichia coli MM294 to give Ap-resistant transformants. The plasmid DNA pTkSJ1 was isolated from one of the transformant strains and subjected to structural analysis by restriction enzyme digestion and to sequencing by the dideoxy method using M13 phage. It was thus confirmed that pTkSJ1 had the desired structure (cf. FIG. 50).

(2) Construction of recombinant plasmid pTkSR18:

About 3 µg of the pTkSJ1 plasmid DNA obtained as described above was dissolved in 30 µl of Y-100 buffer, 10 units of XhoI and 15 units of ScaI were added, and digestion was performed at 37° C. for 2 hours. After 10-minute heat treatment at 65° C., a DNA fragment about 0.5 kb in size was purified by the AFT method. Separately, about 2 µg of the pTrS33 plasmid DNA obtained in Reference Example 5-(2) was dissolved in Y-0 buffer containing 150 mM KCl, 8 units of PvuI and 15 units of SalI were added, and digestion was effected at 37° C. for 2 hours. After 10-minute heat treatment at 65° C., a DNA fragment about 1.0 kb in size was purified by the AFT method. Further, separately, about 2 µg of the pTerm2 plasmid DNA obtained in Reference Example 6 was dissolved in 30 µl of Y-150 buffer, 8 units of PvuI and 8 units of NsiI (New England BioLabs) were added, and digestion was carried out at 37° C. for 2 hours. After 10-minute heat treatment at 65° C., a DNA fragment about 1.85 kb in size was purified by the AFT method. Further, the following two synthetic DNAs (35-mer and 31-mer) were synthesized using Applied Biosystems model 380A DNA synthesizer and respectively 5'-phosphorylated in the same manner as mentioned above:

5'-ACTGTGACGTCCCCAGCTGTTCTGAAG-GAAATGCA-3'

3'-TGACACTGCAGGGGT-CGACAAGACTTCCTTT-5'

The thus-obtained pTkSJ1-derived XhoI-ScaI fragment (about 0.5 kb; about 0.05 µg), pTrS33-derived PvuI-SalI fragment (about 1.0 kb; about 0.1 µg), pTerm2-derived NsiI-PvuI fragment (about 1.85 kb; about 0.1 µg) and two 5'-phosphorylated synthetic DNAs (1 picomole each) were dissolved in 20 µl of T4 ligase buffer, 50 units of T4 DNA ligase was added, and ligation was carried out at 4° C. for 18 hours.

The recombinant plasmid mixture thus obtained was used to transform Escherichia coli MM294 to give Ap-resistant transformants. The plasmid DNA pTkSR18 isolated from one of the transformant strains proved to have the desired structure upon structural analysis by restriction enzyme digestion and sequencing by the dideoxy method using M13 phage (cf. FIG. 51).

REFERENCE EXAMPLE 18

Construction of recombinant plasmid pTkSS4:

(1) Construction of recombinant plasmid pTkSD217:

About 10 µg of the pTA4 plasmid DNA obtained in Reference Example 8 was dissolved in 100 µl of Y-100 buffer, about 30 units of XhoI was added, and digestion was carried out at 37° C. for 2 hours. Then, the reaction mixture was subjected to phenol-chloroform extraction, followed by ethanol precipitation. The DNA fragment thus recovered was dissolved in 50 µl of TE buffer [10 mM Tris-HCl (pH 7.5), 0.5 mM EDTA]. To a 10-µl portion of this DNA solution were added 10 µl of 5-fold concentrated BAL31 buffer [100 mM Tris-HCl (pH 8.0), 3M NaCl, 60 mM $CaCl_2$, 60 mM $MgCl_2$, 5 mM EDTA], 30 µl of water and 0.5 unit of exonuclease BAL31 (Takara Shuzo), and the reaction was carried out at 30° C. for 5 minutes. The reaction conditions employed were such that the DNA could be pared by about 0.5 kb from the XhoI terminus. The reaction was terminated by extraction with phenol. After further extraction with chloroform, the resultant DNA fragment was recovered by precipitation with ethanol. This DNA fragment was dissolved in 30 μl of Y-100 buffer, 10 units of BamHI was added, and digestion was carried out at 37° C. for 2 hours. After 10-minute heat treatment at 65° C., a DNA fragment about 1.5 kb in size was purified by the AFT method.

Separately, about 2 μg of the pTrS33 plasmid DNA (Reference Example 5) was dissolved in 30 μl of Y-0 buffer, about 12 units of SacI was added, and digestion was effected at 37° C. for 2 hours. After phenol extraction and chloroform extraction, the resultant DNA fragment was recovered by ethanol precipitation and dissolved in a total of 40 μl of 50 mM Tris-HCl buffer (pH 7.8) containing 7 mM MgCl₂, 6 mM 2-mercaptoethanol, 0.25 mM dATP, 0.25 mM dCTP, 0.25 mM dGTP and 0.25 mM dTTP (hereinafter referred to as "polymerase buffer" for short), 6 units of the Klenow fragment (Klenow Pol I) (Takara Shuzo) was added, and the reaction was carried out at 15° C. for 1 hour, whereby the SacI cohesive ends were rendered blunt by paring off. The reaction was terminated by phenol extraction. After further extraction with chloroform, ethanol was added for causing DNA precipitation. The DNA fragment thus recovered was dissolved in 30 μl of Y-100 buffer, 10 units of BamHI was added, and digestion was conducted at 37° C. for 2 hours. After 10-minute heat treatment at 65° C., a DNA fragment about 2.8 kb in size was purified by the AFT method.

The thus-obtained pTA4-derived DNA fragment (about 1.5 kb; about 0.2 μg) and pTrS33-derived DNA fragment (about 2.8 kb; about 0.1 μg) were dissolved in a total of 20 μl of T4 ligase buffer, 50 units of T4 DNA ligase was added, and ligation was carried out at 4° C. for 18 hours.

Figure 52:
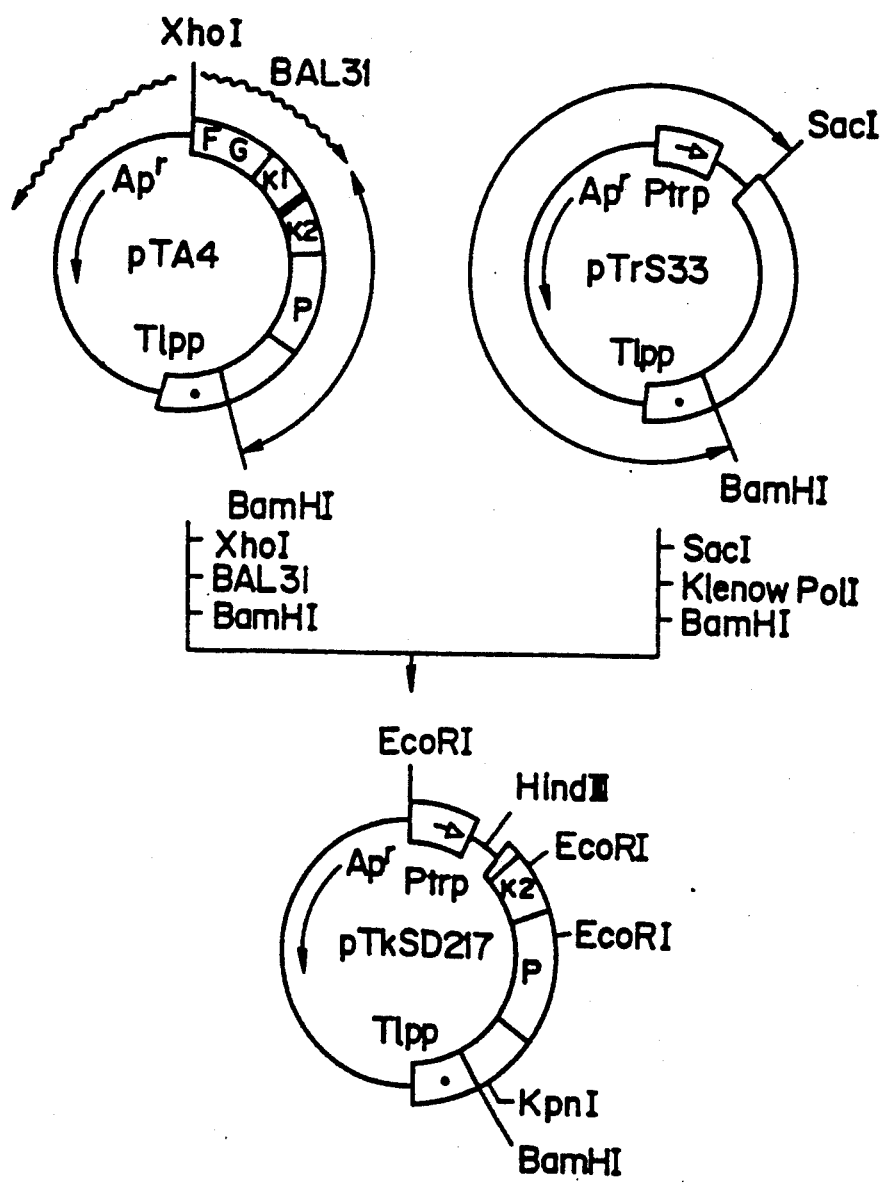
FIG. 52 shows the construction scheme for the plasmid pTkSD217.

The recombinant plasmid mixture obtained was used to transform *Escherichia coli* MM294 to give Ap-resistant transformants. The plasmid DNA pTkSD217 isolated from one of the transformants was subjected to structural analysis by restriction enzyme digestion and to base sequence determination of a region downstream from the *Escherichia coli* tryptophan promoter (Ptrp) by the dideoxy sequence method using M13 phage. As a result, it was confirmed that pTkSD217 had the desired structure and that the base sequence was as follows (cf. FIG. 52):

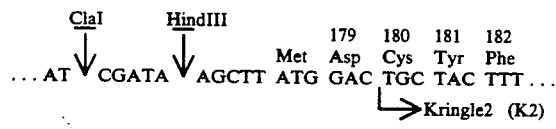

(2) Construction of recombinant plasmid pTkSL11:

About 3 μg of the pTkSD217 plasmid DNA obtained as described above was dissolved in 30 μl of Y-100 buffer, 10 units of HindIII and 15 units of ScaI were added, and digestion was effected at 37° C. for 2 hours. After 10-minute heat treatment at 65° C., a DNA fragment about 0.23 kb in size was purified by the AFT method. Separately, about 2 μg of the pTerm2 plasmid DNA obtained in Reference Example 5 was dissolved in 30 μl of Y-100 buffer, 10 units of HindIII and 10 units of NsiI (New England BioLabs) were added, and digestion was carried out at 37° C. for 2 hours. After 10-minute heat treatment at 65° C., a DNA fragment about 2.8 kb in size was purified by the AFT method. Furthermore, the following two synthetic DNAs (35-mer and 31-mer) were synthesized using Applied Biosystems model 380A DNA synthesizer and respectively 5'-phosphorylated by the method mentioned above:

5'-ACTGTGACGTCCCCAGCTGTTCTGAAG-
GAAATGCA-3'

3'-TGACACTGCAGGGGT-
CGACAAGACTTCCTTT-5'

The thus-obtained pTkSD217-derived DNA fragment (about 0.23 kb; about 0.01 μg), pTerm2-derived DNA fragment (about 2.8 kb; about 0.1 μg) and two 5'-phosphorylated synthetic DNAs (1 picomole each) were dissolved in a total of 20 μl of T4 ligase buffer, 300 units of T4 DNA ligase was added, and ligation was conducted at 4° C. for 18 hours.

Figure 53:
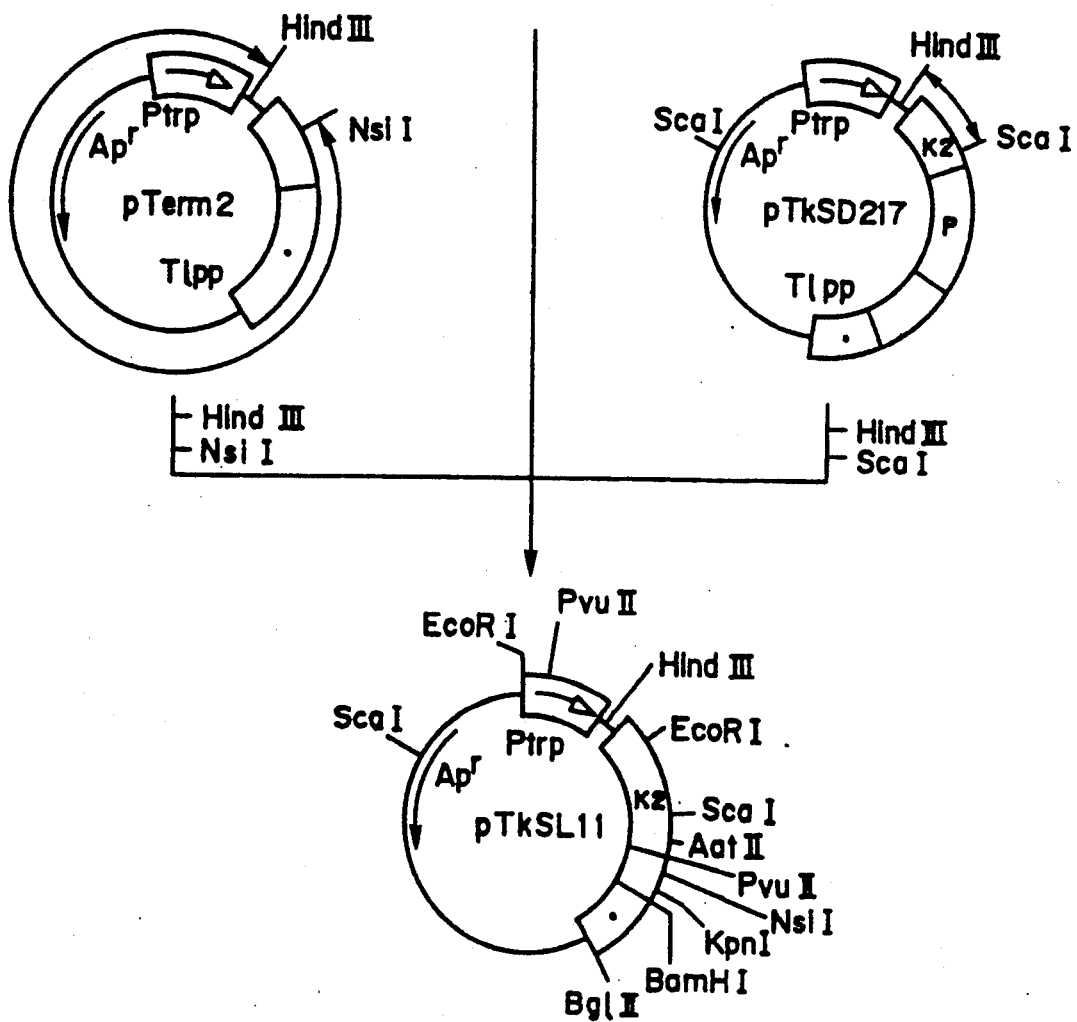
FIG. 53 shows the construction scheme for the plasmid pTkSL11.

The recombinant plasmid mixture obtained was used to transform *Escherichia coli* MM294 to give Ap-resistant transformants. The plasmid DNA pTkSL11 isolated from one of the transformants was subjected to structural analysis by restriction enzyme digestion and to base sequence determination by the M13 dideoxy sequencing method. It was confirmed that pTkSL11 had the desired structure (cf. FIG. 53).

(3) Construction of recombinant plasmid pTkSS4:

About 2 μg of the ptPA7 plasmid DNA obtained in Reference Example 1 was dissolved in 30 μl of Y-100 buffer, 12 units of the restriction enzyme ScaI was added, and digestion was performed at 37° C. for 2 hours. After 10-minute heat treatment at 65° C., a DNA fragment about 2.0 kb in size was purified by the AFT method. Separately, about 2 μg of the pTkSL11 plasmid DNA obtained as described above was digested in the same manner and, after 10-minute heat treatment at 65° C., a DNA fragment about 2.0 kb in size was purified by the AFT method.

The thus-obtained ptPA7-derived DNA fragment (about 2.0 kb; about 0.1 μg) and pTkSL11-derived DNA fragment (about 2.0 kb; about 0.1 μg) were dissolved in 20 μl of T4 ligase buffer, 300 units of T4 DNA ligase was added, and ligation was carried out at 4° C. for 18 hours.

Figure 54:
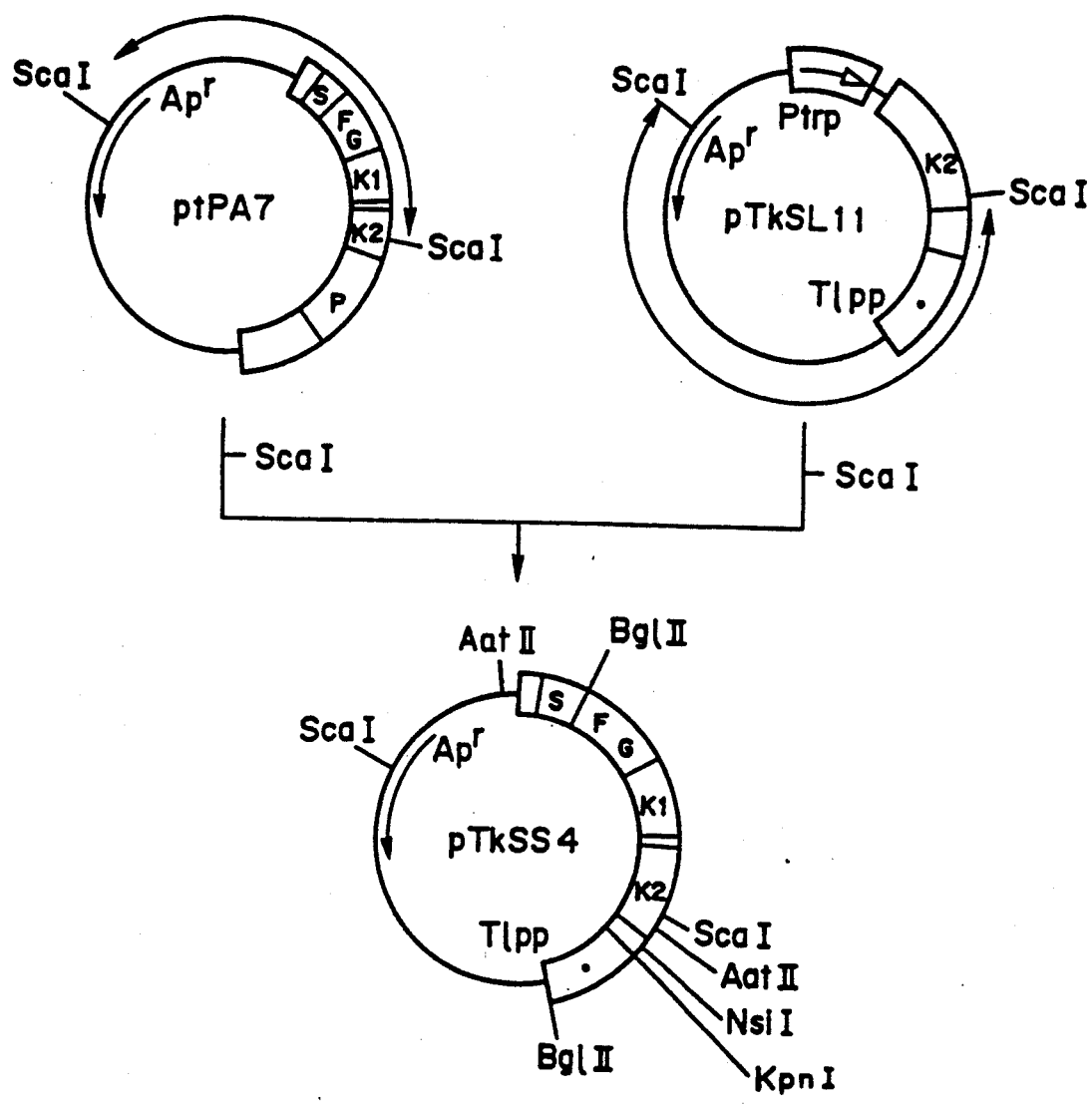
FIG. 54 shows the construction scheme for the plasmid pTkSS4.

The recombinant plasmid mixture obtained was used to transform *Escherichia coli* MM294 to give Ap-resistant transformants. The plasmid DNA pTkSS4 isolated from one of the transformants was subjected to structural analysis by restriction enzyme digestion and it was confirmed that pTkSS4 had the desired structure (cf. FIG. 54).

REFERENCE EXAMPLE 19

Construction of recombinant plasmid pTG3:

About 2 μg of the pTkSS4 plasmid DNA obtained in Reference Example 18 was dissolved in 30 μl of Y-0 buffer, 10 units of the restriction enzyme NarI (New England BioLabs) was added, and digestion was effected at 37° C. for 2 hours. Then, 1.0 μl of 2M NaCl and 12 units of BamHI were added and digestion was further effected at 37° C. for 2 hours. After 10-minute heat treatment at 65° C., a DNA fragment about 3.3 kb in size was purified by the AFT method. Separately, about 3 μg of the pTkSR18 plasmid DNA obtained in Reference Example 17 was subjected to the same digestion reaction as above and, after 10-minute heat treatment at 65° C., a DNA fragment about 0.2 kb in size was purified by the AFT method.

The thus-obtained pTkSS4-derived DNA fragment (about 3.3 kb; about 0.1 µg) and pTkSR18-derived DNA fragment (about 0.2 kb; about 0.01 µg) were dissolved in 20 µl of T4 ligase buffer, 100 units of T4 DNA ligase was added, and ligation was carried out at 4° C. for 18 hours.

Figure 55:
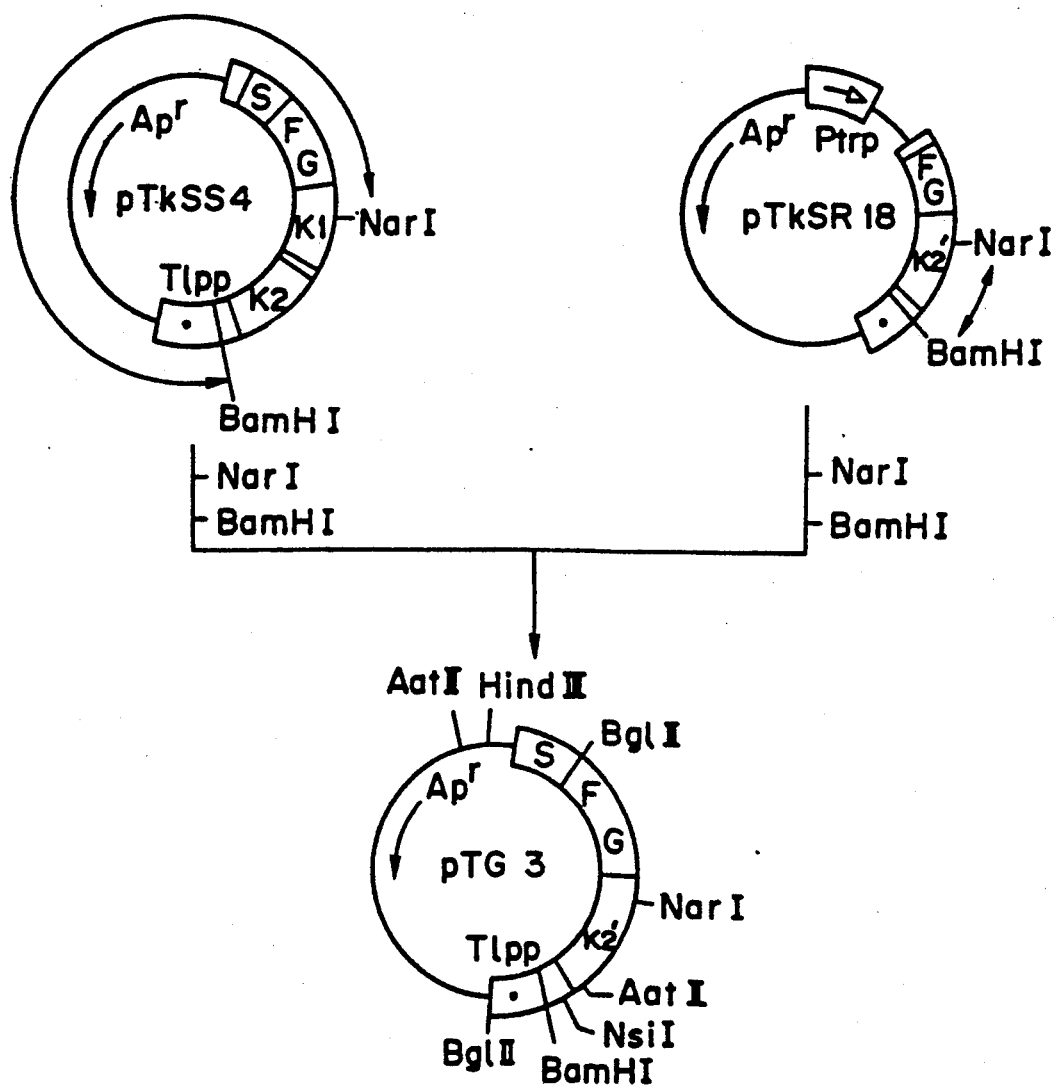
FIG. 55 shows the construction scheme for the plasmid pTG3.

The recombinant plasmid mixture obtained was used to transform *Escherichia coli* MM294 to give Ap-resistant transformants. The plasmid DNA pTG3 isolated from one of the transformants was subjected to structural analysis by restriction enzyme digestion and it was confirmed that pTG3 had the desired structure (cf. FIG. 55).

REFERENCE EXAMPLE 20

Construction of recombinant plasmid phPA2:

About 2 µg of the pTG3 plasmid DNA obtained in Reference Example 19 was dissolved in 30 µl of Y-100 buffer, 10 units each of EcoRI and PvuI were added, and digestion was carried out at 37° C. for 2 hours. After 10-minute heat treatment at 65° C., a DNA fragment about 1.7 kb in size was purified by the AFT method.

Separately, about 2 µg of the pUKB101 plasmid DNA obtained in Reference Example 12 was dissolved in 30 µl of Y-100 buffer, 10 units each of NcoI and PvuI were added, and digestion was carried out at 37° C. for 2 hours. After 10-minute heat treatment at 65° C., a DNA fragment about 3.0 kb in size was purified by the AFT method.

Further, separately, about 2 µg of the pTkSR18 plasmid DNA obtained in Reference Example 17 was dissolved in 30 µl of Y-100 buffer, 10 units each of HindIII and AatII were added, and digestion was carried out at 37° C. for 2 hours. After 10-minute heat treatment at 65° C., a DNA fragment about 0.55 kb in size was purified by the AFT method.

Furthermore, the following four synthetic DNAs (37-mer and 41-mer; 41-mer and 45-mer) were synthesized using Applied Biosystems model 380A DNA synthesizer:

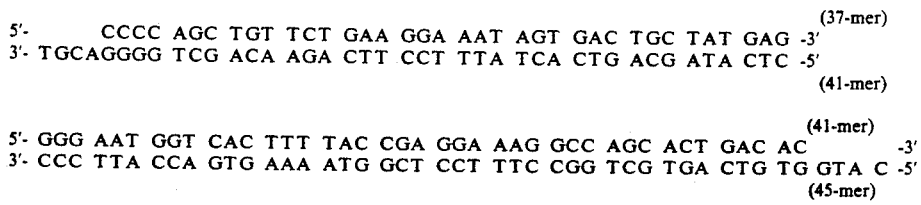

These synthetic DNAs (20 picomoles each) were respectively phosphorylated at the 5' end by carrying out the reaction in 20 µl of T4 kinase buffer in the presence of 5 units of T4 DNA kinase (Takara Shuzo) at 37° C. for 30 minutes.

The thus-obtained pTG3-derived DNA fragment (about 1.7 kb; about 0.05 µg), pUKB101-derived DNA fragment (about 3.0 kb; about 0.05 µg), pTkSR18-derived DNA fragment (about 0.55 kb; about 0.05 µg) and 5'-phosphorylated four synthetic DNAs (1 picomole each) were dissolved in a total of 20 µl of T4 ligase buffer, 300 units of T4 DNA ligase was added, and ligation was carried out at 4° C. for 18 hours.

The recombinant plasmid mixture obtained was used to transform *Escherichia coli* MM294 to give Ap-resistant transformants. The plasmid DNA phPA2 isolated from one of the transformants was subjected to structural analysis by restriction enzyme digestion and to base sequence determination by the M13 dideoxy sequencing method and it was confirmed that phPA2 had the desired As detailedly described hereinabove, the present invention provides polypeptides having such properties as protease resistance and thermal stability on a commercial scale by utilizing recombinant DNA techniques.

While the invention has been described in detail and with reference to specific embodiments thereof, it will be apparent to one skilled in the art that various changes and modifications can be made therein without departing from the spirit and scope thereof.

What is claimed is:

1. A modified granulocyte colony stimulating factor (hG-CSF) glycoprotein, wherein said hG-CSF is hG-CSF-Ala$^1$, Thr$^3$, Tyr$^4$, Arg$^5$, Ser$^{17}$, Asn$^{145}$, and Ser$^{147}$.